US011117955B2

(12) United States Patent
Kyratsous et al.

(10) Patent No.: US 11,117,955 B2
(45) Date of Patent: Sep. 14, 2021

(54) ANTI-ZIKA VIRUS ANTIBODIES AND METHODS OF USE

(71) Applicant: Regeneron Pharmaceuticals, Inc., Tarrytown, NY (US)

(72) Inventors: Christos Kyratsous, Irvington, NY (US); William Olson, Yorktown Heights, NY (US); Peter Mason, Somerville, MA (US)

(73) Assignee: Regeneron Pharmaceuticals, Inc., Tarrytown, NY (US)

(*) Notice: Subject to any disclaimer, the term of this patent is extended or adjusted under 35 U.S.C. 154(b) by 112 days.

(21) Appl. No.: 16/536,531

(22) Filed: Aug. 9, 2019

(65) Prior Publication Data

US 2020/0062831 A1 Feb. 27, 2020

Related U.S. Application Data

(62) Division of application No. 15/651,387, filed on Jul. 17, 2017, now Pat. No. 10,421,804.

(60) Provisional application No. 62/474,753, filed on Mar. 22, 2017, provisional application No. 62/363,546, filed on Jul. 18, 2016.

(51) Int. Cl.
  *C07K 16/10* (2006.01)
  *C07K 16/18* (2006.01)
  *A61K 39/00* (2006.01)

(52) U.S. Cl.
  CPC .......... *C07K 16/1081* (2013.01); *C07K 16/18* (2013.01); *A61K 2039/505* (2013.01); *A61K 2039/507* (2013.01); *C07K 2317/21* (2013.01); *C07K 2317/33* (2013.01); *C07K 2317/52* (2013.01); *C07K 2317/56* (2013.01); *C07K 2317/565* (2013.01); *C07K 2317/76* (2013.01); *C07K 2317/90* (2013.01); *C07K 2317/92* (2013.01); *Y02A 50/30* (2018.01)

(58) Field of Classification Search
  None
  See application file for complete search history.

(56) References Cited

U.S. PATENT DOCUMENTS 10,421,804 B2 9/2019 Kyratsous et al.

FOREIGN PATENT DOCUMENTS

WO PCT/US2017/042447 7/2017
WO 2018/017497 A1 1/2018

OTHER PUBLICATIONS

Morrison and Diamond, Journal of Virology, Apr. 2017, 91(8):e00009-17. (Year: 2017).*
Pattnaik et al., Vaccines, 2020, 8:266, 19 pages. (Year: 2020).*
WIPO Application No. PCT/US2017/042447, PCT Invitation to Pay Additional Fees and, Where Applicable, Protest Fee dated Oct. 5, 2017.
Barba-Spaeth et al., "Structural basis of potent Zika-dengue virus antibody cross-neutralization," Nature, vol. 536; Aug. 4, 2016; 20 pages.
Priyamvada et al., "Human antibody responses after dengue virus infection are highly cross-reactive to Zika virus," PNAS, vol. 113 (No. 28); pp. 7852-7857; Jul. 12, 2016.
WIPO Application No. PCT/US2017/042447, PCT International Search Report and Written Opinion dated Nov. 23, 2017.
U.S. Appl. No. 15/651,387, Requirement for Restriction/Election dated Jul. 18, 2018.
U.S. Appl. No. 15/651,387, Non-Final Office Action dated Nov. 14, 2018.
Blackman et al., "Challenges of Vaccine Development for Zika Virus," Viral Immunology, vol. 31 (No. 2):117-123 (2018). DOI: 10.1089/vim.2017.0145.
Buckley et al., "Detection of Virus-specific Antigen in the Nuclei or Nucleoli of Cells Infected with Zika or Langat Virus," Journal Gen. Virol., vol. 69:1913-1920, (1988).
WIPO Application No. PCT/US2017/042447, PCT International Preliminary Report on Patentability dated Jan. 31, 2019.
U.S. Appl. No. 15/651,387, Notice of Allowance dated May 9, 2019.
Dai et al., "Structures of the Zika Virus Envelope Protein and Its Complex with a Flavivirus Broadly Protective Antibody," Cell Host & Microbe, vol. 19:696-704, May 11, 2016.
U.S. Appl. No. 62/363,546, filed Jul. 18, 2016.
U.S. Appl. No. 62/474,753, filed Mar. 22, 2017.
U.S. Appl. No. 15/651,387, filed Jul. 17, 2017, U.S. Pat. No. 10,421,804.

* cited by examiner

*Primary Examiner* — Stacy B Chen
(74) *Attorney, Agent, or Firm* — Schwabe, Williamson & Wyatt PC; Veronica Mallon

(57) ABSTRACT

The present invention provides monoclonal antibodies, or antigen-binding fragments thereof, that bind to ZIKV glycoproteins, pharmaceutical compositions comprising the antibodies and methods of use. The antibodies of the invention are useful for inhibiting or neutralizing ZIKV activity, thus providing a means of treating or preventing ZIKV infection in humans. In some embodiments, the invention provides for use of one or more antibodies that bind to the ZIKV for preventing viral attachment and/or entry into host cells. The antibodies of the invention may be used prophylactically or therapeutically and may be used alone or in combination with one or more other anti-viral agents or vaccines.

18 Claims, 8 Drawing Sheets

Specification includes a Sequence Listing.

ANTI-ZIKA VIRUS ANTIBODIES AND METHODS OF USE

CROSS-REFERENCE TO RELATED APPLICATIONS

This application is a division of U.S. application Ser. No. 15/651,387, filed Jul. 17, 2017, which claims the benefit under 35 U.S.C § 119(e) of US Provisional Application Nos. 62/363,546, filed Jul. 18, 2016, and 62/474,753, filed Mar. 22, 2017, each of which is herein specifically incorporated by reference in its entirety.

REFERENCE TO A SEQUENCE LISTING

This application incorporates by reference the Sequence Listing submitted in Computer Readable Form as file 10278US02-Sequence.txt, created on Aug. 9, 2019 and containing 212,274 bytes.

FIELD OF THE INVENTION

The present invention relates to antibodies that bind to Zika virus envelope glycoprotein, pharmaceutical compositions comprising these antibodies and methods of use thereof.

BACKGROUND

Zika virus (ZIKV) is a positive-stranded RNA arthropod-borne virus (arbovirus) in the genus Flavivirus, family Flaviviridae (Gubler, D J, et al., In: Knipe, D M, et al., eds., Fields Virology, 5th edn., Philadelphia, Pa.: Lippincott Williams & Wilkins Publishers, 2007:1155-227). It is thought to be principally transmitted to humans by the mosquito, *Aedes aegypti*. In addition to transmission by mosquitoes, ZIKV may be sexually (Foy, B D, et al., (2011), Emerg. Infect. Dis. 17:880-882) and vertically (Mlakar, J. et al., (2016), N. Engl. J. Med. 374:951-958) transmitted, or transmitted via blood products or tissue samples. ZIKV generally causes a mild disease, with a rash and mild febrile illness in the majority of symptomatic individuals. However, when pregnant women are infected with ZIKV, there is an increased risk of developing microcephaly in the fetus (Schuler-Faccini, L. et al., (2016), *MMWR Morb. Mortal. Wkly Rep.* 65:59-62) or other developmental abnormalities (Brasil et al., (2016) N. Engl. J. Med., March 4). There have also been reports that ZIKV is associated with Guillain-Barré syndrome in patients infected with the virus (Cao-Lormeau, V M, et al., (2016), Lancet, April 9; 387(10027):1531-9). In addition, there have also been reports of an association of ZIKV with brain ischemia, myelitis and meningoencephalitis (Carteaux, G. et al. (2016), N. Engl. J. Med. 374(16):1595).

The tropism and pathogenesis of ZIKV are largely unknown. In general, flaviviruses are enveloped viruses containing a single strand RNA genome of about 11,000 bases complexed with multiple copies of the capsid protein, surrounded by an icosahedral shell consisting of 180 copies each of the envelope glycoprotein (E) (~500 amino acids), and the membrane protein (M) (~75 amino acids) or precursor membrane protein (prM) (~165 amino acids), all anchored in a lipid membrane. The genome also codes for seven non-structural proteins that are involved in replication and assembly (Sirohi, D. et al., (2016), Science, 352:467-470).

During their life cycle, flavivirus virions exist in an immature (non-infectious) state and a mature (infectious) state (Lindenbach, B D, In: Fields Virology, Knipe, D M and Howley, P M, eds, Philadelphia, Pa.: Lippincott Williams & Wilkins Publishers, Ed. 6, Vol. 1, 2013, Chapter 25, pp. 712-746).

The ZIKV envelope glycoprotein (E) may be a target for protective antibodies, but to date, no antibodies specific for ZIKV envelope glycoprotein are in clinical testing. Accordingly, there is still a need in the art to identify new antibodies, which can be used to prevent or treat a ZIKV infection.

BRIEF SUMMARY OF THE INVENTION

The present invention provides antibodies and antigen-binding fragments thereof that bind ZIKV E. The antibodies of the present invention are useful for inhibiting or neutralizing the activity of ZIKV. In some embodiments, the antibodies are useful for blocking attachment of ZIKV to the host cell, or for preventing fusion of the virus to the host cell membrane. In so doing, the antibodies of the invention block entry of the virus into host cells. In certain embodiments, the antibodies are useful in preventing, treating or ameliorating at least one symptom of ZIKV infection in a subject. In certain embodiments, the antibodies of the invention may neutralize the virus and in so doing, may prevent transmission of the virus in a pregnant female to her fetus thus preventing microcephaly (or other developmental abnormalities) in the fetus of the pregnant female. In certain embodiments, the antibodies may be administered prophylactically or therapeutically to a subject having, or at risk of acquiring, or at risk of transmitting a ZIKV infection. In certain embodiments, compositions containing at least one antibody of the invention may be administered to a subject for whom a vaccine is contra-indicated, or for whom a vaccine is less efficacious, for example, an elderly patient, a very young patient, a pregnant female patient, a patient who may be allergic to any one or more components of a vaccine, or an immunocompromised patient who may be non-responsive to the immunogens in a vaccine. In certain embodiments, compositions containing at least one antibody of the invention may be administered to a pregnant female, medical staff, hospitalized patients or nursing home residents, an individual traveling to a country known to have a ZIKV outbreak, or traveling to a country know to have mosquitoes carrying the ZIKV, or other high-risk patients during a ZIKV outbreak. In certain embodiments, compositions containing at least one antibody of the invention may be administered as a first line treatment to patients who have already been exposed to ZIKV.

The antibodies of the invention can be full-length (for example, an IgG1 or IgG4 antibody) or may comprise only an antigen-binding portion (for example, a Fab, F(ab')$_2$ or scFv fragment), and may be modified to affect functionality, e.g., to increase persistence in the host or to eliminate residual effector functions (Reddy et al., 2000, J. Immunol. 164:1925-1933). In certain embodiments, the antibodies may be bispecific.

In a first aspect, the present invention provides isolated recombinant monoclonal antibodies or antigen-binding fragments thereof that bind specifically to the ZIKV envelope glycoprotein (E).

In one embodiment, the present invention provides an isolated recombinant antibody or antigen-binding fragment thereof that specifically binds to ZIKV and/or a ZIKV E, wherein the antibody or antigen-binding fragment thereof neutralizes ZIKV in vitro with an IC$_{50}$ less than or equal to $10^{-9}$M and wherein the antibody or antigen-binding fragment thereof demonstrates a protective effect in vivo in a ZIKV infected animal.

In one embodiment, the present invention provides an isolated recombinant antibody or antigen-binding fragment thereof that specifically binds to ZIKV and/or a ZIKV E, wherein the antibody has one or more of the following characteristics:

(a) is a fully human monoclonal antibody;

(b) binds to a VLP expressing Zika prM/E with an $EC_{50}$ ranging from about 80 pM to about 150 nM;

(c) binds to ZIKV E with a dissociation constant ($K_D$) of less than $10^{-7}$M, as measured in a surface plasmon resonance assay; or (d) may or may not demonstrate a change in dissociative half-life (t½) at pH 5 or pH 6 relative to pH 7.4.

Exemplary anti-ZIKV E antibodies of the present invention are listed in Tables 1 and 2 herein. Table 1 sets forth the amino acid sequence identifiers of the heavy chain variable regions (HCVRs), light chain variable regions (LCVRs), heavy chain complementarity determining regions (HCDR1, HCDR2 and HCDR3), and light chain complementarity determining regions (LCDR1, LCDR2 and LCDR3) of exemplary anti-ZIKV E antibodies. Table 2 sets forth the nucleic acid sequence identifiers of the HCVRs, LCVRs, HCDR1, HCDR2 HCDR3, LCDR1, LCDR2 and LCDR3 of the exemplary anti-ZIKV E antibodies.

The present invention provides antibodies, or antigen-binding fragments thereof, comprising an HCVR comprising an amino acid sequence selected from any of the HCVR amino acid sequences listed in Table 1, or a substantially similar sequence thereof having at least 90%, at least 95%, at least 98% or at least 99% sequence identity thereto.

The present invention also provides antibodies, or antigen-binding fragments thereof, comprising an LCVR comprising an amino acid sequence selected from any of the LCVR amino acid sequences listed in Table 1, or a substantially similar sequence thereof having at least 90%, at least 95%, at least 98% or at least 99% sequence identity thereto.

The present invention also provides antibodies, or antigen-binding fragments thereof, comprising an HCVR and an LCVR amino acid sequence pair (HCVR/LCVR) comprising any of the HCVR amino acid sequences listed in Table 1 paired with any of the LCVR amino acid sequences listed in Table 1. According to certain embodiments, the present invention provides antibodies, or antigen-binding fragments thereof, comprising an HCVR/LCVR amino acid sequence pair contained within any of the exemplary anti-ZIKV E antibodies listed in Table 1.

In one embodiment, the isolated anti-ZIKV monoclonal antibodies or antigen-binding fragments comprise the three heavy chain complementarity determining regions (HCDR1, HCDR2 and HCDR3) contained within any one of the heavy chain variable region (HCVR) sequences selected from the group consisting of SEQ ID NOs: 2, 18, 34, 50, 66, 82, 98, 114, 130, 146, 162, 178, 194, 210, 226, 242, 258, 274, 290, 306, 322 and 338; and the three light chain complementarity determining regions (LCDR1, LCDR2 and LCDR3) contained within any one of the light chain variable region (LCVR) sequences selected from the group consisting of SEQ ID NOs: 10, 26, 42, 58, 74, 90, 106, 122, 138, 154, 170, 186, 202, 218, 234, 250, 266, 282, 298, 314, 330 and 346.

In one embodiment, the isolated anti-ZIKV monoclonal antibodies or antigen-binding fragments thereof comprise a HCVR having an amino acid sequence selected from the group consisting of SEQ ID NOs: 2, 18, 34, 50, 66, 82, 98, 114, 130, 146, 162, 178, 194, 210, 226, 242, 258, 274, 290, 306, 322 and 338.

In one embodiment, the isolated anti-ZIKV monoclonal antibodies or antigen-binding fragments thereof comprise a LCVR having an amino acid sequence selected from the group consisting of SEQ ID NOs: 10, 26, 42, 58, 74, 90, 106, 122, 138, 154, 170, 186, 202, 218, 234, 250, 266, 282, 298, 314, 330 and 346.

In one embodiment, the isolated antibody or antigen-binding fragment comprises a HCVR/LCVR amino acid sequence pair selected from the group consisting of SEQ ID NOs: 2/10, 18/26, 34/42, 50/58, 66/74, 82/90, 98/106, 114/122, 130/138, 146/154, 162/170, 178/186, 194/202, 210/218, 226/234, 242/250, 258/266, 274/282, 290/298, 306/314, 322/330 and 338/346.

In certain embodiments, the HCVR/LCVR amino acid sequence pair is selected from the group consisting of SEQ ID NOs: 66/74 (H4H25598P), SEQ ID NOs: 114/122 (H4H25619P), and SEQ ID NOs: 258/266 (H4H25703N). In one embodiment, the HCVR/LCVR amino acid sequence pair is selected from the group consisting of SEQ ID NOs: 114/122 (H4H25619P) and SEQ ID NOs: 258/266 (H4H25703N).

In one embodiment, the isolated antibody or antigen-binding fragment comprises:

(a) a HCDR1 domain having an amino acid sequence selected from the group consisting of SEQ ID NOs: 4, 20, 36, 52, 68, 84, 100, 116, 132, 148, 164, 180, 196, 212, 228, 244, 260, 276, 292, 308, 324 and 340;

(b) a HCDR2 domain having an amino acid sequence selected from the group consisting of SEQ ID NOs: 6, 22, 38, 54, 70, 86, 102, 118, 134, 150, 166, 182, 198, 214, 230, 246, 262, 278, 294, 310, 326 and 342;

(c) a HCDR3 domain having an amino acid sequence selected from the group consisting of SEQ ID NOs: 8, 24, 40, 56, 72, 88, 104, 120, 136, 152, 168, 184, 200, 216, 232, 248, 264, 280, 296, 312, 328 and 344;

(d) a LCDR1 domain having an amino acid sequence selected from the group consisting of SEQ ID NOs: 12, 28, 44, 60, 76, 92, 108, 124, 140, 156, 172, 188, 204, 220, 236, 252, 268, 284, 300, 316, 332 and 348;

(e) a LCDR2 domain having an amino acid sequence selected from the group consisting of SEQ ID NOs: 14, 30, 46, 62, 78, 94, 110, 126, 142, 158, 174, 190, 206, 222, 238, 254, 270, 286, 302, 318, 334 and 350;

(f) a LCDR3 domain having an amino acid sequence selected from the group consisting of SEQ ID NOs: 16, 32, 48, 64, 80, 96, 112, 128, 144, 160, 176, 192, 208, 224, 240, 256, 272, 288, 304, 320, 336 and 352.

In one embodiment, the isolated antibody or antigen-binding fragment thereof comprises an HCDR1 amino acid sequence of SEQ ID NO: 68; an HCDR2 amino acid sequence of SEQ ID NO: 70; an HCDR3 amino acid sequence of SEQ ID NO: 72; an LCDR1 amino acid sequence of SEQ ID NO: 76; an LCDR2 amino acid sequence of SEQ ID NO: 78 and an LCDR3 amino acid sequence of SEQ ID NO: 80.

In one embodiment, the isolated antibody or antigen-binding fragment thereof comprises an HCDR1 amino acid sequence of SEQ ID NO: 116; an HCDR2 amino acid sequence of SEQ ID NO: 118; an HCDR3 amino acid sequence of SEQ ID NO: 120; an LCDR1 amino acid sequence of SEQ ID NO: 124; an LCDR2 amino acid sequence of SEQ ID NO: 126 and an LCDR3 amino acid sequence of SEQ ID NO: 128.

In one embodiment, the isolated antibody or antigen-binding fragment thereof comprises an HCDR1 amino acid sequence of SEQ ID NO: 260; an HCDR2 amino acid sequence of SEQ ID NO: 262; an HCDR3 amino acid sequence of SEQ ID NO: 264; an LCDR1 amino acid sequence of SEQ ID NO: 268; an LCDR2 amino acid sequence of SEQ ID NO: 270 and an LCDR3 amino acid sequence of SEQ ID NO: 272.

The present invention also provides antibodies, or antigen-binding fragments thereof, comprising a heavy chain CDR1 (HCDR1) comprising an amino acid sequence selected from any of the HCDR1 amino acid sequences listed in Table 1 or a substantially similar sequence thereof having at least 90%, at least 95%, at least 98% or at least 99% sequence identity.

The present invention also provides antibodies, or antigen-binding fragments thereof, comprising a heavy chain CDR2 (HCDR2) comprising an amino acid sequence selected from any of the HCDR2 amino acid sequences listed in Table 1 or a substantially similar sequence thereof having at least 90%, at least 95%, at least 98% or at least 99% sequence identity.

The present invention also provides antibodies, or antigen-binding fragments thereof, comprising a heavy chain CDR3 (HCDR3) comprising an amino acid sequence selected from any of the HCDR3 amino acid sequences listed in Table 1 or a substantially similar sequence thereof having at least 90%, at least 95%, at least 98% or at least 99% sequence identity.

The present invention also provides antibodies, or antigen-binding fragments thereof, comprising a light chain CDR1 (LCDR1) comprising an amino acid sequence selected from any of the LCDR1 amino acid sequences listed in Table 1 or a substantially similar sequence thereof having at least 90%, at least 95%, at least 98% or at least 99% sequence identity.

The present invention also provides antibodies, or antigen-binding fragments thereof, comprising a light chain CDR2 (LCDR2) comprising an amino acid sequence selected from any of the LCDR2 amino acid sequences listed in Table 1 or a substantially similar sequence thereof having at least 90%, at least 95%, at least 98% or at least 99% sequence identity.

The present invention also provides antibodies, or antigen-binding fragments thereof, comprising a light chain CDR3 (LCDR3) comprising an amino acid sequence selected from any of the LCDR3 amino acid sequences listed in Table 1 or a substantially similar sequence thereof having at least 90%, at least 95%, at least 98% or at least 99% sequence identity.

The present invention also provides antibodies, or antigen-binding fragments thereof, comprising an HCDR3 and an LCDR3 amino acid sequence pair (HCDR3/LCDR3) comprising any of the HCDR3 amino acid sequences listed in Table 1 paired with any of the LCDR3 amino acid sequences listed in Table 1. According to certain embodiments, the present invention provides antibodies, or antigen-binding fragments thereof, comprising an HCDR3/LCDR3 amino acid sequence pair contained within any of the exemplary anti-ZIKV E antibodies listed in Table 1. In certain embodiments, the HCDR3/LCDR3 amino acid sequence pair is SEQ ID NOs: 72/80 (e.g., H4H25598P) and 264/272 (e.g., H4H25703N).

The present invention also provides antibodies, or antigen-binding fragments thereof, comprising a set of six CDRs HCDR1-HCDR2-HCDR3-LCDR1-LCDR2-LCDR3) contained within any of the exemplary anti-ZIKV E antibodies listed in Table 1. In certain embodiments, the HCDR1-HCDR2-HCDR3-LCDR1-LCDR2-LCDR3 amino acid sequence set is selected from the group consisting of SEQ ID NOs: 68-70-72-76-78-80 (e.g., H4H25598P), SEQ ID NOs: 116, 118, 120, 124, 126 and 128 (H4H25619P), and SEQ ID NOs: 260-262-264-268-270-272 (e.g., H4H25703N).

In a related embodiment, the present invention provides antibodies, or antigen-binding fragments thereof, comprising a set of six CDRs HCDR1-HCDR2-HCDR3-LCDR1-LCDR2-LCDR3) contained within an HCVR/LCVR amino acid sequence pair as defined by any of the exemplary anti-ZIKV E antibodies listed in Table 1. For example, the present invention includes antibodies, or antigen-binding fragments thereof, comprising the HCDR1-HCDR2-HCDR3-LCDR1-LCDR2-LCDR3 amino acid sequences set contained within an HCVR/LCVR amino acid sequence pair selected from the group consisting of SEQ ID NOs: 66/74 (e.g., H4H25598P), SEQ ID NO: 114/122 (e.g. H4H25619P) and 258/266 (e.g., H4H25703N). Methods and techniques for identifying CDRs within HCVR and LCVR amino acid sequences are well known in the art and can be used to identify CDRs within the specified HCVR and/or LCVR amino acid sequences disclosed herein. Exemplary conventions that can be used to identify the boundaries of CDRs include, e.g., the Kabat definition, the Chothia definition, and the AbM definition. In general terms, the Kabat definition is based on sequence variability, the Chothia definition is based on the location of the structural loop regions, and the AbM definition is a compromise between the Kabat and Chothia approaches. See, e.g., Kabat, "Sequences of Proteins of Immunological Interest," National Institutes of Health, Bethesda, Md. (1991); Al-Lazikani et al., *J. Mol. Biol.* 273:927-948 (1997); and Martin et al., *Proc. Natl. Acad. Sci. USA* 86:9268-9272 (1989). Public databases are also available for identifying CDR sequences within an antibody.

In one embodiment, the invention provides an anti-ZIKV antibody that binds specifically to ZIKV and has a heavy chain (HC) amino acid sequence of SEQ ID NO: 367 and a light chain (LC) amino acid sequence of SEQ ID NO: 368.

In one embodiment, the invention provides an anti-ZIKV antibody that binds specifically to ZIKV and has a heavy chain (HC) amino acid sequence of SEQ ID NO: 370 and a light chain (LC) amino acid sequence of SEQ ID NO: 371.

In one embodiment, the invention provides an anti-ZIKV antibody that binds specifically to ZIKV and has a heavy chain (HC) amino acid sequence of SEQ ID NO: 373 and a light chain (LC) amino acid sequence of SEQ ID NO: 374.

In one embodiment, the invention provides an anti-ZIKV antibody that binds specifically to ZIKV and has a heavy chain (HC) amino acid sequence of SEQ ID NO: 369 and a light chain (LC) amino acid sequence of SEQ ID NO: 368.

In one embodiment, the invention provides an anti-ZIKV antibody that binds specifically to ZIKV and has a heavy chain (HC) amino acid sequence of SEQ ID NO: 372 and a light chain (LC) amino acid sequence of SEQ ID NO: 371.

In one embodiment, the invention provides an anti-ZIKV antibody that binds specifically to ZIKV and has a heavy chain (HC) amino acid sequence of SEQ ID NO: 375 and a light chain (LC) amino acid sequence of SEQ ID NO: 374.

In one embodiment, the antibodies of the invention are capable of neutralizing the ZIKV strains selected from the group consisting of MR766 (Uganda 1947), PRVABC59 (Puerto Rico 2015) and FLR (Colombia 2015) strains.

In one aspect of the invention, the invention provides a human antibody, an antibody variant, or an antigen binding fragment thereof that neutralizes ZIKV, wherein the antibody, antibody variant, or antigen binding fragment does not contribute to, cause, or induce, antibody-dependent enhancement (ADE). In one embodiment, the antibody or antigen-binding fragment thereof does not contribute to, cause, or induce, antibody-dependent enhancement (ADE) of a ZIKV infection, or infection with one or more other viruses in the Flavivirus family, e.g. Dengue virus.

In one embodiment, the invention provides an antibody that neutralizes a ZIKV having a wild type E protein (See e.g. SEQ ID NO: 376), but does not neutralize a ZIKV having a mutated form of the E protein, wherein the mutation is a serine to phenylalanine at position 302 of SEQ ID NO: 376 (S302F), a threonine to isoleucine at position 311 of SEQ ID NO: 376 (T311I), or a lysine to glutamic acid at position 369 of SEQ ID NO: 376 (K369E).

In one embodiment, the invention provides a human antibody, an antibody variant, or an antigen binding fragment thereof that neutralizes ZIKV, wherein the antibody, antibody variant, or antigen-binding fragment comprises one or more mutations in the Fc region, wherein the one or more mutations reduce binding of the antibody to an Fc receptor on a cell.

In one embodiment, the invention provides a human antibody, an antibody variant, or an antigen-binding fragment thereof that neutralizes ZIKV, wherein the antibody, antibody variant, or antigen-binding fragment comprises one or more mutations in the Fc region, wherein the one or more mutations result in a longer serum half life of the antibody. In one embodiment, the mutation consists of a YTE modification at positions 131, 133 and 135 of SEQ ID NO: 357 (M131Y, S133T and T135E). These changes are shown at these positions in SEQ ID NO: 358.

In one embodiment, the invention provides a human antibody, an antibody variant, or an antigen binding fragment thereof that neutralizes ZIKV, wherein the antibody, antibody variant, or antigen binding fragment comprises at least one mutation in the Fc region that results in reduced binding of the antibody to an Fc receptor on a cell and at least one mutation that results in an increase in the serum half life of the antibody.

The present invention includes anti-ZIKV antibodies comprising an Fc domain, wherein the Fc domain comprises IgG1 or IgG4 isotypes as described elsewhere herein.

In certain embodiments, an anti-ZIKV antibody of the invention comprises an Fc domain having an amino acid sequence selected from the group consisting of SEQ ID NOs: 356 (IgG1), 357 (IgG4 without a YTE mutation), 358 (IgG4 with a YTE mutation), 365 (IgG4 without a YTE mutation) and 366 (IgG4 with a YTE mutation).

In one embodiment, an anti-ZIKV antibody of the invention comprises an Fc domain having the amino acid sequence of SEQ ID NO: 357.

In one embodiment, an anti-ZIKV antibody of the invention comprises an Fc domain having the amino acid sequence of SEQ ID NO: 358.

In one embodiment, an anti-ZIKV antibody of the invention comprises an HCVR/LVCR amino acid sequence pair of SEQ ID NOs: 258/266 and an Fc domain having the amino acid sequence of SEQ ID NO: 357 or 358.

In one embodiment, an anti-ZIKV antibody of the invention comprises an HCVR/LVCR amino acid sequence pair of SEQ ID NOs: 114/122 and an Fc domain having the amino acid sequence of SEQ ID NO: 357 or 358.

In one embodiment, an anti-ZIKV antibody of the invention comprises an HCVR/LVCR amino acid sequence pair of SEQ ID NOs: 114/122 and an Fc domain having the amino acid sequence of SEQ ID NO: 357.

In one embodiment, an anti-ZIKV antibody of the invention comprises an HCVR/LVCR amino acid sequence pair of SEQ ID NOs: 66/74 and an Fc domain having the amino acid sequence of SEQ ID NO: 357 or 358.

In one embodiment, an anti-ZIKV antibody of the invention comprises an HCVR/LVCR amino acid sequence pair of SEQ ID NOs: 66/74 and an Fc domain having the amino acid sequence of SEQ ID NO: 357.

The present invention includes anti-ZIKV antibodies having a modified glycosylation pattern. In some embodiments, modification to remove undesirable glycosylation sites may be useful, or an antibody lacking a fucose moiety present on the oligosaccharide chain, for example, to increase antibody dependent cellular cytotoxicity (ADCC) function (see Shield et al. (2002) JBC 277:26733). In other applications, modification of galactosylation can be made in order to modify complement dependent cytotoxicity (CDC).

The present invention also provides antibodies and antigen-binding fragments thereof that cross-compete for binding to ZIKV, or that bind the same epitope as a reference antibody or antigen-binding fragment thereof comprising the CDRs of a HCVR and the CDRs of a LCVR, wherein the HCVR and LCVR each has an amino acid sequence selected from the HCVR and LCVR sequences listed in Table 1.

The present invention also provides isolated antibodies and antigen-binding fragments thereof that block ZIKV attachment to a cell, or prevent fusion of the virus to a cell membrane, thereby preventing entry of the virus into a host cell.

In certain embodiments, the antibodies or antigen-binding fragments of the present invention are bispecific comprising a first binding specificity to a first epitope in the ZIKV and a second binding specificity to a second epitope in the ZIKV, wherein the first and second epitopes are distinct and non-overlapping. In certain embodiments the bispecific may comprise a first arm that binds to an epitope in the viral envelope glycoprotein and a second arm that binds to an epitope in a different viral antigen.

In a second aspect, the present invention provides nucleic acid molecules encoding anti-ZIKV antibodies or portions thereof. For example, the present invention provides nucleic acid molecules encoding any of the HCVR amino acid sequences listed in Table 1; in certain embodiments the nucleic acid molecule comprises a polynucleotide sequence selected from any of the HCVR nucleic acid sequences listed in Table 2, or a substantially similar sequence thereof having at least 90%, at least 95%, at least 98% or at least 99% sequence identity thereto.

The present invention also provides nucleic acid molecules encoding any of the LCVR amino acid sequences listed in Table 1; in certain embodiments the nucleic acid molecule comprises a polynucleotide sequence selected from any of the LCVR nucleic acid sequences listed in Table 2, or a substantially similar sequence thereof having at least 90%, at least 95%, at least 98% or at least 99% sequence identity thereto.

The present invention also provides nucleic acid molecules encoding any of the HCDR1 amino acid sequences listed in Table 1; in certain embodiments the nucleic acid molecule comprises a polynucleotide sequence selected from any of the HCDR1 nucleic acid sequences listed in Table 2, or a substantially similar sequence thereof having at least 90%, at least 95%, at least 98% or at least 99% sequence identity thereto.

The present invention also provides nucleic acid molecules encoding any of the HCDR2 amino acid sequences listed in Table 1; in certain embodiments the nucleic acid molecule comprises a polynucleotide sequence selected from any of the HCDR2 nucleic acid sequences listed in Table 2, or a substantially similar sequence thereof having at least 90%, at least 95%, at least 98% or at least 99% sequence identity thereto.

The present invention also provides nucleic acid molecules encoding any of the HCDR3 amino acid sequences listed in Table 1; in certain embodiments the nucleic acid molecule comprises a polynucleotide sequence selected from any of the HCDR3 nucleic acid sequences listed in Table 2, or a substantially similar sequence thereof having at least 90%, at least 95%, at least 98% or at least 99% sequence identity thereto.

The present invention also provides nucleic acid molecules encoding any of the LCDR1 amino acid sequences listed in Table 1; in certain embodiments the nucleic acid molecule comprises a polynucleotide sequence selected from any of the LCDR1 nucleic acid sequences listed in Table 2, or a substantially similar sequence thereof having at least 90%, at least 95%, at least 98% or at least 99% sequence identity thereto.

The present invention also provides nucleic acid molecules encoding any of the LCDR2 amino acid sequences listed in Table 1; in certain embodiments the nucleic acid molecule comprises a polynucleotide sequence selected from any of the LCDR2 nucleic acid sequences listed in Table 2, or a substantially similar sequence thereof having at least 90%, at least 95%, at least 98% or at least 99% sequence identity thereto.

The present invention also provides nucleic acid molecules encoding any of the LCDR3 amino acid sequences listed in Table 1; in certain embodiments the nucleic acid molecule comprises a polynucleotide sequence selected from any of the LCDR3 nucleic acid sequences listed in Table 2, or a substantially similar sequence thereof having at least 90%, at least 95%, at least 98% or at least 99% sequence identity thereto.

The present invention also provides nucleic acid molecules encoding an HCVR, wherein the HCVR comprises a set of three CDRs HCDR1-HCDR2-HCDR3), wherein the HCDR1-HCDR2-HCDR3 amino acid sequence set is as defined by any of the exemplary anti-ZIKV E antibodies listed in Table 1.

The present invention also provides nucleic acid molecules encoding an LCVR, wherein the LCVR comprises a set of three CDRs LCDR1-LCDR2-LCDR3), wherein the LCDR1-LCDR2-LCDR3 amino acid sequence set is as defined by any of the exemplary anti-ZIKV E antibodies listed in Table 1.

The present invention also provides nucleic acid molecules encoding both an HCVR and an LCVR, wherein the HCVR comprises an amino acid sequence of any of the HCVR amino acid sequences listed in Table 1, and wherein the LCVR comprises an amino acid sequence of any of the LCVR amino acid sequences listed in Table 1. In certain embodiments, the nucleic acid molecule comprises a polynucleotide sequence selected from any of the HCVR nucleic acid sequences listed in Table 2, or a substantially similar sequence thereof having at least 90%, at least 95%, at least 98% or at least 99% sequence identity thereto, and a polynucleotide sequence selected from any of the LCVR nucleic acid sequences listed in Table 2, or a substantially similar sequence thereof having at least 90%, at least 95%, at least 98% or at least 99% sequence identity thereto. In certain embodiments according to this aspect of the invention, the nucleic acid molecule encodes an HCVR and LCVR, wherein the HCVR and LCVR are both derived from the same anti-ZIKV E antibody listed in Table 1.

The present invention provides nucleic acid molecules encoding any of the heavy chain amino acid sequences listed in Table 1. The present invention also provides nucleic acid molecules encoding any of the light chain amino acid sequences listed in Table 1.

In a related aspect, the present invention provides recombinant expression vectors capable of expressing a polypeptide comprising a heavy or light chain variable region of an anti-ZIKV E antibody. For example, the present invention includes recombinant expression vectors comprising any of the nucleic acid molecules mentioned above, i.e., nucleic acid molecules encoding any of the HCVR, LCVR, and/or CDR sequences as set forth in Table 1. Also included within the scope of the present invention are host cells into which such vectors have been introduced, as well as methods of producing the antibodies or portions thereof by culturing the host cells under conditions permitting production of the antibodies or antibody fragments, and recovering the antibodies and antibody fragments so produced.

In a third aspect, the invention provides a pharmaceutical composition comprising one or more isolated monoclonal antibodies or antigen-binding fragments thereof which specifically bind to ZIKV E and a pharmaceutically acceptable carrier or diluent. The one or more isolated antibodies comprise an HCVR/LCVR amino acid sequence pair selected from the group consisting of the HCVR and LCVR sequences listed in Table 1. In one embodiment, the one or more isolated monoclonal antibodies tor antigen-binding fragments thereof that bind specifically to ZIKV comprise the three heavy chain complementarity determining regions (HCDR1, HCDR2 and HCDR3) contained within any one of the heavy chain variable region (HCVR) sequences selected from the group consisting of SEQ ID NOs: 2, 18, 34, 50, 66, 82, 98, 114, 130, 146, 162, 178, 194, 210, 226, 242, 258, 274, 290, 306, 322 and 338; and the three light chain complementarity determining regions (LCDR1, LCDR2 and LCDR3) contained within any one of the light chain variable region (LCVR) sequences selected from the group consisting of SEQ ID NOs: 10, 26, 42, 58, 74, 90, 106, 122, 138, 154, 170, 186, 202, 218, 234, 250, 266, 282, 298, 314, 330 and 346. In one embodiment, the HCVR/LCVR amino acid sequence pair is selected from the group consisting of SEQ ID NOs: 2/10, 18/26, 34/42, 50/58, 66/74, 82/90, 98/106, 114/122, 130/138, 146/154, 162/170, 178/186, 194/202, 210/218, 226/234, 242/250, 258/266, 274/282, 290/298, 306/314, 322/330 and 338/346. In one embodiment, the HCVR/LCVR amino acid sequence pair is selected from the group consisting of SEQ ID NOs: 66/74, 114/122 and 258/266. In one embodiment, the HCVR/LCVR amino acid sequence pair is selected from the group consisting of SEQ ID NOs: 114/122 and 258/266.

In one embodiment, the pharmaceutical composition comprises:
a) an isolated first monoclonal antibody, or antigen-binding fragment thereof that binds specifically to ZIKV, comprising a HCDR1 having the amino acid sequence of SEQ ID NO: 116, a HCDR2 having the amino acid sequence of SEQ ID NO: 118, a HCDR3 having the amino acid sequence of SEQ ID NO: 120, a LCDR1 having the amino acid sequence of SEQ ID NO: 124, a LCDR2 having the amino acid sequence of SEQ ID NO: 126, a LCDR3 having the amino acid sequence of SEQ ID NO: 128;

b) an isolated second monoclonal antibody, or antigen-binding fragment thereof that binds specifically to ZIKV, comprising a HCDR1 having the amino acid sequence of SEQ ID NO: 260, a HCDR2 having the amino acid sequence of SEQ ID NO: 262, a HCDR3 having the amino acid sequence of SEQ ID NO: 264, a LCDR1 having the amino acid sequence of SEQ ID NO: 268, a LCDR2 having the amino acid sequence of SEQ ID NO: 270, a LCDR3 having the amino acid sequence of SEQ ID NO: 272; and c) a pharmaceutically acceptable carrier or diluent.

In a related aspect, the invention features a pharmaceutical composition comprising at least two antibodies of the invention and a pharmaceutically acceptable carrier or diluent.

In one embodiment, the pharmaceutical composition comprises at least two isolated monoclonal antibodies or antigen-binding fragments thereof that bind specifically to ZIKV, and a pharmaceutically acceptable carrier or diluent, wherein at least one of the two monoclonal antibodies neutralizes ZIKV in vitro with an $IC_{50}$ equal to or less than about $10^{-9}$M and demonstrates a protective effect in vivo in a ZIKV infected animal.

In one embodiment, the at least two isolated antibodies are selected from a first and a second anti-ZIKV monoclonal antibody or antigen-binding fragment comprising the three heavy chain complementarity determining regions (HCDR1, HCDR2 and HCDR3) contained within any one of the heavy chain variable region (HCVR) sequences selected from the group consisting of SEQ ID NOs: 2, 18, 34, 50, 66, 82, 98, 114, 130, 146, 162, 178, 194, 210, 226, 242, 258, 274, 290, 306, 322 and 338; and the three light chain complementarity determining regions (LCDR1, LCDR2 and LCDR3) contained within any one of the light chain variable region (LCVR) sequences selected from the group consisting of SEQ ID NOs: 10, 26, 42, 58, 74, 90, 106, 122, 138, 154, 170, 186, 202, 218, 234, 250, 266, 282, 298, 314, 330 and 346.

In one embodiment, the at least two isolated antibodies are selected from a first and a second anti-ZIKV monoclonal antibody or antigen-binding fragment thereof, wherein the first anti-ZIKV monoclonal antibody or antigen-binding fragment thereof comprises a HCDR1 having the amino acid sequence of SEQ ID NO: 116, a HCDR2 having the amino acid sequence of SEQ ID NO: 118, a HCDR3 having the amino acid sequence of SEQ ID NO: 120, a LCDR1 having the amino acid sequence of SEQ ID NO: 124, a LCDR2 having the amino acid sequence of SEQ ID NO: 126, and a LCDR3 having the amino acid sequence of SEQ ID NO: 128; and wherein the second anti-ZIKV monoclonal antibody, or antigen-binding fragment thereof that binds specifically to ZIKV, comprises a HCDR1 having the amino acid sequence of SEQ ID NO: 260, a HCDR2 having the amino acid sequence of SEQ ID NO: 262, a HCDR3 having the amino acid sequence of SEQ ID NO: 264, a LCDR1 having the amino acid sequence of SEQ ID NO: 268, a LCDR2 having the amino acid sequence of SEQ ID NO: 270, and a LCDR3 having the amino acid sequence of SEQ ID NO: 272.

In a related aspect, the invention features a composition comprising at least three antibodies of the invention and a pharmaceutically acceptable carrier or diluent.

In certain embodiments, the invention provides a pharmaceutical composition comprising: (a) a first anti-ZIKV antibody comprising an HCVR/LCVR amino acid sequence pair as described in Table 1, or antigen-binding fragment thereof; (b) a second anti-ZIKV antibody comprising an HCVR/LCVR amino acid sequence pair as described in Table 1, or antigen-binding fragment thereof, wherein the first antibody binds to a first epitope on ZIKV E and the second antibody binds to a second different epitope on ZIKV E wherein the first and second epitopes are distinct and non-overlapping; and (c) a pharmaceutically acceptable carrier or diluent.

In another related aspect, the invention features a composition, which comprises a combination of an anti-ZIKV E antibody and a second therapeutic agent.

In one embodiment, the second therapeutic agent is any agent that is advantageously combined with an anti-ZIKV E antibody. Exemplary agents that may be advantageously combined with an anti-ZIKV antibody include, without limitation, other agents that bind and/or inhibit ZIKV activity (including other antibodies or antigen-binding fragments thereof, etc.) and/or agents, which do not directly bind ZIKV but nonetheless inhibit viral activity (including infectivity of host cells) and/or viral pathogenesis.

In certain embodiments, the invention provides a pharmaceutical composition comprising: (a) a first anti-ZIKV antibody or antigen-binding fragment thereof; (b) a second anti-ZIKV antibody or antigen-binding fragment thereof, wherein the first antibody does not cross-compete with the second antibody for binding to ZIKV; and (c) a pharmaceutically acceptable carrier or diluent.

In certain embodiments, the invention provides a pharmaceutical composition comprising: (a) a first anti-ZIKV antibody or antigen-binding fragment thereof; (b) a second anti-ZIKV antibody or antigen-binding fragment thereof, which interacts with a different ZIKV antigen, wherein the first antibody binds to an epitope on ZIKV E and the second antibody binds to an epitope on a different ZIKV antigen; and (c) a pharmaceutically acceptable carrier or diluent.

In certain embodiments, the invention provides a pharmaceutical composition comprising: (a) a first anti-ZIKV antibody or antigen-binding fragment thereof; (b) a second anti-ZIKV antibody or antigen-binding fragment thereof; (c) a third anti-ZIKV antibody or antigen-binding fragment thereof, wherein the first antibody binds to a first epitope on ZIKV E and the second and/or third antibody binds to a different epitope on ZIKV E wherein the first, second and third epitopes are distinct and non-overlapping; and (d) a pharmaceutically acceptable carrier or diluent.

In certain embodiments, the invention provides a pharmaceutical composition comprising: (a) a first anti-ZIKV antibody or antigen-binding fragment thereof; (b) a second anti-ZIKV antibody or antigen-binding fragment thereof; (c) a third anti-ZIKV antibody or an antigen-binding fragment thereof, wherein the first antibody may or may not cross-compete with the second, and/or third antibody for binding to ZIKV; and (d) a pharmaceutically acceptable carrier or diluent.

In certain embodiments, the invention provides a pharmaceutical composition comprising: (a) a first anti-ZIKV antibody or antigen-binding fragment thereof; (b) a second and/or third anti-ZIKV antibody or antigen-binding fragment thereof, which interacts with a different ZIKV antigen, wherein the first antibody binds to an epitope on ZIKV E and the second and/or third antibody binds to an epitope on a different ZIKV antigen; and (c) a pharmaceutically acceptable carrier or diluent.

In one embodiment, the pharmaceutical composition comprises a first anti-ZIKV antibody or an antigen-binding fragment thereof that binds to, or interacts with one epitope on one strain of ZIKV and the second and/or third anti-ZIKV antibody or an antigen-binding fragment thereof that binds to, or interacts with a second and/or a third epitope on the same strain or on a different strain of ZIKV.

In a related aspect, the invention provides a pharmaceutical composition comprising a first isolated monoclonal antibody or an antigen-binding fragment thereof that binds specifically to ZIKV E, wherein the first isolated monoclonal antibody or an antigen-binding fragment thereof comprises an HCDR1 amino acid sequence of SEQ ID NO: 68; an HCDR2 amino acid sequence of SEQ ID NO: 70; an HCDR3 amino acid sequence of SEQ ID NO: 72; an LCDR1 amino acid sequence of SEQ ID NO: 76; an LCDR2 amino acid sequence of SEQ ID NO: 78 and an LCDR3 amino acid sequence of SEQ ID NO: 80, and a pharmaceutically acceptable carrier or diluent. The pharmaceutical composition may further comprise a second isolated monoclonal antibody or an antigen-binding fragment thereof that binds specifically to ZIKV E, wherein the second isolated monoclonal antibody or an antigen-binding fragment thereof comprises an HCDR1 amino acid sequence of SEQ ID NO: 116, or 260; an HCDR2 amino acid sequence of SEQ ID NO: 118, or 262; an HCDR3 amino acid sequence of SEQ ID NO: 120, or 264; an LCDR1 amino acid sequence of SEQ ID NO: 124, or 268; an LCDR2 amino acid sequence of SEQ ID NO: 126, or 270 and an LCDR3 amino acid sequence of SEQ ID NO: 128, or 272.

In one embodiment, the pharmaceutical composition comprises a first isolated monoclonal antibody or an antigen-binding fragment thereof that binds specifically to ZIKV wherein the first isolated monoclonal antibody or an antigen-binding fragment thereof comprises an HCDR1 amino acid sequence of SEQ ID NO: 116; an HCDR2 amino acid sequence of SEQ ID NO: 118; an HCDR3 amino acid sequence of SEQ ID NO: 120; an LCDR1 amino acid sequence of SEQ ID NO: 124; an LCDR2 amino acid sequence of SEQ ID NO: 126 and an LCDR3 amino acid sequence of SEQ ID NO: 128, and a pharmaceutically acceptable carrier or diluent. The pharmaceutical composition may further comprise a second isolated monoclonal antibody or an antigen-binding fragment thereof that binds specifically to ZIKV, wherein the second isolated monoclonal antibody or an antigen-binding fragment thereof comprises an HCDR1 amino acid sequence of SEQ ID NO: 260; an HCDR2 amino acid sequence of SEQ ID NO: 262; an HCDR3 amino acid sequence of SEQ ID NO: 264; an LCDR1 amino acid sequence of SEQ ID NO: 268; an LCDR2 amino acid sequence of SEQ ID NO: 270 and an LCDR3 amino acid sequence of SEQ ID NO: 272. The pharmaceutical composition may further comprise a third isolated monoclonal antibody or an antigen-binding fragment thereof that binds specifically to ZIKV E, wherein the third isolated monoclonal antibody or an antigen-binding fragment thereof comprises an HCDR1 amino acid sequence, an HCDR2 amino acid sequence; an HCDR3 amino acid sequence; an LCDR1 amino acid sequence; an LCDR2 amino acid sequence and an LCDR3 amino acid sequence from any of the antibodies shown in Table 1.

In a related aspect, the invention provides an antibody cocktail comprising a mixture of at least two antibodies that bind specifically to ZIKV, wherein the antibodies comprise the HCVR/LCVR amino acid sequence pairs selected from the group consisting of SEQ ID NOs: 2/10, 18/26, 34/42, 50/58, 66/74, 82/90, 98/106, 114/122, 130/138, 146/154, 162/170, 178/186, 194/202, 210/218, 226/234, 242/250, 258/266, 274/282, 290/298, 306/314, 322/330 and 338/346.

In one embodiment, the cocktail comprises a mixture of two antibodies comprising the HCVR/LCVR amino acid sequence pairs of SEQ ID NO: 114/122 and 258/266. In one embodiment, the antibody cocktail may comprise a third antibody comprising an amino acid sequence pair selected from an antibody shown in Table 1. In one embodiment, the third antibody comprises the HCVR/LCVR amino acid sequence pair of SEQ ID NO: 66/74.

In one embodiment, the antibody cocktail comprises a mixture of two antibodies comprising the heavy chain (HC)/light chain (LC) amino acid sequence pairs of SEQ ID NO: 367/368 and 370/371. In one embodiment, the antibody cocktail may comprise a third antibody comprising a HC/LC amino acid sequence pair of SEQ ID NOs: 373/374.

In certain embodiments, each antibody may be formulated as a separate formulation and if it is determined that more than one antibody is needed to achieve maximal therapeutic efficacy, each of the antibody formulations may be co-administered (concurrently, or sequentially), as needed. Alternatively, the antibody cocktail may be co-formulated.

In certain embodiments, when two or more antibodies are combined together in one pharmaceutical composition, they may or may not bind the same or overlapping epitopes on the ZIKV protein. Additional combination therapies and co-formulations involving the anti-ZIKV antibodies of the present invention are disclosed elsewhere herein.

In certain embodiments, the invention provides a pharmaceutical composition comprising two or more human antibodies, or antigen binding fragments thereof that bind ZIKV E, wherein at least one antibody may prevent attachment of the virus to the cell, and the second antibody may prevent fusion of the virus to the host cell membrane and as such, the composition may provide for prevention of viral entry into the cell and replication within the cell. In a related embodiment, the composition comprising two anti-zika antibodies may provide for prevention of ZIKV entry into the host cell, wherein the antibodies do not contribute to antibody-dependent enhancement (ADE) of ZIKV infection.

In certain embodiments, the anti-ZIKV antibodies of the invention that neutralize Zika virus without contributing to ADE comprise the HCVR/LCVR amino acid sequence pairs selected from the group consisting of SEQ ID NOs: 258/266, 114/122 and 66/74, each having an Fc amino acid sequence as shown in SEQ ID NO: 357.

In certain embodiments, the anti-ZIKV antibodies of the invention that neutralize Zika virus without contributing to ADE comprise the HC/LC amino acid sequence pairs of SEQ ID NOs: 367/368 (H4H25703N) and SEQ ID NOs: 370/371 (H4H25619P).

In certain embodiments, the anti-ZIKV antibodies of the invention that neutralize Zika virus without contributing to ADE and which may have an extended serum half life comprise the HCVR/LCVR amino acid sequence pairs selected from the group consisting of SEQ ID NOs: 258/266, 114/122 and 66/74, each having an Fc amino acid sequence as shown in SEQ ID NO: 358 (IgG4 with YTE mutation described elsewhere herein).

In certain embodiments, the anti-ZIKV antibodies of the invention that neutralize Zika virus without contributing to ADE and which may have an extended serum half life comprise the HC/LC amino acid sequence pairs of SEQ ID NOs: 369/368 (H4H25703N with a YTE mutation described elsewhere herein), SEQ ID NOs: 372/371 (H4H25619P with a YTE mutation described elsewhere herein) and SEQ ID NOs: 375/373 (H4H25598P with a YTE mutation described elsewhere herein).

In a fourth aspect, the invention provides therapeutic methods for treating a disease or disorder associated with ZIKV (such as a viral infection in a subject), or at least one symptom associated with the viral infection, or the frequency or severity of at least one symptom associated with ZIKV infection, using an anti-ZIKV E antibody or antigen-binding portion of an antibody of the invention, or a cocktail of at least two or more antibodies of the invention, wherein the therapeutic methods comprise administering a therapeutically effective amount of one or more antibodies or antigen-binding fragments of the invention to the subject in need thereof. In one embodiment, the methods comprise administering a combination (cocktail) of at least two, or at least three antibodies of the invention. In one embodiment, the antibody cocktail comprises two anti-ZIKV E antibodies having the amino acid sequence pairs as set forth in SEQ ID NOs: 114/122 and 258/266. The disorder treated is any disease or condition, which is improved, ameliorated, inhibited or prevented by inhibition of ZIKV activity. In certain embodiments, the invention provides methods to prevent, treat or ameliorate at least one symptom of ZIKV infection, the method comprising administering a therapeutically effective amount of at least one or more anti-ZIKV E antibodies or antigen-binding fragments thereof of the invention to a subject in need thereof.

In a related aspect, the invention provides a method of neutralizing infectious ZIKV, the method comprising exposing a cell infected with ZIKV to a composition comprising one or more anti-ZIKV antibodies or antigen-binding fragments thereof, wherein the exposing results in enhanced protection of the cell from virus infection, or from cell death. In certain embodiments, the exposing may be in vitro or in vivo. In one embodiment, the one or more anti-ZIKV antibodies or antigen-binding fragments thereof neutralize infectious ZIKV having a wild type E protein, wherein the wild type E protein has a serine at position 302 of SEQ ID NO: 376, a threonine at position 311 of SEQ ID NO: 376, and a lysine at position 369 of SEQ ID NO: 376, but will not neutralize an infectious ZIKV having a mutated form of the E protein, wherein the mutated form of the E protein contains one or more of the following changes: a phenylalanine at position 302 of SEQ ID NO: 376, an isoleucine at position 311 of SEQ ID NO: 376, or a glutamic acid at position 369 of SEQ ID NO: 376. In one embodiment, the methods comprise administering one or more antibodies of the invention. In one embodiment, the methods comprise administering a combination (cocktail) of at least two antibodies of the invention. In one embodiment, the antibody cocktail comprises two anti-ZIKV antibodies having the amino acid sequence pairs as set forth in SEQ ID NOs: 114/122 and 258/266.

In some embodiments, the present invention provides methods to ameliorate or reduce the severity, duration, or frequency of occurrence, of at least one symptom of ZIKV infection in a subject by administering one or more anti-ZIKV E antibodies of the invention, wherein the at least one symptom is selected from the group consisting of fever, headache, arthralgia, myalgia and a maculopapular rash.

In certain embodiments, the invention provides methods to decrease viral load in a subject, the methods comprising administering to the subject an effective amount of one or more antibodies or fragments thereof of the invention that binds ZIKV E and blocks attachment to, or fusion with the cell membrane and/or entry into the host cell, decreasing the likelihood of dissemination into the male reproductive organs.

In one embodiment, the invention provides for reducing the likelihood of transmission of ZIKV from an infected individual to another individual. In one embodiment, transmission of the virus to the fetus from an infected mother may be prevented using at least one antibody of the invention. In a related embodiment, transmission of ZIKV to the fetus from an infected mother may be prevented using at least two antibodies of the invention. In so doing, the treatment of the pregnant female with one or more of the antibodies of the invention may prevent the development of microcephaly (or developmental abnormalities) in the infant.

In a certain embodiment, transmission of ZIKV to a sexual partner may be prevented using at least one antibody of the invention. In a related embodiment, transmission of ZIKV to a sexual partner may be prevented using at least two antibodies of the invention.

In one embodiment, the subject in need thereof is a subject at risk for exposure to, or for acquiring a ZIKV infection, wherein the subject is selected from the group consisting of an a pregnant woman who has been exposed to ZIKV, or who has been bitten by a mosquito suspected of harboring ZIKV, a woman who is living in, or visiting an area where there is a ZIKV outbreak and who is considering conceiving a child, or an immunocompromised individual, a healthcare worker, a person who is suspected of having been exposed to a person harboring the ZIKV, a person who comes into physical contact or close physical proximity with an infected individual, a hospital employee, a pharmaceutical researcher, maintenance personnel responsible for cleaning a hospital facility or institution where a ZIKV patient has been treated, individuals who have visited, or are planning to visit an area or country known to have, or suspected of having an outbreak of ZIKV, or a country that is known to have mosquitoes that may harbor the virus.

In one embodiment, the subject in need thereof may be administered at least one anti-ZIKV antibody of the invention or an antigen-binding fragment thereof, or a pharmaceutical composition comprising at least one antibody or antigen-binding fragment thereof of the invention in combination with a second therapeutic agent. The second therapeutic agent may be selected from the group consisting of an anti-viral drug, an anti-inflammatory drug (such as corticosteroids, and non-steroidal anti-inflammatory drugs, such as antibodies to TNF, a different antibody to ZIKV, a vaccine for ZIKV and/or interferons (alpha/beta/or lambda).

In one embodiment, the pharmaceutical composition may be administered subcutaneously, intravenously, intradermally, intramuscularly, intranasally, or orally.

In a related embodiment, enhanced protection may be observed in a mammal exposed to, or infected with ZIKV when the mammal is treated with a pharmaceutical composition comprising one or more anti-ZIKV antibodies of the invention, or with an antibody cocktail, which comprises at least two or more antibodies of the invention.

In one embodiment, the enhanced protection observed may be measured by a decrease in the severity or frequency of at least one symptom associated with ZIKV infection, or by a decrease in viral load. The at least one symptom may be selected from the group consisting of fever, headache, arthralgia, myalgia and a maculopapular rash.

In one embodiment, enhanced protection is observed in a ZIKV infected mammal treated with one or more antibodies of the invention when there is no substantial loss in weight after viral infection.

In one embodiment, enhanced protection is observed in a ZIKV infected mammal treated with one or more antibodies of the invention, as measured by an increase in survival of the ZIKV infected mammal treated with one or more anti-ZIKV antibodies as compared to a ZIKV virus infected mammal who has not been treated with one or more antibodies of the invention.

The enhanced protection may be observed when one or more of the antibodies is used alone, or when one or more of the antibodies is used in combination with one or more additional therapeutic agents or anti-ZIKV treatment modalities.

The one or more additional therapeutic agents may be selected from the group consisting of an anti-viral drug, an anti-inflammatory drug (such as corticosteroids, and non-steroidal anti-inflammatory drugs, such as an antibody to TNF), a different antibody to ZIKV, a vaccine for ZIKV and/or interferons (alpha/beta/or lambda).

In one embodiment, the one or more additional therapeutic agents comprise one or more anti-ZIKV antibodies.

In one embodiment, the one or more anti-ZIKV antibodies comprise a heavy chain variable region (HCVR) and a light chain variable region (LCVR) amino acid sequence selected from the group consisting of any of the HCVR and LCVR amino acid sequences of Table 1.

In a related embodiment, the one or more anti-ZIKV antibodies comprise a heavy chain variable region (HCVR) and a light chain variable region (LCVR) amino acid sequence pair selected from the group consisting of SEQ ID NOs: 2/10, 18/26, 34/42, 50/58, 66/74, 82/90, 98/106, 114/122, 130/138, 146/154, 162/170, 178/186, 194/202, 210/218, 226/234, 242/250, 258/266, 274/282, 290/298, 306/314, 322/330 and 338/346.

In another related embodiment, the one or more anti-ZIKV antibodies comprise a heavy chain variable region (HCVR) and a light chain variable region (LCVR) amino acid sequence pair selected from the group consisting of SEQ ID NOs: 66/74 and 258/266.

In certain embodiments, the one or more antibodies or antigen-binding fragments thereof may be administered prophylactically or therapeutically to a subject having, or at risk of having, or pre-disposed to developing an ZIKV infection. The subjects at risk include, but are not limited to, a pregnant female who has been exposed to ZIKV, or who has been bitten by a mosquito suspected of harboring the ZIKV, a woman who is living in, or visiting an area where there is a ZIKV outbreak and who is considering conceiving a child, an immunocompromised person, for example, a person who is immunocompromised because of autoimmune disease, or those persons receiving immunosuppressive therapy (for example, following organ transplant), a person who receives a transplant or a blood sample from a person infected with ZIKV, or those persons afflicted with human immunodeficiency syndrome (HIV) or acquired immune deficiency syndrome (AIDS), certain forms of anemia that deplete or destroy white blood cells, those persons receiving radiation or chemotherapy, or those persons afflicted with an inflammatory disorder. Other subjects at risk for acquiring a ZIKV infection include healthcare workers, or any person who comes into physical contact or close physical proximity with an infected individual, or is exposed to bodily fluids or tissues from infected individuals, also has an increased risk of developing a ZIKV infection. Moreover, a subject is at risk of contracting a ZIKV infection due to proximity to an outbreak of the disease, e.g. a subject resides in a densely-populated city or in close proximity to subjects having confirmed or suspected ZIKV infections, or choice of employment, e.g. maintenance personnel responsible for cleaning a hospital facility or institution where a zika patient has been treated, a hospital employee, a pharmaceutical researcher, an individual who has visited or who is planning to visit an area or country known to have or suspected to have an outbreak of ZIKV, or known to have mosquitoes that may harbor the ZIKV.

In certain embodiments, the antibody or antigen-binding fragment thereof of the invention is administered in combination with a second therapeutic agent to the subject in need thereof. The second therapeutic agent may be selected from the group consisting of an anti-inflammatory drug (such as corticosteroids and non-steroidal anti-inflammatory drugs, for example, anti-TNF antibodies), an anti-infective drug, an anti-viral drug, a different antibody to ZIKV, a vaccine for ZIKV, or an interferon, a dietary supplement such as anti-oxidants and any other drug or therapy known in the art useful for ameliorating at least one symptom of the ZIKV infection, or for reducing the viral load in a patient. In certain embodiments, the second therapeutic agent may be an agent that helps to counteract or reduce any possible side effect(s) associated with an antibody or antigen-binding fragment thereof of the invention, if such side effect(s) should occur. The antibody or fragment thereof may be administered subcutaneously, intravenously, intradermally, intraperitoneally, orally, intranasally, intramuscularly, or intracranially. In one embodiment, the antibody may be administered as a single intravenous infusion for maximum concentration of the antibody in the serum of the subject. The antibody or fragment thereof may be administered at a dose of about 0.1 mg/kg of body weight to about 100 mg/kg of body weight of the subject. In certain embodiments, an antibody of the present invention may be administered at one or more doses comprising between 50 mg to 600 mg.

The present invention also includes an anti-ZIKV antibody or antigen-binding fragment thereof of the invention for use in treating a subject who has, or is suspected of having, or has been exposed to ZIKV, or for use in the manufacture of a medicament for the treatment of a disease or disorder that would benefit from the blockade of ZIKV attachment to a cell, or fusion with the cell membrane.

Other embodiments will become apparent from a review of the ensuing detailed description.

DETAILED DESCRIPTION

Figure 1:
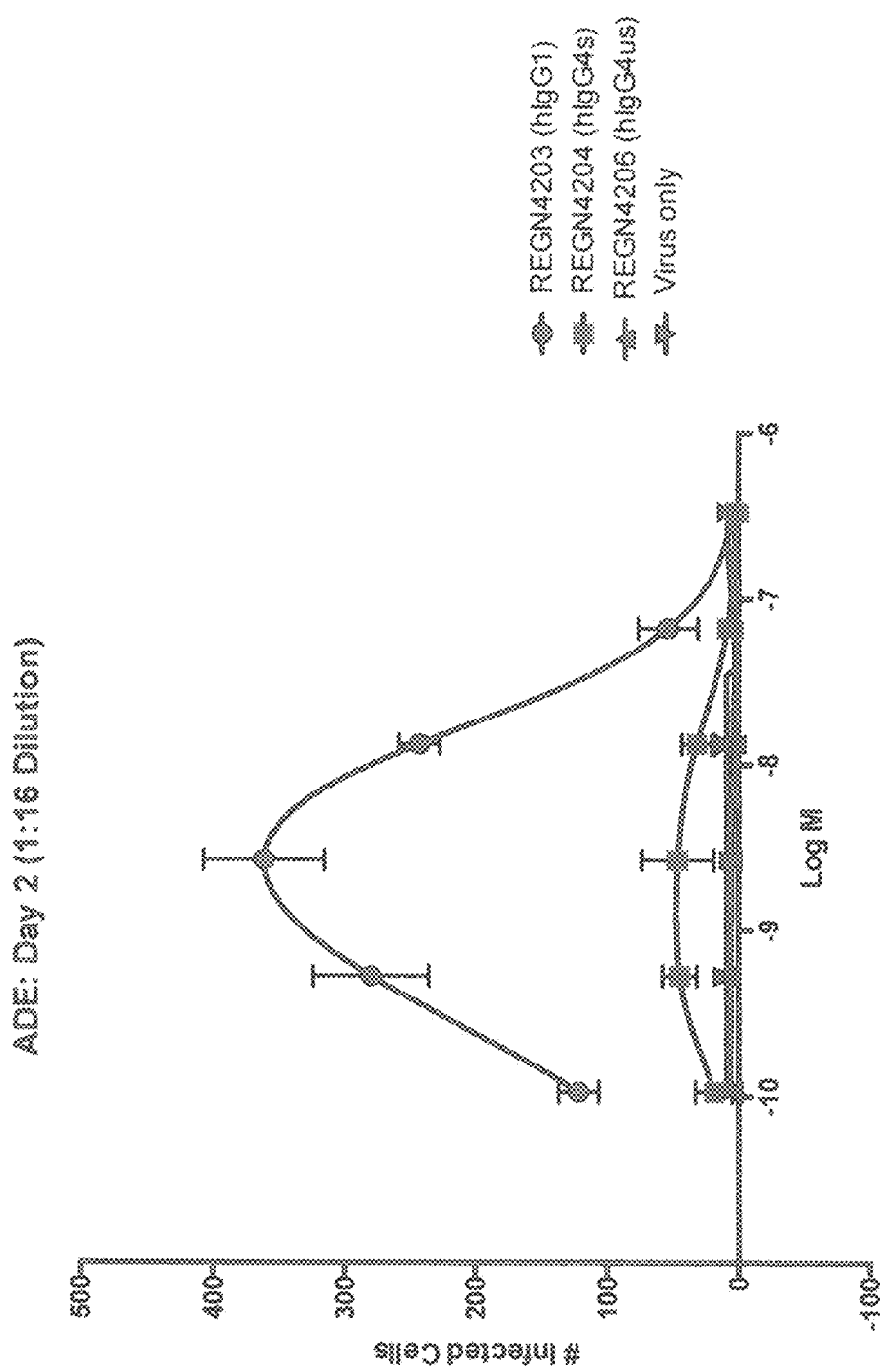
FIG. 1. Shows the results of an immunofluorescence assay for measuring antibody dependent enhancement (ADE) using chimeric antibodies that cross-react with all Flaviviruses.
Figure 2:
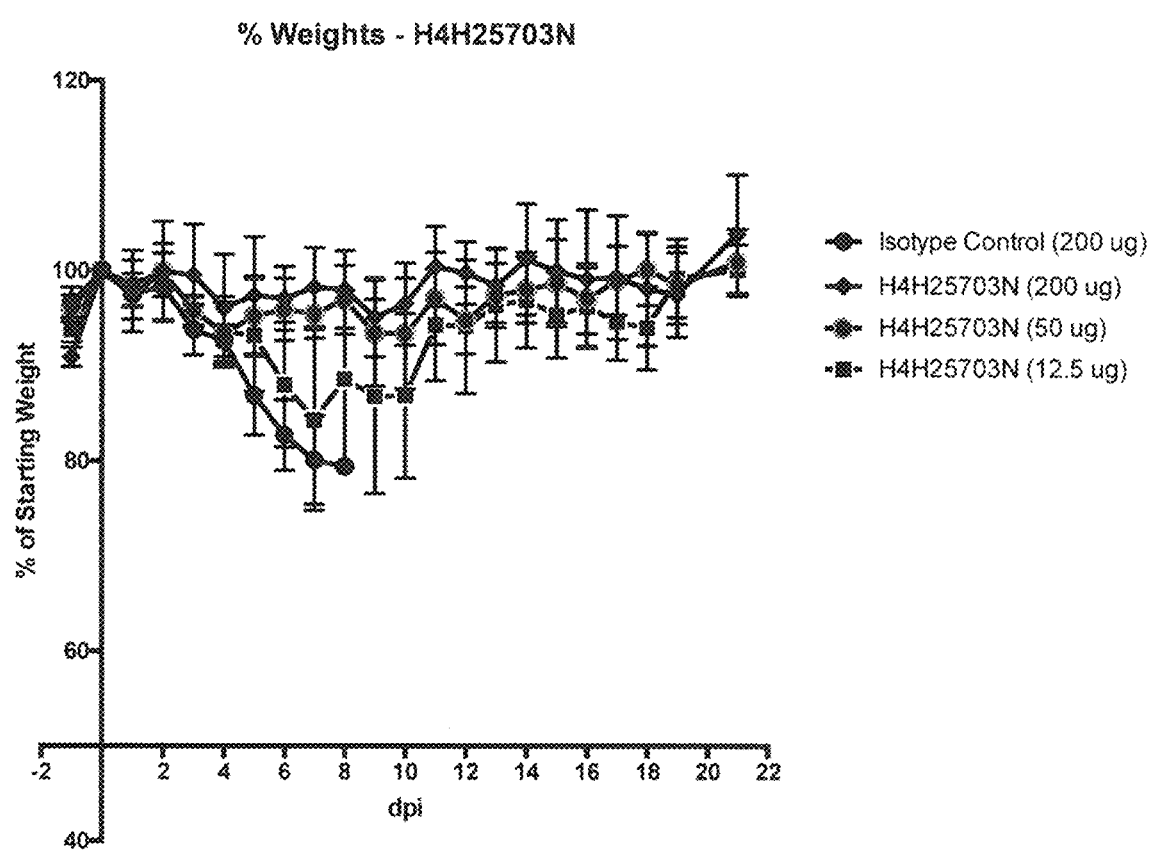
FIG. 2. Shows the protective effect of the anti-Zika antibody, H4H25703N, on prevention of weight loss in Zika virus infected mice.
Figure 3:
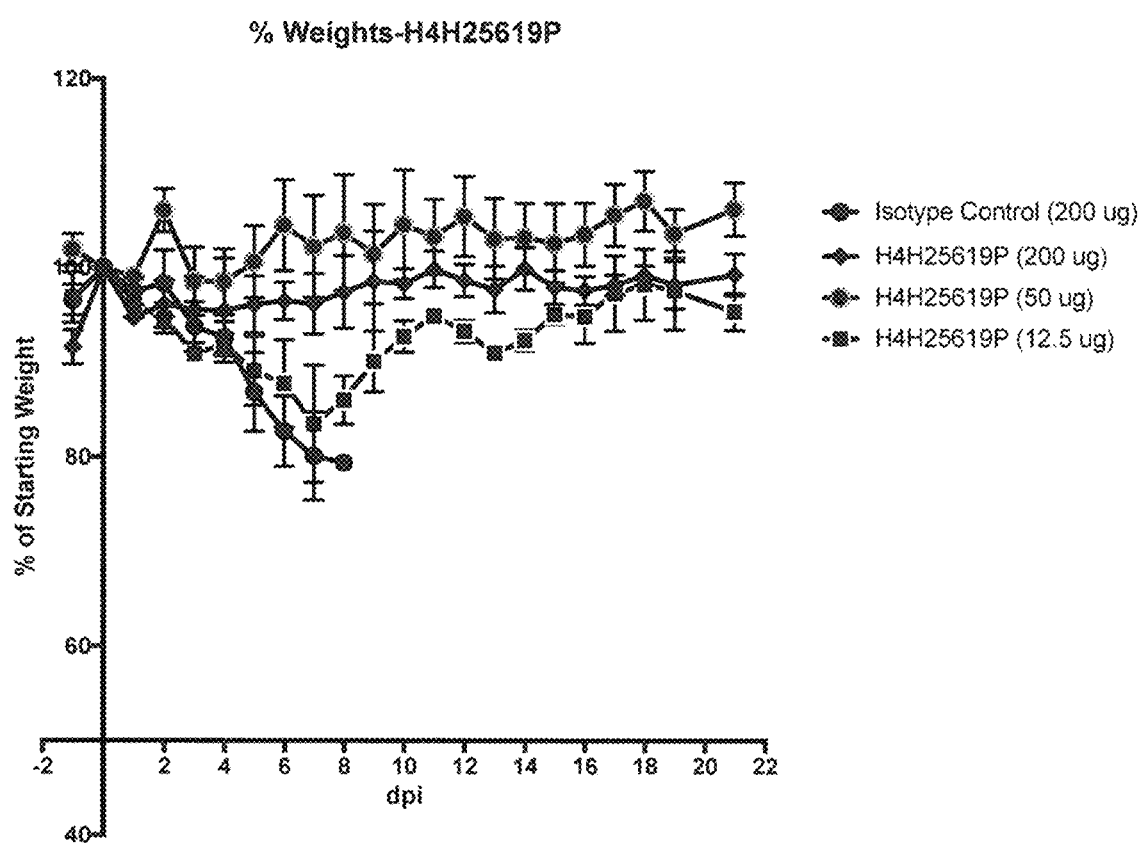
FIG. 3. Shows the protective effect of the anti-Zika antibody, H4H25619P, on prevention of weight loss in Zika virus infected mice.
Figure 4:
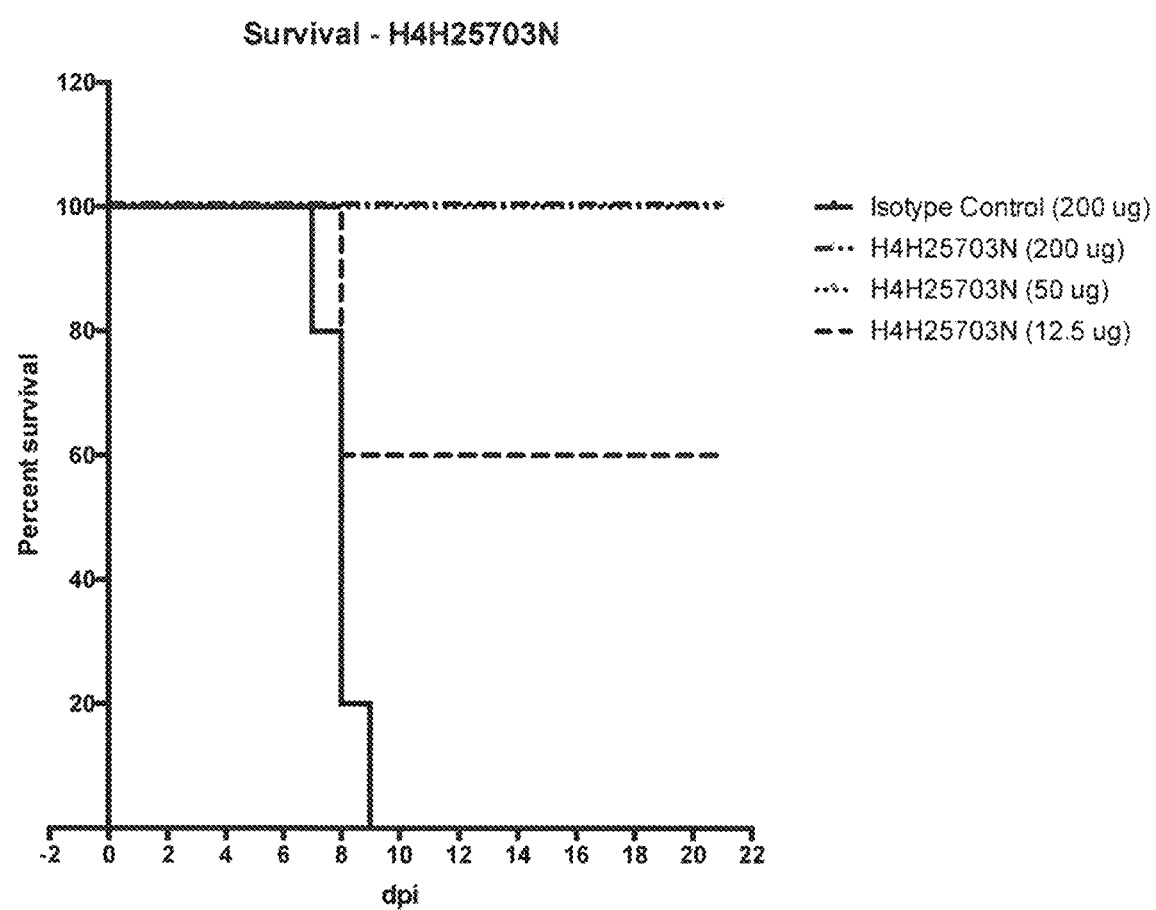
FIG. 4. Shows the protective effect of the anti-Zika antibody, H4H25703N, on survival in Zika virus infected mice.
Figure 5:
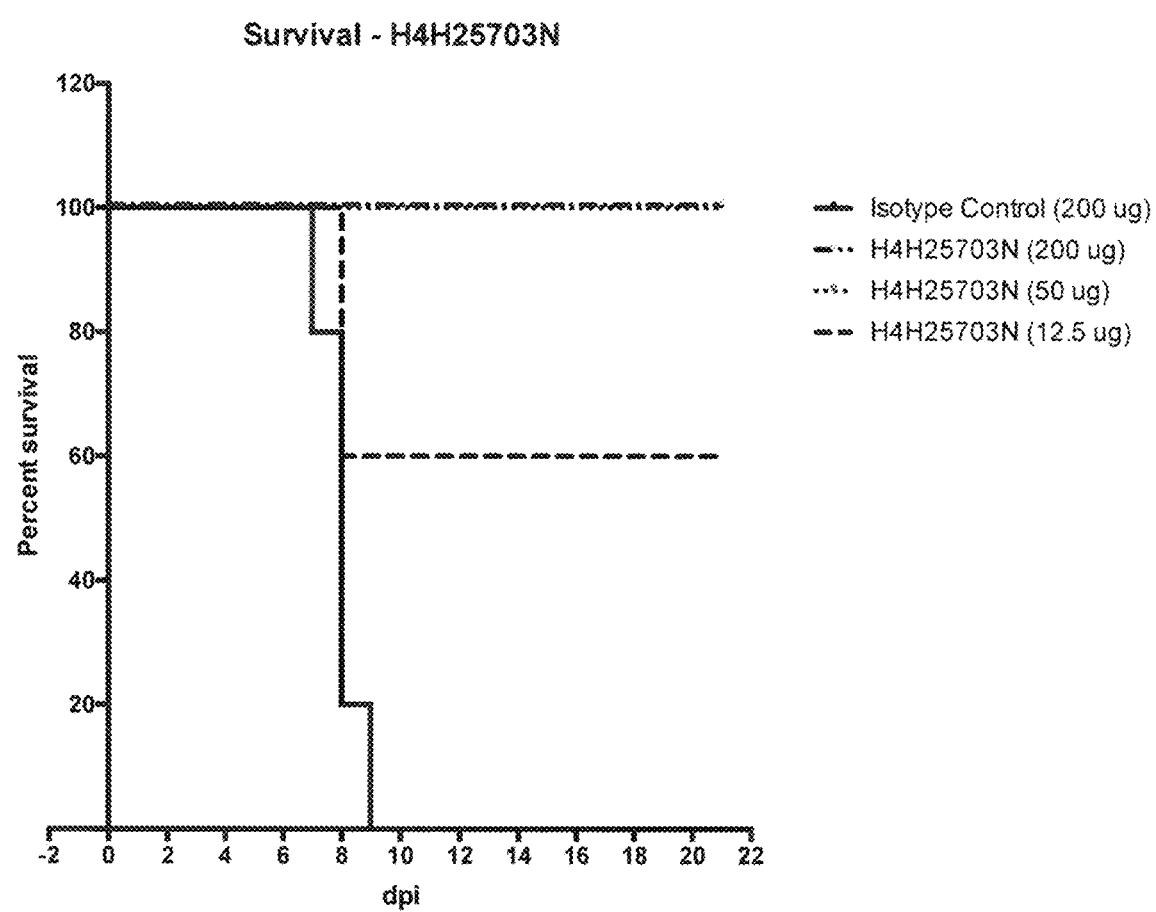
FIG. 5. Shows the protective effect of the anti-Zika antibody, H4H25619P, on survival in Zika virus infected mice.

Before the present methods are described, it is to be understood that this invention is not limited to particular methods, and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, preferred methods and materials are now described. All patents, applications and non-patent publications mentioned in this specification are incorporated herein by reference in their entireties.

Definitions

"Zika virus", or "ZIKV" is a member of the Flaviviridae family, and has been associated with microcephaly and other developmental abnormalities in the fetuses of pregnant women exposed to the virus (Schuler-Faccini, L. et al., (2016), *MMWR Morb. Mortal. Wkly Rep.* 65:59-62) and has also been associated with Guillian-Barré syndrome in adults (Cao-Lormeau, V M, et al., (2016), Lancet, April 9; 387 (10027):1531-9). The term "ZIKV" also includes variants of ZIKV isolated from different ZIKV isolates.

The amino acid sequence of ZIKV envelope glycoprotein (E), noted herein as "ZIKV E" is exemplified within the polyprotein amino acid sequence found in GenBank as accession number ALU33341.1 (See also SEQ ID NO: 353). The term also encompasses ZIKV E or a fragment thereof coupled to, for example, a histidine tag (e.g. see accession number ALU33341.1 with histidine tags (SEQ ID NOs: 354 and 355), mouse or human Fc, or a signal sequence. The amino acid sequence of ZIKV E is also shown in SEQ ID NO: 376. The E protein escape mutation for H4H25703N is shown at position 302 of SEQ ID NO: 377 (S302F). The E protein escape mutations for H4H25619P are shown at position 311 (T311I) and position 369 (K369E) of SEQ ID NO: 378.

The term "ZIKV infection", or "ZIKV infection", as used herein refers to the disease or condition resulting from exposure to the virus (e.g. after being bitten by a mosquito harboring the virus), or to an infected animal, or to an infected human patient, or contact with the bodily fluids or tissues from an animal or human patient having a ZIKV infection. The "symptoms associated with a ZIKV infection" include fever, headache, arthralgia, myalgia and a maculopapular rash. The "condition resulting from exposure to the virus", or "the condition associated with exposure to the virus" also includes microcephaly (or developmental abnormalities) of a fetus in a pregnant woman who was infected with the virus after being bitten by a mosquito harboring the virus. Another "condition resulting from exposure to the virus", or "condition associated with exposure to the virus" includes Guillain-Barré Syndrome.

The term "antibody", as used herein, is intended to refer to immunoglobulin molecules comprised of four polypeptide chains, two heavy (H) chains and two light (L) chains inter-connected by disulfide bonds (i.e., "full antibody molecules"), as well as multimers thereof (e.g. IgM) or antigen-binding fragments thereof. Each heavy chain is comprised of a heavy chain variable region ("HCVR" or "$V_H$") and a heavy chain constant region (comprised of domains $C_H1$, $C_H2$ and $C_H3$). Each light chain is comprised of a light chain variable region ("LCVR or "$V_L$") and a light chain constant region ($C_L$). The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In certain embodiments of the invention, the FRs of the antibody (or antigen binding fragment thereof) may be identical to the human germline sequences, or may be naturally or artificially modified. An amino acid consensus sequence may be defined based on a side-by-side analysis of two or more CDRs.

Substitution of one or more CDR residues or omission of one or more CDRs is also possible. Antibodies have been described in the scientific literature in which one or two CDRs can be dispensed with for binding. Padlan et al. (1995 FASEB J. 9:133-139) analyzed the contact regions between antibodies and their antigens, based on published crystal structures, and concluded that only about one fifth to one third of CDR residues actually contact the antigen. Padlan also found many antibodies in which one or two CDRs had no amino acids in contact with an antigen (see also, Vajdos et al. 2002 J Mol Biol 320:415-428).

CDR residues not contacting antigen can be identified based on previous studies (for example residues H60-H65 in CDRH2 are often not required), from regions of Kabat CDRs lying outside Chothia CDRs, by molecular modeling and/or empirically. If a CDR or residue(s) thereof is omitted, it is usually substituted with an amino acid occupying the corresponding position in another human antibody sequence or a consensus of such sequences. Positions for substitution within CDRs and amino acids to substitute can also be selected empirically. Empirical substitutions can be conservative or non-conservative substitutions.

The fully human anti-ZIKV monoclonal antibodies disclosed herein may comprise one or more amino acid substitutions, insertions and/or deletions in the framework and/or CDR regions of the heavy and light chain variable domains as compared to the corresponding germline sequences. Such mutations can be readily ascertained by comparing the amino acid sequences disclosed herein to germline sequences available from, for example, public antibody sequence databases. The present invention includes antibodies, and antigen-binding fragments thereof, which are derived from any of the amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, can easily produce numerous antibodies and antigen-binding fragments which comprise one or more individual germline mutations or combinations thereof. In certain embodiments, all of the framework and/or CDR residues within the $V_H$ and/or $V_L$ domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antibody was originally derived). Furthermore, the antibodies of the present invention may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antibodies and antigen-binding fragments that contain one or more germline mutations can be easily tested for one or more desired property such as, improved binding specificity, increased binding affinity, improved or enhanced antagonistic or agonistic biological properties (as the case may be), reduced immunogenicity, etc. Antibodies and antigen-binding fragments obtained in this general manner are encompassed within the present invention.

The present invention also includes fully human anti-ZIKV monoclonal antibodies comprising variants of any of the HCVR, LCVR, and/or CDR amino acid sequences disclosed herein having one or more conservative substitutions. For example, the present invention includes anti-ZIKV antibodies having HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences disclosed herein.

The term "human antibody", as used herein, is intended to include antibodies having variable and constant regions derived from human germline immunoglobulin sequences. The human mAbs of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include mAbs in which CDR sequences derived from the germline of another mammalian species (e.g., mouse), have been grafted onto human FR sequences. The term includes antibodies recombinantly produced in a non-human mammal, or in cells of a non-human mammal. The term is not intended to include antibodies isolated from or generated in a human subject.

The term "recombinant", as used herein, refers to antibodies or antigen-binding fragments thereof of the invention created, expressed, isolated or obtained by technologies or methods known in the art as recombinant DNA technology which include, e.g., DNA splicing and transgenic expression. The term refers to antibodies expressed in a non-human mammal (including transgenic non-human mammals, e.g., transgenic mice), or a cell (e.g., CHO cells) expression system or isolated from a recombinant combinatorial human antibody library.

The term "specifically binds," or "binds specifically to", or the like, means that an antibody or antigen-binding fragment thereof forms a complex with an antigen that is relatively stable under physiologic conditions. Specific binding can be characterized by an equilibrium dissociation constant of at least about $1\times10^{-7}$ M or less (e.g., a smaller $K_D$ denotes a tighter binding). Methods for determining whether two molecules specifically bind are well known in the art and include, for example, equilibrium dialysis, surface plasmon resonance, and the like. As described herein, antibodies have been identified by surface plasmon resonance, e.g., BIACORE™, which bind specifically to ZIKV. Moreover, multi-specific antibodies that bind to one domain in ZIKV and one or more additional antigens or a bi-specific that binds to two different regions of ZIKV are nonetheless considered antibodies that "specifically bind", as used herein.

The term "high affinity" antibody refers to those mAbs having a binding affinity to ZIKV, expressed as $K_D$, of at least $10^{-7}$ M; preferably $10^{-8}$ M; more preferably $10^{-9}$M, even more preferably $10^{-10}$ M, even more preferably $10^{-11}$ M, even more preferably $10^{-12}$ M, as measured by surface plasmon resonance, e.g., BIACORE™ or solution-affinity ELISA.

By the term "slow off rate", "Koff" or "kd" is meant an antibody that dissociates from ZIKV, or a virus like particle expressing the ZIKV E, with a rate constant of $1\times10^{-3}$ s$^{-1}$ or less, preferably $1\times10^{-4}$ s$^{-1}$ or less, as determined by surface plasmon resonance, e.g., BIACORE™.

The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. The terms "antigen-binding fragment" of an antibody, or "antibody fragment", as used herein, refers to one or more fragments of an antibody that retain the ability to bind to ZIKV.

In specific embodiments, antibody or antibody fragments of the invention may be conjugated to a moiety such a ligand or a therapeutic moiety ("immunoconjugate"), such as an anti-viral drug, a second anti-ZIKV antibody, or any other therapeutic moiety useful for treating an infection caused by ZIKV.

An "isolated antibody", as used herein, is intended to refer to an antibody that is substantially free of other antibodies (Abs) having different antigenic specificities (e.g., an isolated antibody that specifically binds ZIKV, or a fragment thereof, is substantially free of Abs that specifically bind antigens other than ZIKV.

A "blocking antibody" or a "neutralizing antibody", as used herein (or an "antibody that neutralizes ZIKV activity" or "antagonist antibody"), is intended to refer to an antibody whose binding to ZIKV results in inhibition of at least one biological activity of ZIKV. For example, an antibody of the invention may prevent or block ZIKV attachment to, fusion with, and/or entry into a host cell. In addition, a "neutralizing antibody" is one that can neutralize, i.e., prevent, inhibit, reduce, impede or interfere with, the ability of a pathogen to initiate and/or perpetuate an infection in a host. The terms "neutralizing antibody" and "an antibody that neutralizes" or "antibodies that neutralize" are used interchangeably herein. These antibodies can be used, alone or in combination, as prophylactic or therapeutic agents with other anti-viral agents upon appropriate formulation, or in association with active vaccination, or as a diagnostic tool.

"Antibody-dependent-enhancement" or "ADE" is a mechanism by which a virus, when bound to antiviral antibodies enters cells having Fc receptors, leading to increased infectivity in the cells. ADE is common in cells cultured in the laboratory, but rarely occurs in vivo except for infection with dengue virus, which is a member of the Flaviviridae family. This virus can use this mechanism to infect macrophages, causing a normally mild viral infection to become life-threatening.

The term "surface plasmon resonance", as used herein, refers to an optical phenomenon that allows for the analysis of real-time biomolecular interactions by detection of alterations in protein concentrations within a biosensor matrix, for example using the BIACORE™ system (Pharmacia Biosensor AB, Uppsala, Sweden and Piscataway, N.J.).

The term "$K_D$", as used herein, is intended to refer to the equilibrium dissociation constant of a particular antibody-antigen interaction.

The term "epitope" refers to an antigenic determinant that interacts with a specific antigen-binding site in the variable region of an antibody molecule known as a paratope. A single antigen may have more than one epitope. Thus, different antibodies may bind to different areas on an antigen and may have different biological effects. The term "epitope" also refers to a site on an antigen to which B and/or T cells respond. It also refers to a region of an antigen that is bound by an antibody. Epitopes may be defined as structural or functional. Functional epitopes are generally a subset of the structural epitopes and have those residues that directly contribute to the affinity of the interaction. Epitopes may also be conformational, that is, composed of non-linear amino acids. In certain embodiments, epitopes may include determinants that are chemically active surface groupings of molecules such as amino acids, sugar side chains, phosphoryl groups, or sulfonyl groups, and, in certain embodiments, may have specific three-dimensional structural characteristics, and/or specific charge characteristics.

The term "cross-competes", as used herein, means an antibody or antigen-binding fragment thereof binds to an antigen and inhibits or blocks the binding of another antibody or antigen-binding fragment thereof. The term also includes competition between two antibodies in both orientations, i.e., a first antibody that binds and blocks binding of second antibody and vice-versa. In certain embodiments, the first antibody and second antibody may bind to the same epitope. Alternatively, the first and second antibodies may bind to different, but overlapping epitopes such that binding of one inhibits or blocks the binding of the second antibody, e.g., via steric hindrance. Cross-competition between antibodies may be measured by methods known in the art, for example, by a real-time, label-free bio-layer interferometry assay. To determine if a test antibody cross-competes with a reference anti-ZIKV antibody of the invention, the reference antibody is allowed to bind to an ZIKV E or peptide under saturating conditions. Next, the ability of a test antibody to bind to the ZIKV E is assessed. If the test antibody is able to bind to ZIKV E following saturation binding with the reference anti-ZIKV E antibody, it can be concluded that the test antibody binds to a different epitope than the reference anti-ZIKV antibody. On the other hand, if the test antibody is not able to bind to the ZIKV E following saturation binding with the reference anti-ZIKV E antibody, then the test antibody may bind to the same epitope as the epitope bound by the reference anti-ZIKV E antibody of the invention.

The term "substantial identity" or "substantially identical," when referring to a nucleic acid or fragment thereof, indicates that, when optimally aligned with appropriate nucleotide insertions or deletions with another nucleic acid (or its complementary strand), there is nucleotide sequence identity in at least about 90%, and more preferably at least about 95%, 96%, 97%, 98% or 99% of the nucleotide bases, as measured by any well-known algorithm of sequence identity, such as FASTA, BLAST or GAP, as discussed below. A nucleic acid molecule having substantial identity to a reference nucleic acid molecule may, in certain instances, encode a polypeptide having the same or substantially similar amino acid sequence as the polypeptide encoded by the reference nucleic acid molecule.

As applied to polypeptides, the term "substantial similarity" or "substantially similar" means that two peptide sequences, when optimally aligned, such as by the programs GAP or BESTFIT using default gap weights, share at least 90% sequence identity, even more preferably at least 95%, 98% or 99% sequence identity. Preferably, residue positions, which are not identical, differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent or degree of similarity may be adjusted upwards to correct for the conservative nature of the substitution. Means for making this adjustment are well known to those of skill in the art. See, e.g., Pearson (1994) Methods Mol. Biol. 24: 307-331, which is herein incorporated by reference. Examples of groups of amino acids that have side chains with similar chemical properties include 1) aliphatic side chains: glycine, alanine, valine, leucine and isoleucine; 2) aliphatic-hydroxyl side chains: serine and threonine; 3) amide-containing side chains: asparagine and glutamine; 4) aromatic side chains: phenylalanine, tyrosine, and tryptophan; 5) basic side chains: lysine, arginine, and histidine; 6) acidic side chains: aspartate and glutamate, and 7) sulfur-containing side chains: cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256: 1443 45, herein incorporated by reference. A "moderately conservative" replacement is any change having a nonnegative value in the PAM250 log-likelihood matrix.

Sequence similarity for polypeptides is typically measured using sequence analysis software. Protein analysis software matches similar sequences using measures of similarity assigned to various substitutions, deletions and other modifications, including conservative amino acid substitutions. For instance, GCG software contains programs such as GAP and BESTFIT which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA with default or recommended parameters; a program in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence of the invention to a database containing a large number of sequences from different organisms is the computer program BLAST, especially BLASTP or TBLASTN, using default parameters. See, e.g., Altschul et al. (1990) J. Mol. Biol. 215: 403-410 and (1997) Nucleic Acids Res. 25:3389-3402, each of which is herein incorporated by reference.

By the phrase "therapeutically effective amount" is meant an amount that produces the desired effect for which it is administered. The exact amount will depend on the purpose of the treatment, and will be ascertainable by one skilled in the art using known techniques (see, for example, Lloyd (1999) The Art, Science and Technology of Pharmaceutical Compounding).

As used herein, the term "subject" refers to an animal, preferably a mammal, more preferably a human, in need of amelioration, prevention and/or treatment of a disease or disorder such as a viral infection. The subject may have a ZIKV infection or is predisposed to developing a ZIKV infection. Subjects "predisposed to developing a ZIKV infection", or subjects "who may be at elevated risk for contracting a ZIKV infection", are those subjects with compromised immune systems because of autoimmune disease, those persons receiving immunosuppressive therapy (for example, following organ transplant), those persons afflicted with human immunodeficiency syndrome (HIV) or acquired immune deficiency syndrome (AIDS), pregnant females who have been exposed to, or who may become exposed to the ZIKV if living in, or visiting an area that has an outbreak of ZIKV, in addition to a woman who lives in, or is visiting an area known to have a ZIKV outbreak and is considering conceiving a child, certain forms of anemia that deplete or destroy white blood cells, those persons receiving radiation or chemotherapy, or those persons afflicted with an inflammatory disorder. Additionally, subjects of extreme young or old age are at increased risk. Any person who comes into physical contact or close physical proximity with an infected animal, or human patient, or is exposed to bodily fluids or tissues from an infected animal or human patient, has an increased risk of developing a ZIKV infection. Moreover, a subject is at risk of contracting an ZIKV infection due to proximity to an outbreak of the disease, e.g. subject resides in a densely-populated city or in close proximity to subjects having confirmed or suspected infections of ZIKV, or choice of employment, e.g. hospital worker, pharmaceutical researcher, or an individual who has visited or who is planning to visit an area or country known to have or suspected to have an outbreak of ZIKV. There is also an increased risk of severe outcomes in a subject if they contract a ZIKV infection. When a pregnant woman is infected with ZIKV, there is an increased risk that the baby may be born with microcephaly or other developmental abnormalities. Accordingly, if a woman is pregnant, or is considering conceiving a child, and she is living in an area where there is a ZIKV outbreak, or visiting an area where there is a ZIKV outbreak, or is in an area that is known to have mosquitoes that harbor the ZIKV, she is at risk for contracting a ZIKV infection. There is also an increased risk of developing Guillain-Barré syndrome after exposure of a subject to ZIKV.

As used herein, the terms "treat", "treating", or "treatment" refer to the reduction or amelioration of the severity of at least one symptom or indication of ZIKV infection due to the administration of a therapeutic agent such as an antibody of the present invention to a subject in need thereof. The terms include inhibition of progression of disease or of worsening of infection. The terms also include positive prognosis of disease, i.e., the subject may be free of infection or may have reduced or no viral titers upon administration of a therapeutic agent such as an antibody of the present invention. The therapeutic agent may be administered at a therapeutic dose to the subject.

The terms "prevent", "preventing" or "prevention" refer to inhibition of manifestation of ZIKV infection or any symptoms or indications of ZIKV infection upon administration of an antibody of the present invention. The term includes prevention of spread of infection in a subject exposed to the virus or at risk of having ZIKV infection.

As used herein, the term "anti-viral drug" refers to any anti-infective agent or therapy, whether it be a chemical moiety, or a biological therapy, used to treat, prevent, or ameliorate a viral infection in a subject. For example, in the present invention an anti-viral drug may include, but not be limited to, an antibody to ZIKV (in one embodiment the antibody to ZIKV may be different than those described herein), a vaccine for ZIKV, a direct-acting antiviral agent, and interferons (or other immune modulators). In the present invention, the infection to be treated is caused by a ZIKV.

General Description

ZIKV infection is generally a mild disease in healthy subjects, but pregnant women exposed to the virus are at risk of giving birth to an infant with microcephaly or other developmental abnormalities. The virus is a member of the Flaviviridae family.

The genome of the virus consists of a single strand of positive sense RNA of approximately 11 kb in length and encodes about 10 genes. Zika virions contain three structural proteins: a capsid protein (C), a membrane protein/premembrane protein (M/prM), and an envelope glycoprotein (E). The viral genome also encodes seven non-structural proteins.

Described herein are fully human antibodies and antigen-binding fragments thereof that specifically bind to ZIKV E and modulate the interaction of ZIKV with host cells. The anti-ZIKV E antibodies may bind to the ZIKV with high affinity. In certain embodiments, the antibodies of the present invention may prevent attachment of the virus to the cell, or may block fusion of the virus to the host cell membrane. In so doing, the antibodies block virus entry into the cell and as such inhibit or neutralize viral infection of host cells. In some embodiments, the antibodies may be useful for treating a subject suffering from a ZIKV infection, or a subject who is at risk for acquiring a ZIKV infection (e.g. a pregnant female who is living in, or visiting, a country that has a ZIKV outbreak). The antibodies when administered to a subject in need thereof may reduce the infection by a virus such as ZIKV in the subject. They may be used to decrease viral loads in a subject. They may be used alone or as adjunct therapy with other therapeutic moieties or modalities known in the art for treating a viral infection. The identified antibodies can be used prophylactically (before infection) to protect a mammal from infection, or can be used therapeutically (after infection is established) to ameliorate a previously established infection, or to ameliorate at least one symptom associated with the infection.

The full-length amino acid sequence of an exemplary ZIKV polyprotein is shown in GenBank as accession number ALU33341.1 and also in SEQ ID NO: 353. A fragment of the ZIKV E, may be coupled to a histidine tag, such as shown in SEQ ID NOs: 354 or 355. In certain embodiments, the antibodies of the invention are obtained from mice immunized with a primary immunogen, such as a full-length ZIKV E co-expressed with prM, or with a recombinant form of ZIKV E or fragments thereof, or particles comprised of prM and E followed by immunization with a secondary immunogen, or with an immunogenically active fragment of ZIKV E. In certain embodiments, the antibodies are obtained from mice immunized with DNA encoding the ZIKV prM/E.

The immunogen may be a biologically active and/or immunogenic fragment of ZIKV E or DNA encoding the active fragment thereof. The fragment may be derived from any region of the viral E. The peptides may be modified to include addition or substitution of certain residues for tagging or for purposes of conjugation to carrier molecules, such as, KLH. For example, a cysteine may be added at either the N terminal or C terminal end of a peptide, or a linker sequence may be added to prepare the peptide for conjugation to, for example, KLH for immunization.

Certain anti-ZIKV antibodies of the present invention are able to bind to and neutralize the activity of ZIKV, as determined by in vitro or in vivo assays. The ability of the antibodies of the invention to bind to and neutralize the activity of ZIKV and thus the attachment and/or entry of the virus into a host cell followed by the ensuing viral infection, may be measured using any standard method known to those skilled in the art, including binding assays, or activity assays, as described herein.

Non-limiting, exemplary in vitro assays for measuring binding activity are illustrated in Example 3, herein. In Example 3, the binding of anti-ZIKV E was determined by evaluating binding to virus like particles (VLPs) produced in cells expressing prM/E. In Example 4 the equilibrium dissociation constants were determined using real-time surface plasmon resonance in a Biacore 4000 instrument. Neutralization assays were used to determine the effect of anti-zika antibodies on infectivity of ZIKV in Example 5. Cross-competition assays were conducted in Example 6 to determine cross reactivity of anti-zika antibodies.

The antibodies specific for ZIKV E may contain no additional labels or moieties, or they may contain an N-terminal or C-terminal label or moiety. In one embodiment, the label or moiety is biotin. In a binding assay, the location of a label (if any) may determine the orientation of the peptide relative to the surface upon which the peptide is bound. For example, if a surface is coated with avidin, a peptide containing an N-terminal biotin will be oriented such that the C-terminal portion of the peptide will be distal to the surface. In one embodiment, the label may be a radionuclide, a fluorescent dye or a MRI-detectable label. In certain embodiments, such labeled antibodies may be used in diagnostic assays including imaging assays.

Antigen-Binding Fragments of Antibodies

Unless specifically indicated otherwise, the term "antibody," as used herein, shall be understood to encompass antibody molecules comprising two immunoglobulin heavy chains and two immunoglobulin light chains (i.e., "full antibody molecules") as well as antigen-binding fragments thereof. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. The terms "antigen-binding fragment" of an antibody, or "antibody fragment", as used herein, refers to one or more fragments of an antibody that retain the ability to specifically bind to ZIKV. An antibody fragment may include a Fab fragment, a F(ab')$_2$ fragment, a Fv fragment, a dAb fragment, a fragment containing a CDR, or an isolated CDR. In certain embodiments, the term "antigen-binding fragment" refers to a polypeptide fragment of a multi-specific antigen-binding molecule. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and (optionally) constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR, which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present invention include: (i) $V_H$-$C_H1$; (ii) $V_H$-$C_H2$; (iii) $V_H$-$C_H3$; (iv) $V_H$-$C_H1$-$C_H2$; (v) $V_H$-$C_H1$-$C_H2$-$C_H3$; $V_H$-$C_H2$-$C_H3$; (vii) $V_H$-$C_L$; (viii) $V_L$-$C_H1$; (ix) $V_L$-$C_H2$; (x) $V_L$-$C_H3$; (xi) $V_L$-$C_H1$-$C_H2$; (xii) $V_L$-$C_H1$-$C_H2$-$C_H3$; (xiii) $V_L$-$C_H2$-$C_H3$; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids, which result in a flexible or semi-flexible linkage between adjacent variable and/or constant domains in a single polypeptide molecule. Moreover, an antigen-binding fragment of an antibody of the present invention may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

As with full antibody molecules, antigen-binding fragments may be mono-specific or multi-specific (e.g., bi-specific). A multi-specific antigen-binding fragment of an antibody will typically comprise at least two different variable domains, wherein each variable domain is capable of specifically binding to a separate antigen or to a different epitope on the same antigen. Any multi-specific antibody format, including the exemplary bi-specific antibody formats disclosed herein, may be adapted for use in the context of an antigen-binding fragment of an antibody of the present invention using routine techniques available in the art.

Preparation of Human Antibodies

Methods for generating human antibodies in transgenic mice are known in the art. Any such known methods can be used in the context of the present invention to make human antibodies that specifically bind to ZIKV E. An immunogen comprising any one of the following can be used to generate antibodies to ZIKV. In certain embodiments, the antibodies of the invention are obtained from mice immunized with a fragment of the full-length ZIKV polyprotein (See, for example, GenBank accession numbers ALU33341.1 (SEQ ID NO: 353)), consisting of prM/E or a fragment thereof. Alternatively, the ZIKV E or a fragment thereof may be produced using standard biochemical techniques and modified and used as immunogen. In one embodiment, the immunogen is a recombinantly produced ZIKV E or fragment thereof. In certain embodiments of the invention, the immunogen may be a commercially available ZIKV E. In certain embodiments, one or more booster injections may be administered. In certain embodiments, the booster injections may comprise one or more commercially available ZIKV envelope glycoproteins. In certain embodiments, the immunogen may be a recombinant ZIKV E expressed in $E. coli$ or in any other eukaryotic or mammalian cells such as Chinese hamster ovary (CHO) cells.

Using VELOCIMMUNE® technology (see, for example, U.S. Pat. No. 6,596,541, Regeneron Pharmaceuticals, VELOCIMMUNE®) or any other known method for generating monoclonal antibodies, high affinity chimeric antibodies to ZIKV E are initially isolated having a human variable region and a mouse constant region. The VELOCIMMUNE® technology involves generation of a transgenic mouse having a genome comprising human heavy and light chain variable regions operably linked to endogenous mouse constant region loci such that the mouse produces an antibody comprising a human variable region and a mouse constant region in response to antigenic stimulation. The DNA encoding the variable regions of the heavy and light chains of the antibody are isolated and operably linked to DNA encoding the human heavy and light chain constant regions. The DNA is then expressed in a cell capable of expressing the fully human antibody.

Generally, a VELOCIMMUNE® mouse is challenged with the antigen of interest, and lymphatic cells (such as B-cells) are recovered from the mice that express antibodies. The lymphatic cells may be fused with a myeloma cell line to prepare immortal hybridoma cell lines, and such hybridoma cell lines are screened and selected to identify hybridoma cell lines that produce antibodies specific to the antigen of interest. DNA encoding the variable regions of the heavy chain and light chain may be isolated and linked to desirable isotypic constant regions of the heavy chain and light chain. Such an antibody protein may be produced in a cell, such as a CHO cell. Alternatively, DNA encoding the antigen-specific chimeric antibodies or the variable domains of the light and heavy chains may be isolated directly from antigen-specific lymphocytes.

Initially, high affinity chimeric antibodies are isolated having a human variable region and a mouse constant region. As in the experimental section below, the antibodies are characterized and selected for desirable characteristics, including affinity, selectivity, epitope, etc. The mouse constant regions are replaced with a desired human constant region to generate the fully human antibody of the invention, for example wild-type or modified IgG1 or IgG4. While the constant region selected may vary according to specific use, high affinity antigen-binding and target specificity characteristics reside in the variable region.

Bioequivalents

The anti-ZIKV E antibodies and antibody fragments of the present invention encompass proteins having amino acid sequences that vary from those of the described antibodies, but that retain the ability to react with ZIKV. Such variant antibodies and antibody fragments comprise one or more additions, deletions, or substitutions of amino acids when compared to parent sequence, but exhibit biological activity that is essentially equivalent to that of the described antibodies. Likewise, the antibody-encoding DNA sequences of the present invention encompass sequences that comprise one or more additions, deletions, or substitutions of nucleotides when compared to the disclosed sequence, but that encode an antibody or antibody fragment that is essentially bioequivalent to an antibody or antibody fragment of the invention.

Two antigen-binding proteins, or antibodies, are considered bioequivalent if, for example, they are pharmaceutical equivalents or pharmaceutical alternatives whose rate and extent of absorption do not show a significant difference when administered at the same molar dose under similar experimental conditions, either single dose or multiple doses. Some antibodies will be considered equivalents or pharmaceutical alternatives if they are equivalent in the extent of their absorption but not in their rate of absorption and yet may be considered bioequivalent because such differences in the rate of absorption are intentional and are reflected in the labeling, are not essential to the attainment of effective body drug concentrations on, e.g., chronic use, and are considered medically insignificant for the particular drug product studied.

In one embodiment, two antigen-binding proteins are bioequivalent if there are no clinically meaningful differences in their safety, purity, or potency.

In one embodiment, two antigen-binding proteins are bioequivalent if a patient can be switched one or more times between the reference product and the biological product without an expected increase in the risk of adverse effects, including a clinically significant change in immunogenicity, or diminished effectiveness, as compared to continued therapy without such switching.

In one embodiment, two antigen-binding proteins are bioequivalent if they both act by a common mechanism or mechanisms of action for the condition or conditions of use, to the extent that such mechanisms are known.

Bioequivalence may be demonstrated by in vivo and/or in vitro methods. Bioequivalence measures include, e.g., (a) an in vivo test in humans or other mammals, in which the concentration of the antibody or its metabolites is measured in blood, plasma, serum, or other biological fluid as a function of time; (b) an in vitro test that has been correlated with and is reasonably predictive of human in vivo bioavailability data; (c) an in vivo test in humans or other mammals in which the appropriate acute pharmacological effect of the antibody (or its target) is measured as a function of time; and (d) in a well-controlled clinical trial that establishes safety, efficacy, or bioavailability or bioequivalence of an antibody.

Bioequivalent variants of the antibodies of the invention may be constructed by, for example, making various substitutions of residues or sequences or deleting terminal or internal residues or sequences not needed for biological activity. For example, cysteine residues not essential for biological activity can be deleted or replaced with other amino acids to prevent formation of unnecessary or incorrect intramolecular disulfide bridges upon renaturation. In other contexts, bioequivalent antibodies may include antibody variants comprising amino acid changes, which modify the glycosylation characteristics of the antibodies, e.g., mutations that eliminate or remove glycosylation.

Anti-ZIKV Antibodies Comprising Fc Variants

According to certain embodiments of the present invention, anti-ZIKV antibodies comprising an Fc domain comprising one or more mutations that diminish antibody binding to the FcRn receptor may be prepared.

In one embodiment, the present invention includes anti-ZIKV antibodies comprising a chimeric heavy chain constant ($C_H$) region, wherein the chimeric $C_H$ region comprises segments derived from the $C_H$ regions of more than one immunoglobulin isotype. For example, the antibodies of the invention may comprise a chimeric $C_H$ region comprising part or all of a $C_H2$ domain derived from a human IgG1, human IgG2 or human IgG4 molecule, combined with part or all of a $C_H3$ domain derived from a human IgG1, human IgG2 or human IgG4 molecule. According to certain embodiments, the antibodies of the invention comprise a chimeric $C_H$ region having a chimeric hinge region. For example, a chimeric hinge may comprise an "upper hinge" amino acid sequence (amino acid residues from positions 216 to 227 according to EU numbering) derived from a human IgG1, a human IgG2 or a human IgG4 hinge region, combined with a "lower hinge" sequence (amino acid residues from positions 228 to 236 according to EU numbering) derived from a human IgG1, a human IgG2 or a human IgG4 hinge region. According to certain embodiments, the chimeric hinge region comprises amino acid residues derived from a human IgG1 or a human IgG4 upper hinge and amino acid residues derived from a human IgG2 lower hinge. An antibody comprising a chimeric $C_H$ region as described herein may, in certain embodiments, exhibit modified Fc effector functions without adversely affecting the therapeutic or pharmacokinetic properties of the antibody. (See, e.g., U.S. Pat. No. 9,359,437, the disclosure of which is hereby incorporated by reference in its entirety).

In certain embodiments of the present invention, the modified Fc domain for use in the context of the present invention may comprise an IgG1 Fc comprising the amino acid sequence as shown in SEQ ID NO: 356. Alternatively, a modified Fc for use in the context of the present invention may comprise an IgG4 Fc comprising the amino acid sequence shown in SEQ ID NO: 357, or SEQ ID NO: 358. Non-limiting, exemplary modified Fc regions that can be used in the context of the present invention are set forth in U.S. Pat. No. 9,359,437, and in U.S. 62/140,350, the disclosures of which are hereby incorporated by reference in their entireties, as well as any functionally equivalent variants of the modified Fc regions set forth therein.

In certain embodiments, the present invention also includes anti-ZIKV E antibodies comprising an Fc domain having the following mutations: M131Y, S133T and T135E (based on the residues as numbered in SEQ ID NO: 358), wherein the mutation provides for extended serum half lives of the antibodies.

Other modified Fc domains and Fc modifications that can be used in the context of the present invention include any of the modifications as set forth in US 2014/0171623; U.S. Pat. No. 8,697,396; US 2014/0134162; WO 2014/043361, the disclosures of which are hereby incorporated by reference in their entireties. Methods of constructing antibodies or other antigen-binding fusion proteins comprising a modified Fc domain as described herein are known in the art.

Antibody-Dependent-Enhancement

Antibody-dependent enhancement (ADE) is a mechanism by which a virus, when bound to antiviral antibodies enters cells having Fc receptors, leading to increased infectivity in the cells. ADE has been demonstrated in vitro for many viruses (including ZIKV), but the only compelling data for ADE in man comes from dengue virus infections. This virus can use this mechanism to infect macrophages, causing a normally mild viral infection to become life-threatening. For example, an initial dengue virus infection is clinically manifested for most of the cases by dengue fever (DF), which is a self-limited febrile illness. Although rarely fatal, DF is characterized by often-severe disseminated body pain, headache, fever, rash, lymphadenopathy and leukopenia. Subsequent infection with a heterologous Dengue virus can lead to the much more severe to fatal disease of dengue hemorrhagic fever (DHF) or dengue shock syndrome (DSS). It is hypothesized that the presence of antibodies to the serotype causing the primary infection enhances the infection by a heterologous serotype in secondary infections. During such secondary infection, with a different serotype of dengue virus, cross-reactive antibodies that are not neutralizing form virus-antibody complexes that are taken into monocytes and Langerhans cells (dendritic cells) and increase the number of infected cells. This leads to the activation of cytotoxic lymphocytes, which can result in plasma leakage and the hemorrhagic features characteristic of DHF and DSS. This antibody-dependent enhancement of infection is one reason why the development of a successful vaccine against dengue virus has proven to be so difficult. Although less frequent, DHF/DSS can occur after primary infection, so virus virulence and immune activation are also believed to contribute to the pathogenesis of the disease.

ZIKV infection occurs in areas previously exposed to dengue virus, which is closely related to ZIKV. Furthermore, it has recently been shown that plasma from patients immune to dengue virus shows substantial cross-reactivity to ZIKV. In addition, using a panel of human sera and antibodies that react with the dengue virus envelope protein, it was shown that these antibodies also react with ZIKV. Certain of these antibodies were able to bind ZIKV, but were unable to neutralize the virus, but instead promoted ADE in vitro.

The proposed mechanism by which ADE occurs is by binding the virus to the surface of cells that contain abundant FcγRs, but low levels of other viral attachment factors. This results in cell internalization in the absence of other viral attachment factors, initiating viral infection through the normal infection route.

In certain embodiments, the anti-ZIKV antibodies of the present invention comprise a modified Fc domain having reduced effector function. As used herein, a "modified Fc domain having reduced effector function" means any Fc portion of an immunoglobulin that has been modified, mutated, truncated, etc., relative to a wild-type, naturally occurring Fc domain such that a molecule comprising the modified Fc exhibits a reduction in the severity or extent of at least one effect selected from the group consisting of cell killing (e.g., ADCC and/or CDC), complement activation, phagocytosis and opsonization, relative to a comparator molecule comprising the wild-type, naturally occurring version of the Fc portion. In certain embodiments, a "modified Fc domain having reduced effector function" is an Fc domain with reduced or attenuated binding to an Fc receptor (e.g., FcγR).

Accordingly, in certain embodiments of the invention, the anti-ZIKV antibodies comprise modifications to the Fc region of the antibodies to allow for reduced binding to Fc receptors on macrophages and other cells bearing Fc receptors, while at the same time maintaining the ability to neutralize the virus, and in so doing act to prevent ADE from occurring while at the same time allowing for a decrease in viral infectivity through the normal viral attachment and/or neutralization of fusion.

According to certain embodiments, the modified Fc domain having reduced effector function is a variant IgG4 Fc comprising the amino acid sequence shown in either SEQ ID NO: 357 (without a YTE modification at positions 131, 133 and 135), or SEQ ID NO:358 (having a YTE modification at positions 131, 133 and 135), as described above. As such, an antibody having a variant IgG4 Fc without the YTE modification would not demonstrate antibody dependent enhancement and would not have an extended half-life (e.g. H4H25703N having a HC/LC of SEQ ID NOs: 367/368), whereas an antibody having a variant IgG4 Fc with a YTE modification (e.g. H4H25703 having a HC/LC of SEQ ID NOs: 369/368) would not demonstrate antibody dependent enhancement but would have an extended half-life. As such, Fc modifications can be made that result in either one, or both reduced effector function and longer serum half-life of an antibody, as compared to a wildtype IgG4 Fc.

In one aspect of the invention, the invention comprises a human antibody, an antibody variant, or an antigen binding fragment thereof, that neutralize ZIKV, wherein the antibody, antibody variant, or antigen binding fragment does not contribute to antibody-dependent enhancement of ZIKV infection. In one embodiment, the invention comprises a human antibody, an antibody variant, or an antigen binding fragment thereof, that neutralize ZIKV, wherein the antibody, antibody variant, or antigen binding fragment comprises a mutation in the Fc region, and wherein the mutation reduces binding of the antibody to an Fc receptor.

In another embodiment of the invention, the invention comprises a pharmaceutical composition comprising two or more human antibodies, or antigen binding fragments thereof that bind ZIKV E. The antibodies or antigen binding fragments may prevent attachment of the virus to the cell, or may prevent fusion of the virus to the host cell membrane and as such, prevent viral entry to the cell and replication within the cell and do not contribute to antibody-dependent enhancement of ZIKV infection.

Biological Characteristics of the Antibodies

In general, the antibodies of the present invention function by binding to ZIKV envelope glycoprotein (E). For example, the present invention includes antibodies and antigen-binding fragments of antibodies that bind ZIKV E (e.g., at 25° C. or at 37° C.) with a $K_D$ of less than $10^{-7}$M, as measured by surface plasmon resonance, e.g., using the assay format as described herein. In certain embodiments, the antibodies or antigen-binding fragments thereof bind ZIKV E with a $K_D$ of less than about 100 nM, less than about 50 nM, less than about 5 nM, less than about 1 nM, less than about 500 pM, less than 250 pM, less than about 100 pM, or less than about 1 pM, as measured by surface plasmon resonance, e.g., using the assay format as described herein, or a substantially similar assay.

The present invention also includes antibodies and antigen-binding fragments thereof that bind ZIKV with a dissociative half-life (t½) of greater than about 0.5 minutes as measured by surface plasmon resonance at 25° C., or greater than about 0.3 minutes as measured by surface plasmon resonance at 37° C. and may or may not demonstrate a change in dissociative half life (t½) at pH 5, or pH 6 relative to a pH of 7.4, e.g., using an assay format as defined herein, or a substantially similar assay. In certain embodiments, the antibodies or antigen-binding fragments of the present invention bind ZIKV with a t½ of greater than about 10 minutes, of greater than about 30 minutes, of greater than about 60 minutes, of greater than about 100 minutes, of greater than about 200 minutes, greater than about 300 minutes, greater than about 400 minutes, greater than about 500 minutes, greater than about 600 minutes, greater than about 700 minutes, greater than about 800 minutes, greater than about 900 minutes, or greater than about 1000 minutes as measured by surface plasmon resonance at 25° C., or at 37° C. e.g., using an assay format as defined herein (e.g., mAb-capture or antigen-capture format), or a substantially similar assay.

The present invention also includes antibodies or antigen-binding fragments thereof that neutralize the infectivity of ZIKV for its host cells. In some embodiments, the antibodies exhibit a neutralization potency against ZIKV with an $IC_{50}$ ranging from about $10^{-11}$M to about $10^{-9}$ M. The antibodies of the invention also cross react with ZIKV strains including MR766 (Uganda 1947), PRVABC59 (Puerto Rico 2015), and FLR (Colombia 2015). The antibodies of the invention also bind to VLPs derived from cells expressing ZIKV prM/E with an $EC_{50}$ ranging from about 80 pM to about 150 nM. Furthermore, the antibodies of the invention cross-compete with other antibodies that bind ZIKV E.

In one embodiment, the present invention provides an isolated recombinant antibody or antigen-binding fragment thereof that specifically binds to ZIKV and/or a ZIKV E, wherein the antibody has one or more of the following characteristics:

(a) comprises three heavy chain complementarity determining regions (CDRs) (HCDR1, HCDR2 and HCDR3) contained within any one of the heavy chain variable region (HCVR) sequences selected from the group consisting of SEQ ID NOs: 2, 18, 34, 50, 66, 82, 98, 114, 130, 146, 162, 178, 194, 210, 226, 242, 258, 274, 290, 306, 322 and 338; and three light chain CDRs (LCDR1, LCDR2 and LCDR3) contained within any one of the light chain variable region (LCVR) sequences selected from the group consisting of SEQ ID NOs: 10, 26, 42, 58, 74, 90, 106, 122, 138, 154, 170, 186, 202, 218, 234, 250, 266, 282, 298, 314, 330 and 346;

(b) is a fully human monoclonal antibody;

(c) binds to a VLP expressing Zika prM/E with an $EC_{50}$ ranging from about 80 pM to about 150 nM;

(d) binds to ZIKV E with a dissociation constant ($K_D$) of less than $10^{-7}$M, as measured in a surface plasmon resonance assay;

(e) may or may not demonstrate a change in dissociative half-life (t½) at pH 5 or pH 6 relative to pH 7.4;

(f) demonstrates neutralization of ZIKV with an $IC_{50}$ ranging from about $10^{-11}$ M to about $10^{-9}$M;

(g) demonstrates a protective effect in vivo in a ZIKV infected animal;

(h) cross-competes with a reference antibody, wherein the reference antibody comprises a heavy chain variable region (HCVR) and a light chain variable region (LCVR) amino acid sequence selected from the group consisting of any of the HCVR and LCVR amino acid sequences of Table 1.

The antibodies of the present invention may possess one or more of the aforementioned biological characteristics, or any combinations thereof. Certain of the properties of the antibodies of the invention are summarized below. Other biological characteristics of the antibodies of the present invention will be evident to a person of ordinary skill in the art from a review of the present disclosure including the working Examples herein.

Epitope Mapping and Related Technologies

The present invention includes anti-ZIKV antibodies that interact with one or more amino acids found within the E of ZIKV. The epitope to which the antibodies bind may consist of a single contiguous sequence of 3 or more (e.g., 3, 4, 5, 6, 7, 8, 9, 10, 11, 12, 13, 14, 15, 16, 17, 18, 19, 20 or more) amino acids located within ZIKV E (e.g. a linear epitope in a domain). Alternatively, the epitope may consist of a plurality of non-contiguous amino acids (or amino acid sequences) located within the ZIKV E (e.g. a conformational epitope).

Various techniques known to persons of ordinary skill in the art can be used to determine whether an antibody "interacts with one or more amino acids" within a polypeptide or protein. Exemplary techniques include, for example, routine cross-blocking assays, such as that described in Antibodies, Harlow and Lane (Cold Spring Harbor Press, Cold Spring Harbor, N.Y.). Other methods include alanine scanning mutational analysis, peptide blot analysis (Reineke (2004) Methods Mol. Biol. 248: 443-63), peptide cleavage analysis crystallographic studies and NMR analysis. In addition, methods such as epitope excision, epitope extraction and chemical modification of antigens can be employed (Tomer (2000) Prot. Sci. 9: 487-496). Another method that can be used to identify the amino acids within a polypeptide with which an antibody interacts is hydrogen/deuterium exchange detected by mass spectrometry. In general terms, the hydrogen/deuterium exchange method involves deuterium-labeling the protein of interest, followed by binding the antibody to the deuterium-labeled protein. Next, the protein/antibody complex is transferred to water and exchangeable protons within amino acids that are protected by the antibody complex undergo deuterium-to-hydrogen back-exchange at a slower rate than exchangeable protons within amino acids that are not part of the interface. As a result, amino acids that form part of the protein/antibody interface may retain deuterium and therefore exhibit relatively higher mass compared to amino acids not included in the interface. After dissociation of the antibody, the target protein is subjected to protease cleavage and mass spectrometry analysis, thereby revealing the deuterium-labeled residues that correspond to the specific amino acids with which the antibody interacts. See, e.g., Ehring (1999) Analytical Biochemistry 267: 252-259; Engen and Smith (2001) Anal. Chem. 73: 256A-265A.

The term "epitope" refers to a site on an antigen to which B and/or T cells respond. B-cell epitopes can be formed both from contiguous amino acids or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, and more usually, at least 5 or 8-10 amino acids in a unique spatial conformation.

Modification-Assisted Profiling (MAP), also known as Antigen Structure-based Antibody Profiling (ASAP) is a method that categorizes large numbers of monoclonal antibodies (mAbs) directed against the same antigen according to the similarities of the binding profile of each antibody to chemically or enzymatically modified antigen surfaces (see US 2004/0101920, herein specifically incorporated by reference in its entirety). Each category may reflect a unique epitope either distinctly different from or partially overlapping with epitope represented by another category. This technology allows rapid filtering of genetically identical antibodies, such that characterization can be focused on genetically distinct antibodies. When applied to hybridoma screening, MAP may facilitate identification of rare hybridoma clones that produce mAbs having the desired characteristics. MAP may be used to sort the antibodies of the invention into groups of antibodies binding different epitopes.

In certain embodiments, the ZIKV antibodies or antigen-binding fragments thereof bind an epitope within any one or more of the regions exemplified in ZIKV E, either in natural form, or recombinantly produced, or to a fragment thereof.

In one embodiment, escape mutants were generated using the H4H25703N and the H4H25619P antibodies. The results of these studies demonstrated that the serine at position 302 of SEQ ID NO:376 plays a role in H4H25703N antibody binding to the E protein, since a change from a serine to a phenylalanine resulted in loss of binding of the antibody to the mutated E protein and also resulted in loss of virus neutralization capability of the H4H25703N antibody. Likewise, the results with the escape mutants generated using the H4H25619P antibody demonstrated that the threonine at position 311 of SEQ ID NO: 376 and the lysine at position 369 of SEQ ID NO: 376 play a role in binding of H4H25619P to the E protein, since a change from a threonine to an isoleucine at position 311 of SEQ ID NO: 376 and a change from a lysine to a glutamic acid at position 369 resulted in loss of binding of the antibody to the mutated E protein and also resulted in loss of virus neutralization capability of the H4H25619P antibody.

The present invention includes anti-ZIKV E antibodies that bind to the same epitope, or a portion of the epitope. Likewise, the present invention also includes anti-ZIKV E antibodies that compete for binding to ZIKV E or a fragment thereof with any of the specific exemplary antibodies described herein. For example, the present invention includes anti-ZIKV E antibodies that cross-compete for binding to ZIKV with one or more antibodies obtained from those antibodies described in Tables 1 and 2.

One can easily determine whether an antibody binds to the same epitope as, or competes for binding with, a reference anti-ZIKV E antibody by using routine methods known in the art. For example, to determine if a test antibody binds to the same epitope as a reference anti-ZIKV E antibody of the invention, the reference antibody is allowed to bind to a ZIKV E or peptide under saturating conditions. Next, the ability of a test antibody to bind to the ZIKV E is assessed. If the test antibody is able to bind to ZIKV E following saturation binding with the reference anti-ZIKV E antibody, it can be concluded that the test antibody binds to a different epitope than the reference anti-ZIKV antibody. On the other hand, if the test antibody is not able to bind to the ZIKV E following saturation binding with the reference anti-ZIKV E antibody, then the test antibody may bind to the same epitope as the epitope bound by the reference anti-ZIKV E antibody of the invention.

To determine if an antibody competes for binding with a reference anti-ZIKV E antibody, the above-described binding methodology is performed in two orientations: In a first orientation, the reference antibody is allowed to bind to a ZIKV E under saturating conditions followed by assessment of binding of the test antibody to the ZIKV E. In a second orientation, the test antibody is allowed to bind to an ZIKV E under saturating conditions followed by assessment of binding of the reference antibody to the ZIKV E. If, in both orientations, only the first (saturating) antibody is capable of binding to the ZIKV E, then it is concluded that the test antibody and the reference antibody compete for binding to ZIKV E. As will be appreciated by a person of ordinary skill in the art, an antibody that competes for binding with a reference antibody may not necessarily bind to the identical epitope as the reference antibody, but may sterically block binding of the reference antibody by binding an overlapping or adjacent epitope.

Two antibodies bind to the same or overlapping epitope if each competitively inhibits (blocks) binding of the other to the antigen. That is, a 1-, 5-, 10-, 20- or 100-fold excess of one antibody inhibits binding of the other by at least 50% but preferably 75%, 90% or even 99% as measured in a competitive binding assay (see, e.g., Junghans et al., Cancer Res. 1990 50:1495-1502). Alternatively, two antibodies have the same epitope if essentially all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other.

Additional routine experimentation (e.g., peptide mutation and binding analyses) can then be carried out to confirm whether the observed lack of binding of the test antibody is in fact due to binding to the same epitope as the reference antibody or if steric blocking (or another phenomenon) is responsible for the lack of observed binding. Experiments of this sort can be performed using ELISA, RIA, surface plasmon resonance, flow cytometry or any other quantitative or qualitative antibody-binding assay available in the art.

Immunoconjugates

The invention encompasses a human anti-ZIKV E monoclonal antibody conjugated to a therapeutic moiety ("immunoconjugate"), such as an anti-viral drug to treat ZIKV infection. As used herein, the term "immunoconjugate" refers to an antibody, which is chemically or biologically linked to a radioactive agent, a cytokine, an interferon, a target or reporter moiety, an enzyme, a peptide or protein or a therapeutic agent. The antibody may be linked to the radioactive agent, cytokine, interferon, target or reporter moiety, enzyme, peptide or therapeutic agent at any location along the molecule so long as it is able to bind its target. Examples of immunoconjugates include antibody drug conjugates and antibody-toxin fusion proteins. In one embodiment, the agent may be a second different antibody to ZIKV, or ZIKV E. In certain embodiments, the antibody may be conjugated to an agent specific for a virally infected cell. The type of therapeutic moiety that may be conjugated to the anti-ZIKV antibody and will take into account the condition to be treated and the desired therapeutic effect to be achieved. Examples of suitable agents for forming immunoconjugates are known in the art; see for example, WO 05/103081.

Multi-Specific Antibodies

The antibodies of the present invention may be monospecific, bi-specific, or multi-specific. Multi-specific antibodies may be specific for different epitopes of one target polypeptide or may contain antigen-binding domains specific for more than one target polypeptide. See, e.g., Tutt et al., 1991, J. Immunol. 147:60-69; Kufer et al., 2004, Trends Biotechnol. 22:238-244.

Any of the multi-specific antigen-binding molecules of the invention, or variants thereof, may be constructed using standard molecular biological techniques (e.g., recombinant DNA and protein expression technology), as will be known to a person of ordinary skill in the art.

In some embodiments, ZIKV-specific antibodies are generated in a bi-specific format (a "bi-specific") in which variable regions binding to distinct domains of ZIKV are linked together to confer dual-domain specificity within a single binding molecule. Appropriately designed bi-specifics may enhance overall ZIKV-protein inhibitory efficacy through increasing both specificity and binding avidity. Variable regions with specificity for individual domains, (e.g., segments of the N-terminal domain), or that can bind to different regions within one domain, are paired on a structural scaffold that allows each region to bind simultaneously to the separate epitopes, or to different regions within one domain. In one example for a bi-specific, heavy chain variable regions ($V_H$) from a binder with specificity for one domain are recombined with light chain variable regions ($V_L$) from a series of binders with specificity for a second domain to identify non-cognate $V_L$ partners that can be paired with an original $V_H$ without disrupting the original specificity for that $V_H$. In this way, a single $V_L$ segment (e.g., $V_L1$) can be combined with two different $V_H$ domains (e.g., $V_H1$ and $V_H2$) to generate a bi-specific comprised of two binding "arms" ($V_H1$-$V_L1$ and $V_H2$-$V_L1$). Use of a single $V_L$ segment reduces the complexity of the system and thereby simplifies and increases efficiency in cloning, expression, and purification processes used to generate the bi-specific (See, for example, U.S. Ser. No. 13/022,759 and US2010/0331527).

Alternatively, antibodies that bind more than one domain and a second target, such as, but not limited to, for example, a second different anti-ZIKV antibody, may be prepared in a bi-specific format using techniques described herein, or other techniques known to those skilled in the art. Antibody variable regions binding to distinct regions may be linked together with variable regions that bind to relevant sites on, for example, ZIKV, to confer dual-antigen specificity within a single binding molecule. Appropriately designed bi-specifics of this nature serve a dual function. Variable regions with specificity for the extracellular domain are combined with a variable region with specificity for outside the extracellular domain and are paired on a structural scaffold that allows each variable region to bind to the separate antigens.

An exemplary bi-specific antibody format that can be used in the context of the present invention involves the use of a first immunoglobulin (Ig) $C_H3$ domain and a second Ig $C_H3$ domain, wherein the first and second Ig $C_H3$ domains differ from one another by at least one amino acid, and wherein at least one amino acid difference reduces binding of the bi-specific antibody to Protein A as compared to a bi-specific antibody lacking the amino acid difference. In one embodiment, the first Ig $C_H3$ domain binds Protein A and the second Ig $C_H3$ domain contains a mutation that reduces or abolishes Protein A binding such as an H95R modification (by IMGT exon numbering; H435R by EU numbering). The second $C_H3$ may further comprise a Y96F modification (by IMGT; Y436F by EU). Further modifications that may be found within the second $C_H3$ include: D16E, L18M, N44S, K52N, V57M, and V82I (by IMGT; D356E, L358M, N384S, K392N, V397M, and V422I by EU) in the case of IgG1 antibodies; N44S, K52N, and V82I (IMGT; N384S, K392N, and V422I by EU) in the case of IgG2 antibodies; and Q15R, N44S, K52N, V57M, R69K, E79Q, and V82I (by IMGT; Q355R, N384S, K392N, V397M, R409K, E419Q, and V422I by EU) in the case of IgG4 antibodies. Variations on the bi-specific antibody format described above are contemplated within the scope of the present invention.

Other exemplary bispecific formats that can be used in the context of the present invention include, without limitation, e.g., scFv-based or diabody bispecific formats, IgG-scFv fusions, dual variable domain (DVD)-Ig, Quadroma, knobs-into-holes, common light chain (e.g., common light chain with knobs-into-holes, etc.), CrossMab, CrossFab, (SEED) body, leucine zipper, Duobody, IgG1/IgG2, dual acting Fab (DAF)-IgG, and Mab$^2$ bispecific formats (see, e.g., Klein et al. 2012, mAbs 4:6, 1-11, and references cited therein, for a review of the foregoing formats). Bispecific antibodies can also be constructed using peptide/nucleic acid conjugation, e.g., wherein unnatural amino acids with orthogonal chemical reactivity are used to generate site-specific antibody-oligonucleotide conjugates which then self-assemble into multimeric complexes with defined composition, valency and geometry. (See, e.g., Kazane et al., *J. Am. Chem. Soc.* [Epub: Dec. 4, 2012]).

Therapeutic Administration and Formulations

The invention provides therapeutic compositions comprising the anti-ZIKV E antibodies or antigen-binding fragments thereof of the present invention. Therapeutic compositions in accordance with the invention will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences, Mack Publishing Company, Easton, Pa. These formulations include, for example, powders, pastes, ointments, jellies, waxes, oils, lipids, lipid (cationic or anionic) containing vesicles (such as LIPOFECTIN™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311.

The dose of antibody may vary depending upon the age and the size of a subject to be administered, target disease, conditions, route of administration, and the like. When an antibody of the present invention is used for treating a disease or disorder in an adult patient, or for preventing such a disease, it is advantageous to administer the antibody of the present invention normally at a single dose of about 0.1 to about 60 mg/kg body weight, more preferably about 5 to about 60, about 10 to about 50, or about 20 to about 50 mg/kg body weight. Depending on the severity of the condition, the frequency and the duration of the treatment can be adjusted. In certain embodiments, the antibody or antigen-binding fragment thereof of the invention can be administered as an initial dose of at least about 0.1 mg to about 800 mg, about 1 to about 500 mg, about 5 to about 300 mg, or about 10 to about 200 mg, to about 100 mg, or to about 50 mg. In certain embodiments, the initial dose may be followed by administration of a second or a plurality of subsequent doses of the antibody or antigen-binding fragment thereof in an amount that can be approximately the same or less than that of the initial dose, wherein the subsequent doses are separated by at least 1 day to 3 days; at least one week, at least 2 weeks; at least 3 weeks; at least 4 weeks; at least 5 weeks; at least 6 weeks; at least 7 weeks; at least 8 weeks; at least 9 weeks; at least 10 weeks; at least 12 weeks; or at least 14 weeks.

Various delivery systems are known and can be used to administer the pharmaceutical composition of the invention, e.g., encapsulation in liposomes, microparticles, microcapsules, recombinant cells capable of expressing the mutant viruses, receptor mediated endocytosis (see, e.g., Wu et al. (1987) J. Biol. Chem. 262:4429-4432). Methods of introduction include, but are not limited to, intradermal, transdermal, intramuscular, intraperitoneal, intravenous, subcutaneous, intranasal, epidural and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. The pharmaceutical composition can be also delivered in a vesicle, in particular a liposome (see, for example, Langer (1990) Science 249: 1527-1533).

The use of nanoparticles to deliver the antibodies of the present invention is also contemplated herein. Antibody-conjugated nanoparticles may be used both for therapeutic and diagnostic applications. Antibody-conjugated nanoparticles and methods of preparation and use are described in detail by Arruebo, M., et al. 2009 ("Antibody-conjugated nanoparticles for biomedical applications" in J. Nanomat. Volume 2009, Article ID 439389, 24 pages, doi: 10.1155/ 2009/439389), incorporated herein by reference. Nanoparticles may be developed and conjugated to antibodies contained in pharmaceutical compositions to target virally infected cells. Nanoparticles for drug delivery have also been described in, for example, U.S. Pat. No. 8,257,740, or U.S. Pat. No. 8,246,995, each incorporated herein in its entirety.

In certain situations, the pharmaceutical composition can be delivered in a controlled release system. In one embodiment, a pump may be used. In another embodiment, polymeric materials can be used. In yet another embodiment, a controlled release system can be placed in proximity of the composition's target, thus requiring only a fraction of the systemic dose.

The injectable preparations may include dosage forms for intravenous, subcutaneous, intracutaneous, intracranial, intraperitoneal and intramuscular injections, drip infusions, etc. These injectable preparations may be prepared by methods publicly known. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule.

A pharmaceutical composition of the present invention can be delivered subcutaneously or intravenously with a standard needle and syringe. In addition, with respect to subcutaneous delivery, a pen delivery device readily has applications in delivering a pharmaceutical composition of the present invention. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Numerous reusable pen and autoinjector delivery devices have applications in the subcutaneous delivery of a pharmaceutical composition of the present invention. Examples include, but certainly are not limited to AUTOPEN™ (Owen Mumford, Inc., Woodstock, UK), DISETRONIC™ pen (Disetronic Medical Systems, Burghdorf, Switzerland), HUMALOG MIX 75/25™ pen, HUMALOG™ pen, HUMALIN 70/30™ pen (Eli Lilly and Co., Indianapolis, Ind.), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, N.J.), OPTIPEN™, OPTIPEN PRO™, OPTIPEN STARLET™, and OPTICLIK™ (Sanofi-Aventis, Frankfurt, Germany), to name only a few. Examples of disposable pen delivery devices having applications in subcutaneous delivery of a pharmaceutical composition of the present invention include, but certainly are not limited to the SOLOSTAR™ pen (Sanofi-Aventis), the FLEXPEN™ (Novo Nordisk), and the KWIKPEN™ (Eli Lilly), the SURECLICK™ Autoinjector (Amgen, Thousand Oaks, Calif.), the PENLET™ (Haselmeier, Stuttgart, Germany), the EPI PEN (Dey, L. P.) and the HUMIRA™ Pen (Abbott Labs, Abbott Park, Ill.), to name only a few.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc. The amount of the antibody contained is generally about 5 to about 500 mg per dosage form in a unit dose; especially in the form of injection, it is preferred that the antibody is contained in about 5 to about 100 mg and in about 10 to about 250 mg for the other dosage forms.

Prophylactic or Therapeutic Uses of the Antibodies

The antibodies of the present invention are useful for the treatment, and/or prevention of a disease or disorder or condition associated with ZIKV infection and/or for ameliorating at least one symptom associated with such disease, disorder or condition.

In some embodiments, the antibodies of the invention are useful in decreasing viral titers or reducing viral load in the host. In one embodiment, an antibody or antigen-binding fragment thereof the invention may be administered at a therapeutic dose to a patient with ZIKV infection.

One or more antibodies of the present invention may be administered to relieve or prevent or decrease the severity of one or more of the symptoms or conditions of the disease or disorder. The antibodies may be used to ameliorate or reduce the severity of at least one symptom of ZIKV infection including, but not limited to fever, headache, arthralgia, myalgia, and maculopapular rash.

It is also contemplated herein to use one or more antibodies of the present invention prophylactically to subjects at risk for developing a ZIKV infection such as an immunocompromised individual, a person who has been bitten by a mosquito believed to harbor the ZIKV, a pregnant woman who has been exposed to ZIKV, a woman who lives in, or is visiting a country known to have a ZIKV outbreak and who is considering conceiving a child, an individual visiting, or living in an area known to harbor mosquitoes suspected of carrying the ZIKV, individuals who have visited or are planning to visit an area or country known to have or suspected to have an outbreak of ZIKV.

In a further embodiment of the invention the present antibodies are used for the preparation of a pharmaceutical composition for treating patients suffering from a ZIKV infection, or exposed to ZIKV via a bite by a mosquito harboring the virus. In another embodiment of the invention, the present antibodies are used as adjunct therapy with any other agent or any other therapy known to those skilled in the art useful for treating or ameliorating a ZIKV infection.

Combination Therapies

Combination therapies may include an anti-ZIKV E antibody of the invention and any additional therapeutic agent that may be advantageously combined with an antibody of the invention, or with a biologically active fragment of an antibody of the invention. The antibodies of the present invention may be combined synergistically with one or more drugs or agents used to treat ZIKV infection.

For example, exemplary agents for treating a viral infection may include, e.g., anti-viral drug, an anti-inflammatory drug (such as corticosteroids, and non-steroidal anti-inflammatory drugs, such as anti-TNF), a different antibody to ZIKV, a vaccine for ZIKV, an interferon, an immunomodulator, or any other palliative therapy to treat a ZIKV infection.

In some embodiments, the antibodies of the invention may be combined with a second therapeutic agent to reduce the viral load in a patient with a ZIKV infection, or to ameliorate one or more symptoms of the infection and/or spread to fetus or male reproductive organs.

In certain embodiments, the second therapeutic agent is another different antibody, or antibody cocktail specific for ZIKV E, wherein the different antibody or antibodies within the cocktail may or may not bind to the same epitope, or an overlapping epitope, as an antibody of the present invention. In certain embodiments, the second therapeutic agent is an antibody to a different ZIKV protein. The second antibody may be specific for one or more different ZIKV proteins from different strains of the virus. It is contemplated herein to use a combination ("cocktail") of the antibodies of the invention with neutralization or inhibitory activity against ZIKV. In some embodiments, non-competing antibodies may be combined and administered to a subject in need thereof, to reduce the ability of ZIKV to escape due to mutation. In some embodiments, the antibodies comprising the combination bind to distinct non-overlapping epitopes on the E. The antibodies comprising the combination may block the virus attachment to the cell, and/or may inhibit fusion of the virus with the cell membrane, and in so doing may block ZIKV entry into the host cells. The antibodies may interact with the E from a strain of ZIKV selected from MR766 (Uganda 1947), PRVABC59 (Puerto Rico 2015) and FLR (Colombia 2015) strains, and when used alone, or in combination with any one or more of the agents noted above, may neutralize any one or more of the ZIKV strains noted, or variants thereof.

It is also contemplated herein to use a combination of anti-ZIKV E antibodies of the present invention, wherein the combination comprises one or more antibodies that do not cross-compete. In certain embodiments, the combination includes a cocktail comprising a mixture of at least two, or at least three antibodies of the invention. The antibodies within the cocktail may differ in their ability to neutralize virus or virus infected cells, or in their ability to block attachment of the virus to the cell, or block fusion of the virus to the cell membrane, or in their ability to bind ZIKV E.

As used herein, the term "in combination with" means that additional therapeutically active component(s) may be administered prior to, concurrent with, or after the administration of at least one anti-ZIKV E antibody of the invention, or a cocktail comprising two or more of the antibodies the present invention. The term "in combination with" also includes sequential or concomitant administration of an anti-ZIKV E antibody and a second therapeutic agent.

The additional therapeutically active component(s) may be administered to a subject prior to administration of an anti-ZIKV E antibody of the present invention. For example, a first component may be deemed to be administered "prior to" a second component if the first component is administered 1 week before, 72 hours before, 60 hours before, 48 hours before, 36 hours before, 24 hours before, 12 hours before, 6 hours before, 5 hours before, 4 hours before, 3 hours before, 2 hours before, 1 hour before, 30 minutes before, 15 minutes before, 10 minutes before, 5 minutes before, or less than 1 minute before administration of the second component. In other embodiments, the additional therapeutically active component(s) may be administered to a subject after administration of an anti-ZIKV E antibody of the present invention. For example, a first component may be deemed to be administered "after" a second component if the first component is administered 1 minute after, 5 minutes after, 10 minutes after, 15 minutes after, 30 minutes after, 1 hour after, 2 hours after, 3 hours after, 4 hours after, 5 hours after, 6 hours after, 12 hours after, 24 hours after, 36 hours after, 48 hours after, 60 hours after, 72 hours after administration of the second component. In yet other embodiments, the additional therapeutically active component(s) may be administered to a subject concurrent with administration of an anti-ZIKV E antibody of the present invention. "Concurrent" administration, for purposes of the present invention, includes, e.g., administration of an anti-ZIKV E antibody and an additional therapeutically active component to a subject in a single dosage form, or in separate dosage forms administered to the subject within about 30 minutes or less of each other. If administered in separate dosage forms, each dosage form may be administered via the same route (e.g., both the anti-ZIKV E antibody and the additional therapeutically active component may be administered intravenously, etc.); alternatively, each dosage form may be administered via a different route (e.g., the anti-ZIKV E antibody may be administered intravenously, and the additional therapeutically active component may be administered orally). In any event, administering the components in a single dosage from, in separate dosage forms by the same route, or in separate dosage forms by different routes are all considered "concurrent administration," for purposes of the present disclosure. For purposes of the present disclosure, administration of an anti-ZIKV E antibody "prior to", "concurrent with," or "after" (as those terms are defined herein above) administration of an additional therapeutically active component is considered administration of an anti-ZIKV E antibody "in combination with" an additional therapeutically active component.

The present invention includes pharmaceutical compositions in which an anti-ZIKV E antibody of the present invention is co-formulated with one or more of the additional therapeutically active component(s) as described elsewhere herein.

Administration Regimens

According to certain embodiments, a single dose of an anti-ZIKV E antibody of the invention (or a pharmaceutical composition comprising one or more antibodies of the invention, or a combination of one or more anti-ZIKV E antibodies and any of the additional therapeutically active agents mentioned herein) may be administered to a subject in need thereof. According to certain embodiments of the present invention, multiple doses of an anti-ZIKV E antibody (or a pharmaceutical composition comprising a combination of anti-ZIKV E antibodies or one or more antibodies of the invention and any of the additional therapeutically active agents mentioned herein) may be administered to a subject over a defined time course. The methods according to this aspect of the invention comprise sequentially administering to a subject multiple doses of one or more anti-ZIKV E antibodies of the invention. As used herein, "sequentially administering" means that each dose of anti-ZIKV E antibody is administered to the subject at a different point in time, e.g., on different days separated by a predetermined interval (e.g., hours, days, weeks or months). The present invention includes methods which comprise sequentially administering to the patient a single initial dose of an anti-ZIKV E antibody, followed by one or more secondary doses of the anti-ZIKV E antibody, and optionally followed by one or more tertiary doses of the anti-ZIKV E antibody.

The terms "initial dose," "secondary doses," and "tertiary doses," refer to the temporal sequence of administration of the anti-ZIKV E antibody of the invention. Thus, the "initial dose" is the dose which is administered at the beginning of the treatment regimen (also referred to as the "baseline dose"); the "secondary doses" are the doses which are administered after the initial dose; and the "tertiary doses" are the doses which are administered after the secondary doses. The initial, secondary, and tertiary doses may all contain the same amount of anti-ZIKV E antibody, but generally may differ from one another in terms of frequency of administration. In certain embodiments, however, the amount of anti-ZIKV E antibody contained in the initial, secondary and/or tertiary doses varies from one another (e.g., adjusted up or down as appropriate) during the course of treatment. In certain embodiments, two or more (e.g., 2, 3, 4, or 5) doses are administered at the beginning of the treatment regimen as "loading doses" followed by subsequent doses that are administered on a less frequent basis (e.g., "maintenance doses").

In certain exemplary embodiments of the present invention, each secondary and/or tertiary dose is administered 1 to 48 hours (e.g., 1, 1½, 2, 2½, 3, 3½, 4, 4½, 5, 5½, 6, 6½, 7, 7½, 8, 8½, 9, 9½, 10, 10½, 11, 11½, 12, 12½, 13, 13½, 14, 14½, 15, 15½, 16, 16½, 17, 17½, 18, 18½, 19, 19½, 20, 20½, 21, 21½, 22, 22½, 23, 23½, 24, 24½, 25, 25½, 26, 26½, or more) after the immediately preceding dose. The phrase "the immediately preceding dose," as used herein, means, in a sequence of multiple administrations, the dose of anti-ZIKV E antibody, which is administered to a patient prior to the administration of the very next dose in the sequence with no intervening doses.

The methods according to this aspect of the invention may comprise administering to a patient any number of secondary and/or tertiary doses of an anti-ZIKV E antibody. For example, in certain embodiments, only a single secondary dose is administered to the patient. In other embodiments, two or more (e.g., 2, 3, 4, 5, 6, 7, 8, or more) secondary doses are administered to the patient. Likewise, in certain embodiments, only a single tertiary dose is administered to the patient. In other embodiments, two or more (e.g., 2, 3, 4, 5, 6, 7, 8, or more) tertiary doses are administered to the patient.

In certain embodiments of the invention, the frequency at which the secondary and/or tertiary doses are administered to a patient can vary over the course of the treatment regimen. The frequency of administration may also be adjusted during the course of treatment by a physician depending on the needs of the individual patient following clinical examination.

Diagnostic Uses of the Antibodies

The anti-ZIKV E antibodies of the present invention may be used to detect and/or measure ZIKV in a sample, e.g., for diagnostic purposes. Some embodiments contemplate the use of one or more antibodies of the present invention in assays to detect a disease or disorder such as viral infection. Exemplary diagnostic assays for ZIKV may comprise, e.g., contacting a sample, obtained from a patient, with an anti-ZIKV E antibody of the invention, wherein the anti-ZIKV E antibody is labeled with a detectable label or reporter molecule or used as a capture ligand to selectively isolate ZIKV from patient samples. Alternatively, an unlabeled anti-ZIKV E antibody can be used in diagnostic applications in combination with a secondary antibody which is itself detectably labeled. The detectable label or reporter molecule can be a radioisotope, such as $^3$H, $^{14}$C, $^{32}$P, $^{35}$S, or $^{125}$I; a fluorescent or chemiluminescent moiety such as fluorescein isothiocyanate, or rhodamine; or an enzyme such as alkaline phosphatase, β-galactosidase, horseradish peroxidase, or luciferase. Specific exemplary assays that can be used to detect or measure ZIKV in a sample include enzyme-linked immunosorbent assay (ELISA), radioimmunoassay (RIA), and fluorescence-activated cell sorting (FACS).

Samples that can be used in ZIKV diagnostic assays according to the present invention include any tissue or fluid sample obtainable from a patient, which contains detectable quantities of either ZIKV, or fragments thereof, under normal or pathological conditions. Generally, levels of ZIKV in a particular sample obtained from a healthy patient (e.g., a patient not afflicted with a disease associated with ZIKV will be measured to initially establish a baseline, or standard, level of ZIKV. This baseline level of ZIKV can then be compared against the levels of ZIKV measured in samples obtained from individuals suspected of having a ZIKV-associated condition, or symptoms associated with such condition.

The antibodies specific for ZIKV may contain no additional labels or moieties, or they may contain an N-terminal or C-terminal label or moiety. In one embodiment, the label or moiety is biotin. In a binding assay, the location of a label (if any) may determine the orientation of the peptide relative to the surface upon which the peptide is bound. For example, if a surface is coated with avidin, a peptide containing an N-terminal biotin will be oriented such that the C-terminal portion of the peptide will be distal to the surface.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, room temperature is about 25° C., and pressure is at or near atmospheric.

Example 1: Generation of Human Antibodies to ZIKV

Human antibodies to ZIKV were generated in a mouse comprising DNA encoding human immunoglobulin heavy and kappa light chain variable regions. In one embodiment, the human antibodies to ZIKV were generated in a VELOCIMMUNE® mouse. In one embodiment, VelocImmune® (VI) mice were immunized with DNA encoding the ZIKV prM/E (See also GenBank accession number ALU33341.1 and SEQ ID NO: 353). Antibodies were generated following an accelerated regimen comprising 2 immunizations separated by 2 weeks. The antibody immune response was monitored by a ZIKV E-specific immunoassay. For example, sera were assayed for specific antibody titers to virus-like particles (VLPs) produced from cells expressing ZIKV prM/E. Antibody-producing clones were isolated using both B-cell Sorting Technology (BST) and hybridoma methods. For example, when a desired immune response was achieved, splenocytes were harvested and fused with mouse myeloma cells to preserve their viability and form hybridoma cell lines. The hybridoma cell lines were screened and selected to identify cell lines that produce ZIKV E-specific antibodies. Using this technique, and the various immunogens described above, several chimeric antibodies (i.e., antibodies possessing human variable domains and mouse constant domains) were obtained. Exemplary antibodies generated in this manner were designated as H2 aM25703N, H2 aM25704N, H2 aM25708N, H2 aM25709N, H2 aM25710N, and H2 aM25711N.

Anti-ZIKV antibodies were also isolated directly from antigen-positive mouse B cells without fusion to myeloma cells, as described in U.S. Pat. No. 7,582,298, herein specifically incorporated by reference in its entirety. Using this method, several fully human anti-ZIKV E antibodies (i.e., antibodies possessing human variable domains and human constant domains) were obtained; exemplary antibodies generated in this manner were designated as H4H25566P, H4H25587P, H4H25591P, H4H25592P, H4H25598P, H4H25602P, H4H25617P, H4H25619P, H4H25622P, H4H25626P, H4H25630P, H4H25633P, H4H25634P, H4H25637P, H4H25640P, H4H25641P, H4H25703N, H4H25704N, H4H25708N, H4H25709N, H4H25710N, H4H25711N.

The biological properties of the exemplary antibodies generated in accordance with the methods of this Example are described in detail in the Examples set forth below.

Example 2: Heavy and Light Chain Variable Region Amino Acid and Nucleotide Sequences Table 1 sets forth the amino acid sequence identifiers of the heavy and light chain variable regions and CDRs of selected anti-ZIKV antibodies of the invention. The corresponding nucleic acid sequence identifiers are set forth in Table 2.

TABLE 1

Amino Acid Sequence Identifiers

| Antibody Designation | SEQ ID NOs: | | | | | | | |
|---|---|---|---|---|---|---|---|---|
| | HCVR | HCDR1 | HCDR2 | HCDR3 | LCVR | LCDR1 | LCDR2 | LCDR3 |
| H4H25566P | 2 | 4 | 6 | 8 | 10 | 12 | 14 | 16 |
| H4H25587P | 18 | 20 | 22 | 24 | 26 | 28 | 30 | 32 |
| H4H25591P | 34 | 36 | 38 | 40 | 42 | 44 | 46 | 48 |
| H4H25592P | 50 | 52 | 54 | 56 | 58 | 60 | 62 | 64 |
| H4H25598P | 66 | 68 | 70 | 72 | 74 | 76 | 78 | 80 |
| H4H25602P | 82 | 84 | 86 | 88 | 90 | 92 | 94 | 96 |
| H4H25617P | 98 | 100 | 102 | 104 | 106 | 108 | 110 | 112 |
| H4H25619P | 114 | 116 | 118 | 120 | 122 | 124 | 126 | 128 |
| H4H25622P | 130 | 132 | 134 | 136 | 138 | 140 | 142 | 144 |
| H4H25626P | 146 | 148 | 150 | 152 | 154 | 156 | 158 | 160 |
| H4H25630P | 162 | 164 | 166 | 168 | 170 | 172 | 174 | 176 |
| H4H25633P | 178 | 180 | 182 | 184 | 186 | 188 | 190 | 192 |
| H4H25634P | 194 | 196 | 198 | 200 | 202 | 204 | 206 | 208 |
| H4H25637P | 210 | 212 | 214 | 216 | 218 | 220 | 222 | 224 |
| H4H25640P | 226 | 228 | 230 | 232 | 234 | 236 | 238 | 240 |
| H4H25641P | 242 | 244 | 246 | 248 | 250 | 252 | 254 | 256 |
| H4H25703N | 258 | 260 | 262 | 264 | 266 | 268 | 270 | 272 |
| H4H25704N | 274 | 276 | 278 | 280 | 282 | 284 | 286 | 288 |
| H4H25708N | 290 | 292 | 294 | 296 | 298 | 300 | 302 | 304 |
| H4H25709N | 306 | 308 | 310 | 312 | 314 | 316 | 318 | 320 |
| H4H25710N | 322 | 324 | 326 | 328 | 330 | 332 | 334 | 336 |
| H4H25711N | 338 | 340 | 342 | 344 | 346 | 348 | 350 | 352 |
| H2aM25703N | 258 | 260 | 262 | 264 | 266 | 268 | 270 | 272 |
| H2aM25704N | 274 | 276 | 278 | 280 | 282 | 284 | 286 | 288 |
| H2aM25708N | 290 | 292 | 294 | 296 | 298 | 300 | 302 | 304 |
| H2aM25709N | 306 | 308 | 310 | 312 | 314 | 316 | 318 | 320 |
| H2aM25710N | 322 | 324 | 326 | 328 | 330 | 332 | 334 | 336 |
| H2aM25711N | 338 | 340 | 342 | 344 | 346 | 348 | 350 | 352 |

TABLE 2

Nucleic Acid Sequence Identifiers

| Antibody Designation | SEQ ID NOs: | | | | | | | |
|---|---|---|---|---|---|---|---|---|
| | HCVR | HCDR1 | HCDR2 | HCDR3 | LCVR | LCDR1 | LCDR2 | LCDR3 |
| H4H25566P | 1 | 3 | 5 | 7 | 9 | 11 | 13 | 15 |
| H4H25587P | 17 | 19 | 21 | 23 | 25 | 27 | 29 | 31 |
| H4H25591P | 33 | 35 | 37 | 39 | 41 | 43 | 45 | 47 |
| H4H25592P | 49 | 51 | 53 | 55 | 57 | 59 | 61 | 63 |
| H4H25598P | 65 | 67 | 69 | 71 | 73 | 75 | 77 | 79 |
| H4H25602P | 81 | 83 | 85 | 87 | 89 | 91 | 93 | 95 |
| H4H25617P | 97 | 99 | 101 | 103 | 105 | 107 | 109 | 111 |
| H4H25619P | 113 | 115 | 117 | 119 | 121 | 123 | 125 | 127 |
| H4H25622P | 129 | 131 | 133 | 135 | 137 | 139 | 141 | 143 |
| H4H25626P | 145 | 147 | 149 | 151 | 153 | 155 | 157 | 159 |
| H4H25630P | 161 | 163 | 165 | 167 | 169 | 171 | 173 | 175 |
| H4H25633P | 177 | 179 | 181 | 183 | 185 | 187 | 189 | 191 |
| H4H25634P | 193 | 195 | 197 | 199 | 201 | 203 | 205 | 207 |
| H4H25637P | 209 | 211 | 213 | 215 | 217 | 219 | 221 | 223 |
| H4H25640P | 225 | 227 | 229 | 231 | 233 | 235 | 237 | 239 |
| H4H25641P | 241 | 243 | 245 | 247 | 249 | 251 | 253 | 255 |
| H4H25703N | 257 | 259 | 261 | 263 | 265 | 267 | 269 | 271 |
| H4H25704N | 273 | 275 | 277 | 279 | 281 | 283 | 285 | 287 |
| H4H25708N | 289 | 291 | 293 | 295 | 297 | 299 | 301 | 303 |
| H4H25709N | 305 | 307 | 309 | 311 | 313 | 315 | 317 | 319 |
| H4H25710N | 321 | 323 | 325 | 327 | 329 | 331 | 333 | 335 |
| H4H25711N | 337 | 339 | 341 | 343 | 345 | 347 | 349 | 351 |
| H2aM25703N | 257 | 259 | 261 | 263 | 265 | 267 | 269 | 271 |
| H2aM25704N | 273 | 275 | 277 | 279 | 281 | 283 | 285 | 287 |
| H2aM25708N | 289 | 291 | 293 | 295 | 297 | 299 | 301 | 303 |
| H2aM25709N | 305 | 307 | 309 | 311 | 313 | 315 | 317 | 319 |
| H2aM25710N | 321 | 323 | 325 | 327 | 329 | 331 | 333 | 335 |
| H2aM25711N | 337 | 339 | 341 | 343 | 345 | 347 | 349 | 351 |

Antibodies are typically referred to herein according to the following nomenclature: Fc prefix (e.g. "H1H," "H4H," "H2 aM" etc.), followed by a numerical identifier (e.g. "25566," "25587", "25710" etc., as shown in Table 1 or 2), followed by a "P," "P2," "N", N2, or "B" suffix. The H1H and H4H prefixes on the antibody designations used herein indicate the particular Fc region isotype of the antibody. Thus, according to this nomenclature, an antibody may be referred to herein as, e.g., "H4H25566P", "H2 aM25703N", etc. For example, an "H4H" antibody has a human IgG4 Fc and an "H2 aM" antibody has a mouse IgG2a Fc (all variable regions are fully human as denoted by the first 'H' in the antibody designation). As will be appreciated by a person of ordinary skill in the art, an antibody having a particular Fc isotype can be converted to an antibody with a different Fc isotype (e.g., an antibody with a mouse IgG1 Fc can be converted to an antibody with a human IgG4, etc.), but in any event, the variable domains (including the CDRs)—which are indicated by the numerical identifiers shown in Table 1 or 2—will remain the same, and the binding properties to antigen are expected to be identical or substantially similar regardless of the nature of the Fc domain.

Example 3: Binding Assay to Assess Binding of Monoclonal Antibodies to Zika Pre-Membrane-Envelope Intermediate (prM/E) Polyprotein To investigate the ability of a panel of anti-ZIKV monoclonal antibodies to bind ZIKV E, an in vitro binding assay utilizing ZIKV viral-like particles (VLPs) prepared from prM/E-expressing cells in an electrochemiluminescence based detection platform (MSD) was developed.

VLPs were generated from HEK293T/17 cells transiently expressing the ZIKV prM/E polyprotein (Accession number ALU33341.1 (also shown as SEQ ID NO: 353), amino acid residues 123-795 of ZIKV polyprotein). VLPs prepared from cells expressing the Vesicular stomatitis virus (VSV) glycoprotein (G) were also generated as a negative binding control. Included in the experiment are negative controls for human IgG4 and mouse IgG2a antibodies as irrelevant negative controls for the IgG detection antibodies.

Experiments were carried out according to the following procedure. VLPs from the two sources described above were diluted in PBS, seeded into the 96-well carbon electrode plates (MULTI-ARRAY high bind plate, MSD) and incubated overnight at 4° C. to allow the VLPs to adhere. Nonspecific binding sites were blocked by 2% BSA (w/v) in PBS for 1 hour at room temperature. To the plate-bound particles, anti-ZIKV and control antibodies in serial dilutions ranging from 1.7 pM to 100 nM in 1×PBS+0.5% BSA buffer, and buffer only, were added in duplicate, and the plates were incubated for 1 hour at room temperature. The plates were then washed with 1×PBS to remove the unbound antibodies using an AquaMax2000 plate washer (MDS Analytical Technologies). The plate-bound antibodies were detected with a SULFO-TAG™-conjugated anti-human IgG antibody (Meso Scale Development) or a SULFO-TAG™-conjugated anti-mouse IgG antibody (Jackson Immunoresearch) for 1 hour at room temperature. After washes, the plates were developed with the Read Buffer (MSD) according to manufacturer's recommended procedure and the luminescent signals were recorded with a SECTOR Imager 600 (MSD) instrument. The direct binding signals (in RLU) were analyzed as a function of the antibody concentration and the data were fitted with a sigmoidal (four-parameter logistic) dose-response model using GraphPad Prism™ software. The $EC_{50}$ values, defined as the concentration of antibody at which 50% of the maximal binding signal is detected, was determined for ZIKV prM/E VLPs to indicate potency of each antibody. In addition, ratios of the binding signals of the antibodies at 11.1 nM on ZIKV prM/E VLPs to the irrelevant VSV G VLPs were calculated. The antibodies with the binding ratio less than 2 were marked as NB in Table 3. NB refers to no specific binding observed under assay conditions.

Results Summary and Conclusions:

The ability of the anti-ZIKV monoclonal antibodies to bind specifically ZIKV VLPs prepared form prM/E expressing cells compared with binding to irrelevant VSV G-containing VLPs was assessed using an immunobinding assay. Antibody dose dependent binding to the immobilized VLPs on 96-well High Bind plates (MSD), with antibody concentrations up to 100 nM, were detected using SULFO-TAG™-conjugated anti-human IgG or anti-mouse IgG antibody, and the binding signals in electrochemiluminescence were recorded on a Sector Imager 600 (MSD). RLU values were determined for the antibody binding to VLPs. For the ZIKV prM/E VLPs $EC_{50}$ values were calculated as a measure of potency. For antibodies with irrelevant background affecting ZIKV binding profiles, higher concentrations were excluded from calculation of $EC_{50}$ values and values are italicized in the table. Comparison of the binding signals of the antibodies at 11.1 nM to ZIKV prM/E and irrelevant expressing VLPs was used to evaluate the binding specificity to the ZIKV protein. Specific binding is defined as antibodies having a ratio of 2-fold or higher binding to ZIKV prM/E expressing VLPs compared to irrelevant VLPs at that concentration.

The binding results are summarized in Table 3. $EC_{50}$ values for binding to the ZIKV prM/E VLPs are reported and range from 87 pM to 133 nM for the test antibodies. For antibodies, H4H25640P and H4H25704N, binding values at higher concentrations were excluded from calculation of $EC_{50}$ values to compensate for high background on the irrelevant VSV G VLPs. Ratios of binding on ZIKV prM/E VLPs vs binding to the VSV G VLPs at 11.1 nM concentration are also reported. All test antibodies evaluated bound specifically to ZIKV prM/E VLPs. Negative isotype control antibodies did not bind specifically, as expected (Data not shown).

TABLE 3

| Ab PID | Binding to Zika prM/E VLPs EC50 (M) | Ratio of RLU Zika VLP/VSV G VLP at 11.1 nM |
|---|---|---|
| H4H25566P | 8.20E−10 | 6 |
| H4H25587P | 1.45E−10 | 14 |
| H4H25591P | 1.02E−10 | 3 |
| H4H25592P | 2.13E−10 | 7 |
| H4H25598P | 4.26E−10 | 7 |
| H4H25602P | 1.56E−09 | 5 |
| H4H25617P | 7.55E−10 | 8 |
| H4H25619P | 1.92E−09 | 7 |
| H4H25622P | 2.44E−09 | 7 |
| H4H25626P | 1.59E−09 | 10 |
| H4H25630P | 2.17E−10 | 9 |
| H4H25633P | 4.00E−10 | 9 |
| H4H25634P | 3.23E−10 | 11 |
| H4H25637P | 3.22E−10 | 9 |
| H4H25640P | 1.02E−10 | 2 |
| H4H25641P | 2.87E−09 | 6 |
| H4H25703N | 8.46E−11 | 8 |
| H4H25708N | 1.33E−07 | 4 |
| H4H25704N | 1.80E−10 | 4 |
| H4H25710N | 5.42E−10 | 13 |
| H2aM25710N | 2.44E−10 | 107 |
| H2aM25709N | 3.62E−10 | 244 |
| H2aM25711N | 4.68E−10 | 263 |

Italicized values have high antibody concentrations excluded from $EC_{50}$ calculations.

Example 4: Antibody Binding to ZIKV prM80E as Determined by Surface Plasmon Resonance A. pH Dependent Dissociation Rate Constants Dissociation rate constants for zika (prM80E)-mmH binding to purified anti-ZIKV mAbs were determined using a real-time surface plasmon resonance biosensor using a Biacore 4000 instrument (Catalog nr. 28-9643-21). The Biacore CM5 sensor surface was derivatized by amine coupling with a polyclonal goat anti-human Fc antibody (Jackson Laboratories, #BR-109005-098) to capture anti-ZIKV antibodies expressed with human constant regions. Biacore pH chase studies were performed in a buffer composed of 0.01M $Na_2HPO_4/NaH_2PO_4$, 0.15M NaCl, 0.05% v/v Surfactant P20 (PBS-P running buffer) at pH 7.4, 6.0, 5.5 and 5.0. ZIKV (prM80E) with a C-terminal myc-myc-his tag (SEQ ID NO: 354), hereby referred to as ZIKV-mmH, was prepared in PBS-P running buffer (at a concentration of 30 nM) and was injected over the anti-ZIKV mAb captured surface at a flow rate of 30 μL/minute. Association of ZIKV-mmH to the captured monoclonal antibody was monitored for 3 minutes at in PBS-P running buffer at pH7.4 and the dissociation of ZIKV-mmH in PBS-P running buffer at pH7.4, pH6.0, pH5.5 or pH5.0 was monitored for 10 minutes. All of the pH chase experiments were performed at 37° C. Kinetic dissociation ($k_d$) rate constants were determined by fitting the real-time sensorgrams to a 1:1 binding model using Scrubber 2.0c curve fitting software. Dissociative half-lives (t½) were calculated from the kinetic rate constants as:

$$t_{1/2} \text{ (min)} = \ln 2/(60 \times k_d)$$

Binding kinetic parameters for ZIKV-mmH binding to purified anti-ZIKV mAbs at 37° C. are shown in Tables 4A and 4B.

TABLE 4A

37° C. Binding Kinetics Results at pH 7.4 and 6.0

| | pH 7.4 | | | | pH 6.0 | | | | |
| --- | --- | --- | --- | --- | --- | --- | --- | --- | --- |
| REGN Nr/Ab PID # | mAb Capture (RU) | 30 nM Zika prM80E Bound (RU) | kd (1/s) | t½ (min) | mAb Capture (RU) | 30 nM Zika prM80E Bound (RU) | kd (1/s) | t½ (min) | t½ pH 7.4/ t½ pH 6.0 |
| H4H25566P | 113.3 | 14.1 | 5.42E−02 | 0.21 | 111.5 | 6.9 | 2.99E−01 | 0.04 | 5.5 |
| H4H25587P | 65.4 | 20.1 | 1.80E−02 | 0.64 | 62.2 | 22.1 | 1.51E−02 | 0.77 | 0.8 |
| H4H25591P | 159.9 | 62.7 | 6.30E−03 | 1.83 | 161.8 | 62.3 | 1.36E−02 | 0.85 | 2.2 |
| H4H25592P | 126.7 | 57.9 | 1.74E−03 | 6.63 | 123 | 59.6 | 5.03E−03 | 2.3 | 2.9 |
| H4H25598P | 65.5 | 29.3 | 3.97E−04 | 29.13 | 59.8 | 28.8 | 1.29E−02 | 0.9 | 32.4 |
| H4H25602P | 95.4 | 31.5 | 3.56E−04 | 32.46 | 92.5 | 32.2 | 1.22E−02 | 0.95 | 34.1 |
| H4H25617P | 28.3 | 13.6 | 6.02E−03 | 1.92 | 19.2 | 14.1 | 4.94E−03 | 2.34 | 0.8 |
| H4H25619P | 79.2 | 15.8 | 1.93E−03 | 6 | 73.8 | 18.4 | 1.02E−02 | 11.29 | 0.5 |
| H4H25622P | 66.8 | 18 | 3.18E−03 | 3.63 | 56.8 | 16.5 | 2.34E−03 | 4.93 | 0.7 |
| H4H25626P | 8 | 1.3 | IC | IC | 4.1 | 1.5 | IC | IC | IC |
| H4H25630P | −11.6 | −0.5 | IC | IC | −21.6 | −1.5 | IC | IC | IC |
| H4H25633P | 8.6 | 0.6 | IC | IC | 4.7 | 1.5 | IC | IC | IC |
| H4H25634P | 26.3 | 15 | 1.19E−02 | 0.97 | 15.4 | 15 | 5.85E−03 | 1.98 | 0.5 |
| H4H25637P | 119.9 | 37.6 | 1.18E−02 | 0.98 | 116.4 | 38.5 | 3.92E−03 | 2.95 | 0.3 |
| H4H25640P | 104.7 | 55.6 | 1.72E−03 | 6.72 | 102.2 | 58.5 | 3.23E−03 | 3.58 | 1.9 |
| H4H25641P | 85.9 | 23.4 | 1.91E−02 | 0.61 | 79.7 | 25.1 | 1.59E−02 | 0.73 | 0.8 |
| H4H25703N | 153.4 | 74.6 | 2.11E−03 | 5.47 | 158.7 | 77.3 | 2.83E−03 | 4.08 | 1.3 |
| H4H25708N | 69.9 | 22.5 | 2.60E−03 | 4.45 | 67.8 | 25.4 | 1.44E−03 | 8.02 | 0.6 |
| H4H25704N | 78.1 | 46.6 | 1.21E−03 | 9.56 | 74.9 | 49.7 | 1.31E−03 | 8.85 | 1.1 |
| H4H25710N | 82.7 | 21.3 | 5.41E−03 | 2.14 | 81.1 | 21.1 | 1.30E−01 | 0.09 | 24 |

IC = inconclusive
NB no binding

TABLE 4B

37° C. Binding Kinetics Results at pH 5.5 and 5.0

| | pH 5.5 | | | | pH 5.0 | | | | |
| --- | --- | --- | --- | --- | --- | --- | --- | --- | --- |
| REGN Nr/Ab PID # | mAb Capture (RU) | 30 nM Zika prM80E Bound (RU) | kd (1/s) | t½ (min) | t½ pH 7.4/ t½ pH 5.5 | mAb Capture (RU) | 30 nM Zika prM80E Bound (RU) | kd (1/s) | t½ (min) | t½ pH 7.4/ t½ pH 5.0 |
| H4H25566P | 96.8 | 6.4 | 3.92E−01 | 0.03 | 7.2 | 101.5 | 6.1 | 3.68E−01 | 0.03 | 6.8 |
| H4H25587P | 63.7 | 27.2 | 1.74E−02 | 0.66 | 1 | 46.2 | 23.6 | 1.77E−02 | 0.7 | 1 |
| H4H25591P | 145 | 62.1 | 1.84E−02 | 0.63 | 2.9 | 151.6 | 57.7 | 1.48E−02 | 0.8 | 2.4 |
| H4H25592P | 124.6 | 66.7 | 7.36E−03 | 1.57 | 4.2 | 111.7 | 61.5 | 6.58E−03 | 1.8 | 3.8 |
| H4H25598P | 44.9 | 26.9 | 7.41E−02 | 0.16 | 187 | 54 | 22.4 | 1.14E−01 | 0.1 | 288 |
| H4H25602P | 94.3 | 37 | 4.76E−02 | 0.24 | 134 | 81.8 | 30.4 | 9.70E−02 | 0.1 | 272 |
| H4H25617P | −0.2 | 15.2 | 4.65E−03 | 2.48 | 0.8 | 10.4 | 13.4 | 4.64E−03 | 2.5 | 0.8 |
| H4H25619P | 71.9 | 24.6 | 9.53E−04 | 12.12 | 0.5 | 59.1 | 21.2 | 5.48E−04 | 21.1 | 0.3 |
| H4H25622P | 42.8 | 19.3 | 1.78E−03 | 6.49 | 0.6 | 49.8 | 16.9 | 7.04E−04 | 16.4 | 0.2 |
| H4H25626P | −1.1 | 5 | IC | IC | IC | −6.5 | 1 | IC | IC | IC |

TABLE 4B-continued

37° C. Binding Kinetics Results at pH 5.5 and 5.0

| | pH 5.5 | | | | | pH 5.0 | | | | |
|---|---|---|---|---|---|---|---|---|---|---|
| REGN Nr/Ab PID # | mAb Capture (RU) | 30 nM Zika prM80E Bound (RU) | kd (1/s) | t½ (min) | t½ pH 7.4/ t½ pH 5.5 | mAb Capture (RU) | 30 nM Zika prM80E Bound (RU) | kd (1/s) | t½ (min) | t½ pH 7.4/ t½ pH 5.0 |
| H4H25630P | −35.2 | −2.6 | IC | IC | IC | −22.7 | −3.9 | IC | IC | IC |
| H4H25633P | 0.5 | 1.7 | IC | IC | IC | −8.3 | −2.9 | IC | IC | IC |
| H4H25634P | −4 | 17.3 | 6.11E−03 | 1.89 | 0.5 | 6.4 | 14 | 5.53E−03 | 2.1 | 0.5 |
| H4H25637P | 118.2 | 42.6 | 4.14E−03 | 2.79 | 0.4 | 105.1 | 38.9 | 2.28E−03 | 5.1 | 0.2 |
| H4H25640P | 86.1 | 60 | 4.02E−03 | 2.87 | 2.3 | 92.4 | 55.3 | 3.37E−03 | 3.4 | 2 |
| H4H25641P | 79.5 | 29.9 | 2.04E−02 | 0.57 | 1.1 | 65.4 | 24.8 | 1.33E−02 | 0.9 | 0.7 |
| H4H25703N | 145.5 | 79.9 | 3.26E−03 | 3.54 | 1.5 | 148.6 | 73 | 2.80E−03 | 4.1 | 1.3 |
| H4H25708N | 68.2 | 31.1 | 1.57E−03 | 7.37 | 0.6 | 51.4 | 25.9 | 1.29E−03 | 8.9 | 0.5 |
| H4H25704N | 59.2 | 52.4 | 1.07E−03 | 10.77 | 0.9 | 65.8 | 49.4 | 9.59E−04 | 12 | 0.8 |
| H4H25710N | 81 | 20 | 1.81E−01 | 0.06 | 33.4 | 65.9 | 11.5 | 3.39E−01 | 0.03 | 62.6 |

IC = inconclusive
NB no binding

Results and Summary

The effect of pH on the dissociation (kd and t½) of ZIKV.mmH from anti-ZIKV antibodies were studied at pH 7.4, 6.0, 5.5 and 5.0, at 37° C. The anti-ZIKV antibodies H4H25710N, H4H25602P and H4H25598P of the invention showed the highest pH dependent changes in dissociation. Anti-ZIKV antibody H4H25566P showed moderate pH dependent changes in dissociation while the rest of the ZIKV-antibodies did not show significant pH dependent changes in dissociation.

B. Binding Affinity and Kinetics at 25° C. and 37° C.

Equilibrium dissociation constants ($K_D$ values) for ZIKV (prM80E)-mmH protein binding to purified anti-ZIKV monoclonal antibodies were determined using a real-time surface plasmon resonance biosensor assay on a Biacore 4000 instrument. The Biacore sensor surface was derivatized by amine coupling with a polyclonal goat anti-human Fc antibody (Jackson Laboratories, #BR-109005-098) to capture anti-ZIKV antibodies expressed with human constant regions. Biacore binding studies were performed in HBS-P running buffer (0.01M HEPES pH 7.4, 0.15M NaCl, 0.05% v/v Surfactant P20). ZIKV (prM80E) protein with a C-terminal myc-myc-hexahistidine tag (mmH) was prepared in-house and here by referred to as ZIKV-mmH (See SEQ ID NO: 354). Different concentrations (3-fold dilutions) of ZIKV-mmH (ranging from 30 nM to 0.37 nM), prepared in HBS-P running buffer were injected over the anti-ZIKV antibody captured surface at a flow rate of 30 μL/min. Association of ZIKV-mmH to each of the captured monoclonal antibodies was monitored for 3 minutes and dissociation was monitored for 8 minutes in HBS-P running buffer. All binding kinetics experiments were performed at either 25° C. or 37° C. Kinetic association ($k_a$) and dissociation ($k_d$) rate constants were determined by fitting the real-time sensorgrams to a 1:1 binding model using Scrubber 2.0c curve fitting software. Binding dissociation equilibrium constants ($K_D$) and dissociative half-lives (t½) were calculated from the kinetic rate constants as:

$$K_D(M) = \frac{kd}{ka} \bigg/ k_a, \text{ and } t_{1/2}(\min) = \frac{\ln(2)}{60 * kd}$$

Binding kinetic parameters for ZIKV-mmH binding to anti-ZIKV antibodies at 25° C. and 37° C. are shown in Tables 5 and 6.

TABLE 5

Binding kinetics parameters of anti-ZIKV monoclonal antibodies binding to ZIKV (prM80E)-mmH at 25° C.

| Antibody | Amount of antibody captured (RU) | 30 nM ZIKV-mmH bound (RU) | $k_a$ (1/Ms) | $k_d$ (1/s) | $K_D$ (M) | t½ (min) |
|---|---|---|---|---|---|---|
| H4H25566P | 218.4 ± 0.9 | 49.5 | 5.90E+05 | 1.63E−02 | 2.77E−08 | 0.7 |
| H4H25587P | 151.2 ± 2.1 | 68.8 | 8.22E+05 | 4.22E−03 | 5.13E−09 | 2.7 |
| H4H25591P | 291.6 ± 5.1 | 103.6 | 6.49E+05 | 3.18E−03 | 4.90E−09 | 3.6 |
| H4H25592P | 263.4 ± 3.2 | 123.3 | 1.35E+06 | 6.76E−04 | 5.02E−10 | 17.1 |
| H4H25598P | 206.8 ± 1.7 | 64.7 | 2.89E+05 | 4.49E−05 | 1.56E−10 | 257.3 |
| H4H25602P | 218.4 ± 4.8 | 68.8 | 2.86E+05 | 1.95E−05 | 7.00E−11 | 592.0 |
| H4H25617P | 144.6 ± 2.3 | 41.6 | 2.50E+05 | 1.97E−03 | 7.90E−09 | 5.9 |
| H4H25619P | 202.5 ± 3.2 | 39.3 | 1.64E+05 | 5.16E−04 | 3.14E−09 | 22.4 |
| H4H25622P | 186.0 ± 2.7 | 32.5 | 2.51E+05 | 1.33E−03 | 5.31E−09 | 8.7 |
| H4H25626P | 354.7 ± 6.3 | 55.1 | 1.47E+05 | 9.05E−04 | 6.17E−09 | 12.8 |
| H4H25630P | 252.6 ± 2.8 | 140.7 | 1.67E+06 | 3.50E−04 | 2.10E−10 | 33.0 |
| H4H25633P | 258.4 ± 3.1 | 76.1 | 4.11E+05 | 8.02E−04 | 1.95E−09 | 14.4 |
| H4H25634P | 142.2 ± 2.0 | 54.7 | 6.47E+05 | 5.44E−03 | 8.41E−09 | 2.1 |
| H4H25637P | 331.7 ± 3.3 | 126.8 | 6.17E+05 | 3.91E−03 | 6.33E−09 | 3.0 |
| H4H25640P | 291.5 ± 7.7 | 129.3 | 1.21E+06 | 7.22E−04 | 5.97E−10 | 16.0 |

TABLE 5-continued

Binding kinetics parameters of anti-ZIKV monoclonal antibodies binding to ZIKV (prM80E)-mmH at 25° C.

| Antibody | Amount of antibody captured (RU) | 30 nM ZIKV-mmH bound (RU) | $k_a$ (1/Ms) | $k_d$ (1/s) | $K_D$ (M) | $t^{1/2}$ (min) |
|---|---|---|---|---|---|---|
| H4H25641P | 189.5 ± 3.1 | 57.8 | 1.05E+06 | 9.22E−03 | 8.75E−09 | 1.3 |
| H4H25703N | 390.8 ± 6.6 | 169.1 | 5.66E+05 | 3.07E−04 | 5.42E−10 | 37.6 |
| H4H25708N | 176.3 ± 1.6 | 56.0 | 4.17E+05 | 5.04E−04 | 1.21E−09 | 22.9 |
| H4H25704N | 222.0 ± 3.6 | 110.0 | 1.33E+06 | 3.59E−04 | 2.70E−10 | 32.2 |
| H4H25710N | 186.4 ± 1.1 | 48.4 | 2.99E+05 | 2.09E−03 | 6.99E−09 | 5.5 |

TABLE 6

Binding kinetics parameters of anti-ZIKV monoclonal antibodies binding to ZIKV (prM80E)-mmH at 37° C.

| Antibody | Amount of antibody captured (RU) | 30 nM ZIKV-mmH bound (RU) | $k_a$ (1/Ms) | $k_d$ (1/s) | $K_D$ (M) | $t^{1/2}$ (min) |
|---|---|---|---|---|---|---|
| H4H25566P | 178.0 ± 9.6 | 20.8 | 6.87E+05 | 3.60E−02 | 5.25E−08 | 0.3 |
| H4H25587P | 100.1 ± 7.9 | 51.3 | 1.10E+06 | 1.45E−02 | 1.32E−08 | 0.8 |
| H4H25591P | 271.8 ± 11.8 | 112.0 | 8.16E+05 | 6.82E−03 | 8.37E−09 | 1.7 |
| H4H25592P | 216.4 ± 10.9 | 120.0 | 1.61E+06 | 1.65E−03 | 1.02E−09 | 7.0 |
| H4H25598P | 168.9 ± 9.9 | 75.3 | 4.06E+05 | 2.84E−04 | 7.00E−10 | 40.7 |
| H4H25602P | 193.0 ± 10.6 | 83.7 | 3.81E+05 | 2.84E−04 | 7.45E−10 | 40.6 |
| H4H25617P | 112.1 ± 7.1 | 34.3 | 4.52E+05 | 7.29E−03 | 1.61E−08 | 1.6 |
| H4H25619P | 166.3 ± 9.6 | 44.3 | 1.93E+05 | 1.08E−03 | 5.59E−09 | 10.7 |
| H4H25622P | 120.3 ± 3.5 | 30.1 | 2.95E+05 | 2.67E−03 | 9.07E−09 | 4.3 |
| H4H25626P | 237.2 ± 6.5 | 61.5 | 3.03E+05 | 1.87E−03 | 6.18E−09 | 6.2 |
| H4H25630P | 164.6 ± 4.6 | 102.5 | 1.98E+06 | 2.29E−03 | 1.16E−09 | 5.1 |
| H4H25633P | 152.1 ± 4.4 | 53.4 | 6.78E+05 | 5.01E−03 | 7.39E−09 | 2.3 |
| H4H25634P | 87.3 ± 2.5 | 36.8 | 8.66E+05 | 1.01E−02 | 1.17E−08 | 1.1 |
| H4H25637P | 240.5 ± 5.5 | 93.7 | 9.92E+05 | 9.89E−03 | 9.97E−09 | 1.2 |
| H4H25640P | 221.8 ± 7.9 | 109.6 | 1.47E+06 | 1.86E−03 | 1.27E−09 | 6.2 |
| H4H25641P | 142.2 ± 4.0 | 45.6 | 1.59E+06 | 1.88E−02 | 1.19E−08 | 0.6 |
| H4H25703N | 267.5 ± 6.8 | 134.8 | 7.38E+05 | 1.77E−03 | 2.39E−09 | 6.5 |
| H4H25708N | 93.9 ± 2.3 | 47.7 | 7.81E+05 | 2.32E−03 | 2.97E−09 | 5.0 |
| H4H25704N | 142.5 ± 2.6 | 83.3 | 1.93E+06 | 1.20E−03 | 6.21E−10 | 9.6 |
| H4H25710N | 119.2 ± 2.1 | 36.2 | 5.19E+05 | 6.40E−03 | 1.24E−08 | 1.8 |

Results and Summary

At 25° C., all 20 anti-zika antibodies of the invention bound to ZIKV-.mmH with $K_D$ values ranging from 70 pM to 27.7 nM (Table 5). At 37° C., the anti-ZIKV antibodies of the invention bound to ZIKV-mmH with $K_D$ values ranging from 621 pM to 52.5 nM (Table 6). As expected, the negative isotype control showed no binding (data not shown).

Example 5: Neutralization of ZIKV with Antibodies Specific for ZIKV E

Vero cells (African Green Monkey kidney—AMC® CCL81) were seeded 1 day prior to infection with ZIKV, at 10,000 cells per well in Corning black 96-well cell culture plates with a clear bottom in MEM-alpha complete medium containing 10% heat inactivated FBS and penicillin/streptomycin/L-glutamine.

The strains of ZIKV used for infection of Vero cells were MR766 (Isolated from a sentinel rhesus monkey in Uganda, 1947. Accession #AY632535), FLR (Isolated from a human in Colombia in December 2015. Accession #KU820897) and PRVABC59 (Isolated from a human in Puerto Rico in December 2015. Accession #KU501215).

On the day of neutralization/infection, test antibodies were diluted to 2× concentration in DMEM containing 2% heat inactivated FBS penicillin/streptomycin/L-glutamine and mixed 1:1 with ZIKV for 30 minutes at 37° C.

Media was removed from the plated Vero cells, which were then incubated with 1:1 mixture of antibody and virus for 1 hour at 37° C., with gentle agitation of the assay plates every 15 minutes. Antibody treated virus inoculum was removed and the cells were overlaid with 100 uL of DMEM containing 1% heat inactivated FBS, penicillin/streptomycin/L-glutamine and 1% methyl cellulose and incubated overnight (12-16 hours) at 37° C. at 5% CO2.

The following day, the overlay media was aspirated off the cells, which were washed twice with PBS, then fixed with an ice cold 1:1 mixture of acetone and methanol for 30 minutes at 4° C. Fixed cells were washed twice with PBS, then permeabilized with PBS containing 0.1% Triton-X and 5% FBS for 15 minutes at room temperature. Cells were washed once with PBS alone, followed by incubation with PBS containing 5% FBS for 30 minutes at room temperature to block non-specific binding. Cells were then incubated with a polyclonal antibody (Zika Mouse Immune Ascitic Fluid-obtained from UTMB) at a 1:10,000 dilution in PBS containing 5% FBS and 0.1% Tween-20 for 1 hour at room temperature. Cells were washed 6 times with 300 uL PBS using the Molecular Devices AquaMax 4000 plate washer, then incubated with secondary antibody (Life Technologies Alexa-488 conjugated goat-anti-mouse IgG) for 1 hour at room temperature in the dark. Cells were washed 6 times on the plate washer and 100 uL PBS was added prior to analysis. Analysis was completed using the SpectraMax with Mini Max plate reader by imaging each well and using settings to count distinct fluorescent foci.

Neutralization % was calculated as follows:

$$\% \text{ Neutralization} = \frac{\text{\# of infected cells at each } mAb \text{ concentration} - \text{assay background}}{\text{\# of infected cells in virus only control} - \text{assay background}}$$

The results, expressed as % neutralization, were analyzed using nonlinear regression (4-parameter logistics) with Prism 5 software (GraphPad Software, Inc.) to obtain $IC_{50}$ values. Results are shown in Tables 7 and 8 below.

Results Summary and Conclusions:

The data shown below in Table 7 and 8 show that 18 out of the 20 anti-ZIKV virus antibodies of the present invention, using the experimental design described herein, potently neutralize infectivity of ZIKV strains MR766, PRVABC59 (Puerto Rico 2015) and FLP (Colombia 2015) with an $IC_{50}$ ranging from about $10^{-11}$ M to about $10^{-9}$M. As expected, the negative isotype control showed no neutralization (data not shown).

TABLE 7

| Ab PID | MR766 Uganda 1947 IC50 (M) | PRVABC59 Puerto Rico 2015 IC50 (M) | FLR Colombia 2015 IC50 (M) |
| --- | --- | --- | --- |
| H4H25587P | 1.50E−10 | 3.21E−10 | 9.55E−10 |
| H4H25598P | 5.45E−11 | 3.98E−10 | 5.53E−10 |
| H4H25602P | 5.31E−11 | 5.01E−10 | 6.30E−10 |
| H4H25630P | 1.47E−10 | 5.39E−10 | 2.83E−10 |
| H4H25633P | 1.02E−10 | 6.52E−10 | 4.40E−10 |
| H4H25710N | 4.71E−11 | 1.24E−09 | 1.06E−09 |
| H4H25591P | 3.43E−11 | 2.54E−10 | 3.30E−10 |
| H4H25592P | 4.26E−11 | 2.18E−10 | 5.53E−10 |
| H4H25634P | 1.39E−10 | 1.45E−10 | 2.07E−10 |
| H4H25637P | 6.71E−11 | 2.39E−10 | 1.34E−10 |
| H4H25640P | 2.79E−11 | 1.66E−10 | 9.90E−11 |
| H4H25641P | 3.71E−11 | 3.56E−10 | 2.12E−10 |
| H4H25703N | 4.45E−11 | 2.51E−10 | 6.19E−11 |
| H4H25704N | 4.60E−11 | 2.78E−10 | 7.58E−11 |
| H4H25617P | 1.66E−10 | 5.43E−10 | 5.52E−10 |
| H4H25566P | Partial neutralization | Partial neutralization | 1.55E−09 |
| H4H25619P | 1.71E−10 | 1.14E−09 | 1.26E−09 |
| H4H25622P | 1.88E−10 | 1.28E−09 | 1.58E−09 |
| H4H25626P | 1.59E−10 | 1.17E−09 | 1.09E−09 |
| H4H25708N | 3.49E−10 | non neutralizing | non neutralizing |

TABLE 8

| Ab PID | MR766 IC50 (M) |
| --- | --- |
| H2aM25703N | ~2.095e−011 |
| H2aM25708N | 1.07E−10 |
| H2aM25710N | 1.70E−11 |
| H2aM25704N | 2.21E−10 |

Example 6: Octet Cross Competition Assay

To assess whether two antibodies compete with one another for binding to their epitopes on ZIKV (prM80E)-mmH hereby referred to as ZIKV.mmH (SEQ ID NO: 354), binding competition between anti-ZIKV monoclonal antibodies was determined using a real time, label-free bio-layer interferometry assay on an Octet RED384 biosensor (Pall ForteBio Corp.). Cross competition experiments were performed at 25° C. in 0.01 M HEPES pH7.4, 0.15M NaCl, 0.05% v/v Surfactant Tween-20, 0.1 mg/mL BSA (HBS-P buffer) with the plate shaking at the speed of 1000 rpm. All anti-ZIKV antibody and ZIKV-mmH solutions tested were prepared in Octet HBS-P buffer. To assess whether 2 antibodies were able to compete with one another for binding to their respective epitopes on ZIKV-mmH, approximately ~0.97-0.112 nm of ZIKV-mmH was first captured on anti-His coated Octet biosensor tips from wells containing 10 μg/mL of ZIKV-mmH for 90 seconds. The ZIKV-mmH captured Octet biosensor tips were saturated by submerging for 5 minutes into wells containing 20 ug/ml of the first anti-ZIKV monoclonal antibody (hereby referred to as mAb-1), followed by submerging in wells containing the second anti-ZIKV monoclonal antibody (hereby referred to as mAb-2). Between steps, the Octet biosensor tips were washed in HBS-P buffer for 30 seconds.

The real-time binding response was monitored during the course of the experiment and the binding response at the end of every step was recorded. The response of ZIKV-mmH binding to mAb-1 and then to the blocking mAb was corrected for background binding, compared and competitive/non-competitive behavior of different anti-ZIKV monoclonal antibodies was determined.

Table 9 explicitly defines the relationships of antibodies competing in both directions, independent of the order of binding. Two anti-ZIKV monoclonal antibodies, H4H25619P and H4H25703N did not cross compete with the remaining antibodies described in this invention.

TABLE 9

Cross-competition of anti-ZIKV antibodies for binding to ZIKV-mmH.

| mAb-1 | mAb-2 |
|---|---|
| H4H25710N | H4H25633P |
| | H4H25602P |
| | H4H25598P |
| | H4H25630P |
| | H4H25587P |
| H4H25633P | H4H25710N |
| | H4H25602P |
| | H4H25598P |
| | H4H25630P |
| | H4H25587P |
| H4H25602P | H4H25710N |
| | H4H25633P |
| | H4H25598P |
| | H4H25630P |
| | H4H25587P |
| H4H25598P | H4H25710N |
| | H4H25633P |
| | H4H25602P |
| | H4H25630P |
| | H4H25587P |
| H4H25630P | H4H25710N |
| | H4H25633P |
| | H4H25602P |
| | H4H25598P |
| | H4H25587P |
| H4H25587P | H4H25710N |
| | H4H25633P |

TABLE 9-continued

Cross-competition of anti-ZIKV antibodies for binding to ZIKV-mmH.

| mAb-1 | mAb-2 |
|---|---|
| | H4H25602P |
| | H4H25598P |
| | H4H25630P |
| H4H25634P | H4H25641P |
| | H4H25703N |
| | H4H25592P |
| | H4H25591P |
| | H4H25704N |
| | H4H25640P |
| | H4H25637P |
| | H4H25617P |
| H4H25641P | H4H25634P |
| | H4H25703N |
| | H4H25592P |
| | H4H25591P |
| | H4H25704N |
| | H4H25640P |
| | H4H25637P |
| | H4H25617P |
| H4H25703N | H4H25634P |
| | H4H25641P |
| | H4H25592P |
| | H4H25591P |
| | H4H25704N |
| | H4H25640P |
| | H4H25637P |
| | H4H25617P |
| H4H25592P | H4H25634P |
| | H4H25641P |
| | H4H25703N |
| | H4H25591P |
| | H4H25704N |
| | H4H25640P |
| | H4H25637P |
| | H4H25617P |
| H4H25591P | H4H25634P |
| | H4H25641P |
| | H4H25703N |
| | H4H25592P |
| | H4H25704N |
| | H4H25640P |
| | H4H25637P |
| | H4H25617P |
| H4H25704N | H4H25634P |
| | H4H25641P |
| | H4H25703N |
| | H4H25592P |
| | H4H25591P |
| | H4H25640P |
| | H4H25637P |
| | H4H25617P |
| H4H25640P | H4H25634P |
| | H4H25641P |
| | H4H25703N |
| | H4H25592P |
| | H4H25591P |
| | H4H25704N |
| | H4H25637P |
| | H4H25617P |
| H4H25637P | H4H25634P |
| | H4H25641P |
| | H4H25703N |
| | H4H25592P |
| | H4H25591P |
| | H4H25704N |
| | H4H25640P |
| | H4H25617P |
| H4H25617P | H4H25634P |
| | H4H25641P |
| | H4H25703N |
| | H4H25592P |
| | H4H25591P |
| | H4H25704N |
| | H4H25640P |
| | H4H25637P |

TABLE 9-continued

Cross-competition of anti-ZIKV antibodies for binding to ZIKV-mmH.

| mAb-1 | mAb-2 |
|---|---|
| H4H25619P | H4H25622P |
| | H4H25626P |
| | H4H25566P |
| H4H25622P | H4H25619P |
| | H4H25626P |
| | H4H25566P |
| H4H25626P | H4H25619P |
| | H4H25622P |
| | H4H25566P |
| H4H25566P | H4H25619P |
| | H4H25622P |
| | H4H25526P |

Example 7: Measurement of Antibody Dependent Enhancement (ADE) Using an Immunofluorescence Assay Experiments were conducted to determine the effect of ZIKV antibodies on Antibody Dependent Enhancement (ADE) using an immunofluorescence assay (described below).

In one experiment, chimeric antibodies that cross-react with all Flaviviruses were made using the heavy chain and light chain sequences found in GenBank accession numbers KJ438784 (kappa light chain) and KJ438785.1 (heavy chain). Three antibodies were made, designated REGN4203 (hIgG1), REGN4204 (hIgG4s) and REGN4206 (hIgG4us). REGN4203 has a heavy chain (HC) shown in SEQ ID NO: 359 and a light chain (LC) shown in SEQ ID NO: 360. REGN4204 has a heavy chain (HC) shown in SEQ ID NO: 361 and a light chain (LC) shown in SEQ ID NO: 362 and REGN4206 has a heavy chain (HC) shown in SEQ ID NO: 363 and a light chain (LC) shown in SEQ ID NO: 364.

In another experiment, two anti-Zika virus antibodies designated H4H25703N (HCVR/LCVR amino acid sequence pairs of SEQ ID NOs: 258/266) and H4H25619P (HCVR/LCVR amino acid sequence pairs of SEQ ID NOs: 114/122) were tested for their effects on ADE using the same immunofluorescence assay. Each of the anti-Zika antibodies, H4H25703N and H4H25619P, was prepared as either an IgG1 having an Fc comprising the amino acid sequence of SEQ ID NO: 356, or as an IgG4 having an Fc comprising the amino acid sequence shown in SEQ ID NO: 357. The full-length amino acid sequence of the heavy chain (HC) of H4H25703N is shown as SEQ ID NO: 367 and the full length amino acid sequence of the light chain (LC) of H4H25703N is shown as SEQ ID NO: 368. The full-length amino acid sequence of the heavy chain (HC) of H4H25619P is shown as SEQ ID NO: 370 and the full-length amino acid sequence of the light chain (LC) of H4H25619P is shown as SEQ ID NO: 371.

Antibodies were diluted to 2× for final concentrations of 50, 10, 2, 0.4, and 0.08 ug/mL in RPMI+10% FBS, 1× Penicillin/Streptomycin/Glutamine. 100 uL of each antibody was then mixed 1:1 with RPMI complete media containing 2500 ffu (fluorescence focus units) virus for 30 minutes at 37° C., 5% $CO_2$. 80,000 K562 cells in 300 uL RPMI complete media was then added to the antibody/virus mixture and incubated at 37° C., 5% $CO_2$ for 3 days. At 1 and 2 days post-infection, 100 uL supernatant was removed and frozen to −80° C. At day 3, the remainder of the supernatant was collected and frozen to −80° C.

To detect the viral load of the supernatant, Vero cells were seeded at 10,000 cells/well in black/clear-bottom 96-well cell culture plates in MEM-alpha containing 10% FBS, 1× Penicillin/Streptomycin/Glutamine. Cells were incubated at 37° C., 5% $CO_2$ overnight. On the day of infection, supernatant samples from above were diluted in RPMI complete media. 50 uL of each dilution was added to Vero cells and incubated for 1 hour at 37° C., 5% $CO_2$ with gentle agitation of the plates every 15 minutes. Inoculum was removed from the cells and cells were overlaid with 100 uL DMEM+1% FBS, 1× Penicillin/Streptomycin/Glutamine, 1% methyl cellulose and incubated at 37° C., 5% $CO_2$ overnight.

Infected cells were quantitated by an immunofluorescence assay as previously described in Example 5.

Results

As shown in FIG. 1, REGN4203 demonstrated an increase in ADE as shown by the increase in virus yield when the concentration of antibody increased from $10^{-10}$M to $10^{-7}$M. REGN4204 showed a modest increase in virus yield as the concentration of antibody increased from $10^{-10}$M to $10^{-7}$M. However, REGN4206 had no effect on ADE as shown by its inability to increase virus yield as the concentration of antibody increased from $10^{-10}$M to $10^{-7}$M. In fact, REGN4206 showed no difference as compared to the virus only control.

Figure 6:
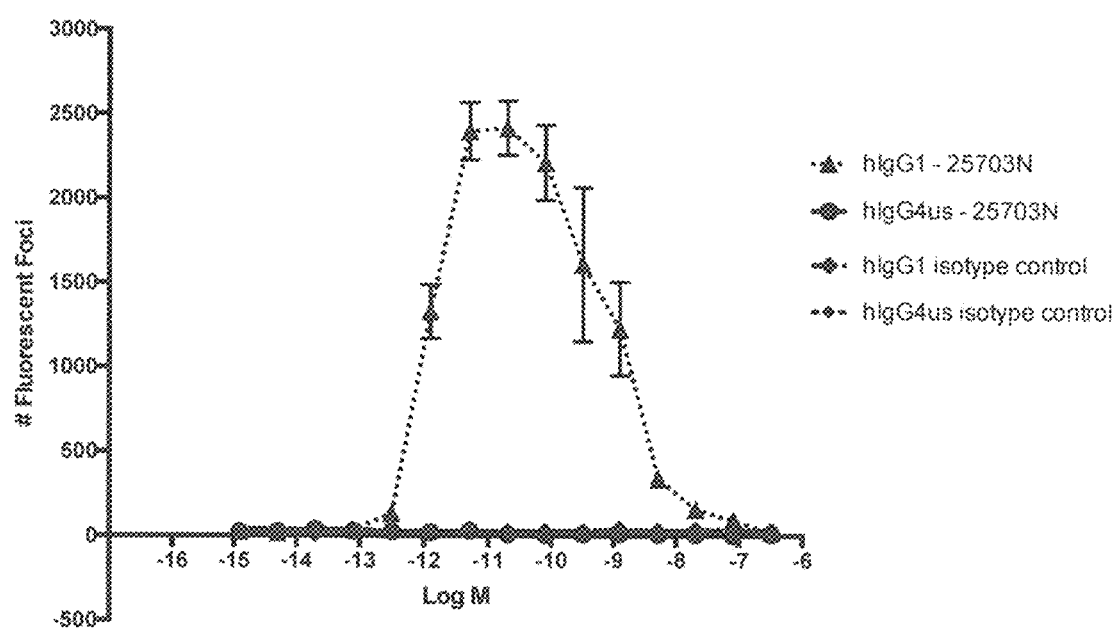
FIG. 6. Shows the results of an assay for measuring antibody dependent enhancement (ADE) using an anti-Zika virus antibody, H4H25703N, prepared as either an IgG1, or an IgG4.
Figure 7:
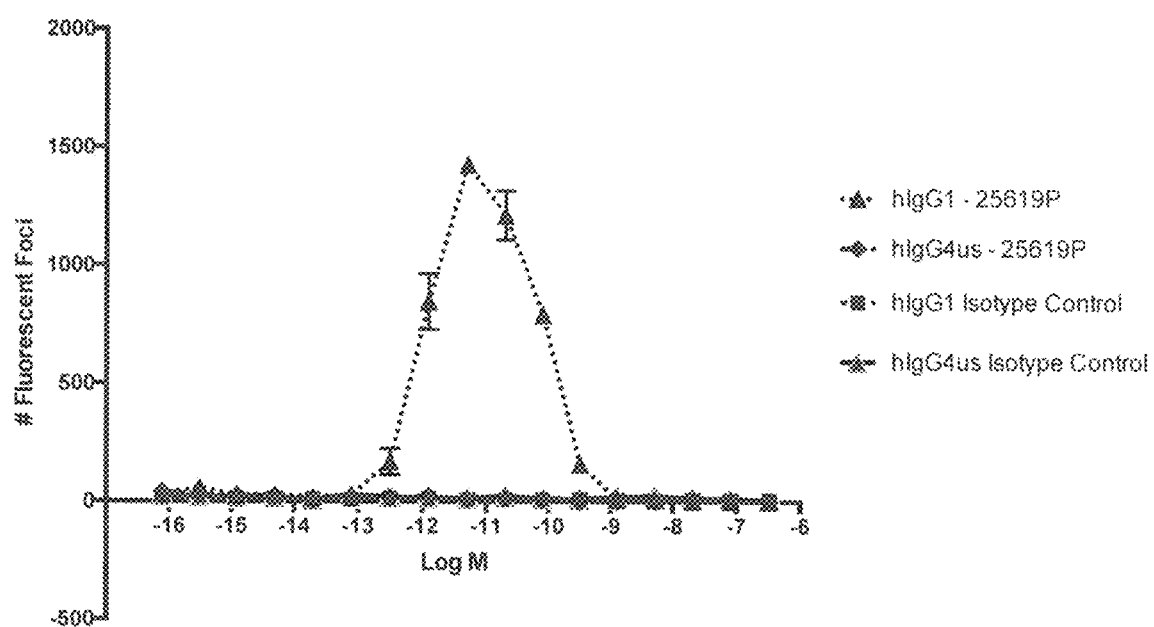
FIG. 7. Shows the results of an assay for measuring antibody dependent enhancement (ADE) using an anti-Zika virus antibody, H4H25619P, prepared as either an IgG1, or an IgG4.

As shown in FIGS. 6 and 7, unlike their IgG1 versions, the anti-ZIKV antibodies, when prepared as an IgG4 having an Fc comprising the amino acid sequence shown in SEQ ID NO: 357, do not induce ADE activity.

Example 8: Effect of Anti-ZIKV Antibodies on Protection in ZIKV Infected Mice

A study was done to determine the effect of anti-ZIKV antibodies in a mouse model of ZIKV infection.

Briefly, one day prior to infection, two anti-ZIKV antibodies, designated H4H25703N and H4H25619P, were diluted in PBS for final concentrations of 200, 50, or 12.5 μg per 200 μL dose. One day later, interferon alpha/beta receptor 1 (IFNAR1) KO mice were dosed with the antibodies via subcutaneous injection into the loose dorsal scruff area. On the day of infection, ZIKV, strain FSS13025, was diluted in DMEM media containing 2% heat-inactivated fetal bovine serum with 1× penicillin/streptomycin/glutamine to $10^5$ ffu per 200 μL dose. The mice were dosed with the virus via intraperitoneal injection. The mice were monitored for weight loss throughout the course of the experiment up to 21 days post-infection. Animals whose body weight dropped below an 80% threshold or those experiencing extreme morbidity (shaking, weakness, and non-responsiveness) were euthanized. Those animals, which were euthanized, show date of death as one day post-euthanasia (for example, an animal culled at 6 days post-infection is denoted as surviving until day 7).

Results

The results, as shown in FIGS. 2-5, show that all mice receiving the isotype control antibody lost greater than 20% of their body weight by day 9 after infection and had to be sacrificed according to IACUC guidelines. Mice receiving either the H4H25703 anti-ZIKV antibody (FIG. 2) or the H4H25619P anti-ZIKV antibody (FIG. 3) were able to better control their body weight loss up to 21 days post infection; no mice in the 200 ug and 50 ug groups and 40% of the mice in the 12.5 ug groups displayed a weight loss of more than the 20% threshold. Pre-treatment of mice with H4H25703N (FIG. 4) or H4H25619 (FIG. 5) also improved their survival; 100% of mice treated with 200 ug or 50 ug of either antibody or 60% of mice treated with 12.5 ug of each antibody survived challenge with ZIKV.

Example 9: In Vitro Generation of ZIKV Escape Mutants to Determine the Binding Sites for H4H25703N and H4H25619P $4 \times 10^5$ ffu MR766 ZIKV was combined with increasing concentrations of H4H25703N or H4H25619P (or isotype control antibody) at each antibody's IC50, IC75, IC85, IC99, IC99, and IC99.99 as calculated from the IC50 and hill slope of the neutralization curve analysis when plotted in GraphPad Prism (log(inhibitor) vs. response—variable slope (four parameter)). The calculations were completed as follows where f=the desired fraction (for IC85, f=85) and H=hill slope:

$$IC_f = \left(\frac{F}{100-F}\right)^{1/H}$$

Virus and antibody were incubated together for 30 minutes at 37° C. prior to addition onto $2 \times 10^5$ Vero cells* that had been seeded one day prior to infection in a 24-well plate. Cells were incubated at 37° C., 5% CO2 and checked daily for cytopathic effect. Once cytopathic effect was evident in the wells treated with isotype control antibody, the viral supernatant was collected from the H4H25703N and H4H25619P treated wells and cleared of debris by centrifugation. The viral supernatant from the well with the highest concentration of antibody where cytopathic effect was seen was then incubated with fresh antibody and passed onto fresh pre-seeded cells, and again incubated at 37° C., 5% CO2 until cytopathic effect was evident. This cycle was repeated until cytopathic effect was seen at the highest antibody concentration (1099.99). Viral supernatant was collected from the IC99.99 well and passed to a T25 flask pre-seeded with $6 \times 10^6$ Vero cells. Once cytopathic effect was visible on these cells, the virus was collected, cleared by centrifugation, and used in a neutralization assay to verify its escape, and also to determine whether the virus was still able to be neutralized by the second antibody. The infected cells from this virus expansion were also collected into 1 mL Trizol for RNA isolation and sequence analysis of the virus.

Neutralization Assay**

To confirm whether the escape mutants generated under the pressure of H4H25703N and H4H25619P were resistant to neutralization, a neutralization assay in Vero cells was performed. Briefly, to complete the neutralization, virus was combined with decreasing concentrations of either H4H25703N, H4H25619P, or isotype control antibody at concentrations from 10 ug/mL diluted 3-fold down to 200 pg/mL for an 11-point curve. Virus and antibodies were incubated together at 37° C. for 30 minutes prior to addition onto 10,000 Vero cells pre-seeded in black, clear-bottom 96-well cell culture plates. Cells were incubated with virus/antibody mixture for 1 hour with gentle agitation periodically throughout the incubation. After the incubation, the inoculum was removed and the cells were overlaid with DMEM containing 1% methyl cellulose*** and incubated at 37° C., 5% CO2 overnight. The methyl cellulose overlay was aspirated from the cells, which were then washed twice with PBS and fixed with an ice cold 1:1 mixture of acetone and methanol for 30 minutes at 4 C. Fixed cells were washed twice with PBS, then permeabilized with PBS containing 5% FBS and 0.1% Triton-X for 15 minutes at room temperature. Cells were washed with PBS then incubated with PBS containing 5% FBS to block nonspecific binding for 30 minutes at room temperature. Cells were then incubated with primary antibody (polyclonal immunized mouse ascites fluid) at a 1:10,000 dilution in PBS+5% FBS and 0.1% Tween-20 for 1 hour at room temperature. Cells were washed 6 times with PBS using a Molecular Devices Aqua-Max 4000 plate washer, then incubated with secondary antibody (Alexa-488 conjugated goat-anti-mouse IgG) at 1 ug/mL in PBS+5% FBS and 0.1% Tween-20 for 1 hour in the dark at room temperature. Cells were washed 6 times on the plate washer and left in 100 uL PBS for analysis on the Spectramax with MiniMax plate reader to count fluorescent foci. Percent neutralization is calculated as follows and was plotted in GraphPad Prism in a nonlinear regression (log (inhibitor) vs. response—variable slope (four parameter)):

% Neutralization=(1-((well value-media only control)/(virus only control-media only control)))*100

Once neutralization was confirmed, RNA was isolated from the infected cells from the virus expansion using Trizol (Life Technologies), following the manufacturer's protocol. The resulting RNA was used for cDNA synthesis using the Life Technologies SuperScript III First Strand Synthesis system. This cDNA was used as template in a PCR to amplify the Zika E sequence using the following parameters:

```
Primers:
MR766 PCR Fwd:
TGGGTTGTGTACGGAACCTG (SEQ ID NO: 379)

MR766 PCR Rev:
GGCACTGGCAATCTTTGTGG (SEQ ID NO: 380)

1 uL cDNA
1 uL each primer (100 uM)
4 uL 10% DMSO
33 uL AccuPrime Pfx Supermix
Cycling: 95C for 5 minutes
3 cycles of:       95C for 15 seconds
                   54C for 15 seconds
                   72C for 2 minutes
35 cycles of:      95C for 15 seconds
                   56C for 15 seconds
                   72C for 2 minutes
```

*Vero cells cultured and seeded in DMEM high glucose media containing 10% heat-inactivated FBS and penicillin/streptomycin/L-glutamine
**Neutralization reactions and virus growth were completed in DMEM high glucose media containing 2% heat-inactivated FBS and penicillin/streptomycin/L-glutamine
***Methyl cellulose overlay contains 1x DMEM with 1% heat-inactivated FBS, penicillin/streptomycin/L-glutamine, and 1% methyl cellulose The resulting PCR product (expected size: 2113 bp) was run on a 1% agarose TBE gel containing 1× Sybr Safe DNA Stain (Life Technologies) at 120V for 1 hour. The amplicon was cut out and purified using the Qiagen QiaQuick Gel Extraction Kit following the manufacturer's instructions. The resulting purified product sequenced using the Sanger method using the following primers:

```
MR766 seq1:
                                          (SEQ ID NO: 381)
    TGATACTGCTGATTGCCCCG MR766 seq2:
                                          (SEQ ID NO: 382)
    AACACAAGGTGAAGCCTAC MR766 seq3:
                                          (SEQ ID NO: 383)
    AAGAGGCAAACCGTCGTCGTTC MR766 seq4:
                                          (SEQ ID NO: 384)
    CCCGTGATTACTGAAAGCAC MR766 seq5:
                                          (SEQ ID NO: 385)
    GTTCAACTCACTGGGTAAGG
```

Sequences were analyzed and assembled to compose the full Zika E sequence. Translation of the sequence assembly revealed escape mutations.

Results

Figure 8A:
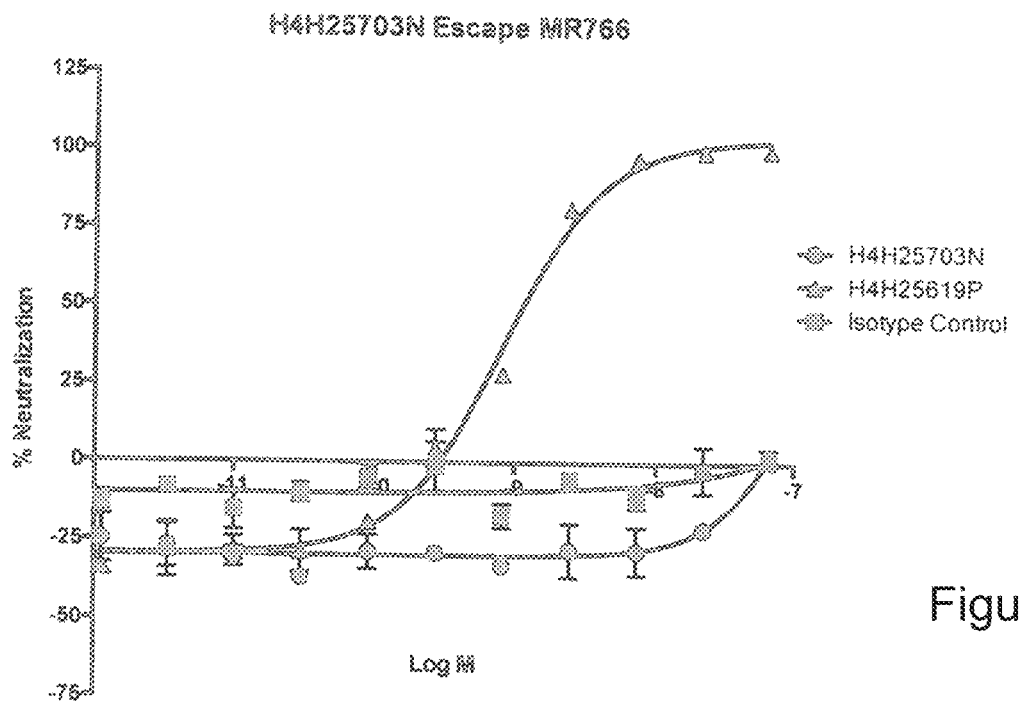
FIGS. 8A and 8B. Show ZIKV neutralization using escape mutants generated in the presence of antibodies H4H25703N and H4H25619P.
Figure 8B:
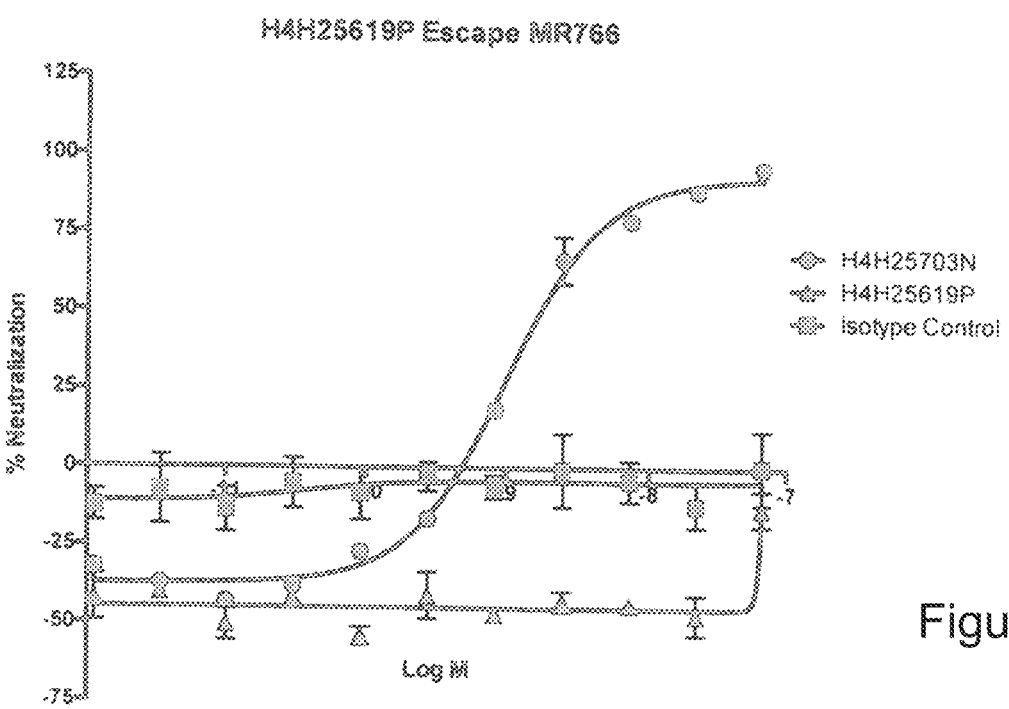

Sequence analysis confirmed that the escape mutation for H4H25703N was found at position 302 of the Zika virus E protein (SEQ ID NO: 376; S302E). The escape mutations for H4H25619P were found at amino acid positions 311 and 369 of the Zika virus E protein (SEQ ID NO: 376; T311I and K369E, respectively). The amino acid sequence showing the E protein escape mutation (S302F) for H4H25703N is shown as SEQ ID NO: 377. The amino acid sequence showing the E protein escape mutations (T311I and K369E) for H4H25619P is shown as SEQ ID NO: 378. The data from these studies suggest binding sites for H4H25703N and H4H25619P on ZIKV E protein that may play a major role in viral neutralization. In addition, the results shown in FIGS. 8A and 8B demonstrate that while one antibody may not neutralize ZIKV because of a mutation in the E protein, a second antibody may be capable of neutralizing that virus containing a mutation in the E protein, thus providing support for the use of an antibody cocktail.

Example 10: Effect of Anti-ZIKV Antibody Combinations on Protection in ZIKV Infected Mice A study was done to determine the effect of anti-ZIKV antibodies, when used alone or in combination in a mouse model of ZIKV infection.

Interferon alpha/beta receptor 1 (IFNAR1) KO mice were received at 6-8 weeks of age and injected subcutaneously with 200 μL PBS containing either a negative isotype control antibody, or anti-ZIKV antibodies for final doses of 200, 50, or 12.5 pg antibody per mouse. When two of the antibodies were combined, each antibody was given at a dose of 100, 25, or 6.25 μg, so that the total dose of both antibodies when combined was 200, 50 or 12.5 μg. One day post-treatment, the mice were infected via intraperitoneal injection with 105 ffu Zika virus strain F5513025 diluted in DMEM+2% FBS, 1× Penicillin/Streptomycin/Glutamine (PSG). The animals were monitored for up to 3 weeks for weight loss or extreme sickness. Animals were euthanized if they dropped below a weight threshold of 80% of starting weight or exhibited extreme sickness (qualified by tremors or non-responsiveness—animals with hind limb paralysis were monitored for recovery in the experiment).

Results

The results showed that all mice receiving the isotype control antibody lost greater than 20% of their body weight by day 9 after infection and had to be sacrificed according to IACUC guidelines. Pre-treatment of mice with H4H25703N or H4H25619 at doses of 200 ug or 50 ug resulted in 100% survival. 60% of mice treated with 12.5 ug of H4H25703 survived challenge with ZIKV. 75% of mice treated with 12.5 ug of H4H25619 survived challenge with ZIKV. Pretreatment of mice with both antibodies at total doses of 200 ug (100 ug of each antibody) or 50 ug (25 ug of each antibody) resulted in 100% survival. Pretreatment of mice with a total dose of 12.5 ug (6.25 ug of each antibody) also resulted in 100% survival. These results suggest that a lower dose of each antibody can be used in combination to achieve greater efficacy, as compared to that attained when each antibody is used alone. The results are shown in Table 10 below.

TABLE 10

| Antibody Identification | % Survival Final Dose of Ab used (in ug) | | |
|---|---|---|---|
| Number | 200 | 50 | 12.5 |
| H4H25703 | 100% | 100% | 60% |
| H4H25619 | 100% | 100% | 75% |
| H4H25703 + H4H25619 | 100% | 100% | 100% |

What is claimed is:

1. A method of neutralizing infectious ZIKV, the method comprising exposing a cell infected with ZIKV to a composition comprising an isolated recombinant monoclonal antibody or antigen-binding fragment thereof that specifically binds to ZIKA virus (ZIKV) and/or a ZIKV envelope glycoprotein (E), wherein the antibody or antigen-binding fragment thereof comprises three complementarity determining regions (CDRs) of a heavy chain variable region (HCVR) comprising the amino acid sequence of SEQ ID NO: 114, and three CDRs of a light chain variable region (LCVR) comprising the amino acid sequence of SEQ ID NO: 122, and wherein the exposing results in enhanced protection of the cell from virus infection, or from cell death.

2. The method of claim 1, wherein the one or more anti-ZIKV antibodies or antigen-binding fragments thereof neutralize infectious ZIKV having a wild type E protein, wherein the wild type E protein has a serine at position 302 of SEQ ID NO: 376, a threonine at position 311 of SEQ ID NO: 376, and a lysine at position 369 of SEQ ID NO: 376, but will not neutralize an infectious ZIKV having a mutated form of the E protein, wherein the mutated form of the E protein contains one or more of the following changes: a phenylalanine at position 302 of SEQ ID NO: 376, an isoleucine at position 311 of SEQ ID NO: 376, or a glutamic acid at position 369 of SEQ ID NO: 376.

3. The method of claim 1, wherein the enhanced protection is observed when the antibody is used alone, or when it is used in combination with one or more additional therapeutic agents or anti-ZIKV treatment modalities, wherein the one or more additional therapeutic agents is selected from the group consisting of an anti-viral drug, an anti-inflammatory drug, one or more different isolated monoclonal anti-ZIKV antibodies or antigen-binding fragments thereof, an immunomodulator and an interferon.

4. The method of claim 3, wherein the enhanced protection is observed when the antibody is used in combination with one or more different isolated monoclonal anti-ZIKV antibodies or antigen-binding fragments thereof, wherein the one or more different anti-ZIKV antibodies or antigen-binding fragments comprise a heavy chain variable region (HCVR) and a light chain variable region (LCVR) amino acid sequence pair selected from the group consisting of SEQ ID NOs: 2/10, 18/26, 34/42, 50/58, 66/74, 82/90, 98/106, 130/138, 146/154, 162/170, 178/186, 194/202, 210/218, 226/234, 242/250, 258/266, 274/282, 290/298, 306/314, 322/330 and 338/346.

5. The method of claim 1, wherein the antibody or antigen-binding fragment comprises a HCVR comprising the amino acid sequence of SEQ ID NO: 114, and a LCVR comprising the amino acid sequence of SEQ ID NO: 122.

6. The method of claim 1, wherein the antibody or antigen-binding fragment comprises an HCDR1 amino acid sequence of SEQ ID NO: 116; an HCDR2 amino acid sequence of SEQ ID NO: 118; an HCDR3 amino acid sequence of SEQ ID NO: 120; an LCDR1 amino acid sequence of SEQ ID NO: 124; an LCDR2 amino acid sequence of SEQ ID NO: 126 and an LCDR3 amino acid sequence of SEQ ID NO: 128.

7. The method of claim 1, wherein the antibody further comprises an Fc domain having the amino acid sequence of SEQ ID NO: 357.

8. The method of claim 1, wherein the antibody or antigen-binding fragment does not contribute to Antibody Dependent Enhancement (ADE).

9. The method of claim 1, wherein the antibody or antigen-binding fragment has one or more of the following characteristics:
  (a) is a fully human monoclonal antibody;
  (b) binds to a VLP expressing ZIKV prM/E with an $EC_{50}$ ranging from about 80 pM to about 150 nM;
  (c) binds to ZIKV E with a dissociation constant ($K_D$) of less than $10^{-7}$M, as measured in a surface plasmon resonance assay; or
  (d) may or may not demonstrate a change in dissociative half-life (t½) at pH 5 or pH 6 relative to pH 7.4.

10. The method of claim 3, wherein the enhanced protection is observed when the antibody is used in combination with one or more different isolated monoclonal anti-ZIKV antibodies or antigen-binding fragments thereof, wherein the one or more different anti-ZIKV antibodies or antigen-binding fragments comprise the three heavy chain complementarity determining regions (HCDR1, HCDR2 and HCDR3) contained within any one of the heavy chain variable region (HCVR) sequences selected from the group consisting of SEQ ID NOs: 2, 18, 34, 50, 66, 82, 98, 130, 146, 162, 178, 194, 210, 226, 242, 258, 274, 290, 306, 322 and 338; and the three light chain complementarity determining regions (LCDR1, LCDR2 and LCDR3) contained within any one of the light chain variable region (LCVR) sequences selected from the group consisting of SEQ ID NOs: 10, 26, 42, 58, 74, 90, 106, 138, 154, 170, 186, 202, 218, 234, 250, 266, 282, 298, 314, 330 and 346.

11. The method of claim 4, wherein the one or more different anti-ZIKV antibodies or antigen-binding fragments comprise an HCVR/LCVR amino acid sequence pair selected from the group consisting of SEQ ID NOs: 66/74, and 258/266.

12. The method of claim 1, further comprising administering an anti-ZIKV antibody or antigen-binding fragment thereof comprising a HCVR comprising the amino acid sequence of SEQ ID NO: 258 and a LCVR comprising the amino acid sequence of SEQ ID NO: 266.

13. The method of claim 1, further comprising administering an isolated anti-ZIKV antibody or antigen-binding fragment thereof comprising a HCDR1 having the amino acid sequence of SEQ ID NO: 260, a HCDR2 having the amino acid sequence of SEQ ID NO: 262, a HCDR3 having the amino acid sequence of SEQ ID NO: 264, a LCDR1 having the amino acid sequence of SEQ ID NO: 268, a LCDR2 having the amino acid sequence of SEQ ID NO: 270, a LCDR3 having the amino acid sequence of SEQ ID NO: 272.

14. The method of claim 1, wherein the antibody or antigen-binding fragment neutralizes one or more ZIKV strains selected from the group consisting of MR766 (Uganda 1947), PRVABC59 (Puerto Rico 2015) and FLR (Colombia 2015) strains, as measured in an in vitro neutralization assay.

15. The method of claim 1, wherein the antibody or antigen-binding fragment is a fully human antibody or antigen-binding fragment.

16. The method of claim 15, wherein the fully human antibody or antigen-binding fragment is an antibody.

17. The method of claim 16, wherein the fully human antibody comprises an Fc domain comprising the amino acid sequence of SEQ ID NO: 357.

18. The method of claim 16, wherein the fully human antibody comprises an Fc domain comprising the amino acid sequence of SEQ ID NO: 358.

* * * * *

SEQUENCE LISTING

```
<160> NUMBER OF SEQ ID NOS: 375

<210> SEQ ID NO 1
<211> LENGTH: 357
<212> TYPE: DNA
<213> ORGANISM: Artificial Sequence
<220> FEATURE:
<223> OTHER INFORMATION: synthetic

<400> SEQUENCE: 1
caggtgcagc tgcaggagtc gggcccagga ctggtgaagc cttcacagac cctgtccctc     60
acctgcactg tctctggtgg ctccatcagc agtggtggtt actactggag ctggatccgc    120
cagcacccag ggaagggcct ggagtggatt gggtacatct attacagtgg gagcacctac    180
tacaacccgt ccctcaagag tcgaattacc atatcaatag acacgtctaa gaaccagttc    240
tccctgaagc tgacctctgt gactgccgcg gacacggccg tgtactactg tgcgaggggg    300
caacagctgc tttcctttga ctactggggc cagggaaccc tggtcaccgt ctcctca       357

<210> SEQ ID NO 2
<211> LENGTH: 119
<212> TYPE: PRT
<213> ORGANISM: Artificial Sequence
<220> FEATURE:
<223> OTHER INFORMATION: synthetic

<400> SEQUENCE: 2

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Ile Thr Ile Ser Ile Asp Thr Ser Lys Asn Gln Phe
65                  70                  75                  80

Ser Leu Lys Leu Thr Ser Val Thr Ala Ala Asp Thr Ala Val Tyr Tyr
                85                  90                  95

Cys Ala Arg Gly Gln Gln Leu Leu Ser Phe Asp Tyr Trp Gly Gln Gly
            100                 105                 110

Thr Leu Val Thr Val Ser Ser
        115

<210> SEQ ID NO 3
<211> LENGTH: 30
<212> TYPE: DNA
<213> ORGANISM: Artificial Sequence
```

<220> FEATURE:
<223> OTHER INFORMATION: synthetic

<400> SEQUENCE: 3
ggtggctcca tcagcagtgg tggttactac                                30

<210> SEQ ID NO 4
<211> LENGTH: 10
<212> TYPE: PRT
<213> ORGANISM: Artificial Sequence
<220> FEATURE:
<223> OTHER INFORMATION: synthetic

<400> SEQUENCE: 4

Gly Gly Ser Ile Ser Ser Gly Gly Tyr Tyr
1               5                   10

<210> SEQ ID NO 5
<211> LENGTH: 21
<212> TYPE: DNA
<213> ORGANISM: Artificial Sequence
<220> FEATURE:
<223> OTHER INFORMATION: synthetic

<400> SEQUENCE: 5
atctattaca gtgggagcac c                                         21

<210> SEQ ID NO 6
<211> LENGTH: 7
<212> TYPE: PRT
<213> ORGANISM: Artificial Sequence
<220> FEATURE:
<223> OTHER INFORMATION: synthetic

<400> SEQUENCE: 6

Ile Tyr Tyr Ser Gly Ser Thr
1               5

<210> SEQ ID NO 7
<211> LENGTH: 33
<212> TYPE: DNA
<213> ORGANISM: Artificial Sequence
<220> FEATURE:
<223> OTHER INFORMATION: synthetic

<400> SEQUENCE: 7
gcgagggggc aacagctgct ttcctttgac tac                            33

<210> SEQ ID NO 8
<211> LENGTH: 11
<212> TYPE: PRT
<213> ORGANISM: Artificial Sequence
<220> FEATURE:
<223> OTHER INFORMATION: synthetic

<400> SEQUENCE: 8

Ala Arg Gly Gln Gln Leu Leu Ser Phe Asp Tyr
1               5                   10

<210> SEQ ID NO 9
<211> LENGTH: 321
<212> TYPE: DNA
<213> ORGANISM: Artificial Sequence
<220> FEATURE:
<223> OTHER INFORMATION: synthetic

<400> SEQUENCE: 9

```
gacatccaga tgacccagtc tccatcctcc gtgtctgcat ctgtaggaga cagagtcacc    60
atcacctgtc gggcgagtca gggaattagc aggtggttag cctggtatca gctgaaacca   120
gggaaacccc ctacgcccct gatctatgct gcatccagtt tgcaaagtgg ggccccatca   180
aggttcagcg gcagggggtc tgggacagat ttcactctca ccatcagcag cctgcagcct   240
gaagattttg caacttacta ttgtcaacag gctaacagtt tcccgtacac ttttggccag   300
gggaccaagc tggagatcaa a                                             321
```

<210> SEQ ID NO 10
<211> LENGTH: 107
<212> TYPE: PRT
<213> ORGANISM: Artificial Sequence
<220> FEATURE:
<223> OTHER INFORMATION: synthetic

<400> SEQUENCE: 10

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Arg Trp
            20                  25                  30

Leu Ala Trp Tyr Gln Leu Lys Pro Gly Lys Pro Thr Pro Leu Ile
        35                  40                  45

Tyr Ala Ala Ser Ser Leu Gln Ser Gly Ala Pro Ser Arg Phe Ser Gly
    50                  55                  60

Arg Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Tyr
                85                  90                  95

Thr Phe Gly Gln Gly Thr Lys Leu Glu Ile Lys
            100                 105

<210> SEQ ID NO 11
<211> LENGTH: 18
<212> TYPE: DNA
<213> ORGANISM: Artificial Sequence
<220> FEATURE:
<223> OTHER INFORMATION: synthetic

<400> SEQUENCE: 11
cagggaatta gcaggtgg                                                  18

<210> SEQ ID NO 12
<211> LENGTH: 6
<212> TYPE: PRT
<213> ORGANISM: Artificial Sequence
<220> FEATURE:
<223> OTHER INFORMATION: synthetic

<400> SEQUENCE: 12

Gln Gly Ile Ser Arg Trp
1               5

<210> SEQ ID NO 13
<211> LENGTH: 9
<212> TYPE: DNA
<213> ORGANISM: Artificial Sequence
<220> FEATURE:
<223> OTHER INFORMATION: synthetic

<400> SEQUENCE: 13

```
gctgcatcc                                                                9
```

<210> SEQ ID NO 14
<211> LENGTH: 3
<212> TYPE: PRT
<213> ORGANISM: Artificial Sequence
<220> FEATURE:
<223> OTHER INFORMATION: synthetic

<400> SEQUENCE: 14

Ala Ala Ser
1

<210> SEQ ID NO 15
<211> LENGTH: 27
<212> TYPE: DNA
<213> ORGANISM: Artificial Sequence
<220> FEATURE:
<223> OTHER INFORMATION: synthetic

<400> SEQUENCE: 15

```
caacaggcta acagtttccc gtacact                                           27
```

<210> SEQ ID NO 16
<211> LENGTH: 9
<212> TYPE: PRT
<213> ORGANISM: Artificial Sequence
<220> FEATURE:
<223> OTHER INFORMATION: synthetic

<400> SEQUENCE: 16

Gln Gln Ala Asn Ser Phe Pro Tyr Thr
1               5

<210> SEQ ID NO 17
<211> LENGTH: 363
<212> TYPE: DNA
<213> ORGANISM: Artificial Sequence
<220> FEATURE:
<223> OTHER INFORMATION: synthetic

<400> SEQUENCE: 17

```
gaagtgcagc tggtggagtc tgggggaggc ttggtacagc ctggcaggtc cctgacactc       60
tcctgtgcag cctctggatt cacctttgat gattatgtca tgcactgggt ccggcaagct      120
ccagggaagg gcctggagtg ggtctcaggt attagttgga atagtgatac cattgactat      180
gcggactctg tgaagggccg attcaccatc tccagagaca cgccaagaa ctccctgtat      240 ctgcaaatga acagtctgag agctgaggac acggccttgt attactgtgc aaaagatagg      300
cgcagctggt acggagggta ctttgactac tggggccagg gaaccctggt caccgtctcc      360
tca                                                                   363
```

<210> SEQ ID NO 18
<211> LENGTH: 121
<212> TYPE: PRT
<213> ORGANISM: Artificial Sequence
<220> FEATURE:
<223> OTHER INFORMATION: synthetic

<400> SEQUENCE: 18

Glu Val Gln Leu Val Glu Ser Gly Gly Gly Leu Val Gln Pro Gly Arg
1               5                   10                  15

Ser Leu Thr Leu Ser Cys Ala Ala Ser Gly Phe Thr Phe Asp Asp Tyr
            20                  25                  30

```
Val Met His Trp Val Arg Gln Ala Pro Gly Lys Gly Leu Glu Trp Val
         35                  40                  45

Ser Gly Ile Ser Trp Asn Ser Asp Thr Ile Asp Tyr Ala Asp Ser Val
     50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Leu Tyr Tyr Cys
                 85                  90                  95

Ala Lys Asp Arg Arg Ser Trp Tyr Gly Tyr Phe Asp Tyr Trp Gly
                100                 105                 110        Gly

Gln Gly Thr Leu Val Thr Val Ser Ser
        115                 120

<210> SEQ ID NO 19
<211> LENGTH: 24
<212> TYPE: DNA
<213> ORGANISM: Artificial Sequence
<220> FEATURE:
<223> OTHER INFORMATION: synthetic

<400> SEQUENCE: 19
ggattcacct ttgatgatta tgtc                                          24

<210> SEQ ID NO 20
<211> LENGTH: 8
<212> TYPE: PRT
<213> ORGANISM: Artificial Sequence
<220> FEATURE:
<223> OTHER INFORMATION: synthetic

<400> SEQUENCE: 20

Gly Phe Thr Phe Asp Asp Tyr Val
 1               5

<210> SEQ ID NO 21
<211> LENGTH: 24
<212> TYPE: DNA
<213> ORGANISM: Artificial Sequence
<220> FEATURE:
<223> OTHER INFORMATION: synthetic

<400> SEQUENCE: 21
attagttgga atagtgatac catt                                          24

<210> SEQ ID NO 22
<211> LENGTH: 8
<212> TYPE: PRT
<213> ORGANISM: Artificial Sequence
<220> FEATURE:
<223> OTHER INFORMATION: synthetic

<400> SEQUENCE: 22

Ile Ser Trp Asn Ser Asp Thr Ile
 1               5

<210> SEQ ID NO 23
<211> LENGTH: 42
<212> TYPE: DNA
<213> ORGANISM: Artificial Sequence
<220> FEATURE:
<223> OTHER INFORMATION: synthetic

<400> SEQUENCE: 23
```
gcaaaagata ggcgcagctg gtacggaggg tactttgact ac                42

<210> SEQ ID NO 24
<211> LENGTH: 14
<212> TYPE: PRT
<213> ORGANISM: Artificial Sequence
<220> FEATURE:
<223> OTHER INFORMATION: synthetic

<400> SEQUENCE: 24

Ala Lys Asp Arg Arg Ser Trp Tyr Gly Gly Tyr Phe Asp Tyr
1               5                   10

<210> SEQ ID NO 25
<211> LENGTH: 321
<212> TYPE: DNA
<213> ORGANISM: Artificial Sequence
<220> FEATURE:
<223> OTHER INFORMATION: synthetic

<400> SEQUENCE: 25
gacatccaga tgacccagtc tccatcctcc ctgtctgcat ctgtaggaga cagagtcacc    60
atcacttgcc gggcgagtca gggcattagc agttatttag cctggtatca gcagaaacca   120
gggaaagttc ctaagctcct gatctatgct gcatccactt tgcaatcagg ggtcccatct   180
cggttcagtg gcagtggatc tgggacagat ttctctctca ccatcagcag cctgcagcct   240
gaagatgttg caacttatta ctgtcaaaag tataacagtg ccccgctcac tttcggcgga   300
gggaccaagg tggagatcaa a                                             321

<210> SEQ ID NO 26
<211> LENGTH: 107
<212> TYPE: PRT
<213> ORGANISM: Artificial Sequence
<220> FEATURE:
<223> OTHER INFORMATION: synthetic

<400> SEQUENCE: 26

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Tyr
                20                  25                  30

Leu Ala Trp Tyr Gln Gln Lys Pro Gly Lys Val Pro Lys Leu Leu Ile
            35                  40                  45

Tyr Ala Ala Ser Thr Leu Gln Ser Gly Val Pro Ser Arg Phe Ser Gly
        50                  55                  60

Ser Gly Ser Gly Thr Asp Phe Ser Leu Thr Ile Ser Ser Leu Gln Pro
65                  70                  75                  80

Glu Asp Val Ala Thr Tyr Tyr Cys Gln Lys Tyr Asn Ser Ala Pro Leu
                85                  90                  95

Thr Phe Gly Gly Gly Thr Lys Val Glu Ile Lys
            100                 105

<210> SEQ ID NO 27
<211> LENGTH: 18
<212> TYPE: DNA
<213> ORGANISM: Artificial Sequence
<220> FEATURE:
<223> OTHER INFORMATION: synthetic

<400> SEQUENCE: 27
cagggcatta gcagttat                                                  18

<210> SEQ ID NO 28
<211> LENGTH: 6
<212> TYPE: PRT
<213> ORGANISM: Artificial Sequence
<220> FEATURE:
<223> OTHER INFORMATION: synthetic

<400> SEQUENCE: 28

Gln Gly Ile Ser Ser Tyr
1               5

<210> SEQ ID NO 29
<211> LENGTH: 9
<212> TYPE: DNA
<213> ORGANISM: Artificial Sequence
<220> FEATURE:
<223> OTHER INFORMATION: synthetic

<400> SEQUENCE: 29 gctgcatcc                                                              9

<210> SEQ ID NO 30
<211> LENGTH: 3
<212> TYPE: PRT
<213> ORGANISM: Artificial Sequence
<220> FEATURE:
<223> OTHER INFORMATION: synthetic

<400> SEQUENCE: 30

Ala Ala Ser
1

<210> SEQ ID NO 31
<211> LENGTH: 27
<212> TYPE: DNA
<213> ORGANISM: Artificial Sequence
<220> FEATURE:
<223> OTHER INFORMATION: synthetic

<400> SEQUENCE: 31
caaaagtata acagtgcccc gctcact                                         27

<210> SEQ ID NO 32
<211> LENGTH: 9
<212> TYPE: PRT
<213> ORGANISM: Artificial Sequence
<220> FEATURE:
<223> OTHER INFORMATION: synthetic

<400> SEQUENCE: 32

Gln Lys Tyr Asn Ser Ala Pro Leu Thr
1               5

<210> SEQ ID NO 33
<211> LENGTH: 351
<212> TYPE: DNA
<213> ORGANISM: Artificial Sequence
<220> FEATURE:
<223> OTHER INFORMATION: synthetic

<400> SEQUENCE: 33
caggtgcagc tggtggagtc tgggggaggc gtggtccagc ctggagggtc cctgagactc      60
tcctgtgcag cctctggatt caccttcagt tattctggca tgcactgggt ccgccaggct     120
ccaggcaagg ggctggagtg ggtggcagtt atatcatatg atggaattaa taaatactat     180

```
gcagactccg tgaagggccg attcaccatc tccagagaca attccaagaa cacgctgtat      240
ctgcaaatga acagcctgag acctgaggac acggctgttt attactgtgc gaaagatagg      300
ggtggaaggt tcgacccctg gggccaggga accctggtca ccgtctcctc a               351
```

```
<210> SEQ ID NO 34
<211> LENGTH: 117
<212> TYPE: PRT
<213> ORGANISM: Artificial Sequence
<220> FEATURE:
<223> OTHER INFORMATION: synthetic

<400> SEQUENCE: 34
```

Gln Val Gln Leu Val Glu Ser Gly Gly Gly Val Val Gln Pro Gly Arg
1               5                  10                  15

Ser Leu Arg Leu Ser Cys Ala Ala Ser Gly Phe Thr Phe Ser Tyr Ser
            20                  25                  30

Gly Met His Trp Val Arg Gln Ala Pro Gly Lys Gly Leu Glu Trp Val
        35                  40                  45

Ala Val Ile Ser Tyr Asp Gly Ile Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Ala Lys Asp Arg Gly Gly Arg Phe Asp Pro Trp Gly Gln Gly Thr Leu
            100                 105                 110

Val Thr Val Ser Ser
        115

```
<210> SEQ ID NO 35
<211> LENGTH: 24
<212> TYPE: DNA
<213> ORGANISM: Artificial Sequence
<220> FEATURE:
<223> OTHER INFORMATION: synthetic

<400> SEQUENCE: 35
ggattcacct tcagttattc tggc                                              24

<210> SEQ ID NO 36
<211> LENGTH: 8
<212> TYPE: PRT
<213> ORGANISM: Artificial Sequence
<220> FEATURE:
<223> OTHER INFORMATION: synthetic

<400> SEQUENCE: 36
```

Gly Phe Thr Phe Ser Tyr Ser Gly
1               5

```
<210> SEQ ID NO 37
<211> LENGTH: 24
<212> TYPE: DNA
<213> ORGANISM: Artificial Sequence
<220> FEATURE:
<223> OTHER INFORMATION: synthetic

<400> SEQUENCE: 37
atatcatatg atggaattaa taaa                                              24
```

<210> SEQ ID NO 38
<211> LENGTH: 8
<212> TYPE: PRT
<213> ORGANISM: Artificial Sequence
<220> FEATURE:
<223> OTHER INFORMATION: synthetic

<400> SEQUENCE: 38

Ile Ser Tyr Asp Gly Ile Asn Lys
1               5

<210> SEQ ID NO 39
<211> LENGTH: 30
<212> TYPE: DNA
<213> ORGANISM: Artificial Sequence
<220> FEATURE:
<223> OTHER INFORMATION: synthetic

<400> SEQUENCE: 39
gcgaaagata ggggtggaag gttcgacccc                                    30

<210> SEQ ID NO 40
<211> LENGTH: 10
<212> TYPE: PRT
<213> ORGANISM: Artificial Sequence
<220> FEATURE:
<223> OTHER INFORMATION: synthetic

<400> SEQUENCE: 40

Ala Lys Asp Arg Gly Gly Arg Phe Asp Pro
1               5                   10

<210> SEQ ID NO 41
<211> LENGTH: 321
<212> TYPE: DNA
<213> ORGANISM: Artificial Sequence
<220> FEATURE:
<223> OTHER INFORMATION: synthetic

<400> SEQUENCE: 41
gacatccaga tgacccagtc tccatcctcc ctgtctgcat ctgtaggaga cagagtcacc    60
atcacttgcc gggcgagtca gggcattagc aattatttag cctggtatca gcagaaacca   120
gggaaagttc ctaacctcct gatctatggt gcatccactt tgcattcagg ggtcccatct   180
cggttcagtg gcagtggatc tgggacagat ttcactctca ccatcagcag cctgcagcct   240
gcagatgttg caacttatta ctgtcaaaag tataacagtg ccccactcac tttcggcgga   300
gggaccaagg tggagatcaa a                                             321

<210> SEQ ID NO 42
<211> LENGTH: 107
<212> TYPE: PRT
<213> ORGANISM: Artificial Sequence
<220> FEATURE:
<223> OTHER INFORMATION: synthetic

<400> SEQUENCE: 42

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Val Pro Asn Leu Leu Ile
        35                  40                  45

Tyr Gly Ala Ser Thr Leu His Ser Gly Val Pro Ser Arg Phe Ser Gly

```
                    50                  55                  60
Ser Gly Ser Gly Thr Asp Phe Thr Leu Thr Ile Ser Ser Leu Gln Pro
 65                  70                  75                  80

Ala Asp Val Ala Thr Tyr Tyr Cys Gln Lys Tyr Asn Ser Ala Pro Leu
                 85                  90                  95

Thr Phe Gly Gly Gly Thr Lys Val Glu Ile Lys
            100                 105
```

<210> SEQ ID NO 43
<211> LENGTH: 18
<212> TYPE: DNA
<213> ORGANISM: Artificial Sequence
<220> FEATURE:
<223> OTHER INFORMATION: synthetic

<400> SEQUENCE: 43
cagggcatta gcaattat                                                   18

<210> SEQ ID NO 44
<211> LENGTH: 6
<212> TYPE: PRT
<213> ORGANISM: Artificial Sequence
<220> FEATURE:
<223> OTHER INFORMATION: synthetic

<400> SEQUENCE: 44

```
Gln Gly Ile Ser Asn Tyr
 1               5
```

<210> SEQ ID NO 45
<211> LENGTH: 9
<212> TYPE: DNA
<213> ORGANISM: Artificial Sequence
<220> FEATURE:
<223> OTHER INFORMATION: synthetic

<400> SEQUENCE: 45 ggtgcatcc                                                              9

<210> SEQ ID NO 46
<211> LENGTH: 3
<212> TYPE: PRT
<213> ORGANISM: Artificial Sequence
<220> FEATURE:
<223> OTHER INFORMATION: synthetic

<400> SEQUENCE: 46

```
Gly Ala Ser
 1
```

<210> SEQ ID NO 47
<211> LENGTH: 27
<212> TYPE: DNA
<213> ORGANISM: Artificial Sequence
<220> FEATURE:
<223> OTHER INFORMATION: synthetic

<400> SEQUENCE: 47
caaaagtata acagtgcccc actcact                                         27

<210> SEQ ID NO 48
<211> LENGTH: 9
<212> TYPE: PRT
<213> ORGANISM: Artificial Sequence
<220> FEATURE:

<223> OTHER INFORMATION: synthetic

<400> SEQUENCE: 48

Gln Lys Tyr Asn Ser Ala Pro Leu Thr
1               5

<210> SEQ ID NO 49
<211> LENGTH: 351
<212> TYPE: DNA
<213> ORGANISM: Artificial Sequence
<220> FEATURE:
<223> OTHER INFORMATION: synthetic

<400> SEQUENCE: 49

```
caggtgcagc tggtggagtc tgggggaggc gtggtccagc ctgggaggtc cctgagactc    60
tcctgtgcag cctctggatt caccttcagt tactctggca tgcactgggt ccgccaggct   120
ccaggcaagg ggctggagtg ggtggcagtt atatcatatg atggaagtaa taatactat   180
gcagactccg tgaagggccg attcaccatc tccagagaca attccaacaa cattctatat   240
ctgcaaatga acagcctgag agctgaggac acggctgtgt attactgtgc gaaagattgg   300
ggtggaaggt tcgacccctg gggccaggga accctggtca ccgtctcctc a            351
```

<210> SEQ ID NO 50
<211> LENGTH: 117
<212> TYPE: PRT
<213> ORGANISM: Artificial Sequence
<220> FEATURE:
<223> OTHER INFORMATION: synthetic

<400> SEQUENCE: 50

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Tyr Ser
                20                  25                  30

Gly Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
        50                  55                  60

Lys Gly Arg Phe Thr Ile Ser Arg Asp Asn Ser Asn Asn Ile Leu Tyr
65                  70                  75                  80

Leu Gln Met Asn Ser Leu Arg Ala Glu Asp Thr Ala Val Tyr Tyr Cys
                85                  90                  95

Ala Lys Asp Trp Gly Gly Arg Phe Asp Pro Trp Gly Gln Gly Thr Leu
            100                 105                 110

Val Thr Val Ser Ser
        115

<210> SEQ ID NO 51
<211> LENGTH: 24
<212> TYPE: DNA
<213> ORGANISM: Artificial Sequence
<220> FEATURE:
<223> OTHER INFORMATION: synthetic

<400> SEQUENCE: 51

```
ggattcacct tcagttactc tggc                                           24
```

<210> SEQ ID NO 52
<211> LENGTH: 8
<212> TYPE: PRT

```
<213> ORGANISM: Artificial Sequence
<220> FEATURE:
<223> OTHER INFORMATION: synthetic

<400> SEQUENCE: 52

Gly Phe Thr Phe Ser Tyr Ser Gly
1               5

<210> SEQ ID NO 53
<211> LENGTH: 24
<212> TYPE: DNA
<213> ORGANISM: Artificial Sequence
<220> FEATURE:
<223> OTHER INFORMATION: synthetic

<400> SEQUENCE: 53
atatcatatg atggaagtaa taaa                                           24

<210> SEQ ID NO 54
<211> LENGTH: 8
<212> TYPE: PRT
<213> ORGANISM: Artificial Sequence
<220> FEATURE:
<223> OTHER INFORMATION: synthetic

<400> SEQUENCE: 54

Ile Ser Tyr Asp Gly Ser Asn Lys
1               5

<210> SEQ ID NO 55
<211> LENGTH: 30
<212> TYPE: DNA
<213> ORGANISM: Artificial Sequence
<220> FEATURE:
<223> OTHER INFORMATION: synthetic

<400> SEQUENCE: 55
gcgaaagatt ggggtggaag gttcgacccc                                     30

<210> SEQ ID NO 56
<211> LENGTH: 10
<212> TYPE: PRT
<213> ORGANISM: Artificial Sequence
<220> FEATURE:
<223> OTHER INFORMATION: synthetic

<400> SEQUENCE: 56

Ala Lys Asp Trp Gly Gly Arg Phe Asp Pro
1               5                   10

<210> SEQ ID NO 57
<211> LENGTH: 321
<212> TYPE: DNA
<213> ORGANISM: Artificial Sequence
<220> FEATURE:
<223> OTHER INFORMATION: synthetic

<400> SEQUENCE: 57
gacatccaga tgacccagtc tccatcctcc ctgtctgcat ctgtaggaga cagagtcacc    60
atcacttgcc gggcgagtca gggcattagc agttatttag cctggtatca gcagatacca   120
gggaaagttc ctaagctcct gatctatgct gcatccactt tgcattcagg agtcccatct   180
cggttcagtg gcagtggctc tgggacagat tcactctca ccatcagcag cctgcagcct   240
gcagatgttg caacttatta ctgtcaaaag tataacagtg ccccgctcac tttcggcgga   300
```
gggaccaagg tggagatcaa a                                                     321

<210> SEQ ID NO 58
<211> LENGTH: 107
<212> TYPE: PRT
<213> ORGANISM: Artificial Sequence
<220> FEATURE:
<223> OTHER INFORMATION: synthetic

<400> SEQUENCE: 58

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Ile Pro Gly Lys Val Pro Lys Leu Leu Ile
        35                  40                  45

Tyr Ala Ala Ser Thr Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Ala Asp Val Ala Thr Tyr Tyr Cys Gln Lys Tyr Asn Ser Ala Pro Leu
                85                  90                  95

Thr Phe Gly Gly Gly Thr Lys Val Glu Ile Lys
            100                 105

<210> SEQ ID NO 59
<211> LENGTH: 18
<212> TYPE: DNA
<213> ORGANISM: Artificial Sequence
<220> FEATURE:
<223> OTHER INFORMATION: synthetic

<400> SEQUENCE: 59
cagggcatta gcagttat                                                          18

<210> SEQ ID NO 60
<211> LENGTH: 6
<212> TYPE: PRT
<213> ORGANISM: Artificial Sequence
<220> FEATURE:
<223> OTHER INFORMATION: synthetic

<400> SEQUENCE: 60

Gln Gly Ile Ser Ser Tyr
1               5

<210> SEQ ID NO 61
<211> LENGTH: 9
<212> TYPE: DNA
<213> ORGANISM: Artificial Sequence
<220> FEATURE:
<223> OTHER INFORMATION: synthetic

<400> SEQUENCE: 61 gctgcatcc                                                                     9

<210> SEQ ID NO 62
<211> LENGTH: 3
<212> TYPE: PRT
<213> ORGANISM: Artificial Sequence
<220> FEATURE:
<223> OTHER INFORMATION: synthetic

<400> SEQUENCE: 62

```
<210> SEQ ID NO 63
<211> LENGTH: 27
<212> TYPE: DNA
<213> ORGANISM: Artificial Sequence
<220> FEATURE:
<223> OTHER INFORMATION: synthetic

<400> SEQUENCE: 63
caaaagtata acagtgcccc gctcact                                              27

<210> SEQ ID NO 64
<211> LENGTH: 9
<212> TYPE: PRT
<213> ORGANISM: Artificial Sequence
<220> FEATURE:
<223> OTHER INFORMATION: synthetic

<400> SEQUENCE: 64

Gln Lys Tyr Asn Ser Ala Pro Leu Thr
1               5

<210> SEQ ID NO 65
<211> LENGTH: 369
<212> TYPE: DNA
<213> ORGANISM: Artificial Sequence
<220> FEATURE:
<223> OTHER INFORMATION: synthetic

<400> SEQUENCE: 65
gaggtgcagc tggtggagtc tggaggaggc ttggtccagc cggggggtc cctgagactc          60 tcctgtgcag cctctgggtt caccgtcagt agcaactaca tgagttgggt ccgccaggct        120
ccagggagcg gctggagtg gtctcagtc atatatagcg gtggtatcac acactatata         180
ggctccgtga agggccgatt caccatctcc agacacaatt ccaagaacac gctgtatctt       240
caaatgaaca gcctgagagc tgaggacacg gccatgtact actgtgcgcg ggaacggtac       300
tccggtataa ctggaaaccc gtatggtttt gattttggg gccaagggac aatggtcacc        360
gtctcttca                                                              369

<210> SEQ ID NO 66
<211> LENGTH: 123
<212> TYPE: PRT
<213> ORGANISM: Artificial Sequence
<220> FEATURE:
<223> OTHER INFORMATION: synthetic

<400> SEQUENCE: 66

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Ser Gly Leu Glu Trp Val
        35                  40                  45

Ser Val Ile Tyr Ser Gly Gly Ile Thr His Tyr Ile Gly Ser Val Lys
    50                  55                  60

Gly Arg Phe Thr Ile Ser Arg His Asn Ser Lys Asn Thr Leu Tyr Leu
65                  70                  75                  80

Gln Met Asn Ser Leu Arg Ala Glu Asp Thr Ala Met Tyr Tyr Cys Ala
```

Ala Ala Ser
1

85                  90                  95

Arg Glu Arg Tyr Ser Gly Ile Thr Gly Asn Pro Tyr Gly Phe Asp Phe
            100                 105                 110

Trp Gly Gln Gly Thr Met Val Thr Val Ser Ser
        115                 120

<210> SEQ ID NO 67
<211> LENGTH: 24
<212> TYPE: DNA
<213> ORGANISM: Artificial Sequence
<220> FEATURE:
<223> OTHER INFORMATION: synthetic

<400> SEQUENCE: 67
gggttcaccg tcagtagcaa ctac                                              24

<210> SEQ ID NO 68
<211> LENGTH: 8
<212> TYPE: PRT
<213> ORGANISM: Artificial Sequence
<220> FEATURE:
<223> OTHER INFORMATION: synthetic

<400> SEQUENCE: 68

Gly Phe Thr Val Ser Ser Asn Tyr
1               5

<210> SEQ ID NO 69
<211> LENGTH: 21
<212> TYPE: DNA
<213> ORGANISM: Artificial Sequence
<220> FEATURE:
<223> OTHER INFORMATION: synthetic

<400> SEQUENCE: 69
atatatagcg gtggtatcac a                                                 21

<210> SEQ ID NO 70
<211> LENGTH: 7
<212> TYPE: PRT
<213> ORGANISM: Artificial Sequence
<220> FEATURE:
<223> OTHER INFORMATION: synthetic

<400> SEQUENCE: 70

Ile Tyr Ser Gly Gly Ile Thr
1               5

<210> SEQ ID NO 71
<211> LENGTH: 51
<212> TYPE: DNA
<213> ORGANISM: Artificial Sequence
<220> FEATURE:
<223> OTHER INFORMATION: synthetic

<400> SEQUENCE: 71
gcgcgggaac ggtactccgg tataactgga aaccgtatg gttttgattt t                  51

<210> SEQ ID NO 72
<211> LENGTH: 17
<212> TYPE: PRT
<213> ORGANISM: Artificial Sequence
<220> FEATURE:
<223> OTHER INFORMATION: synthetic

<400> SEQUENCE: 72

Ala Arg Glu Arg Tyr Ser Gly Ile Thr Gly Asn Pro Tyr Gly Phe Asp
1               5                   10                  15

Phe

<210> SEQ ID NO 73
<211> LENGTH: 321
<212> TYPE: DNA
<213> ORGANISM: Artificial Sequence
<220> FEATURE:
<223> OTHER INFORMATION: synthetic

<400> SEQUENCE: 73
gacatccagt tgacccagtc tccatccttc ctgtctgcat ctgtaggaga cagagtcacc    60
atcacttgct gggccagtca ggacattagc agttatttag cctggtatca gcaaaaacca   120
gggatagccc ctaaactcct gatctattct gcatccactt tgcaaagtgg agtcccatca   180
agtttcagcg gcagtggatc tgggaccgaa ttcactctca caatcagcag cctgcagcct   240
gaagattttg caacttatta ctgtcaacag cttaatattt acccattcac tttcggccct   300
gggaccaaag tggatatcaa a                                              321

<210> SEQ ID NO 74
<211> LENGTH: 107
<212> TYPE: PRT
<213> ORGANISM: Artificial Sequence
<220> FEATURE:
<223> OTHER INFORMATION: synthetic

<400> SEQUENCE: 74

Asp Ile Gln Leu Thr Gln Ser Pro Ser Phe Leu Ser Ala Ser Val Gly
1               5                   10                  15

Asp Arg Val Thr Ile Thr Cys Trp Ala Ser Gln Asp Ile Ser Ser Tyr
            20                  25                  30

Leu Ala Trp Tyr Gln Gln Lys Pro Gly Ile Ala Pro Lys Leu Leu Ile
        35                  40                  45

Tyr Ser Ala Ser Thr Leu Gln Ser Gly Val Pro Ser Ser Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Leu Asn Ile Tyr Pro Phe
                85                  90                  95

Thr Phe Gly Pro Gly Thr Lys Val Asp Ile Lys
            100                 105

<210> SEQ ID NO 75
<211> LENGTH: 18
<212> TYPE: DNA
<213> ORGANISM: Artificial Sequence
<220> FEATURE:
<223> OTHER INFORMATION: synthetic

<400> SEQUENCE: 75
caggacatta gcagttat                                                  18

<210> SEQ ID NO 76
<211> LENGTH: 6
<212> TYPE: PRT
<213> ORGANISM: Artificial Sequence
<220> FEATURE:
<223> OTHER INFORMATION: synthetic

<400> SEQUENCE: 76

Gln Asp Ile Ser Ser Tyr
1               5

<210> SEQ ID NO 77
<211> LENGTH: 9
<212> TYPE: DNA
<213> ORGANISM: Artificial Sequence
<220> FEATURE:
<223> OTHER INFORMATION: synthetic

<400> SEQUENCE: 77 tctgcatcc                                                                  9

<210> SEQ ID NO 78
<211> LENGTH: 3
<212> TYPE: PRT
<213> ORGANISM: Artificial Sequence
<220> FEATURE:
<223> OTHER INFORMATION: synthetic

<400> SEQUENCE: 78

Ser Ala Ser
1

<210> SEQ ID NO 79
<211> LENGTH: 27
<212> TYPE: DNA
<213> ORGANISM: Artificial Sequence
<220> FEATURE:
<223> OTHER INFORMATION: synthetic

<400> SEQUENCE: 79
caacagctta atatttaccc attcact                                             27

<210> SEQ ID NO 80
<211> LENGTH: 9
<212> TYPE: PRT
<213> ORGANISM: Artificial Sequence
<220> FEATURE:
<223> OTHER INFORMATION: synthetic

<400> SEQUENCE: 80

Gln Gln Leu Asn Ile Tyr Pro Phe Thr
1               5

<210> SEQ ID NO 81
<211> LENGTH: 369
<212> TYPE: DNA
<213> ORGANISM: Artificial Sequence
<220> FEATURE:
<223> OTHER INFORMATION: synthetic

<400> SEQUENCE: 81
gaggtgcagc tggtggagtc tggaggaggt ttggtccagc cggggggtc cctgagactc           60 tcctgtgcag cctctgggtt caccgtcagt agcaactaca tgagctgggt ccgccaggct         120
ccagggagcg ggctggagtg ggtctcagtt atttatagcg gtggtatcac acactatgta         180
gactccgtga agggccgatt caccatctcc agacacaatt ccaagaacac gctgtatctt         240
caaatgaaca gcctgagagc tgaggacacg gccatgtatt actgtgcgcg ggaacggtac         300
tccggtataa ctggaaaccc ttatggtttt gatatttggg gccaagggac aatggtcacc         360
gtctcttca                                                                369

<210> SEQ ID NO 82
<211> LENGTH: 123
<212> TYPE: PRT
<213> ORGANISM: Artificial Sequence
<220> FEATURE:
<223> OTHER INFORMATION: synthetic

<400> SEQUENCE: 82

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Ser Gly Leu Glu Trp Val
        35                  40                  45

Ser Val Ile Tyr Ser Gly Gly Ile Thr His Tyr Val Asp Ser Val Lys
    50                  55                  60

Gly Arg Phe Thr Ile Ser Arg His Asn Ser Lys Asn Thr Leu Tyr Leu
65                  70                  75                  80

Gln Met Asn Ser Leu Arg Ala Glu Asp Thr Ala Met Tyr Tyr Cys Ala
                85                  90                  95

Arg Glu Arg Tyr Ser Gly Ile Thr Gly Asn Pro Tyr Gly Phe Asp Ile
            100                 105                 110

Trp Gly Gln Gly Thr Met Val Thr Val Ser Ser
        115                 120
```

<210> SEQ ID NO 83
<211> LENGTH: 24
<212> TYPE: DNA
<213> ORGANISM: Artificial Sequence
<220> FEATURE:
<223> OTHER INFORMATION: synthetic

<400> SEQUENCE: 83
gggttcaccg tcagtagcaa ctac        24

<210> SEQ ID NO 84
<211> LENGTH: 8
<212> TYPE: PRT
<213> ORGANISM: Artificial Sequence
<220> FEATURE:
<223> OTHER INFORMATION: synthetic

<400> SEQUENCE: 84

```
Gly Phe Thr Val Ser Ser Asn Tyr
1               5
```

<210> SEQ ID NO 85
<211> LENGTH: 21
<212> TYPE: DNA
<213> ORGANISM: Artificial Sequence
<220> FEATURE:
<223> OTHER INFORMATION: synthetic

<400> SEQUENCE: 85
atttatagcg gtggtatcac a        21

<210> SEQ ID NO 86
<211> LENGTH: 7
<212> TYPE: PRT
<213> ORGANISM: Artificial Sequence
<220> FEATURE:
<223> OTHER INFORMATION: synthetic

<400> SEQUENCE: 86

Ile Tyr Ser Gly Gly Ile Thr
1               5

<210> SEQ ID NO 87
<211> LENGTH: 51
<212> TYPE: DNA
<213> ORGANISM: Artificial Sequence
<220> FEATURE:
<223> OTHER INFORMATION: synthetic

<400> SEQUENCE: 87
gcgcgggaac ggtactccgg tataactgga aacccttatg gttttgatat t         51

<210> SEQ ID NO 88
<211> LENGTH: 17
<212> TYPE: PRT
<213> ORGANISM: Artificial Sequence
<220> FEATURE:
<223> OTHER INFORMATION: synthetic

<400> SEQUENCE: 88

Ala Arg Glu Arg Tyr Ser Gly Ile Thr Gly Asn Pro Tyr Gly Phe Asp
1               5                   10                  15

Ile

<210> SEQ ID NO 89
<211> LENGTH: 321
<212> TYPE: DNA
<213> ORGANISM: Artificial Sequence
<220> FEATURE:
<223> OTHER INFORMATION: synthetic

<400> SEQUENCE: 89
gacatccagt tgacccagtc tccatccttc ctgtctgcat ctgtaggaga cagagtcacc    60
atcacttgct gggccagtca ggacattagc agttatttag cctggtatca gcaaaaacca   120
gggatagccc ctaaactcct gatctatgct gcatccactt tgcaaagtgg ggtcccatca   180
aggttcagcg gcagtggatc tgggacagaa ttcactctca caatcagcag cctgcagcct   240
gaagattttg caacttatta ctgtcaacag cttaatattt acccattcac tttcggccct   300
gggaccaaag tggatatcaa a                                             321

<210> SEQ ID NO 90
<211> LENGTH: 107
<212> TYPE: PRT
<213> ORGANISM: Artificial Sequence
<220> FEATURE:
<223> OTHER INFORMATION: synthetic

<400> SEQUENCE: 90

Asp Ile Gln Leu Thr Gln Ser Pro Ser Phe Leu Ser Ala Ser Val Gly
1               5                   10                  15

Asp Arg Val Thr Ile Thr Cys Trp Ala Ser Gln Asp Ile Ser Ser Tyr
            20                  25                  30

Leu Ala Trp Tyr Gln Gln Lys Pro Gly Ile Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Leu Asn Ile Tyr Pro Phe
                85                  90                  95

Thr Phe Gly Pro Gly Thr Lys Val Asp Ile Lys
            100                 105

<210> SEQ ID NO 91
<211> LENGTH: 18
<212> TYPE: DNA
<213> ORGANISM: Artificial Sequence
<220> FEATURE:
<223> OTHER INFORMATION: synthetic

<400> SEQUENCE: 91
caggacatta gcagttat                                                      18

<210> SEQ ID NO 92
<211> LENGTH: 6
<212> TYPE: PRT
<213> ORGANISM: Artificial Sequence
<220> FEATURE:
<223> OTHER INFORMATION: synthetic

<400> SEQUENCE: 92

Gln Asp Ile Ser Ser Tyr
1               5

<210> SEQ ID NO 93
<211> LENGTH: 9
<212> TYPE: DNA
<213> ORGANISM: Artificial Sequence
<220> FEATURE:
<223> OTHER INFORMATION: synthetic

<400> SEQUENCE: 93 gctgcatcc                                                                 9

<210> SEQ ID NO 94
<211> LENGTH: 3
<212> TYPE: PRT
<213> ORGANISM: Artificial Sequence
<220> FEATURE:
<223> OTHER INFORMATION: synthetic

<400> SEQUENCE: 94

Ala Ala Ser
1

<210> SEQ ID NO 95
<211> LENGTH: 27
<212> TYPE: DNA
<213> ORGANISM: Artificial Sequence
<220> FEATURE:
<223> OTHER INFORMATION: synthetic

<400> SEQUENCE: 95
caacagctta atatttaccc attcact                                            27

<210> SEQ ID NO 96
<211> LENGTH: 9
<212> TYPE: PRT
<213> ORGANISM: Artificial Sequence
<220> FEATURE:
<223> OTHER INFORMATION: synthetic

<400> SEQUENCE: 96

Gln Gln Leu Asn Ile Tyr Pro Phe Thr

<210> SEQ ID NO 97
<211> LENGTH: 345
<212> TYPE: DNA
<213> ORGANISM: Artificial Sequence
<220> FEATURE:
<223> OTHER INFORMATION: synthetic

<400> SEQUENCE: 97

```
gaggtgcagc tggtggagtc tgggggaggc ttggtacagc ctggggggtc cctgagactc      60
tcctgttcag cctctggatt cacctttacc acctatgcca tgagctgggt ccgccaggct     120
ccagggaggg gctggagtg gtctcatct attagtggta ctggtgttag cacatactac       180
gcagactccg tgaagggccg gttcaccatc tccagagaca attccaagaa tgcgctgtat     240
ctgcaaatga acagcctgac agccgaggac acggccgtat attactgtgc gaaggatagt    300
gggacctatc actggggcca gggaaccctg gtcaccgtct cctca                     345
```

<210> SEQ ID NO 98
<211> LENGTH: 115
<212> TYPE: PRT
<213> ORGANISM: Artificial Sequence
<220> FEATURE:
<223> OTHER INFORMATION: synthetic

<400> SEQUENCE: 98

Glu Val Gln Leu Val Glu Ser Gly Gly Gly Leu Val Gln Pro Gly Gly
1               5                   10                  15

Ser Leu Arg Leu Ser Cys Ser Ala Ser Gly Phe Thr Phe Thr Thr Tyr
            20                  25                  30

Ala Met Ser Trp Val Arg Gln Ala Pro Gly Arg Gly Leu Glu Trp Val
        35                  40                  45

Ser Ser Ile Ser Gly Thr Gly Val Ser Thr Tyr Tyr Ala Asp Ser Val
    50                  55                  60

Lys Gly Arg Phe Thr Ile Ser Arg Asp Asn Ser Lys Asn Ala Leu Tyr
65                  70                  75                  80

Leu Gln Met Asn Ser Leu Thr Ala Glu Asp Thr Ala Val Tyr Tyr Cys
                85                  90                  95

Ala Lys Asp Ser Gly Thr Tyr His Trp Gly Gln Gly Thr Leu Val Thr
            100                 105                 110

Val Ser Ser
        115

<210> SEQ ID NO 99
<211> LENGTH: 24
<212> TYPE: DNA
<213> ORGANISM: Artificial Sequence
<220> FEATURE:
<223> OTHER INFORMATION: synthetic

<400> SEQUENCE: 99

```
ggattcacct ttaccaccta tgcc                                             24
```

<210> SEQ ID NO 100
<211> LENGTH: 8
<212> TYPE: PRT
<213> ORGANISM: Artificial Sequence
<220> FEATURE:
<223> OTHER INFORMATION: synthetic

<400> SEQUENCE: 100

```
Gly Phe Thr Phe Thr Thr Tyr Ala
1               5

<210> SEQ ID NO 101
<211> LENGTH: 24
<212> TYPE: DNA
<213> ORGANISM: Artificial Sequence
<220> FEATURE:
<223> OTHER INFORMATION: synthetic

<400> SEQUENCE: 101
attagtggta ctggtgttag caca                                          24

<210> SEQ ID NO 102
<211> LENGTH: 8
<212> TYPE: PRT
<213> ORGANISM: Artificial Sequence
<220> FEATURE:
<223> OTHER INFORMATION: synthetic

<400> SEQUENCE: 102

Ile Ser Gly Thr Gly Val Ser Thr
1               5

<210> SEQ ID NO 103
<211> LENGTH: 24
<212> TYPE: DNA
<213> ORGANISM: Artificial Sequence
<220> FEATURE:
<223> OTHER INFORMATION: synthetic

<400> SEQUENCE: 103
gcgaaggata gtgggaccta tcac                                          24

<210> SEQ ID NO 104
<211> LENGTH: 8
<212> TYPE: PRT
<213> ORGANISM: Artificial Sequence
<220> FEATURE:
<223> OTHER INFORMATION: synthetic

<400> SEQUENCE: 104

Ala Lys Asp Ser Gly Thr Tyr His
1               5

<210> SEQ ID NO 105
<211> LENGTH: 324
<212> TYPE: DNA
<213> ORGANISM: Artificial Sequence
<220> FEATURE:
<223> OTHER INFORMATION: synthetic

<400> SEQUENCE: 105
gaaattgtgt tgacacagtc tccagccacc ctgtctttgt ctccagggga aagagccacc    60
ctctcctgca gggccagtca gagtgttgac agctacttag cctggtacca acagaaacct   120
ggccaggctc ccagactcct catctatgat gcatccaaca gggccactgg catcccagcc   180
aggttcagtg gcagtgggtc tgggacagac ttcactctca ccatcagcag cctagagtct   240
gaagattttg cagtttatta ctgtcagcag cgtcgcaact ggccgcagtt cactttcggc   300
ggagggacca aggtggagat caaa                                         324

<210> SEQ ID NO 106
<211> LENGTH: 108
```

<212> TYPE: PRT
<213> ORGANISM: Artificial Sequence
<220> FEATURE:
<223> OTHER INFORMATION: synthetic

<400> SEQUENCE: 106

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Asp Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Ser
65                  70                  75                  80

Glu Asp Phe Ala Val Tyr Tyr Cys Gln Gln Arg Arg Asn Trp Pro Gln
                85                  90                  95

Phe Thr Phe Gly Gly Gly Thr Lys Val Glu Ile Lys
            100                 105

<210> SEQ ID NO 107
<211> LENGTH: 18
<212> TYPE: DNA
<213> ORGANISM: Artificial Sequence
<220> FEATURE:
<223> OTHER INFORMATION: synthetic

<400> SEQUENCE: 107
cagagtgttg acagctac                                                      18

<210> SEQ ID NO 108
<211> LENGTH: 6
<212> TYPE: PRT
<213> ORGANISM: Artificial Sequence
<220> FEATURE:
<223> OTHER INFORMATION: synthetic

<400> SEQUENCE: 108

Gln Ser Val Asp Ser Tyr
1               5

<210> SEQ ID NO 109
<211> LENGTH: 9
<212> TYPE: DNA
<213> ORGANISM: Artificial Sequence
<220> FEATURE:
<223> OTHER INFORMATION: synthetic

<400> SEQUENCE: 109 gatgcatcc                                                                 9

<210> SEQ ID NO 110
<211> LENGTH: 3
<212> TYPE: PRT
<213> ORGANISM: Artificial Sequence
<220> FEATURE:
<223> OTHER INFORMATION: synthetic

<400> SEQUENCE: 110

Asp Ala Ser
1

<210> SEQ ID NO 111
<211> LENGTH: 30
<212> TYPE: DNA
<213> ORGANISM: Artificial Sequence
<220> FEATURE:
<223> OTHER INFORMATION: synthetic

<400> SEQUENCE: 111
cagcagcgtc gcaactggcc gcagttcact                    30

<210> SEQ ID NO 112
<211> LENGTH: 10
<212> TYPE: PRT
<213> ORGANISM: Artificial Sequence
<220> FEATURE:
<223> OTHER INFORMATION: synthetic

<400> SEQUENCE: 112

Gln Gln Arg Arg Asn Trp Pro Gln Phe Thr
1               5                   10

<210> SEQ ID NO 113
<211> LENGTH: 360
<212> TYPE: DNA
<213> ORGANISM: Artificial Sequence
<220> FEATURE:
<223> OTHER INFORMATION: synthetic

<400> SEQUENCE: 113
caggtgcagc tggtggagtc tgggggaggc gtggtccagc ctggagagtc cctgagactc      60
tcctgtacag cgtctggatt caccttcagt acctatggca tgcactgggt ccgccacgtt     120
ccaggcaagg gactggagtg ggtggcaatt gtttggtatg atggaagtga taaatcctat     180
gcagcctccg tgaagggccg attcaccatc tccagagaca attccaagaa cacgctgttt     240
ctgcaaatga acagtttgag agccgaggac acggctgtgt attactgtgc gcgacagggg     300
acctactact actacggtat ggacgtctgg ggccaaggga ccacggtcac cgtctcctca     360

<210> SEQ ID NO 114
<211> LENGTH: 120
<212> TYPE: PRT
<213> ORGANISM: Artificial Sequence
<220> FEATURE:
<223> OTHER INFORMATION: synthetic

<400> SEQUENCE: 114

Gln Val Gln Leu Val Glu Ser Gly Gly Gly Val Val Gln Pro Gly Arg
1               5                   10                  15

Ser Leu Arg Leu Ser Cys Thr Ala Ser Gly Phe Thr Phe Ser Thr Tyr
                20                  25                  30

Gly Met His Trp Val Arg His Val Pro Gly Lys Gly Leu Glu Trp Val
            35                  40                  45

Ala Ile Val Trp Tyr Asp Gly Ser Asp Lys Ser Tyr Ala Ala Ser Val
        50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Arg Gln Gly Thr Tyr Tyr Tyr Tyr Gly Met Asp Val Trp Gly Gln
                100                 105                 110

Gly Thr Thr Val Thr Val Ser Ser
            115                 120

<210> SEQ ID NO 115
<211> LENGTH: 24
<212> TYPE: DNA
<213> ORGANISM: Artificial Sequence
<220> FEATURE:
<223> OTHER INFORMATION: synthetic

<400> SEQUENCE: 115
ggattcacct tcagtaccta tggc        24

<210> SEQ ID NO 116
<211> LENGTH: 8
<212> TYPE: PRT
<213> ORGANISM: Artificial Sequence
<220> FEATURE:
<223> OTHER INFORMATION: synthetic

<400> SEQUENCE: 116

Gly Phe Thr Phe Ser Thr Tyr Gly
1               5

<210> SEQ ID NO 117
<211> LENGTH: 24
<212> TYPE: DNA
<213> ORGANISM: Artificial Sequence
<220> FEATURE:
<223> OTHER INFORMATION: synthetic

<400> SEQUENCE: 117
gtttggtatg atggaagtga taaa        24

<210> SEQ ID NO 118
<211> LENGTH: 8
<212> TYPE: PRT
<213> ORGANISM: Artificial Sequence
<220> FEATURE:
<223> OTHER INFORMATION: synthetic

<400> SEQUENCE: 118

Val Trp Tyr Asp Gly Ser Asp Lys
1               5

<210> SEQ ID NO 119
<211> LENGTH: 39
<212> TYPE: DNA
<213> ORGANISM: Artificial Sequence
<220> FEATURE:
<223> OTHER INFORMATION: synthetic

<400> SEQUENCE: 119
gcgcgacagg ggacctacta ctactacggt atggacgtc        39

<210> SEQ ID NO 120
<211> LENGTH: 13
<212> TYPE: PRT
<213> ORGANISM: Artificial Sequence
<220> FEATURE:
<223> OTHER INFORMATION: synthetic

<400> SEQUENCE: 120

Ala Arg Gln Gly Thr Tyr Tyr Tyr Tyr Gly Met Asp Val
1               5                   10

<210> SEQ ID NO 121
<211> LENGTH: 324

<212> TYPE: DNA
<213> ORGANISM: Artificial Sequence
<220> FEATURE:
<223> OTHER INFORMATION: synthetic

<400> SEQUENCE: 121

```
gacatccaga tgacccagtc tccttcctct ctgtctgcat ctgtaggaga cagagtcacc    60
atcacttgcc ggtcaagtca gaccattact aactatttaa attggtatca gcagagaccg   120
gggaaagccc ctaagctcct gatctatgct gcgtccagtt tgcaaagtgg ggtcccatca   180
aggttcagtg gcagtggatc tgggacagat ttcactctca ccatcagcag tctgcaacct   240
gaagattttg caacttacta ctgtcaacag agttacagta cccctccgat caccttcggc   300
caagggacca agctggagat caaa                                          324
```

<210> SEQ ID NO 122
<211> LENGTH: 108
<212> TYPE: PRT
<213> ORGANISM: Artificial Sequence
<220> FEATURE:
<223> OTHER INFORMATION: synthetic

<400> SEQUENCE: 122

```
Asp Ile Gln Met Thr Gln Ser Pro Ser Ser Leu Ser Ala Ser Val Gly
1               5                   10                  15
Asp Arg Val Thr Ile Thr Cys Arg Ser Ser Gln Thr Ile Thr Asn Tyr
            20                  25                  30
Leu Asn Trp Tyr Gln Gln Arg Pro Gly Lys Ala Pro Lys Leu Leu Ile
        35                  40                  45
Tyr Ala Ala Ser Ser Leu Gln Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Ser Tyr Ser Thr Pro Pro
                85                  90                  95
Ile Thr Phe Gly Gln Gly Thr Lys Leu Glu Ile Lys
            100                 105
```

<210> SEQ ID NO 123
<211> LENGTH: 18
<212> TYPE: DNA
<213> ORGANISM: Artificial Sequence
<220> FEATURE:
<223> OTHER INFORMATION: synthetic

<400> SEQUENCE: 123

```
cagaccatta ctaactat                                                  18
```

<210> SEQ ID NO 124
<211> LENGTH: 6
<212> TYPE: PRT
<213> ORGANISM: Artificial Sequence
<220> FEATURE:
<223> OTHER INFORMATION: synthetic

<400> SEQUENCE: 124

```
Gln Thr Ile Thr Asn Tyr
1               5
```

<210> SEQ ID NO 125
<211> LENGTH: 9
<212> TYPE: DNA

```
<213> ORGANISM: Artificial Sequence
<220> FEATURE:
<223> OTHER INFORMATION: synthetic

<400> SEQUENCE: 125 gctgcgtcc                                                              9

<210> SEQ ID NO 126
<211> LENGTH: 3
<212> TYPE: PRT
<213> ORGANISM: Artificial Sequence
<220> FEATURE:
<223> OTHER INFORMATION: synthetic

<400> SEQUENCE: 126

Ala Ala Ser
1

<210> SEQ ID NO 127
<211> LENGTH: 30
<212> TYPE: DNA
<213> ORGANISM: Artificial Sequence
<220> FEATURE:
<223> OTHER INFORMATION: synthetic

<400> SEQUENCE: 127
caacagagtt acagtacccc tccgatcacc                                      30

<210> SEQ ID NO 128
<211> LENGTH: 10
<212> TYPE: PRT
<213> ORGANISM: Artificial Sequence
<220> FEATURE:
<223> OTHER INFORMATION: synthetic

<400> SEQUENCE: 128

Gln Gln Ser Tyr Ser Thr Pro Pro Ile Thr
1               5                   10

<210> SEQ ID NO 129
<211> LENGTH: 360
<212> TYPE: DNA
<213> ORGANISM: Artificial Sequence
<220> FEATURE:
<223> OTHER INFORMATION: synthetic

<400> SEQUENCE: 129
caggtgcagc tggtggagtc tgggggaggc gtggtccagc ctgggaggtc cctgagactc      60
tcctgtgcag cgtctggatt caccttcagt agttatggca tgcactgggt ccgccaggct     120
ccaggcaagg ggctggagtg gttggcaatt atatggtatg atggaactaa taaacagtat     180
gtagactccg tgaagggccg attcaccatc tccagagaca attccaagaa cacgctgtat     240
ctgcaattga acagcctgag agccgaggac acggctgtgt attactgtgc gcgacaggac     300
ttctactact actacggtat ggacgtctgg ggccaaggga ccacggtcac cgtctcctca     360

<210> SEQ ID NO 130
<211> LENGTH: 120
<212> TYPE: PRT
<213> ORGANISM: Artificial Sequence
<220> FEATURE:
<223> OTHER INFORMATION: synthetic

<400> SEQUENCE: 130

Gln Val Gln Leu Val Glu Ser Gly Gly Gly Val Val Gln Pro Gly Arg
```

```
                1               5                   10                  15
Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Leu
            35                  40                  45

Ala Ile Ile Trp Tyr Asp Gly Thr Asn Lys Gln Tyr Val Asp Ser Val
    50                  55                  60

Lys Gly Arg Phe Thr Ile Ser Arg Asp Asn Ser Lys Asn Thr Leu Tyr
65                  70                  75                  80

Leu Gln Leu Asn Ser Leu Arg Ala Glu Asp Thr Ala Val Tyr Tyr Cys
                85                  90                  95

Ala Arg Gln Asp Phe Tyr Tyr Tyr Gly Met Asp Val Trp Gly Gln
                100                 105                 110

Gly Thr Thr Val Thr Val Ser Ser
            115                 120
```

<210> SEQ ID NO 131
<211> LENGTH: 24
<212> TYPE: DNA
<213> ORGANISM: Artificial Sequence
<220> FEATURE:
<223> OTHER INFORMATION: synthetic

<400> SEQUENCE: 131
ggattcacct tcagtagtta tggc                                      24

<210> SEQ ID NO 132
<211> LENGTH: 8
<212> TYPE: PRT
<213> ORGANISM: Artificial Sequence
<220> FEATURE:
<223> OTHER INFORMATION: synthetic

<400> SEQUENCE: 132

Gly Phe Thr Phe Ser Ser Tyr Gly
1               5

<210> SEQ ID NO 133
<211> LENGTH: 24
<212> TYPE: DNA
<213> ORGANISM: Artificial Sequence
<220> FEATURE:
<223> OTHER INFORMATION: synthetic

<400> SEQUENCE: 133
atatggtatg atggaactaa taaa                                      24

<210> SEQ ID NO 134
<211> LENGTH: 8
<212> TYPE: PRT
<213> ORGANISM: Artificial Sequence
<220> FEATURE:
<223> OTHER INFORMATION: synthetic

<400> SEQUENCE: 134

Ile Trp Tyr Asp Gly Thr Asn Lys
1               5

<210> SEQ ID NO 135
<211> LENGTH: 39
<212> TYPE: DNA
<213> ORGANISM: Artificial Sequence
<220> FEATURE:

<223> OTHER INFORMATION: synthetic

<400> SEQUENCE: 135
gcgcgacagg acttctacta ctactacggt atggacgtc                              39

<210> SEQ ID NO 136
<211> LENGTH: 13
<212> TYPE: PRT
<213> ORGANISM: Artificial Sequence
<220> FEATURE:
<223> OTHER INFORMATION: synthetic

<400> SEQUENCE: 136

Ala Arg Gln Asp Phe Tyr Tyr Tyr Tyr Gly Met Asp Val
1               5                   10

<210> SEQ ID NO 137
<211> LENGTH: 324
<212> TYPE: DNA
<213> ORGANISM: Artificial Sequence
<220> FEATURE:
<223> OTHER INFORMATION: synthetic

<400> SEQUENCE: 137
gacatccaga tgacccagtc tccatcctcc ctgtctgcat ctgtaggaga cagagtcacc        60
atcacttgcc gggcaagtca gagcattagc agctatttaa actggtatca gcagaaacca      120
gggaaagccc ctaaggtcct gatctatgct gcatccagtt tgcaaagtgg ggtcccatca      180
aggttcagtg gcagtggatc tgggacagat ttcactctca ccatcagcag tctgcaacct      240
gaagattttg caacttacta ctgtcaacag agttacagta cccctccgat caccttcggc      300
caagggacca gctggagat caaa                                              324

<210> SEQ ID NO 138
<211> LENGTH: 108
<212> TYPE: PRT
<213> ORGANISM: Artificial Sequence
<220> FEATURE:
<223> OTHER INFORMATION: synthetic

<400> SEQUENCE: 138

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Val Leu Ile
            35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Lys Leu Glu Ile Lys
            100                 105

<210> SEQ ID NO 139
<211> LENGTH: 18
<212> TYPE: DNA
<213> ORGANISM: Artificial Sequence
<220> FEATURE:
<223> OTHER INFORMATION: synthetic

```
<400> SEQUENCE: 139
cagagcatta gcagctat                                                      18

<210> SEQ ID NO 140
<211> LENGTH: 6
<212> TYPE: PRT
<213> ORGANISM: Artificial Sequence
<220> FEATURE:
<223> OTHER INFORMATION: synthetic

<400> SEQUENCE: 140

Gln Ser Ile Ser Ser Tyr
1               5

<210> SEQ ID NO 141
<211> LENGTH: 9
<212> TYPE: DNA
<213> ORGANISM: Artificial Sequence
<220> FEATURE:
<223> OTHER INFORMATION: synthetic

<400> SEQUENCE: 141 gctgcatcc                                                                 9

<210> SEQ ID NO 142
<211> LENGTH: 3
<212> TYPE: PRT
<213> ORGANISM: Artificial Sequence
<220> FEATURE:
<223> OTHER INFORMATION: synthetic

<400> SEQUENCE: 142

Ala Ala Ser
1

<210> SEQ ID NO 143
<211> LENGTH: 30
<212> TYPE: DNA
<213> ORGANISM: Artificial Sequence
<220> FEATURE:
<223> OTHER INFORMATION: synthetic

<400> SEQUENCE: 143
caacagagtt acagtacccc tccgatcacc                                         30

<210> SEQ ID NO 144
<211> LENGTH: 10
<212> TYPE: PRT
<213> ORGANISM: Artificial Sequence
<220> FEATURE:
<223> OTHER INFORMATION: synthetic

<400> SEQUENCE: 144

Gln Gln Ser Tyr Ser Thr Pro Pro Ile Thr
1               5                   10

<210> SEQ ID NO 145
<211> LENGTH: 360
<212> TYPE: DNA
<213> ORGANISM: Artificial Sequence
<220> FEATURE:
<223> OTHER INFORMATION: synthetic

<400> SEQUENCE: 145
caggtgcagc tggtggagtc tgggggaggc gtggtccagc ctggggaggtc cctgagactc       60
```

```
tcctgtgcag cgtctggatt caccttcagt agctatggca tgcactgggt ccgccaggct    120
ccaggcaagg ggctggagtg ggtggcactt atatggtatg atggaagtga taaacactat    180
gtagactcca tgaagggccg attcaccatc tccagagaca actccaagaa cacgctgtat    240
ctgcaaatga acagcctgag agccgatgac acggctgtgt attactgtgc gagacaagct    300
tactacttct actacggtat ggacgtctgg ggccaaggga ccacggtcac cgtctcctca    360
```

<210> SEQ ID NO 146
<211> LENGTH: 120
<212> TYPE: PRT
<213> ORGANISM: Artificial Sequence
<220> FEATURE:
<223> OTHER INFORMATION: synthetic

<400> SEQUENCE: 146

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Leu Ile Trp Tyr Asp Gly Ser Asp Lys His Tyr Val Asp Ser Met
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Asp Asp Thr Ala Val Tyr Tyr Cys
                85                  90                  95

Ala Arg Gln Ala Tyr Tyr Phe Tyr Tyr Gly Met Asp Val Trp Gly Gln
            100                 105                 110

Gly Thr Thr Val Thr Val Ser Ser
        115                 120
```

<210> SEQ ID NO 147
<211> LENGTH: 24
<212> TYPE: DNA
<213> ORGANISM: Artificial Sequence
<220> FEATURE:
<223> OTHER INFORMATION: synthetic

<400> SEQUENCE: 147

```
ggattcacct tcagtagcta tggc                                            24
```

<210> SEQ ID NO 148
<211> LENGTH: 8
<212> TYPE: PRT
<213> ORGANISM: Artificial Sequence
<220> FEATURE:
<223> OTHER INFORMATION: synthetic

<400> SEQUENCE: 148

```
Gly Phe Thr Phe Ser Ser Tyr Gly
1               5
```

<210> SEQ ID NO 149
<211> LENGTH: 24
<212> TYPE: DNA
<213> ORGANISM: Artificial Sequence
<220> FEATURE:
<223> OTHER INFORMATION: synthetic

<400> SEQUENCE: 149

```
atatggtatg atggaagtga taaa                                            24
```

<210> SEQ ID NO 150
<211> LENGTH: 8
<212> TYPE: PRT
<213> ORGANISM: Artificial Sequence
<220> FEATURE:
<223> OTHER INFORMATION: synthetic

<400> SEQUENCE: 150

```
Ile Trp Tyr Asp Gly Ser Asp Lys
1               5
```

<210> SEQ ID NO 151
<211> LENGTH: 39
<212> TYPE: DNA
<213> ORGANISM: Artificial Sequence
<220> FEATURE:
<223> OTHER INFORMATION: synthetic

<400> SEQUENCE: 151

```
gcgagacaag cttactactt ctactacggt atggacgtc                            39
```

<210> SEQ ID NO 152
<211> LENGTH: 13
<212> TYPE: PRT
<213> ORGANISM: Artificial Sequence
<220> FEATURE:
<223> OTHER INFORMATION: synthetic

<400> SEQUENCE: 152

```
Ala Arg Gln Ala Tyr Tyr Phe Tyr Tyr Gly Met Asp Val
1               5                   10
```

<210> SEQ ID NO 153
<211> LENGTH: 324
<212> TYPE: DNA
<213> ORGANISM: Artificial Sequence
<220> FEATURE:
<223> OTHER INFORMATION: synthetic

<400> SEQUENCE: 153

```
gacatccaga tgacccagtc tccatcctcc ctgtctgcat ctgtaggaga cagagtcacc     60
atcacttgcc ggtcaagtca gagcattagc agctatttaa attggtatca gcagaaacca   120
gggaaagccc ctaagctcct gatctatgct gcatccagtt tgcaaagtgg ggtcccatca   180
aggttcagtg gcagtggatc tgggacagat ttcactctca ccatcagcag tctgcaacct   240
gaagattttg caacttacta ctgtcaacag agttacagta cccctccgat caccttcggc   300
caagggacca gctggagat caaa                                           324
```

<210> SEQ ID NO 154
<211> LENGTH: 108
<212> TYPE: PRT
<213> ORGANISM: Artificial Sequence
<220> FEATURE:
<223> OTHER INFORMATION: synthetic

<400> SEQUENCE: 154

```
Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Ile Ser Ser Tyr
            20                  25                  30
```

Leu Asn Trp Tyr Gln Gln Lys Pro Gly Lys Ala Pro Lys Leu Leu Ile
                35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Lys Leu Glu Ile Lys
            100                 105

<210> SEQ ID NO 155
<211> LENGTH: 18
<212> TYPE: DNA
<213> ORGANISM: Artificial Sequence
<220> FEATURE:
<223> OTHER INFORMATION: synthetic

<400> SEQUENCE: 155
cagagcatta gcagctat                                                 18

<210> SEQ ID NO 156
<211> LENGTH: 6
<212> TYPE: PRT
<213> ORGANISM: Artificial Sequence
<220> FEATURE:
<223> OTHER INFORMATION: synthetic

<400> SEQUENCE: 156

Gln Ser Ile Ser Ser Tyr
1               5

<210> SEQ ID NO 157
<211> LENGTH: 9
<212> TYPE: DNA
<213> ORGANISM: Artificial Sequence
<220> FEATURE:
<223> OTHER INFORMATION: synthetic

<400> SEQUENCE: 157 gctgcatcc                                                            9

<210> SEQ ID NO 158
<211> LENGTH: 3
<212> TYPE: PRT
<213> ORGANISM: Artificial Sequence
<220> FEATURE:
<223> OTHER INFORMATION: synthetic

<400> SEQUENCE: 158

Ala Ala Ser
1

<210> SEQ ID NO 159
<211> LENGTH: 30
<212> TYPE: DNA
<213> ORGANISM: Artificial Sequence
<220> FEATURE:
<223> OTHER INFORMATION: synthetic

<400> SEQUENCE: 159
caacagagtt acagtacccc tccgatcacc                                    30

<210> SEQ ID NO 160

```
<211> LENGTH: 10
<212> TYPE: PRT
<213> ORGANISM: Artificial Sequence
<220> FEATURE:
<223> OTHER INFORMATION: synthetic

<400> SEQUENCE: 160

Gln Gln Ser Tyr Ser Thr Pro Pro Ile Thr
1               5                   10

<210> SEQ ID NO 161
<211> LENGTH: 354
<212> TYPE: DNA
<213> ORGANISM: Artificial Sequence
<220> FEATURE:
<223> OTHER INFORMATION: synthetic

<400> SEQUENCE: 161
caggttcagc tggtgcagtc tggagctgaa gtgaagaggc ctggggcctc agtgaaggtc    60
tcctgtaagg cttctgatta cacctttacc gactatggta tcagctgggt gcgacaggcc   120
cctggacaag gacttgagtg gatgggatgg ttcaatactt acaatggtaa cacaaactac   180
gcacagaagt tccagggcag aatcaccatg accacagaca catccacgag cacagcctac   240
atggaactga ggagcctaag atctgacgac acggccatat attactgtgc gagagattgg   300
ggcctccact actttgaaaa ctggggccag ggaaccctgg tcaccgtctc ctca          354

<210> SEQ ID NO 162
<211> LENGTH: 118
<212> TYPE: PRT
<213> ORGANISM: Artificial Sequence
<220> FEATURE:
<223> OTHER INFORMATION: synthetic

<400> SEQUENCE: 162

Gln Val Gln Leu Val Gln Ser Gly Ala Glu Val Lys Arg Pro Gly Ala
1               5                   10                  15

Ser Val Lys Val Ser Cys Lys Ala Ser Asp Tyr Thr Phe Thr Asp Tyr
            20                  25                  30

Gly Ile Ser Trp Val Arg Gln Ala Pro Gly Gln Gly Leu Glu Trp Met
        35                  40                  45

Gly Trp Phe Asn Thr Tyr Asn Gly Asn Thr Asn Tyr Ala Gln Lys Phe
    50                  55                  60

Gln Gly Arg Ile Thr Met Thr Thr Asp Thr Ser Thr Ser Thr Ala Tyr
65                  70                  75                  80

Met Glu Leu Arg Ser Leu Arg Ser Asp Asp Thr Ala Ile Tyr Tyr Cys
                85                  90                  95

Ala Arg Asp Trp Gly Leu His Tyr Phe Glu Asn Trp Gly Gln Gly Thr
            100                 105                 110

Leu Val Thr Val Ser Ser
        115

<210> SEQ ID NO 163
<211> LENGTH: 24
<212> TYPE: DNA
<213> ORGANISM: Artificial Sequence
<220> FEATURE:
<223> OTHER INFORMATION: synthetic

<400> SEQUENCE: 163
gattacacct ttaccgacta tggt                                            24
```

<210> SEQ ID NO 164
<211> LENGTH: 8
<212> TYPE: PRT
<213> ORGANISM: Artificial Sequence
<220> FEATURE:
<223> OTHER INFORMATION: synthetic

<400> SEQUENCE: 164

Asp Tyr Thr Phe Thr Asp Tyr Gly
1               5

<210> SEQ ID NO 165
<211> LENGTH: 24
<212> TYPE: DNA
<213> ORGANISM: Artificial Sequence
<220> FEATURE:
<223> OTHER INFORMATION: synthetic

<400> SEQUENCE: 165
ttcaatactt acaatggtaa caca                                          24

<210> SEQ ID NO 166
<211> LENGTH: 8
<212> TYPE: PRT
<213> ORGANISM: Artificial Sequence
<220> FEATURE:
<223> OTHER INFORMATION: synthetic

<400> SEQUENCE: 166

Phe Asn Thr Tyr Asn Gly Asn Thr
1               5

<210> SEQ ID NO 167
<211> LENGTH: 33
<212> TYPE: DNA
<213> ORGANISM: Artificial Sequence
<220> FEATURE:
<223> OTHER INFORMATION: synthetic

<400> SEQUENCE: 167
gcgagagatt ggggcctcca ctactttgaa aac                                33

<210> SEQ ID NO 168
<211> LENGTH: 11
<212> TYPE: PRT
<213> ORGANISM: Artificial Sequence
<220> FEATURE:
<223> OTHER INFORMATION: synthetic

<400> SEQUENCE: 168

Ala Arg Asp Trp Gly Leu His Tyr Phe Glu Asn
1               5                   10

<210> SEQ ID NO 169
<211> LENGTH: 324
<212> TYPE: DNA
<213> ORGANISM: Artificial Sequence
<220> FEATURE:
<223> OTHER INFORMATION: synthetic

<400> SEQUENCE: 169
gaaattgtgt tgacgcagtc tccaggcacc ctgtctttgt ctccagggga aagagccacc    60
ctctcctgca gggccagtca gagtgttcgc aacagctact tagcctggta ccaacagaaa   120
cctggccagg ctcccaggct cctcatctat ggtgcatcca gcagggacac tggcatccca   180

```
gacaggttca gtggcagtgg gtctgggaca gacttcactc tcaccatcag cagactggag    240
cctgaagatt ttgcagtgta ttactgtcag cagtatggtc gctcacccttg gacgttcggc   300 caagggacca aggtggaaat caaa                                           324
```

<210> SEQ ID NO 170
<211> LENGTH: 108
<212> TYPE: PRT
<213> ORGANISM: Artificial Sequence
<220> FEATURE:
<223> OTHER INFORMATION: synthetic

<400> SEQUENCE: 170

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Arg Asn Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Asp Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Arg Ser Pro
                85                  90                  95

Trp Thr Phe Gly Gln Gly Thr Lys Val Glu Ile Lys
            100                 105
```

<210> SEQ ID NO 171
<211> LENGTH: 21
<212> TYPE: DNA
<213> ORGANISM: Artificial Sequence
<220> FEATURE:
<223> OTHER INFORMATION: synthetic

<400> SEQUENCE: 171

```
cagagtgttc gcaacagcta c                                              21
```

<210> SEQ ID NO 172
<211> LENGTH: 7
<212> TYPE: PRT
<213> ORGANISM: Artificial Sequence
<220> FEATURE:
<223> OTHER INFORMATION: synthetic

<400> SEQUENCE: 172

```
Gln Ser Val Arg Asn Ser Tyr
1               5
```

<210> SEQ ID NO 173
<211> LENGTH: 9
<212> TYPE: DNA
<213> ORGANISM: Artificial Sequence
<220> FEATURE:
<223> OTHER INFORMATION: synthetic

<400> SEQUENCE: 173

```
ggtgcatcc                                                            9
```

<210> SEQ ID NO 174
<211> LENGTH: 3
<212> TYPE: PRT
<213> ORGANISM: Artificial Sequence
<220> FEATURE:
<223> OTHER INFORMATION: synthetic

<400> SEQUENCE: 174

Gly Ala Ser
1

<210> SEQ ID NO 175
<211> LENGTH: 27
<212> TYPE: DNA
<213> ORGANISM: Artificial Sequence
<220> FEATURE:
<223> OTHER INFORMATION: synthetic

<400> SEQUENCE: 175
cagcagtatg gtcgctcacc ttggacg        27

<210> SEQ ID NO 176
<211> LENGTH: 9
<212> TYPE: PRT
<213> ORGANISM: Artificial Sequence
<220> FEATURE:
<223> OTHER INFORMATION: synthetic

<400> SEQUENCE: 176

Gln Gln Tyr Gly Arg Ser Pro Trp Thr
1               5

<210> SEQ ID NO 177
<211> LENGTH: 366
<212> TYPE: DNA
<213> ORGANISM: Artificial Sequence
<220> FEATURE:
<223> OTHER INFORMATION: synthetic

<400> SEQUENCE: 177
gaagtgcagc tggtggagtc ggggggaggc ttggttcagc ctggcaggtc cctgagactc        60
tcctgtgcag cctctggatt cacctttgat gattatgcca tacactgggt ccgtcaagct       120
ccagggaagg gcctggagtg ggtctcaggt attagttgga atagtggtta cctaggctat       180
gcggactctg tgaagggccg attcaccatc tccagagaca cgccaagaa ctccctgtat        240 ctgcaaatga acagtctgag agctgaggac acggccttct attactgtgc aaaagatgtg       300
gcctggggct cggtgcgcca tgtctttgaa atctggggcc aagggacaat ggtcaccgtc       360
tcttca                                                                  366

<210> SEQ ID NO 178
<211> LENGTH: 122
<212> TYPE: PRT
<213> ORGANISM: Artificial Sequence
<220> FEATURE:
<223> OTHER INFORMATION: synthetic

<400> SEQUENCE: 178

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Ile His Trp Val Arg Gln Ala Pro Gly Lys Gly Leu Glu Trp Val
        35                  40                  45

Ser Gly Ile Ser Trp Asn Ser Gly Tyr Leu Gly Tyr Ala Asp Ser Val
    50                  55                  60

```
Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Phe Tyr Tyr Cys
                 85                  90                  95

Ala Lys Asp Val Ala Trp Gly Ser Val Arg His Val Phe Glu Ile Trp
            100                 105                 110

Gly Gln Gly Thr Met Val Thr Val Ser Ser
            115                 120
```

```
<210> SEQ ID NO 179
<211> LENGTH: 24
<212> TYPE: DNA
<213> ORGANISM: Artificial Sequence
<220> FEATURE:
<223> OTHER INFORMATION: synthetic

<400> SEQUENCE: 179
ggattcacct ttgatgatta tgcc                                          24
```

```
<210> SEQ ID NO 180
<211> LENGTH: 8
<212> TYPE: PRT
<213> ORGANISM: Artificial Sequence
<220> FEATURE:
<223> OTHER INFORMATION: synthetic

<400> SEQUENCE: 180

Gly Phe Thr Phe Asp Asp Tyr Ala
1               5
```

```
<210> SEQ ID NO 181
<211> LENGTH: 24
<212> TYPE: DNA
<213> ORGANISM: Artificial Sequence
<220> FEATURE:
<223> OTHER INFORMATION: synthetic

<400> SEQUENCE: 181
attagttgga atagtggtta ccta                                          24
```

```
<210> SEQ ID NO 182
<211> LENGTH: 8
<212> TYPE: PRT
<213> ORGANISM: Artificial Sequence
<220> FEATURE:
<223> OTHER INFORMATION: synthetic

<400> SEQUENCE: 182

Ile Ser Trp Asn Ser Gly Tyr Leu
1               5
```

```
<210> SEQ ID NO 183
<211> LENGTH: 45
<212> TYPE: DNA
<213> ORGANISM: Artificial Sequence
<220> FEATURE:
<223> OTHER INFORMATION: synthetic

<400> SEQUENCE: 183
gcaaaagatg tggcctgggg ctcggtgcgc catgtctttg aaatc                   45
```

```
<210> SEQ ID NO 184
<211> LENGTH: 15
<212> TYPE: PRT
<213> ORGANISM: Artificial Sequence
```

<220> FEATURE:
<223> OTHER INFORMATION: synthetic

<400> SEQUENCE: 184

Ala Lys Asp Val Ala Trp Gly Ser Val Arg His Val Phe Glu Ile
1               5                   10                  15

<210> SEQ ID NO 185
<211> LENGTH: 324
<212> TYPE: DNA
<213> ORGANISM: Artificial Sequence
<220> FEATURE:
<223> OTHER INFORMATION: synthetic

<400> SEQUENCE: 185
gaaattgtgt tgacgcagtc tccaggcacc ctgtctttgt ctccaggaga aagagccacc      60
ctctcctgca gggccagtca aactattacc ggcaaccagt tagcctggta ccagcagaaa     120
cctggccagg ctcccaggct cctcatctat tttacatcca gcagggccac tggcatccca     180
gacaggttca gtggcagtgg gtctgggaca gacttctctc tcaccatcag cagactggag     240
cctgaagatt ttgcagtgta tttctgtcag cagtttggtt actcaccttg acgttcggc     300 caagggacca aggtggaaat caaa                                            324

<210> SEQ ID NO 186
<211> LENGTH: 108
<212> TYPE: PRT
<213> ORGANISM: Artificial Sequence
<220> FEATURE:
<223> OTHER INFORMATION: synthetic

<400> SEQUENCE: 186

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Thr Ile Thr Gly Asn
            20                  25                  30

Gln Leu Ala Trp Tyr Gln Gln Lys Pro Gly Gln Ala Pro Arg Leu Leu
        35                  40                  45

Ile Tyr Phe Thr Ser Ser Arg Ala Thr Gly Ile Pro Asp Arg Phe Ser
    50                  55                  60

Gly Ser Gly Ser Gly Thr Asp Phe Ser Leu Thr Ile Ser Arg Leu Glu
65                  70                  75                  80

Pro Glu Asp Phe Ala Val Tyr Phe Cys Gln Gln Phe Gly Tyr Ser Pro
                85                  90                  95

Trp Thr Phe Gly Gln Gly Thr Lys Val Glu Ile Lys
            100                 105

<210> SEQ ID NO 187
<211> LENGTH: 21
<212> TYPE: DNA
<213> ORGANISM: Artificial Sequence
<220> FEATURE:
<223> OTHER INFORMATION: synthetic

<400> SEQUENCE: 187
caaactatta ccggcaacca g                                                21

<210> SEQ ID NO 188
<211> LENGTH: 7
<212> TYPE: PRT
<213> ORGANISM: Artificial Sequence
<220> FEATURE:

<223> OTHER INFORMATION: synthetic

<400> SEQUENCE: 188

Gln Thr Ile Thr Gly Asn Gln
1               5

<210> SEQ ID NO 189
<211> LENGTH: 9
<212> TYPE: DNA
<213> ORGANISM: Artificial Sequence
<220> FEATURE:
<223> OTHER INFORMATION: synthetic

<400> SEQUENCE: 189 tttacatcc                                                              9

<210> SEQ ID NO 190
<211> LENGTH: 3
<212> TYPE: PRT
<213> ORGANISM: Artificial Sequence
<220> FEATURE:
<223> OTHER INFORMATION: synthetic

<400> SEQUENCE: 190

Phe Thr Ser
1

<210> SEQ ID NO 191
<211> LENGTH: 27
<212> TYPE: DNA
<213> ORGANISM: Artificial Sequence
<220> FEATURE:
<223> OTHER INFORMATION: synthetic

<400> SEQUENCE: 191
cagcagtttg gttactcacc ttggacg                                          27

<210> SEQ ID NO 192
<211> LENGTH: 9
<212> TYPE: PRT
<213> ORGANISM: Artificial Sequence
<220> FEATURE:
<223> OTHER INFORMATION: synthetic

<400> SEQUENCE: 192

Gln Gln Phe Gly Tyr Ser Pro Trp Thr
1               5

<210> SEQ ID NO 193
<211> LENGTH: 372
<212> TYPE: DNA
<213> ORGANISM: Artificial Sequence
<220> FEATURE:
<223> OTHER INFORMATION: synthetic

<400> SEQUENCE: 193
caggtgcagc tgcaggagtc gggcccagga ctggtgcagc cttcacagac cctgtccctc      60
acctgcactg tctctggtgg ctccatcacc agtggtggtt acttctggac ctggatccgc     120
cagcacccag ggaggggcct ggagtggctt gggaacatct ttaacagcgg ggacacctac     180
tactacccgt ccctcaagag tcaaattgcc atatcagtag acacgtctaa gaaccagttc     240
tccctgaagc tgacctctgt gactgccgcg gacacggccg tgtattactg tgcgagaggg     300
gtcctttact acgattttg gagtggttat attgactact ggggcctggg aaccctggtc     360
accgtctcct ca 372

<210> SEQ ID NO 194
<211> LENGTH: 124
<212> TYPE: PRT
<213> ORGANISM: Artificial Sequence
<220> FEATURE:
<223> OTHER INFORMATION: synthetic

<400> SEQUENCE: 194

Gln Val Gln Leu Gln Glu Ser Gly Pro Gly Leu Val Gln Pro Ser Gln
1               5                   10                  15

Thr Leu Ser Leu Thr Cys Thr Val Ser Gly Gly Ser Ile Thr Ser Gly
            20                  25                  30

Gly Tyr Phe Trp Thr Trp Ile Arg Gln His Pro Gly Arg Gly Leu Glu
        35                  40                  45

Trp Leu Gly Asn Ile Phe Asn Ser Gly Asp Thr Tyr Tyr Tyr Pro Ser
    50                  55                  60

Leu Lys Ser Gln Ile Ala Ile Ser Val Asp Thr Ser Lys Asn Gln Phe
65                  70                  75                  80

Ser Leu Lys Leu Thr Ser Val Thr Ala Ala Asp Thr Ala Val Tyr Tyr
                85                  90                  95

Cys Ala Arg Gly Val Leu Tyr Tyr Asp Phe Trp Ser Gly Tyr Ile Asp
            100                 105                 110

Tyr Trp Gly Leu Gly Thr Leu Val Thr Val Ser Ser
        115                 120

<210> SEQ ID NO 195
<211> LENGTH: 30
<212> TYPE: DNA
<213> ORGANISM: Artificial Sequence
<220> FEATURE:
<223> OTHER INFORMATION: synthetic

<400> SEQUENCE: 195
ggtggctcca tcaccagtgg tggttacttc 30

<210> SEQ ID NO 196
<211> LENGTH: 10
<212> TYPE: PRT
<213> ORGANISM: Artificial Sequence
<220> FEATURE:
<223> OTHER INFORMATION: synthetic

<400> SEQUENCE: 196

Gly Gly Ser Ile Thr Ser Gly Gly Tyr Phe
1               5                   10

<210> SEQ ID NO 197
<211> LENGTH: 21
<212> TYPE: DNA
<213> ORGANISM: Artificial Sequence
<220> FEATURE:
<223> OTHER INFORMATION: synthetic

<400> SEQUENCE: 197
atctttaaca gcggggacac c 21

<210> SEQ ID NO 198
<211> LENGTH: 7
<212> TYPE: PRT
<213> ORGANISM: Artificial Sequence
<220> FEATURE:

<223> OTHER INFORMATION: synthetic

<400> SEQUENCE: 198

Ile Phe Asn Ser Gly Asp Thr
1               5

<210> SEQ ID NO 199
<211> LENGTH: 48
<212> TYPE: DNA
<213> ORGANISM: Artificial Sequence
<220> FEATURE:
<223> OTHER INFORMATION: synthetic

<400> SEQUENCE: 199
gcgagagggg tcctttacta cgattttggg agtggttata ttgactac        48

<210> SEQ ID NO 200
<211> LENGTH: 16
<212> TYPE: PRT
<213> ORGANISM: Artificial Sequence
<220> FEATURE:
<223> OTHER INFORMATION: synthetic

<400> SEQUENCE: 200

Ala Arg Gly Val Leu Tyr Tyr Asp Phe Trp Ser Gly Tyr Ile Asp Tyr
1               5                   10                  15

<210> SEQ ID NO 201
<211> LENGTH: 324
<212> TYPE: DNA
<213> ORGANISM: Artificial Sequence
<220> FEATURE:
<223> OTHER INFORMATION: synthetic

<400> SEQUENCE: 201
gaaattgtgt tgacgcagtc tccaggcacc ctgtctttgt ctccagggga aagagccacc        60
ctctcctgca gggccagtca gagtgttagc agcatctact tagcctggta ccagcagaaa       120
cctggccagg ctcccaggct cctcatctat ggtgcgtcca gcagggccac tggcatccca       180
gacaggttca gtggcagtgg gtctgggaca gacttcactc tcataatcag cagactggag       240
cctgaagatt ttgcagtgta ttactgtcag cagtatggta gttcaccttg gacgttcggc       300
caagggacca aggtggaaat caaa                                              324

<210> SEQ ID NO 202
<211> LENGTH: 108
<212> TYPE: PRT
<213> ORGANISM: Artificial Sequence
<220> FEATURE:
<223> OTHER INFORMATION: synthetic

<400> SEQUENCE: 202

Glu Ile Val Leu Thr Gln Ser Pro Gly Thr Leu Ser Leu Ser Pro Gly
1               5                   10                  15
Glu Arg Ala Thr Leu Ser Cys Arg Ala Ser Gln Ser Val Ser Ser Ile
                20                  25                  30
Tyr Leu Ala Trp Tyr Gln Gln Lys Pro Gly Gln Ala Pro Arg Leu Leu
            35                  40                  45
Ile Tyr Gly Ala Ser Ser Arg Ala Thr Gly Ile Pro Asp Arg Phe Ser
        50                  55                  60
Gly Ser Gly Ser Gly Thr Asp Phe Thr Leu Ile Ile Ser Arg Leu Glu
65                  70                  75                  80

Pro Glu Asp Phe Ala Val Tyr Tyr Cys Gln Gln Tyr Gly Ser Ser Pro
            85                  90                  95

Trp Thr Phe Gly Gln Gly Thr Lys Val Glu Ile Lys
            100                 105

<210> SEQ ID NO 203
<211> LENGTH: 21
<212> TYPE: DNA
<213> ORGANISM: Artificial Sequence
<220> FEATURE:
<223> OTHER INFORMATION: synthetic

<400> SEQUENCE: 203
cagagtgtta gcagcatcta c                                              21

<210> SEQ ID NO 204
<211> LENGTH: 7
<212> TYPE: PRT
<213> ORGANISM: Artificial Sequence
<220> FEATURE:
<223> OTHER INFORMATION: synthetic

<400> SEQUENCE: 204

Gln Ser Val Ser Ser Ile Tyr
1               5

<210> SEQ ID NO 205
<211> LENGTH: 9
<212> TYPE: DNA
<213> ORGANISM: Artificial Sequence
<220> FEATURE:
<223> OTHER INFORMATION: synthetic

<400> SEQUENCE: 205 ggtgcgtcc                                                            9

<210> SEQ ID NO 206
<211> LENGTH: 3
<212> TYPE: PRT
<213> ORGANISM: Artificial Sequence
<220> FEATURE:
<223> OTHER INFORMATION: synthetic

<400> SEQUENCE: 206

Gly Ala Ser
1

<210> SEQ ID NO 207
<211> LENGTH: 27
<212> TYPE: DNA
<213> ORGANISM: Artificial Sequence
<220> FEATURE:
<223> OTHER INFORMATION: synthetic

<400> SEQUENCE: 207
cagcagtatg gtagttcacc ttggacg                                        27

<210> SEQ ID NO 208
<211> LENGTH: 9
<212> TYPE: PRT
<213> ORGANISM: Artificial Sequence
<220> FEATURE:
<223> OTHER INFORMATION: synthetic

<400> SEQUENCE: 208

Gln Gln Tyr Gly Ser Ser Pro Trp Thr

<210> SEQ ID NO 209
<211> LENGTH: 372
<212> TYPE: DNA
<213> ORGANISM: Artificial Sequence
<220> FEATURE:
<223> OTHER INFORMATION: synthetic

<400> SEQUENCE: 209

```
cagctgcagc tgcaggagtc gggcccagga ctggtgaagc cttcggagac cctgtccctc      60
acctgcactg tctctggtga ctccatcagc agtagtaatt acttctgggg ctggatccgc     120
cagcccccag ggaagggcct ggagtggatt gggaatatct attatagtgg agacacctac     180
tacaacccgt ccctcaagag tcgagtcacc atgtccgttg acacgtccaa gaaacagttc     240
tccctgaagc tgaggtctgt gaccgccgca gacacggctg tatattactg tgcgagaggg     300
aggccttatt acgattttg gagtggttat tttgactact ggggccaggg aaccctggtc     360
accgtctcct ca                                                        372
```

<210> SEQ ID NO 210
<211> LENGTH: 124
<212> TYPE: PRT
<213> ORGANISM: Artificial Sequence
<220> FEATURE:
<223> OTHER INFORMATION: synthetic

<400> SEQUENCE: 210

Gln Leu Gln Leu Gln Glu Ser Gly Pro Gly Leu Val Lys Pro Ser Glu
1               5                   10                  15
Thr Leu Ser Leu Thr Cys Thr Val Ser Gly Asp Ser Ile Ser Ser Ser
            20                  25                  30
Asn Tyr Phe Trp Gly Trp Ile Arg Gln Pro Pro Gly Lys Gly Leu Glu
        35                  40                  45
Trp Ile Gly Asn Ile Tyr Tyr Ser Gly Asp Thr Tyr Tyr Asn Pro Ser
    50                  55                  60
Leu Lys Ser Arg Val Thr Met Ser Val Asp Thr Ser Lys Lys Gln Phe
65                  70                  75                  80
Ser Leu Lys Leu Arg Ser Val Thr Ala Ala Asp Thr Ala Val Tyr Tyr
                85                  90                  95
Cys Ala Arg Gly Arg Pro Tyr Tyr Asp Phe Trp Ser Gly Tyr Phe Asp
            100                 105                 110
Tyr Trp Gly Gln Gly Thr Leu Val Thr Val Ser Ser
        115                 120

<210> SEQ ID NO 211
<211> LENGTH: 30
<212> TYPE: DNA
<213> ORGANISM: Artificial Sequence
<220> FEATURE:
<223> OTHER INFORMATION: synthetic

<400> SEQUENCE: 211
ggtgactcca tcagcagtag taattacttc                                       30

<210> SEQ ID NO 212
<211> LENGTH: 10
<212> TYPE: PRT
<213> ORGANISM: Artificial Sequence
<220> FEATURE:
<223> OTHER INFORMATION: synthetic

<400> SEQUENCE: 212

Gly Asp Ser Ile Ser Ser Ser Asn Tyr Phe
1               5                   10

<210> SEQ ID NO 213
<211> LENGTH: 21
<212> TYPE: DNA
<213> ORGANISM: Artificial Sequence
<220> FEATURE:
<223> OTHER INFORMATION: synthetic

<400> SEQUENCE: 213
atctattata gtggagacac c                                            21

<210> SEQ ID NO 214
<211> LENGTH: 7
<212> TYPE: PRT
<213> ORGANISM: Artificial Sequence
<220> FEATURE:
<223> OTHER INFORMATION: synthetic

<400> SEQUENCE: 214

Ile Tyr Tyr Ser Gly Asp Thr
1               5

<210> SEQ ID NO 215
<211> LENGTH: 48
<212> TYPE: DNA
<213> ORGANISM: Artificial Sequence
<220> FEATURE:
<223> OTHER INFORMATION: synthetic

<400> SEQUENCE: 215
gcgagaggga ggccttatta cgattttttgg agtggttatt ttgactac              48

<210> SEQ ID NO 216
<211> LENGTH: 16
<212> TYPE: PRT
<213> ORGANISM: Artificial Sequence
<220> FEATURE:
<223> OTHER INFORMATION: synthetic

<400> SEQUENCE: 216

Ala Arg Gly Arg Pro Tyr Tyr Asp Phe Trp Ser Gly Tyr Phe Asp Tyr
1               5                   10                  15

<210> SEQ ID NO 217
<211> LENGTH: 324
<212> TYPE: DNA
<213> ORGANISM: Artificial Sequence
<220> FEATURE:
<223> OTHER INFORMATION: synthetic

<400> SEQUENCE: 217
gaaattgtgt tgacacagtc tccaggcacc ctgtctttgt ctccagggga aagagccacc    60
ctcccctgca gggccagtca gagtgttagc agcagctact tagcctggta ccagcagaaa   120
cctggccagg ctcccaggct cctcatatat ggtgcatcta gcagggccac tggcatccca   180
gacaggttca gaggcagtgg gtctgggaca gacttcactc tcaccatcag tagactggag   240
cctgaagatt ttgcagtgta ttactgtcag cagtatggaa ccgcaccttg gacgttcggc   300
caagggacca aggtggaaat caaa                                         324

-continued

```
<210> SEQ ID NO 218
<211> LENGTH: 108
<212> TYPE: PRT
<213> ORGANISM: Artificial Sequence
<220> FEATURE:
<223> OTHER INFORMATION: synthetic

<400> SEQUENCE: 218
```

Glu Ile Val Leu Thr Gln Ser Pro Gly Thr Leu Ser Leu Ser Pro Gly
1               5                   10                  15

Glu Arg Ala Thr Leu Pro Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Arg
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Thr Ala Pro
                85                  90                  95

Trp Thr Phe Gly Gln Gly Thr Lys Val Glu Ile Lys
            100                 105

```
<210> SEQ ID NO 219
<211> LENGTH: 21
<212> TYPE: DNA
<213> ORGANISM: Artificial Sequence
<220> FEATURE:
<223> OTHER INFORMATION: synthetic

<400> SEQUENCE: 219
cagagtgtta gcagcagcta c                                              21

<210> SEQ ID NO 220
<211> LENGTH: 7
<212> TYPE: PRT
<213> ORGANISM: Artificial Sequence
<220> FEATURE:
<223> OTHER INFORMATION: synthetic

<400> SEQUENCE: 220
```

Gln Ser Val Ser Ser Ser Tyr
1               5

```
<210> SEQ ID NO 221
<211> LENGTH: 9
<212> TYPE: DNA
<213> ORGANISM: Artificial Sequence
<220> FEATURE:
<223> OTHER INFORMATION: synthetic

<400> SEQUENCE: 221 ggtgcatct                                                             9

<210> SEQ ID NO 222
<211> LENGTH: 3
<212> TYPE: PRT
<213> ORGANISM: Artificial Sequence
<220> FEATURE:
<223> OTHER INFORMATION: synthetic

<400> SEQUENCE: 222
```

Gly Ala Ser
1

<210> SEQ ID NO 223
<211> LENGTH: 27
<212> TYPE: DNA
<213> ORGANISM: Artificial Sequence
<220> FEATURE:
<223> OTHER INFORMATION: synthetic

<400> SEQUENCE: 223
cagcagtatg gaaccgcacc ttggacg                                         27

<210> SEQ ID NO 224
<211> LENGTH: 9
<212> TYPE: PRT
<213> ORGANISM: Artificial Sequence
<220> FEATURE:
<223> OTHER INFORMATION: synthetic

<400> SEQUENCE: 224

Gln Gln Tyr Gly Thr Ala Pro Trp Thr
1               5

<210> SEQ ID NO 225
<211> LENGTH: 351
<212> TYPE: DNA
<213> ORGANISM: Artificial Sequence
<220> FEATURE:
<223> OTHER INFORMATION: synthetic

<400> SEQUENCE: 225
caggtgcagc tggtggagtc tgggggaggc gtggtccagc ctggggaggtc cctgagactc     60 tcctgtgcag cctctggatt caccttcagt tactatggca tgcactgggt ccgccaggct    120
ccaggcaagg gactggagtg gtggcagtt atattatatg atggaagtaa taaattctat    180
tcagactccg tgaagggccg attcaccatc tccagagaca attccaggaa cacgctgtat    240
ctgcaaatga acagcctgag acttgaggac acggctgtgt attactgtgc gaaagactac    300
ggtggccgct ttgactactg gggccaggga accctggtca ccgtctcctc a             351

<210> SEQ ID NO 226
<211> LENGTH: 117
<212> TYPE: PRT
<213> ORGANISM: Artificial Sequence
<220> FEATURE:
<223> OTHER INFORMATION: synthetic

<400> SEQUENCE: 226

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Tyr Tyr
            20                  25                  30

Gly Met His Trp Val Arg Gln Ala Pro Gly Lys Gly Leu Glu Trp Val
        35                  40                  45

Ala Val Ile Leu Tyr Asp Gly Ser Asn Lys Phe Tyr Ser Asp Ser Val
    50                  55                  60

Lys Gly Arg Phe Thr Ile Ser Arg Asp Asn Ser Arg Asn Thr Leu Tyr
65                  70                  75                  80

Leu Gln Met Asn Ser Leu Arg Leu Glu Asp Thr Ala Val Tyr Tyr Cys
                85                  90                  95

Ala Lys Asp Tyr Gly Gly Arg Phe Asp Tyr Trp Gly Gln Gly Thr Leu
            100                 105                 110

Val Thr Val Ser Ser
        115

<210> SEQ ID NO 227
<211> LENGTH: 24
<212> TYPE: DNA
<213> ORGANISM: Artificial Sequence
<220> FEATURE:
<223> OTHER INFORMATION: synthetic

<400> SEQUENCE: 227
ggattcacct tcagttacta tggc                                          24

<210> SEQ ID NO 228
<211> LENGTH: 8
<212> TYPE: PRT
<213> ORGANISM: Artificial Sequence
<220> FEATURE:
<223> OTHER INFORMATION: synthetic

<400> SEQUENCE: 228

Gly Phe Thr Phe Ser Tyr Tyr Gly
1               5

<210> SEQ ID NO 229
<211> LENGTH: 24
<212> TYPE: DNA
<213> ORGANISM: Artificial Sequence
<220> FEATURE:
<223> OTHER INFORMATION: synthetic

<400> SEQUENCE: 229
atattatatg atggaagtaa taaa                                          24

<210> SEQ ID NO 230
<211> LENGTH: 8
<212> TYPE: PRT
<213> ORGANISM: Artificial Sequence
<220> FEATURE:
<223> OTHER INFORMATION: synthetic

<400> SEQUENCE: 230

Ile Leu Tyr Asp Gly Ser Asn Lys
1               5

<210> SEQ ID NO 231
<211> LENGTH: 30
<212> TYPE: DNA
<213> ORGANISM: Artificial Sequence
<220> FEATURE:
<223> OTHER INFORMATION: synthetic

<400> SEQUENCE: 231
gcgaaagact acggtggccg ctttgactac                                    30

<210> SEQ ID NO 232
<211> LENGTH: 10
<212> TYPE: PRT
<213> ORGANISM: Artificial Sequence
<220> FEATURE:
<223> OTHER INFORMATION: synthetic

<400> SEQUENCE: 232

Ala Lys Asp Tyr Gly Gly Arg Phe Asp Tyr
1               5                   10

```
<210> SEQ ID NO 233
<211> LENGTH: 324
<212> TYPE: DNA
<213> ORGANISM: Artificial Sequence
<220> FEATURE:
<223> OTHER INFORMATION: synthetic

<400> SEQUENCE: 233
gaaattgtgt tgacgcagtc tccaggcacc ctgtctttgt cttcagggga aagagccacc      60
ctctcctgca gggccagtca gagtgttagc aacaaatact tagcctggta ccagcagaaa     120
cctggccagg ttcccaggct cctcatctat ggtgcatcca acagggccac tggcatccca     180
gacaggttca gtggcagtgg gtctgggaca gacttcactc tcaccatcaa cagactggag     240
cctgaagatt ttgctgtgtt ctactgtcag caatatggta gtacaccttc gacgttcggc     300
caagggacca aggtggaaat caaa                                            324

<210> SEQ ID NO 234
<211> LENGTH: 108
<212> TYPE: PRT
<213> ORGANISM: Artificial Sequence
<220> FEATURE:
<223> OTHER INFORMATION: synthetic

<400> SEQUENCE: 234

Glu Ile Val Leu Thr Gln Ser Pro Gly Thr Leu Ser Leu Ser Ser Gly
1               5                  10                  15

Glu Arg Ala Thr Leu Ser Cys Arg Ala Ser Gln Ser Val Ser Asn Lys
            20                  25                  30

Tyr Leu Ala Trp Tyr Gln Gln Lys Pro Gly Gln Val Pro Arg Leu Leu
        35                  40                  45

Ile Tyr Gly Ala Ser Asn Arg Ala Thr Gly Ile Pro Asp Arg Phe Ser
    50                  55                  60

Gly Ser Gly Ser Gly Thr Asp Phe Thr Leu Thr Ile Asn Arg Leu Glu
65                  70                  75                  80

Pro Glu Asp Phe Ala Val Phe Tyr Cys Gln Gln Tyr Gly Ser Thr Pro
                85                  90                  95

Ser Thr Phe Gly Gln Gly Thr Lys Val Glu Ile Lys
            100                 105

<210> SEQ ID NO 235
<211> LENGTH: 21
<212> TYPE: DNA
<213> ORGANISM: Artificial Sequence
<220> FEATURE:
<223> OTHER INFORMATION: synthetic

<400> SEQUENCE: 235
cagagtgtta gcaacaaata c                                                21

<210> SEQ ID NO 236
<211> LENGTH: 7
<212> TYPE: PRT
<213> ORGANISM: Artificial Sequence
<220> FEATURE:
<223> OTHER INFORMATION: synthetic

<400> SEQUENCE: 236

Gln Ser Val Ser Asn Lys Tyr
1               5

<210> SEQ ID NO 237
```

<211> LENGTH: 9
<212> TYPE: DNA
<213> ORGANISM: Artificial Sequence
<220> FEATURE:
<223> OTHER INFORMATION: synthetic

<400> SEQUENCE: 237 ggtgcatcc                                                                   9

<210> SEQ ID NO 238
<211> LENGTH: 3
<212> TYPE: PRT
<213> ORGANISM: Artificial Sequence
<220> FEATURE:
<223> OTHER INFORMATION: synthetic

<400> SEQUENCE: 238

Gly Ala Ser
1

<210> SEQ ID NO 239
<211> LENGTH: 27
<212> TYPE: DNA
<213> ORGANISM: Artificial Sequence
<220> FEATURE:
<223> OTHER INFORMATION: synthetic

<400> SEQUENCE: 239
cagcaatatg gtagtacacc ttcgacg                                              27

<210> SEQ ID NO 240
<211> LENGTH: 9
<212> TYPE: PRT
<213> ORGANISM: Artificial Sequence
<220> FEATURE:
<223> OTHER INFORMATION: synthetic

<400> SEQUENCE: 240

Gln Gln Tyr Gly Ser Thr Pro Ser Thr
1               5

<210> SEQ ID NO 241
<211> LENGTH: 351
<212> TYPE: DNA
<213> ORGANISM: Artificial Sequence
<220> FEATURE:
<223> OTHER INFORMATION: synthetic

<400> SEQUENCE: 241
caggtgcagc tggtggagtc tgggggaggc gtggtccagc ctggggaggtc cctgagactc         60 tcctgtgcag cctctggatt caccttcagt tactatggca tgcactgggt ccgccaggct        120
ccaggcaagg ggctggagtg ggtggcagtt atatcatatg atggcagtaa taactattat        180
gtagactccg tgaagggccg attcaccatc tccagagaca attccaagaa cacgctgtat        240
ctgcaaatga acagcctgag agctgaggac acggctgtgt attactgtgc gaaggattac        300
ggtggccgct ttgactactg gggccaggga accctggtca ccgtctcctc a                 351

<210> SEQ ID NO 242
<211> LENGTH: 117
<212> TYPE: PRT
<213> ORGANISM: Artificial Sequence
<220> FEATURE:
<223> OTHER INFORMATION: synthetic

<400> SEQUENCE: 242

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Tyr Tyr
            20                  25                  30

Gly Met His Trp Val Arg Gln Ala Pro Gly Lys Gly Leu Glu Trp Val
        35                  40                  45

Ala Val Ile Ser Tyr Asp Ala Ser Asn Asn Tyr Tyr Val Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Tyr Gly Gly Arg Phe Asp Tyr Trp Gly Gln Gly Thr Leu
            100                 105                 110

Val Thr Val Ser Ser
        115

<210> SEQ ID NO 243
<211> LENGTH: 24
<212> TYPE: DNA
<213> ORGANISM: Artificial Sequence
<220> FEATURE:
<223> OTHER INFORMATION: synthetic

<400> SEQUENCE: 243
ggattcacct tcagttacta tggc                                            24

<210> SEQ ID NO 244
<211> LENGTH: 8
<212> TYPE: PRT
<213> ORGANISM: Artificial Sequence
<220> FEATURE:
<223> OTHER INFORMATION: synthetic

<400> SEQUENCE: 244

Gly Phe Thr Phe Ser Tyr Tyr Gly
1               5

<210> SEQ ID NO 245
<211> LENGTH: 24
<212> TYPE: DNA
<213> ORGANISM: Artificial Sequence
<220> FEATURE:
<223> OTHER INFORMATION: synthetic

<400> SEQUENCE: 245
atatcatatg atgccagtaa taac                                            24

<210> SEQ ID NO 246
<211> LENGTH: 8
<212> TYPE: PRT
<213> ORGANISM: Artificial Sequence
<220> FEATURE:
<223> OTHER INFORMATION: synthetic

<400> SEQUENCE: 246

Ile Ser Tyr Asp Ala Ser Asn Asn
1               5

<210> SEQ ID NO 247
<211> LENGTH: 30
<212> TYPE: DNA

```
<213> ORGANISM: Artificial Sequence
<220> FEATURE:
<223> OTHER INFORMATION: synthetic

<400> SEQUENCE: 247
gcgaaggatt acggtggccg ctttgactac                                              30

<210> SEQ ID NO 248
<211> LENGTH: 10
<212> TYPE: PRT
<213> ORGANISM: Artificial Sequence
<220> FEATURE:
<223> OTHER INFORMATION: synthetic

<400> SEQUENCE: 248

Ala Lys Asp Tyr Gly Gly Arg Phe Asp Tyr
1               5                   10

<210> SEQ ID NO 249
<211> LENGTH: 321
<212> TYPE: DNA
<213> ORGANISM: Artificial Sequence
<220> FEATURE:
<223> OTHER INFORMATION: synthetic

<400> SEQUENCE: 249
gaaattgtgt tgacgcagtc tccaggcacc ctgtctttgt ctccagggga aagagccacc          60
ctctcctgcg gggccagtca gagtgttagc agctacttag cctggtacca gcagaaacct         120
ggccagactc ccaggctcct catctatggt gcatccagca gggccactgg catcccagac         180
aggttcagtg gcagtgggtc tgggactgac ttcactctca ccattagcag actggagcct         240
gaagattttg cagtgtatta ttgtcagcag tatggtagct caccttggac gttcggccaa         300
gggaccaagg tggaaatcaa a                                                    321

<210> SEQ ID NO 250
<211> LENGTH: 107
<212> TYPE: PRT
<213> ORGANISM: Artificial Sequence
<220> FEATURE:
<223> OTHER INFORMATION: synthetic

<400> SEQUENCE: 250

Glu Ile Val Leu Thr Gln Ser Pro Gly Thr Leu Ser Leu Ser Pro Gly
1               5                   10                  15

Glu Arg Ala Thr Leu Ser Cys Gly Ala Ser Gln Ser Val Ser Ser Tyr
            20                  25                  30

Leu Ala Trp Tyr Gln Gln Lys Pro Gly Gln Thr Pro Arg Leu Leu Ile
        35                  40                  45

Tyr Gly Ala Ser Ser Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Gly Ser Ser Pro Trp
                85                  90                  95

Thr Phe Gly Gln Gly Thr Lys Val Glu Ile Lys
            100                 105

<210> SEQ ID NO 251
<211> LENGTH: 18
<212> TYPE: DNA
<213> ORGANISM: Artificial Sequence
```

<220> FEATURE:
<223> OTHER INFORMATION: synthetic

<400> SEQUENCE: 251
cagagtgtta gcagctac                                                    18

<210> SEQ ID NO 252
<211> LENGTH: 6
<212> TYPE: PRT
<213> ORGANISM: Artificial Sequence
<220> FEATURE:
<223> OTHER INFORMATION: synthetic

<400> SEQUENCE: 252

Gln Ser Val Ser Ser Tyr
1               5

<210> SEQ ID NO 253
<211> LENGTH: 9
<212> TYPE: DNA
<213> ORGANISM: Artificial Sequence
<220> FEATURE:
<223> OTHER INFORMATION: synthetic

<400> SEQUENCE: 253 ggtgcatcc                                                               9

<210> SEQ ID NO 254
<211> LENGTH: 3
<212> TYPE: PRT
<213> ORGANISM: Artificial Sequence
<220> FEATURE:
<223> OTHER INFORMATION: synthetic

<400> SEQUENCE: 254

Gly Ala Ser
1

<210> SEQ ID NO 255
<211> LENGTH: 27
<212> TYPE: DNA
<213> ORGANISM: Artificial Sequence
<220> FEATURE:
<223> OTHER INFORMATION: synthetic

<400> SEQUENCE: 255
cagcagtatg gtagctcacc ttggacg                                          27

<210> SEQ ID NO 256
<211> LENGTH: 9
<212> TYPE: PRT
<213> ORGANISM: Artificial Sequence
<220> FEATURE:
<223> OTHER INFORMATION: synthetic

<400> SEQUENCE: 256

Gln Gln Tyr Gly Ser Ser Pro Trp Thr
1               5

<210> SEQ ID NO 257
<211> LENGTH: 351
<212> TYPE: DNA
<213> ORGANISM: Artificial Sequence
<220> FEATURE:
<223> OTHER INFORMATION: synthetic

<400> SEQUENCE: 257

```
caggtgcagc tggtggagtc ggggggaggc gtggtccagc ctgggaggtc cctgagactc      60
tcctgtgcag cctctggatt caccttcaat tactatggca tgcactgggt ccgccaggct     120
ccaggcaagg ggctggagtg gtggcagtc atatcatatg atggaactaa taaatactat     180
gcagactccg tgaagggccg attcaccacc tccagagaca attccaagaa cacgctgtat     240
ctgcagatga acagcctgag agctgaggac acggctctgt attactgtgc gagagatcgc     300
ggtggccgct ttgactactg gggccaggga atccaggtca ccgtctcctc a              351
```

<210> SEQ ID NO 258
<211> LENGTH: 117
<212> TYPE: PRT
<213> ORGANISM: Artificial Sequence
<220> FEATURE:
<223> OTHER INFORMATION: synthetic

<400> SEQUENCE: 258

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Asn Tyr Tyr
            20                  25                  30

Gly Met His Trp Val Arg Gln Ala Pro Gly Lys Gly Leu Glu Trp Val
        35                  40                  45

Ala Val Ile Ser Tyr Asp Gly Thr Asn Lys Tyr Tyr Ala Asp Ser Val
    50                  55                  60

Lys Gly Arg Phe Thr Thr Ser Arg Asp Asn Ser Lys Asn Thr Leu Tyr
65                  70                  75                  80

Leu Gln Met Asn Ser Leu Arg Ala Glu Asp Thr Ala Leu Tyr Tyr Cys
                85                  90                  95

Ala Arg Asp Arg Gly Gly Arg Phe Asp Tyr Trp Gly Gln Gly Ile Gln
            100                 105                 110

Val Thr Val Ser Ser
        115
```

<210> SEQ ID NO 259
<211> LENGTH: 24
<212> TYPE: DNA
<213> ORGANISM: Artificial Sequence
<220> FEATURE:
<223> OTHER INFORMATION: synthetic

<400> SEQUENCE: 259

```
ggattcacct caattacta tggc                                              24
```

<210> SEQ ID NO 260
<211> LENGTH: 8
<212> TYPE: PRT
<213> ORGANISM: Artificial Sequence
<220> FEATURE:
<223> OTHER INFORMATION: synthetic

<400> SEQUENCE: 260

```
Gly Phe Thr Phe Asn Tyr Tyr Gly
1               5
```

<210> SEQ ID NO 261
<211> LENGTH: 24
<212> TYPE: DNA
<213> ORGANISM: Artificial Sequence
<220> FEATURE:
<223> OTHER INFORMATION: synthetic

<400> SEQUENCE: 261
atatcatatg atggaactaa taaa                                              24

<210> SEQ ID NO 262
<211> LENGTH: 8
<212> TYPE: PRT
<213> ORGANISM: Artificial Sequence
<220> FEATURE:
<223> OTHER INFORMATION: synthetic

<400> SEQUENCE: 262

Ile Ser Tyr Asp Gly Thr Asn Lys
1               5

<210> SEQ ID NO 263
<211> LENGTH: 30
<212> TYPE: DNA
<213> ORGANISM: Artificial Sequence
<220> FEATURE:
<223> OTHER INFORMATION: synthetic

<400> SEQUENCE: 263
gcgagagatc gcggtggccg ctttgactac                                        30

<210> SEQ ID NO 264
<211> LENGTH: 10
<212> TYPE: PRT
<213> ORGANISM: Artificial Sequence
<220> FEATURE:
<223> OTHER INFORMATION: synthetic

<400> SEQUENCE: 264

Ala Arg Asp Arg Gly Gly Arg Phe Asp Tyr
1               5                   10

<210> SEQ ID NO 265
<211> LENGTH: 324
<212> TYPE: DNA
<213> ORGANISM: Artificial Sequence
<220> FEATURE:
<223> OTHER INFORMATION: synthetic

<400> SEQUENCE: 265
gaaattgtgt tgacgcagtc tccagacacc ctgtctttgt ctccagggga aagagccacc        60
ctctcctgca gggccagtca gagtgttagc agcaactact tagcctggta ccagcagaaa       120
cctggccagg ctcccaggct cctcatctat ggtgcatcca gcagggccac tggcatccca       180
gacaggttca gtggcagtgg gtctgggaca gacttcactc tcaccatcag cagactggag       240
cctgaagatt ttgcagtgta ttactgtcag cggtatggta cctcaccgct cactttcggc       300
ggagggacca aggtggagat caaa                                              324

<210> SEQ ID NO 266
<211> LENGTH: 108
<212> TYPE: PRT
<213> ORGANISM: Artificial Sequence
<220> FEATURE:
<223> OTHER INFORMATION: synthetic

<400> SEQUENCE: 266

Glu Ile Val Leu Thr Gln Ser Pro Asp Thr Leu Ser Leu Ser Pro Gly
1               5                   10                  15

Glu Arg Ala Thr Leu Ser Cys Arg Ala Ser Gln Ser Val Ser Ser Asn

```
            20                  25                  30
Tyr Leu Ala Trp Tyr Gln Gln Lys Pro Gly Gln Ala Pro Arg Leu Leu
         35                  40                  45

Ile Tyr Gly Ala Ser Ser Arg Ala Thr Gly Ile Pro Asp Arg Phe Ser
     50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Arg Tyr Gly Thr Ser Pro
                 85                  90                  95

Leu Thr Phe Gly Gly Gly Thr Lys Val Glu Ile Lys
            100                 105
```

<210> SEQ ID NO 267
<211> LENGTH: 21
<212> TYPE: DNA
<213> ORGANISM: Artificial Sequence
<220> FEATURE:
<223> OTHER INFORMATION: synthetic

<400> SEQUENCE: 267
cagagtgtta gcagcaacta c                                          21

<210> SEQ ID NO 268
<211> LENGTH: 7
<212> TYPE: PRT
<213> ORGANISM: Artificial Sequence
<220> FEATURE:
<223> OTHER INFORMATION: synthetic

<400> SEQUENCE: 268

Gln Ser Val Ser Ser Asn Tyr
1               5

<210> SEQ ID NO 269
<211> LENGTH: 9
<212> TYPE: DNA
<213> ORGANISM: Artificial Sequence
<220> FEATURE:
<223> OTHER INFORMATION: synthetic

<400> SEQUENCE: 269 ggtgcatcc                                                         9

<210> SEQ ID NO 270
<211> LENGTH: 3
<212> TYPE: PRT
<213> ORGANISM: Artificial Sequence
<220> FEATURE:
<223> OTHER INFORMATION: synthetic

<400> SEQUENCE: 270

Gly Ala Ser
1

<210> SEQ ID NO 271
<211> LENGTH: 27
<212> TYPE: DNA
<213> ORGANISM: Artificial Sequence
<220> FEATURE:
<223> OTHER INFORMATION: synthetic

<400> SEQUENCE: 271
cagcggtatg gtacctcacc gctcact                                    27

```
<210> SEQ ID NO 272
<211> LENGTH: 9
<212> TYPE: PRT
<213> ORGANISM: Artificial Sequence
<220> FEATURE:
<223> OTHER INFORMATION: synthetic

<400> SEQUENCE: 272

Gln Arg Tyr Gly Thr Ser Pro Leu Thr
1               5

<210> SEQ ID NO 273
<211> LENGTH: 351
<212> TYPE: DNA
<213> ORGANISM: Artificial Sequence
<220> FEATURE:
<223> OTHER INFORMATION: synthetic

<400> SEQUENCE: 273
caggtgcagc tggtggagtc agggggaggc gtggtccagt ctggggaggtc cctgagactc      60 tcctgtgcag cctctggatt caccttcatt tactatggca tgcactgggt ccgccaggct     120
ccaggcaagg ggctagagtg ggtggcagtt atatcatatg atggaagtga tagatactat     180
gcagactctg tgaagggccg attcaccatc tccagagacg attccaagaa cacgctgtat     240
ctgcaaatga acagcctgag acctgaggac acggctgtgt attactgtgc gaaagaccgc     300
ggtggccgtt ttgactactg gggccaggga accctggtca ccgtctcctc a              351

<210> SEQ ID NO 274
<211> LENGTH: 117
<212> TYPE: PRT
<213> ORGANISM: Artificial Sequence
<220> FEATURE:
<223> OTHER INFORMATION: synthetic

<400> SEQUENCE: 274

Gln Val Gln Leu Val Glu Ser Gly Gly Gly Val Val Gln Ser Gly Arg
1               5                   10                  15

Ser Leu Arg Leu Ser Cys Ala Ala Ser Gly Phe Thr Phe Ile Tyr Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asp Arg Tyr Tyr Ala Asp Ser Val
    50                  55                  60

Lys Gly Arg Phe Thr Ile Ser Arg Asp Asp Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Ala Lys Asp Arg Gly Gly Arg Phe Asp Tyr Trp Gly Gln Gly Thr Leu
            100                 105                 110

Val Thr Val Ser Ser
        115

<210> SEQ ID NO 275
<211> LENGTH: 24
<212> TYPE: DNA
<213> ORGANISM: Artificial Sequence
<220> FEATURE:
<223> OTHER INFORMATION: synthetic

<400> SEQUENCE: 275
```

```
ggattcacct tcatttacta tggc                                              24
```

<210> SEQ ID NO 276
<211> LENGTH: 8
<212> TYPE: PRT
<213> ORGANISM: Artificial Sequence
<220> FEATURE:
<223> OTHER INFORMATION: synthetic

<400> SEQUENCE: 276

Gly Phe Thr Phe Ile Tyr Tyr Gly
1               5

<210> SEQ ID NO 277
<211> LENGTH: 24
<212> TYPE: DNA
<213> ORGANISM: Artificial Sequence
<220> FEATURE:
<223> OTHER INFORMATION: synthetic

<400> SEQUENCE: 277

```
atatcatatg atggaagtga taga                                              24
```

<210> SEQ ID NO 278
<211> LENGTH: 8
<212> TYPE: PRT
<213> ORGANISM: Artificial Sequence
<220> FEATURE:
<223> OTHER INFORMATION: synthetic

<400> SEQUENCE: 278

Ile Ser Tyr Asp Gly Ser Asp Arg
1               5

<210> SEQ ID NO 279
<211> LENGTH: 30
<212> TYPE: DNA
<213> ORGANISM: Artificial Sequence
<220> FEATURE:
<223> OTHER INFORMATION: synthetic

<400> SEQUENCE: 279

```
gcgaaagacc gcggtggccg ttttgactac                                        30
```

<210> SEQ ID NO 280
<211> LENGTH: 10
<212> TYPE: PRT
<213> ORGANISM: Artificial Sequence
<220> FEATURE:
<223> OTHER INFORMATION: synthetic

<400> SEQUENCE: 280

Ala Lys Asp Arg Gly Gly Arg Phe Asp Tyr
1               5                   10

<210> SEQ ID NO 281
<211> LENGTH: 324
<212> TYPE: DNA
<213> ORGANISM: Artificial Sequence
<220> FEATURE:
<223> OTHER INFORMATION: synthetic

<400> SEQUENCE: 281

```
gaaattgtgt tgacgcagtc tccaggcacc ctgtctttgt ctccagggga aagagccacc       60
ctctcctgca gggccagtca gagtgttaac aacaactact tagcctggta ccagcagaaa      120
```

-continued

```
cctggccagg ctcccaggct cctcatctat ggtgcatcca gcagggccac tggcatccca    180
gacaggttcg gtggcggtgg gtctgggaca gacttcactc tcaccatcag cagactggag    240
cctgaagatt ttgcagtgta ttactgtcag cggtatggta actctccgct cactttcggc    300
ggagggacca aggtggagat caaa                                           324
```

```
<210> SEQ ID NO 282
<211> LENGTH: 108
<212> TYPE: PRT
<213> ORGANISM: Artificial Sequence
<220> FEATURE:
<223> OTHER INFORMATION: synthetic

<400> SEQUENCE: 282

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Asn Asn Asn
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Gly
    50                  55                  60

Gly Gly Gly Ser Gly Thr Asp Phe Thr Leu Thr Ile Ser Arg Leu Glu
65                  70                  75                  80

Pro Glu Asp Phe Ala Val Tyr Tyr Cys Gln Arg Tyr Gly Asn Ser Pro
                85                  90                  95

Leu Thr Phe Gly Gly Gly Thr Lys Val Glu Ile Lys
            100                 105
```

```
<210> SEQ ID NO 283
<211> LENGTH: 21
<212> TYPE: DNA
<213> ORGANISM: Artificial Sequence
<220> FEATURE:
<223> OTHER INFORMATION: synthetic

<400> SEQUENCE: 283
cagagtgtta acaacaacta c                                              21
```

```
<210> SEQ ID NO 284
<211> LENGTH: 7
<212> TYPE: PRT
<213> ORGANISM: Artificial Sequence
<220> FEATURE:
<223> OTHER INFORMATION: synthetic

<400> SEQUENCE: 284

Gln Ser Val Asn Asn Asn Tyr
1               5
```

```
<210> SEQ ID NO 285
<211> LENGTH: 9
<212> TYPE: DNA
<213> ORGANISM: Artificial Sequence
<220> FEATURE:
<223> OTHER INFORMATION: synthetic

<400> SEQUENCE: 285 ggtgcatcc                                                            9
```

```
<210> SEQ ID NO 286
<211> LENGTH: 3
```

```
<212> TYPE: PRT
<213> ORGANISM: Artificial Sequence
<220> FEATURE:
<223> OTHER INFORMATION: synthetic

<400> SEQUENCE: 286

Gly Ala Ser
1

<210> SEQ ID NO 287
<211> LENGTH: 27
<212> TYPE: DNA
<213> ORGANISM: Artificial Sequence
<220> FEATURE:
<223> OTHER INFORMATION: synthetic

<400> SEQUENCE: 287
cagcggtatg gtaactctcc gctcact                                            27

<210> SEQ ID NO 288
<211> LENGTH: 9
<212> TYPE: PRT
<213> ORGANISM: Artificial Sequence
<220> FEATURE:
<223> OTHER INFORMATION: synthetic

<400> SEQUENCE: 288

Gln Arg Tyr Gly Asn Ser Pro Leu Thr
1               5

<210> SEQ ID NO 289
<211> LENGTH: 372
<212> TYPE: DNA
<213> ORGANISM: Artificial Sequence
<220> FEATURE:
<223> OTHER INFORMATION: synthetic

<400> SEQUENCE: 289
gaggtgcagc tgttggagtc tgggggagac ttggtacagc ctggggggtc cctgagactc        60
tcctgtgcag cctctggatt cacctttagt agctatgcca tgagctgggt ccgccaggct       120
ccagggaagg gcctggagtg gtctcagct attagtgtta gtggtgatag cacatactac        180
gcagactccg tgaagggccg gttcaccatc tccagagaca attccaagaa cacgctgtat       240
ctgcaaatga acagcctgag agccgaggac acggccgtat attactgtgc gaaagatcgc       300
gggtatacct ggaactacta ctactacggt atggacgtct ggggccaagg gaccacggtc       360
accgtctcct ca                                                          372

<210> SEQ ID NO 290
<211> LENGTH: 124
<212> TYPE: PRT
<213> ORGANISM: Artificial Sequence
<220> FEATURE:
<223> OTHER INFORMATION: synthetic

<400> SEQUENCE: 290

Glu Val Gln Leu Leu Glu Ser Gly Gly Asp Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Val Ser Gly Asp Ser Thr Tyr Tyr Ala Asp Ser Val
```

```
                50                  55                  60
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Arg Gly Tyr Thr Trp Asn Tyr Tyr Tyr Gly Met Asp
            100                 105                 110

Val Trp Gly Gln Gly Thr Thr Val Thr Val Ser Ser
        115                 120
```

<210> SEQ ID NO 291
<211> LENGTH: 24
<212> TYPE: DNA
<213> ORGANISM: Artificial Sequence
<220> FEATURE:
<223> OTHER INFORMATION: synthetic

<400> SEQUENCE: 291
ggattcacct ttagtagcta tgcc                                        24

<210> SEQ ID NO 292
<211> LENGTH: 8
<212> TYPE: PRT
<213> ORGANISM: Artificial Sequence
<220> FEATURE:
<223> OTHER INFORMATION: synthetic

<400> SEQUENCE: 292

```
Gly Phe Thr Phe Ser Ser Tyr Ala
 1               5
```

<210> SEQ ID NO 293
<211> LENGTH: 24
<212> TYPE: DNA
<213> ORGANISM: Artificial Sequence
<220> FEATURE:
<223> OTHER INFORMATION: synthetic

<400> SEQUENCE: 293
attagtgtta gtggtgatag caca                                        24

<210> SEQ ID NO 294
<211> LENGTH: 8
<212> TYPE: PRT
<213> ORGANISM: Artificial Sequence
<220> FEATURE:
<223> OTHER INFORMATION: synthetic

<400> SEQUENCE: 294

```
Ile Ser Val Ser Gly Asp Ser Thr
 1               5
```

<210> SEQ ID NO 295
<211> LENGTH: 51
<212> TYPE: DNA
<213> ORGANISM: Artificial Sequence
<220> FEATURE:
<223> OTHER INFORMATION: synthetic

<400> SEQUENCE: 295
gcgaaagatc gcgggtatac ctggaactac tactactacg gtatggacgt c          51

<210> SEQ ID NO 296
<211> LENGTH: 17

```
<212> TYPE: PRT
<213> ORGANISM: Artificial Sequence
<220> FEATURE:
<223> OTHER INFORMATION: synthetic

<400> SEQUENCE: 296

Ala Lys Asp Arg Gly Tyr Thr Trp Asn Tyr Tyr Tyr Gly Met Asp
1               5                   10                  15

Val

<210> SEQ ID NO 297
<211> LENGTH: 336
<212> TYPE: DNA
<213> ORGANISM: Artificial Sequence
<220> FEATURE:
<223> OTHER INFORMATION: synthetic

<400> SEQUENCE: 297
gatattgtga tgacccagac tccactctcc tcacctgtca cccttggaca gccggcctcc    60
atctcctgca ggtctagtca aagcctcgta cacagtgatg gaaacaccta cttgagttgg   120
cttcagcaga ggccaggcca gcctccaaga ctcctaattt ataagatttc taaccgattc   180
tctggggtcc cagacagatt cagtggcagt ggggcaggga cagatttcac actgaaaatc   240
agcagggtgg aagctgagga tgtcggggtt tattactgca tgcaagctac acaatttccg   300
tacacttttg gccaggggac caaactggag atcaaa                             336

<210> SEQ ID NO 298
<211> LENGTH: 112
<212> TYPE: PRT
<213> ORGANISM: Artificial Sequence
<220> FEATURE:
<223> OTHER INFORMATION: synthetic

<400> SEQUENCE: 298

Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Ser Leu Val His Ser
                20                  25                  30

Asp Gly Asn Thr Tyr Leu Ser Trp Leu Gln Gln Arg Pro Gly Gln Pro
            35                  40                  45

Pro Arg Leu Leu Ile Tyr Lys Ile Ser Asn Arg Phe Ser Gly Val Pro
        50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Thr Gln Phe Pro Tyr Thr Phe Gly Gln Gly Thr Lys Leu Glu Ile Lys
                100                 105                 110

<210> SEQ ID NO 299
<211> LENGTH: 33
<212> TYPE: DNA
<213> ORGANISM: Artificial Sequence
<220> FEATURE:
<223> OTHER INFORMATION: synthetic

<400> SEQUENCE: 299
caaagcctcg tacacagtga tggaaacacc tac                                 33

<210> SEQ ID NO 300
```

```
<211> LENGTH: 11
<212> TYPE: PRT
<213> ORGANISM: Artificial Sequence
<220> FEATURE:
<223> OTHER INFORMATION: synthetic

<400> SEQUENCE: 300

Gln Ser Leu Val His Ser Asp Gly Asn Thr Tyr
1               5                   10

<210> SEQ ID NO 301
<211> LENGTH: 9
<212> TYPE: DNA
<213> ORGANISM: Artificial Sequence
<220> FEATURE:
<223> OTHER INFORMATION: synthetic

<400> SEQUENCE: 301 aagatttct                                                            9

<210> SEQ ID NO 302
<211> LENGTH: 3
<212> TYPE: PRT
<213> ORGANISM: Artificial Sequence
<220> FEATURE:
<223> OTHER INFORMATION: synthetic

<400> SEQUENCE: 302

Lys Ile Ser
1

<210> SEQ ID NO 303
<211> LENGTH: 27
<212> TYPE: DNA
<213> ORGANISM: Artificial Sequence
<220> FEATURE:
<223> OTHER INFORMATION: synthetic

<400> SEQUENCE: 303
atgcaagcta cacaatttcc gtacact                                       27

<210> SEQ ID NO 304
<211> LENGTH: 9
<212> TYPE: PRT
<213> ORGANISM: Artificial Sequence
<220> FEATURE:
<223> OTHER INFORMATION: synthetic

<400> SEQUENCE: 304

Met Gln Ala Thr Gln Phe Pro Tyr Thr
1               5

<210> SEQ ID NO 305
<211> LENGTH: 369
<212> TYPE: DNA
<213> ORGANISM: Artificial Sequence
<220> FEATURE:
<223> OTHER INFORMATION: synthetic

<400> SEQUENCE: 305
gaggtgcagc tggtggagtc tgaggaggc ttggtccagc ctggggggtc cctgagactc     60
tcctgtgcag cctctgggtt caccgtcagt agcaactaca tgagctgggt ccgccaggct    120
ccagggaagg ggctggagtg ggtctcagtt atttatagcg gtggtagaac aaactacgga    180
gactccgtga agggccgatt caccatctcc agagacaatt ccaagaacac gctgtatctt    240
```

```
caaatgaaca gcctgagagc tgaggacacg gccgtgtatt actgtgcgag agagaattac    300
gatttttgga gtggtgaccc ctacggtttg gacgtctggg gccaagggac cacggtcacc    360
gtctcctca                                                            369
```

<210> SEQ ID NO 306
<211> LENGTH: 123
<212> TYPE: PRT
<213> ORGANISM: Artificial Sequence
<220> FEATURE:
<223> OTHER INFORMATION: synthetic

<400> SEQUENCE: 306

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Ser Gly Gly Arg Thr Asn Tyr Gly Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Glu Asn Tyr Asp Phe Trp Ser Gly Asp Pro Tyr Gly Trp Asp Val
            100                 105                 110

Trp Gly Gln Gly Thr Thr Val Thr Val Ser Ser
        115                 120
```

<210> SEQ ID NO 307
<211> LENGTH: 24
<212> TYPE: DNA
<213> ORGANISM: Artificial Sequence
<220> FEATURE:
<223> OTHER INFORMATION: synthetic

<400> SEQUENCE: 307

```
gggttcaccg tcagtagcaa ctac                                            24
```

<210> SEQ ID NO 308
<211> LENGTH: 8
<212> TYPE: PRT
<213> ORGANISM: Artificial Sequence
<220> FEATURE:
<223> OTHER INFORMATION: synthetic

<400> SEQUENCE: 308

```
Gly Phe Thr Val Ser Ser Asn Tyr
1               5
```

<210> SEQ ID NO 309
<211> LENGTH: 21
<212> TYPE: DNA
<213> ORGANISM: Artificial Sequence
<220> FEATURE:
<223> OTHER INFORMATION: synthetic

<400> SEQUENCE: 309

```
atttatagcg gtggtagaac a                                               21
```

<210> SEQ ID NO 310

```
<211> LENGTH: 7
<212> TYPE: PRT
<213> ORGANISM: Artificial Sequence
<220> FEATURE:
<223> OTHER INFORMATION: synthetic

<400> SEQUENCE: 310

Ile Tyr Ser Gly Gly Arg Thr
1               5

<210> SEQ ID NO 311
<211> LENGTH: 51
<212> TYPE: DNA
<213> ORGANISM: Artificial Sequence
<220> FEATURE:
<223> OTHER INFORMATION: synthetic

<400> SEQUENCE: 311
gcgagagaga attacgattt ttggagtggt gacccctacg gttgggacgt c         51

<210> SEQ ID NO 312
<211> LENGTH: 17
<212> TYPE: PRT
<213> ORGANISM: Artificial Sequence
<220> FEATURE:
<223> OTHER INFORMATION: synthetic

<400> SEQUENCE: 312

Ala Arg Glu Asn Tyr Asp Phe Trp Ser Gly Asp Pro Tyr Gly Trp Asp
1               5                  10                  15
Val

<210> SEQ ID NO 313
<211> LENGTH: 321
<212> TYPE: DNA
<213> ORGANISM: Artificial Sequence
<220> FEATURE:
<223> OTHER INFORMATION: synthetic

<400> SEQUENCE: 313
gacatccaga tgacccagtc tccatcctca ctgtctgcat ctgtaggaga cagagtcacc     60
atcacttgtc gggcgagtca ggacattagc aattatttag cctggtttca gcagaaacca    120
gggaaagccc ctaagtccct gatatatggt gcatccagtt tgcaaagagg ggtcccatca    180 agttcagcg gcagtggatc tgggacagat ttcactctca ccatcagcag cctgcagcct    240
gaagattttg caacttatta ctgccaacag tataatagtt acccatacac ttttggccag    300
gggaccaagc tggagatcaa a                                              321

<210> SEQ ID NO 314
<211> LENGTH: 107
<212> TYPE: PRT
<213> ORGANISM: Artificial Sequence
<220> FEATURE:
<223> OTHER INFORMATION: synthetic

<400> SEQUENCE: 314

Asp Ile Gln Met Thr Gln Ser Pro Ser Ser Leu Ser Ala Ser Val Gly
1               5                  10                  15

Asp Arg Val Thr Ile Thr Cys Arg Ala Ser Gln Asp Ile Ser Asn Tyr
                20                  25                  30

Leu Ala Trp Phe Gln Gln Lys Pro Gly Lys Ala Pro Lys Ser Leu Ile
        35                  40                  45
```

-continued

```
Tyr Gly Ala Ser Ser Leu Gln Arg Gly Val Pro Ser Lys Phe Ser Gly
        50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asn Ser Tyr Pro Tyr
                 85                  90                  95

Thr Phe Gly Gln Gly Thr Lys Leu Glu Ile Lys
            100                 105
```

<210> SEQ ID NO 315
<211> LENGTH: 18
<212> TYPE: DNA
<213> ORGANISM: Artificial Sequence
<220> FEATURE:
<223> OTHER INFORMATION: synthetic

<400> SEQUENCE: 315
caggacatta gcaattat                                                18

<210> SEQ ID NO 316
<211> LENGTH: 6
<212> TYPE: PRT
<213> ORGANISM: Artificial Sequence
<220> FEATURE:
<223> OTHER INFORMATION: synthetic

<400> SEQUENCE: 316

```
Gln Asp Ile Ser Asn Tyr
 1               5
```

<210> SEQ ID NO 317
<211> LENGTH: 9
<212> TYPE: DNA
<213> ORGANISM: Artificial Sequence
<220> FEATURE:
<223> OTHER INFORMATION: synthetic

<400> SEQUENCE: 317 ggtgcatcc                                                           9

<210> SEQ ID NO 318
<211> LENGTH: 3
<212> TYPE: PRT
<213> ORGANISM: Artificial Sequence
<220> FEATURE:
<223> OTHER INFORMATION: synthetic

<400> SEQUENCE: 318

```
Gly Ala Ser
 1
```

<210> SEQ ID NO 319
<211> LENGTH: 27
<212> TYPE: DNA
<213> ORGANISM: Artificial Sequence
<220> FEATURE:
<223> OTHER INFORMATION: synthetic

<400> SEQUENCE: 319
caacagtata atagttaccc atacact                                      27

<210> SEQ ID NO 320
<211> LENGTH: 9
<212> TYPE: PRT
<213> ORGANISM: Artificial Sequence

```
<220> FEATURE:
<223> OTHER INFORMATION: synthetic

<400> SEQUENCE: 320

Gln Gln Tyr Asn Ser Tyr Pro Tyr Thr
1               5

<210> SEQ ID NO 321
<211> LENGTH: 369
<212> TYPE: DNA
<213> ORGANISM: Artificial Sequence
<220> FEATURE:
<223> OTHER INFORMATION: synthetic

<400> SEQUENCE: 321
gaggtgcagc tgctggagtc tggaggaggc ttggtccagc ctgggggtc cctgagactc      60 tcctgtgcag cctctgggtt caccgtcagt aataactaca tgagctgggt ccgccaggct    120
ccagggaagg gactggagtg ggtctcagtt atttatagcg gtggtagaac aaactacgga    180
gactccgtga agggccgatt caccatctcc agagacaatt ccaagaacac gctgtatctt    240
caaatgaaca gcctaagagc tgaggacacg gccgtgtatt actgtgcgag agagaattac    300
gattttggga gtggtgaccc ctacggttgg gacgtctggg gccaagggac cacggtcacc    360
gtctcctca                                                             369

<210> SEQ ID NO 322
<211> LENGTH: 123
<212> TYPE: PRT
<213> ORGANISM: Artificial Sequence
<220> FEATURE:
<223> OTHER INFORMATION: synthetic

<400> SEQUENCE: 322

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Val Ser Asn Asn
            20                  25                  30

Tyr Met Ser Trp Val Arg Gln Ala Pro Gly Lys Gly Leu Glu Trp Val
        35                  40                  45

Ser Val Ile Tyr Ser Gly Gly Arg Thr Asn Tyr Gly Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Glu Asn Tyr Asp Phe Trp Ser Gly Asp Pro Tyr Gly Trp Asp Val
            100                 105                 110

Trp Gly Gln Gly Thr Thr Val Thr Val Ser Ser
        115                 120

<210> SEQ ID NO 323
<211> LENGTH: 24
<212> TYPE: DNA
<213> ORGANISM: Artificial Sequence
<220> FEATURE:
<223> OTHER INFORMATION: synthetic

<400> SEQUENCE: 323
gggttcaccg tcagtaataa ctac                                             24
```

<210> SEQ ID NO 324
<211> LENGTH: 8
<212> TYPE: PRT
<213> ORGANISM: Artificial Sequence
<220> FEATURE:
<223> OTHER INFORMATION: synthetic

<400> SEQUENCE: 324

Gly Phe Thr Val Ser Asn Asn Tyr
1               5

<210> SEQ ID NO 325
<211> LENGTH: 21
<212> TYPE: DNA
<213> ORGANISM: Artificial Sequence
<220> FEATURE:
<223> OTHER INFORMATION: synthetic

<400> SEQUENCE: 325
atttatagcg gtggtagaac a                                              21

<210> SEQ ID NO 326
<211> LENGTH: 7
<212> TYPE: PRT
<213> ORGANISM: Artificial Sequence
<220> FEATURE:
<223> OTHER INFORMATION: synthetic

<400> SEQUENCE: 326

Ile Tyr Ser Gly Gly Arg Thr
1               5

<210> SEQ ID NO 327
<211> LENGTH: 51
<212> TYPE: DNA
<213> ORGANISM: Artificial Sequence
<220> FEATURE:
<223> OTHER INFORMATION: synthetic

<400> SEQUENCE: 327
gcgagagaga attacgattt ttggagtggt gacccctacg gttgggacgt c             51

<210> SEQ ID NO 328
<211> LENGTH: 17
<212> TYPE: PRT
<213> ORGANISM: Artificial Sequence
<220> FEATURE:
<223> OTHER INFORMATION: synthetic

<400> SEQUENCE: 328

Ala Arg Glu Asn Tyr Asp Phe Trp Ser Gly Asp Pro Tyr Gly Trp Asp
1               5                   10                  15

Val

<210> SEQ ID NO 329
<211> LENGTH: 321
<212> TYPE: DNA
<213> ORGANISM: Artificial Sequence
<220> FEATURE:
<223> OTHER INFORMATION: synthetic

<400> SEQUENCE: 329
gacatccaga tgacccagtc tccatcctca ctgtctgcat ctgtaggaga cagagtcacc    60
atcacttgtc gggcgagtca ggacattagc aattatttag cctggtttca gcagaaacca   120
gggaaagccc ctaagtccct gatatatggt gcatccagtt tgcaaagagg ggtcccatca   180
aagttcagag gcagtggatc tgggacagat ttcactctca ccatcagcag cctgcagcct      240
gaagattttg caagttatta ctgccaacag tataatagtt acccatacac ttttggccag      300
gggaccaagc tggagatcaa a      321

<210> SEQ ID NO 330
<211> LENGTH: 107
<212> TYPE: PRT
<213> ORGANISM: Artificial Sequence
<220> FEATURE:
<223> OTHER INFORMATION: synthetic

<400> SEQUENCE: 330

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Ala Trp Phe Gln Gln Lys Pro Gly Lys Ala Pro Lys Ser Leu Ile
        35                  40                  45

Tyr Gly Ala Ser Ser Leu Gln Arg Gly Val Pro Ser Lys Phe Arg Gly
    50                  55                  60

Ser Gly Ser Gly Thr Asp Phe Thr Leu Thr Ile Ser Ser Leu Gln Pro
65                  70                  75                  80

Glu Asp Phe Ala Ser Tyr Tyr Cys Gln Gln Tyr Asn Ser Tyr Pro Tyr
                85                  90                  95

Thr Phe Gly Gln Gly Thr Lys Leu Glu Ile Lys
            100                 105

<210> SEQ ID NO 331
<211> LENGTH: 18
<212> TYPE: DNA
<213> ORGANISM: Artificial Sequence
<220> FEATURE:
<223> OTHER INFORMATION: synthetic

<400> SEQUENCE: 331
caggacatta gcaattat      18

<210> SEQ ID NO 332
<211> LENGTH: 6
<212> TYPE: PRT
<213> ORGANISM: Artificial Sequence
<220> FEATURE:
<223> OTHER INFORMATION: synthetic

<400> SEQUENCE: 332

Gln Asp Ile Ser Asn Tyr
1               5

<210> SEQ ID NO 333
<211> LENGTH: 9
<212> TYPE: DNA
<213> ORGANISM: Artificial Sequence
<220> FEATURE:
<223> OTHER INFORMATION: synthetic

<400> SEQUENCE: 333 ggtgcatcc      9

<210> SEQ ID NO 334
<211> LENGTH: 3
<212> TYPE: PRT

```
<213> ORGANISM: Artificial Sequence
<220> FEATURE:
<223> OTHER INFORMATION: synthetic

<400> SEQUENCE: 334

Gly Ala Ser
1

<210> SEQ ID NO 335
<211> LENGTH: 27
<212> TYPE: DNA
<213> ORGANISM: Artificial Sequence
<220> FEATURE:
<223> OTHER INFORMATION: synthetic

<400> SEQUENCE: 335
caacagtata atagttaccc atacact                                          27

<210> SEQ ID NO 336
<211> LENGTH: 9
<212> TYPE: PRT
<213> ORGANISM: Artificial Sequence
<220> FEATURE:
<223> OTHER INFORMATION: synthetic

<400> SEQUENCE: 336

Gln Gln Tyr Asn Ser Tyr Pro Tyr Thr
1               5

<210> SEQ ID NO 337
<211> LENGTH: 369
<212> TYPE: DNA
<213> ORGANISM: Artificial Sequence
<220> FEATURE:
<223> OTHER INFORMATION: synthetic

<400> SEQUENCE: 337
gaggtgcagc tggtggagtc tggaggaggc ttggtccagc ctgggggtc cctgagactc       60 tcctgtgcag cctctgggtt caccgtcagt agcaactaca tgagctgggt ccgccaggct      120
ccagggaagg ggctggagtg ggtctcagtt atttatagcg gtggtagaac aaactacgga      180
gactccgtga agggccgatt caccatctcc agagacaatt ccaagaacac gctgtatctt      240
caaatgaaca gcctgagagc tgaggacacg gccgtgtatt actgtgcgag agaaattac       300 gattttgga gtggtgaccc ctacggttgg gacgtctggg gccaagggac cacggtcacc       360
gtctcctca                                                             369

<210> SEQ ID NO 338
<211> LENGTH: 123
<212> TYPE: PRT
<213> ORGANISM: Artificial Sequence
<220> FEATURE:
<223> OTHER INFORMATION: synthetic

<400> SEQUENCE: 338

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Ser Gly Gly Arg Thr Asn Tyr Gly Asp Ser Val Lys
    50                  55                  60
```

```
Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                 85                  90                  95

Arg Glu Asn Tyr Asp Phe Trp Ser Gly Asp Pro Tyr Gly Trp Asp Val
            100                 105                 110

Trp Gly Gln Gly Thr Thr Val Thr Val Ser Ser
        115                 120
```

<210> SEQ ID NO 339
<211> LENGTH: 24
<212> TYPE: DNA
<213> ORGANISM: Artificial Sequence
<220> FEATURE:
<223> OTHER INFORMATION: synthetic

<400> SEQUENCE: 339
gggttcaccg tcagtagcaa ctac                                          24

<210> SEQ ID NO 340
<211> LENGTH: 8
<212> TYPE: PRT
<213> ORGANISM: Artificial Sequence
<220> FEATURE:
<223> OTHER INFORMATION: synthetic

<400> SEQUENCE: 340

```
Gly Phe Thr Val Ser Ser Asn Tyr
 1               5
```

<210> SEQ ID NO 341
<211> LENGTH: 21
<212> TYPE: DNA
<213> ORGANISM: Artificial Sequence
<220> FEATURE:
<223> OTHER INFORMATION: synthetic

<400> SEQUENCE: 341
atttatagcg gtggtagaac a                                             21

<210> SEQ ID NO 342
<211> LENGTH: 7
<212> TYPE: PRT
<213> ORGANISM: Artificial Sequence
<220> FEATURE:
<223> OTHER INFORMATION: synthetic

<400> SEQUENCE: 342

```
Ile Tyr Ser Gly Gly Arg Thr
 1               5
```

<210> SEQ ID NO 343
<211> LENGTH: 51
<212> TYPE: DNA
<213> ORGANISM: Artificial Sequence
<220> FEATURE:
<223> OTHER INFORMATION: synthetic

<400> SEQUENCE: 343
gcgagagaga attacgattt ttggagtggt gacccctacg gttgggacgt c             51

<210> SEQ ID NO 344
<211> LENGTH: 17
<212> TYPE: PRT

```
<213> ORGANISM: Artificial Sequence
<220> FEATURE:
<223> OTHER INFORMATION: synthetic

<400> SEQUENCE: 344

Ala Arg Glu Asn Tyr Asp Phe Trp Ser Gly Asp Pro Tyr Gly Trp Asp
1               5                   10                  15
Val

<210> SEQ ID NO 345
<211> LENGTH: 321
<212> TYPE: DNA
<213> ORGANISM: Artificial Sequence
<220> FEATURE:
<223> OTHER INFORMATION: synthetic

<400> SEQUENCE: 345
gacatccaga tgacccagtc tccatcctca ctgtctgcat ctgtaggaga cagagtcacc      60
atcacttgtc gggcgagtca ggacattagc aattatttag cctggtttca gcagaaacca    120
gggaaagccc ctaagtccct gatatatggt gcatccagtt tgcaaagagg ggtcccatca    180
aagttcagcg gcagtggatc tgggacagat ttcactctca ccatcagcag cctgcagcct    240
gaagattttg caacttatta ctgccaacag tataatagtt acccatacac ttttggccag    300
gggaccaagc tggagatcaa a                                              321

<210> SEQ ID NO 346
<211> LENGTH: 107
<212> TYPE: PRT
<213> ORGANISM: Artificial Sequence
<220> FEATURE:
<223> OTHER INFORMATION: synthetic

<400> SEQUENCE: 346

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
                20                  25                  30

Leu Ala Trp Phe Gln Gln Lys Pro Gly Lys Ala Pro Lys Ser Leu Ile
            35                  40                  45

Tyr Gly Ala Ser Ser Leu Gln Arg Gly Val Pro Ser Lys Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Tyr
                85                  90                  95

Thr Phe Gly Gln Gly Thr Lys Leu Glu Ile Lys
            100                 105

<210> SEQ ID NO 347
<211> LENGTH: 18
<212> TYPE: DNA
<213> ORGANISM: Artificial Sequence
<220> FEATURE:
<223> OTHER INFORMATION: synthetic

<400> SEQUENCE: 347
caggacatta gcaattat                                                   18

<210> SEQ ID NO 348
<211> LENGTH: 6
```

<212> TYPE: PRT
<213> ORGANISM: Artificial Sequence
<220> FEATURE:
<223> OTHER INFORMATION: synthetic

<400> SEQUENCE: 348

Gln Asp Ile Ser Asn Tyr
1               5

<210> SEQ ID NO 349
<211> LENGTH: 9
<212> TYPE: DNA
<213> ORGANISM: Artificial Sequence
<220> FEATURE:
<223> OTHER INFORMATION: synthetic

<400> SEQUENCE: 349 ggtgcatcc                                                                 9

<210> SEQ ID NO 350
<211> LENGTH: 3
<212> TYPE: PRT
<213> ORGANISM: Artificial Sequence
<220> FEATURE:
<223> OTHER INFORMATION: synthetic

<400> SEQUENCE: 350

Gly Ala Ser
1

<210> SEQ ID NO 351
<211> LENGTH: 27
<212> TYPE: DNA
<213> ORGANISM: Artificial Sequence
<220> FEATURE:
<223> OTHER INFORMATION: synthetic

<400> SEQUENCE: 351
caacagtata atagttaccc atacact                                            27

<210> SEQ ID NO 352
<211> LENGTH: 9
<212> TYPE: PRT
<213> ORGANISM: Artificial Sequence
<220> FEATURE:
<223> OTHER INFORMATION: synthetic

<400> SEQUENCE: 352

Gln Gln Tyr Asn Ser Tyr Pro Tyr Thr
1               5

<210> SEQ ID NO 353
<211> LENGTH: 3423
<212> TYPE: PRT
<213> ORGANISM: Artificial Sequence
<220> FEATURE:
<223> OTHER INFORMATION: Zika Virus polyprotein (GenBank No. ALU33341.1)

<400> SEQUENCE: 353

Met Lys Asn Pro Lys Lys Lys Ser Gly Gly Phe Arg Ile Val Asn Met
1               5                   10                  15

Leu Lys Arg Gly Val Ala Arg Val Ser Pro Phe Gly Gly Leu Lys Arg
                20                  25                  30

Leu Pro Ala Gly Leu Leu Leu Gly His Gly Pro Ile Arg Met Val Leu
35 40 45

```
Ala Ile Leu Ala Phe Leu Arg Phe Thr Ala Ile Lys Pro Ser Leu Gly
 50                  55                  60

Leu Ile Asn Arg Trp Gly Ser Val Gly Lys Lys Glu Ala Met Glu Ile
 65                  70                  75                  80

Ile Lys Lys Phe Lys Lys Asp Leu Ala Ala Met Leu Arg Ile Ile Asn
                 85                  90                  95

Ala Arg Lys Glu Lys Lys Arg Arg Gly Ala Asp Thr Ser Val Gly Ile
                100                 105                 110

Val Gly Leu Leu Leu Thr Thr Ala Met Ala Ala Glu Val Thr Arg Arg
                115                 120                 125

Gly Ser Ala Tyr Tyr Met Tyr Leu Asp Arg Asn Asp Ala Gly Glu Ala
130                 135                 140

Ile Ser Phe Pro Thr Thr Leu Gly Met Asn Lys Cys Tyr Ile Gln Ile
145                 150                 155                 160

Met Asp Leu Gly His Met Cys Asp Ala Thr Met Ser Tyr Glu Cys Pro
                165                 170                 175

Met Leu Asp Glu Gly Val Glu Pro Asp Asp Val Asp Cys Trp Cys Asn
                180                 185                 190

Thr Thr Ser Thr Trp Val Val Tyr Gly Thr Cys His His Lys Lys Gly
                195                 200                 205

Glu Ala Arg Arg Ser Arg Arg Ala Val Thr Leu Pro Ser His Ser Thr
210                 215                 220

Arg Lys Leu Gln Thr Arg Ser Gln Thr Trp Leu Glu Ser Arg Glu Tyr
225                 230                 235                 240

Thr Lys His Leu Ile Arg Val Glu Asn Trp Ile Phe Arg Asn Pro Gly
                245                 250                 255

Phe Ala Leu Ala Ala Ala Ala Ile Ala Trp Leu Leu Gly Ser Ser Thr
                260                 265                 270

Ser Gln Lys Val Ile Tyr Leu Val Met Ile Leu Leu Ile Ala Pro Ala
                275                 280                 285

Tyr Ser Ile Arg Cys Ile Gly Val Ser Asn Arg Asp Phe Val Glu Gly
                290                 295                 300

Met Ser Gly Gly Thr Trp Val Asp Ile Val Leu Glu His Gly Gly Cys
305                 310                 315                 320

Val Thr Val Met Ala Gln Asp Lys Pro Thr Val Asp Ile Glu Leu Val
                325                 330                 335

Thr Thr Thr Val Ser Asn Met Ala Glu Val Arg Ser Tyr Cys Tyr Glu
                340                 345                 350

Ala Ser Ile Ser Asp Met Ala Ser Asp Ser Arg Cys Pro Thr Gln Gly
                355                 360                 365

Glu Ala Tyr Leu Asp Lys Gln Ser Asp Thr Gln Tyr Val Cys Lys Arg
370                 375                 380

Thr Leu Val Asp Arg Gly Trp Gly Asn Gly Cys Gly Leu Phe Gly Lys
385                 390                 395                 400

Gly Ser Leu Val Thr Cys Ala Lys Phe Ala Cys Ser Lys Lys Met Thr
                405                 410                 415

Gly Lys Ser Ile Gln Pro Glu Asn Leu Glu Tyr Arg Ile Met Leu Ser
                420                 425                 430

Val His Gly Ser Gln His Ser Gly Met Ile Val Asn Asp Thr Gly His
                435                 440                 445

Glu Thr Asp Glu Asn Arg Ala Lys Val Glu Ile Thr Pro Asn Ser Pro
450                 455                 460

Arg Ala Glu Ala Thr Leu Gly Gly Phe Gly Ser Leu Gly Leu Asp Cys
```

```
            465                 470                 475                 480
        Glu Pro Arg Thr Gly Leu Asp Phe Ser Asp Leu Tyr Tyr Leu Thr Met
                            485                 490                 495

Asn Asn Lys His Trp Leu Val His Lys Glu Trp Phe His Asp Ile Pro
                        500                 505                 510

Leu Pro Trp His Ala Gly Ala Asp Thr Gly Thr Pro His Trp Asn Asn
                    515                 520                 525

Lys Glu Ala Leu Val Glu Phe Lys Asp Ala His Ala Lys Arg Gln Thr
                530                 535                 540

Val Val Val Leu Gly Ser Gln Glu Gly Ala Val His Thr Ala Leu Ala
        545                 550                 555                 560

Gly Ala Leu Glu Ala Glu Met Asp Gly Ala Lys Gly Arg Leu Ser Ser
                            565                 570                 575

Gly His Leu Lys Cys Arg Leu Lys Met Asp Lys Leu Arg Leu Lys Gly
                        580                 585                 590

Val Ser Tyr Ser Leu Cys Thr Ala Ala Phe Thr Phe Thr Lys Ile Pro
                    595                 600                 605

Ala Glu Thr Leu His Gly Thr Val Thr Val Glu Val Gln Tyr Ala Gly
                610                 615                 620

Thr Asp Gly Pro Cys Lys Val Pro Ala Gln Met Ala Val Asp Met Gln
        625                 630                 635                 640

Thr Leu Thr Pro Val Gly Arg Leu Ile Thr Ala Asn Pro Val Ile Thr
                            645                 650                 655

Glu Ser Thr Glu Asn Ser Lys Met Met Leu Glu Leu Asp Pro Pro Phe
                        660                 665                 670

Gly Asp Ser Tyr Ile Val Ile Gly Val Gly Glu Lys Lys Ile Thr His
                    675                 680                 685

His Trp His Arg Ser Gly Ser Thr Ile Gly Lys Ala Phe Glu Ala Thr
                690                 695                 700

Val Arg Gly Ala Lys Arg Met Ala Val Leu Gly Asp Thr Ala Trp Asp
        705                 710                 715                 720

Phe Gly Ser Val Gly Gly Ala Leu Asn Ser Leu Gly Lys Gly Ile His
                            725                 730                 735

Gln Ile Phe Gly Ala Ala Phe Lys Ser Leu Phe Gly Gly Met Ser Trp
                        740                 745                 750

Phe Ser Gln Ile Leu Ile Gly Thr Leu Leu Met Trp Leu Gly Leu Asn
                    755                 760                 765

Thr Lys Asn Gly Ser Ile Ser Leu Met Cys Leu Ala Leu Gly Gly Val
                770                 775                 780

Leu Ile Phe Leu Ser Thr Ala Val Ser Ala Asp Val Gly Cys Ser Val
        785                 790                 795                 800

Asp Phe Ser Lys Lys Glu Thr Arg Cys Gly Thr Gly Val Phe Val Tyr
                            805                 810                 815

Asn Asp Val Glu Ala Trp Arg Asp Arg Tyr Lys Tyr His Pro Asp Ser
                        820                 825                 830

Pro Arg Arg Leu Ala Ala Ala Val Lys Gln Ala Trp Glu Asp Gly Ile
                    835                 840                 845

Cys Gly Ile Ser Ser Val Ser Arg Met Glu Asn Ile Met Trp Arg Ser
                850                 855                 860

Val Glu Gly Glu Leu Asn Ala Ile Leu Glu Glu Asn Gly Val Gln Leu
        865                 870                 875                 880

Thr Val Val Val Gly Ser Val Lys Asn Pro Met Trp Arg Gly Pro Gln
                            885                 890                 895
```

```
Arg Leu Pro Val Pro Val Asn Glu Leu Pro His Gly Trp Lys Ala Trp
            900                 905                 910

Gly Lys Ser His Phe Val Arg Ala Ala Lys Thr Asn Asn Ser Phe Val
            915                 920                 925

Val Asp Gly Asp Thr Leu Lys Glu Cys Pro Leu Lys His Arg Ala Trp
            930                 935                 940

Asn Ser Phe Leu Val Glu Asp His Gly Phe Gly Val Phe His Thr Ser
945                 950                 955                 960

Val Trp Leu Lys Val Arg Glu Asp Tyr Ser Leu Glu Cys Asp Pro Ala
            965                 970                 975

Val Ile Gly Thr Ala Val Lys Gly Lys Glu Ala Val His Ser Asp Leu
            980                 985                 990

Gly Tyr Trp Ile Glu Ser Glu Lys Asn Asp Thr Trp Arg Leu Lys Arg
            995                 1000                1005

Ala His Leu Ile Glu Met Lys Thr Cys Glu Trp Pro Lys Ser His Thr
            1010                1015                1020

Leu Trp Thr Asp Gly Ile Glu Glu Ser Asp Leu Ile Ile Pro Lys Ser
1025                1030                1035                1040

Leu Ala Gly Pro Leu Ser His His Asn Thr Arg Glu Gly Tyr Arg Thr
            1045                1050                1055

Gln Met Lys Gly Pro Trp His Ser Glu Glu Leu Glu Ile Arg Phe Glu
            1060                1065                1070

Glu Cys Pro Gly Thr Lys Val His Val Glu Glu Thr Cys Gly Thr Arg
            1075                1080                1085

Gly Pro Ser Leu Arg Ser Thr Thr Ala Ser Gly Arg Val Ile Glu Glu
            1090                1095                1100

Trp Cys Cys Arg Glu Cys Thr Met Pro Pro Leu Ser Phe Arg Ala Lys
1105                1110                1115                1120

Asp Gly Cys Trp Tyr Gly Met Glu Ile Arg Pro Arg Lys Glu Pro Glu
            1125                1130                1135

Ser Asn Leu Val Arg Ser Met Val Thr Ala Gly Ser Thr Asp His Met
            1140                1145                1150

Asp His Phe Ser Leu Gly Val Leu Val Ile Leu Leu Met Val Gln Glu
            1155                1160                1165

Gly Leu Lys Lys Arg Met Thr Thr Lys Ile Ile Ile Ser Thr Ser Met
            1170                1175                1180

Ala Val Leu Val Ala Met Ile Leu Gly Gly Phe Ser Met Ser Asp Leu
1185                1190                1195                1200

Ala Lys Leu Ala Ile Leu Met Gly Ala Thr Phe Ala Glu Met Asn Thr
            1205                1210                1215

Gly Gly Asp Val Ala His Leu Ala Leu Ile Ala Ala Phe Lys Val Arg
            1220                1225                1230

Pro Ala Leu Leu Val Ser Phe Ile Phe Arg Ala Asn Trp Thr Pro Arg
            1235                1240                1245

Glu Ser Met Leu Leu Ala Leu Ala Ser Cys Leu Leu Gln Thr Ala Ile
            1250                1255                1260

Ser Ala Leu Glu Gly Asp Leu Met Val Leu Ile Asn Gly Phe Ala Leu
1265                1270                1275                1280

Ala Trp Leu Ala Ile Arg Ala Met Val Val Pro Arg Thr Asp Asn Ile
            1285                1290                1295

Thr Leu Ala Ile Leu Ala Ala Leu Thr Pro Leu Ala Arg Gly Thr Leu
            1300                1305                1310
```

Leu Val Ala Trp Arg Ala Gly Leu Ala Thr Cys Gly Phe Met Leu
1315                1320            1325

Leu Ser Leu Lys Gly Lys Gly Ser Val Lys Lys Asn Leu Pro Phe Val
1330                1335            1340

Met Ala Leu Gly Leu Thr Ala Val Arg Leu Val Asp Pro Ile Asn Val
1345                1350            1355            1360

Val Gly Leu Leu Leu Leu Thr Arg Ser Gly Lys Arg Ser Trp Pro Pro
                1365            1370            1375

Ser Glu Val Leu Thr Ala Val Gly Leu Ile Cys Ala Leu Ala Gly Gly
            1380            1385            1390

Phe Ala Lys Ala Asp Ile Glu Met Ala Gly Pro Met Ala Ala Val Gly
                1395            1400            1405

Leu Leu Ile Val Ser Tyr Val Val Ser Gly Lys Ser Val Asp Met Tyr
            1410            1415            1420

Ile Glu Arg Ala Gly Asp Ile Thr Trp Glu Lys Asp Ala Glu Val Thr
1425                1430            1435            1440

Gly Asn Ser Pro Arg Leu Asp Val Ala Leu Asp Glu Ser Gly Asp Phe
                1445            1450            1455

Ser Leu Val Glu Asp Asp Gly Pro Pro Met Arg Glu Ile Ile Leu Lys
            1460            1465            1470

Val Val Leu Met Thr Ile Cys Gly Met Asn Pro Ile Ala Ile Pro Phe
            1475            1480            1485

Ala Ala Gly Ala Trp Tyr Val Tyr Val Lys Thr Gly Lys Arg Ser Gly
            1490            1495            1500

Ala Leu Trp Asp Val Pro Ala Pro Lys Glu Val Lys Lys Gly Glu Thr
1505                1510            1515            1520

Thr Asp Gly Val Tyr Arg Val Met Thr Arg Arg Leu Leu Gly Ser Thr
                1525            1530            1535

Gln Val Gly Val Gly Val Met Gln Glu Gly Val Phe His Thr Met Trp
            1540            1545            1550

His Val Thr Lys Gly Ser Ala Leu Arg Ser Gly Glu Gly Arg Leu Asp
            1555            1560            1565

Pro Tyr Trp Gly Asp Val Lys Gln Asp Leu Val Ser Tyr Cys Gly Pro
1570                1575            1580

Trp Lys Leu Asp Ala Ala Trp Asp Gly His Ser Glu Val Gln Leu Leu
1585                1590            1595            1600

Ala Val Pro Pro Gly Glu Arg Ala Arg Asn Ile Gln Thr Leu Pro Gly
                1605            1610            1615

Ile Phe Lys Thr Lys Asp Gly Asp Ile Gly Ala Val Ala Leu Asp Tyr
            1620            1625            1630

Pro Ala Gly Thr Ser Gly Ser Pro Ile Leu Asp Lys Cys Gly Arg Val
            1635            1640            1645

Ile Gly Leu Tyr Gly Asn Gly Val Val Ile Lys Asn Gly Ser Tyr Val
            1650            1655            1660

Ser Ala Ile Thr Gln Gly Arg Arg Glu Glu Thr Pro Val Glu Cys
1665                1670            1675            1680

Phe Glu Pro Ser Met Leu Lys Lys Lys Gln Leu Thr Val Leu Asp Leu
                1685            1690            1695

His Pro Gly Ala Gly Lys Thr Arg Arg Val Leu Pro Glu Ile Val Arg
                1700            1705            1710

Glu Ala Ile Lys Thr Arg Leu Arg Thr Val Ile Leu Ala Pro Thr Arg
            1715            1720            1725

Val Val Ala Ala Glu Met Glu Glu Ala Leu Arg Gly Leu Pro Val Arg

```
            1730            1735            1740
Tyr Met Thr Thr Ala Val Asn Val Thr His Ser Gly Thr Glu Ile Val
1745            1750            1755            1760

Asp Leu Met Cys His Ala Thr Phe Thr Ser Arg Leu Leu Gln Pro Ile
            1765            1770            1775

Arg Val Pro Asn Tyr Asn Leu Tyr Ile Met Asp Glu Ala His Phe Thr
            1780            1785            1790

Asp Pro Ser Ser Ile Ala Ala Arg Gly Tyr Ile Ser Thr Arg Val Glu
            1795            1800            1805

Met Gly Glu Ala Ala Ala Ile Phe Met Thr Ala Thr Pro Pro Gly Thr
            1810            1815            1820

Arg Asp Ala Phe Pro Asp Ser Asn Ser Pro Ile Met Asp Thr Glu Val
1825            1830            1835            1840

Glu Val Pro Glu Arg Ala Trp Ser Ser Gly Phe Asp Trp Val Thr Asp
            1845            1850            1855

Tyr Ser Gly Lys Thr Val Trp Phe Val Pro Ser Val Arg Asn Gly Asn
            1860            1865            1870

Glu Ile Ala Ala Cys Leu Thr Lys Ala Gly Lys Arg Val Ile Gln Leu
            1875            1880            1885

Ser Arg Lys Thr Phe Glu Thr Glu Phe Gln Lys Thr Lys His Gln Glu
            1890            1895            1900

Trp Asp Phe Val Val Thr Thr Asp Ile Ser Glu Met Gly Ala Asn Phe
1905            1910            1915            1920

Lys Ala Asp Arg Val Ile Asp Ser Arg Arg Cys Leu Lys Pro Val Ile
            1925            1930            1935

Leu Asp Gly Glu Arg Val Ile Leu Ala Gly Pro Met Pro Val Thr His
            1940            1945            1950

Ala Ser Ala Ala Gln Arg Arg Gly Arg Ile Gly Arg Asn Pro Asn Lys
            1955            1960            1965

Pro Gly Asp Glu Tyr Leu Tyr Gly Gly Gly Cys Ala Glu Thr Asp Glu
            1970            1975            1980

Asp His Ala His Trp Leu Glu Ala Arg Met Leu Leu Asp Asn Ile Tyr
1985            1990            1995            2000

Leu Gln Asp Gly Leu Ile Ala Ser Leu Tyr Arg Pro Glu Ala Asp Lys
            2005            2010            2015

Val Ala Ala Ile Glu Gly Glu Phe Lys Leu Arg Thr Glu Gln Arg Lys
            2020            2025            2030

Thr Phe Val Glu Leu Met Lys Arg Gly Asp Leu Pro Val Trp Leu Ala
            2035            2040            2045

Tyr Gln Val Ala Ser Ala Gly Ile Thr Tyr Thr Asp Arg Arg Trp Cys
            2050            2055            2060

Phe Asp Gly Thr Thr Asn Asn Thr Ile Met Glu Asp Ser Val Pro Ala
2065            2070            2075            2080

Glu Val Trp Thr Arg His Gly Glu Lys Arg Val Leu Lys Pro Arg Trp
            2085            2090            2095

Met Asp Ala Arg Val Cys Ser Asp His Ala Ala Leu Lys Ser Phe Lys
            2100            2105            2110

Glu Phe Ala Ala Gly Lys Arg Gly Ala Ala Phe Gly Val Met Glu Ala
            2115            2120            2125

Leu Gly Thr Leu Pro Gly His Met Thr Glu Arg Phe Gln Glu Ala Ile
            2130            2135            2140

Asp Asn Leu Ala Val Leu Met Arg Ala Glu Thr Gly Ser Arg Pro Tyr
2145            2150            2155            2160
```

-continued

Lys Ala Ala Ala Ala Gln Leu Pro Glu Thr Leu Glu Thr Ile Met Leu
              2165                2170                2175

Leu Gly Leu Leu Gly Thr Val Ser Leu Gly Ile Phe Phe Val Leu Met
              2180                2185                2190

Arg Asn Lys Gly Ile Gly Lys Met Gly Phe Gly Met Val Thr Leu Gly
              2195                2200                2205

Ala Ser Ala Trp Leu Met Trp Leu Ser Glu Ile Glu Pro Ala Arg Ile
              2210                2215                2220

Ala Cys Val Leu Ile Val Val Phe Leu Leu Leu Val Val Leu Ile Pro
2225                2230                2235                2240

Glu Pro Glu Lys Gln Arg Ser Pro Gln Asp Asn Gln Met Ala Ile Ile
              2245                2250                2255

Ile Met Val Ala Val Gly Leu Leu Gly Leu Ile Thr Ala Asn Glu Leu
              2260                2265                2270

Gly Trp Leu Glu Arg Thr Lys Ser Asp Leu Ser His Leu Met Gly Arg
              2275                2280                2285

Arg Glu Glu Gly Ala Thr Met Gly Phe Ser Met Asp Ile Asp Leu Arg
              2290                2295                2300

Pro Ala Ser Ala Trp Ala Ile Tyr Ala Ala Leu Thr Thr Phe Ile Thr
2305                2310                2315                2320

Pro Ala Val Gln His Ala Val Thr Thr Ser Tyr Asn Asn Tyr Ser Leu
              2325                2330                2335

Met Ala Met Ala Thr Gln Ala Gly Val Leu Phe Gly Met Gly Lys Gly
              2340                2345                2350

Met Pro Phe Tyr Ala Trp Asp Phe Gly Val Pro Leu Leu Met Ile Gly
              2355                2360                2365

Cys Tyr Ser Gln Leu Thr Pro Leu Thr Leu Ile Val Ala Ile Ile Leu
              2370                2375                2380

Leu Val Ala His Tyr Met Tyr Leu Ile Pro Gly Leu Gln Ala Ala Ala
2385                2390                2395                2400

Ala Arg Ala Ala Gln Lys Arg Thr Ala Ala Gly Ile Met Lys Asn Pro
              2405                2410                2415

Val Val Asp Gly Ile Val Val Thr Asp Ile Asp Thr Met Thr Ile Asp
              2420                2425                2430

Pro Gln Val Glu Lys Lys Met Gly Gln Val Leu Leu Met Ala Val Ala
              2435                2440                2445

Val Ser Ser Ala Ile Leu Ser Arg Thr Ala Trp Gly Trp Gly Glu Ala
              2450                2455                2460

Gly Ala Leu Ile Thr Ala Ala Thr Ser Thr Leu Trp Glu Gly Ser Pro
2465                2470                2475                2480

Asn Lys Tyr Trp Asn Ser Ser Thr Ala Thr Ser Leu Cys Asn Ile Phe
              2485                2490                2495

Arg Gly Ser Tyr Leu Ala Gly Ala Ser Leu Ile Tyr Thr Val Thr Arg
              2500                2505                2510

Asn Ala Gly Leu Val Lys Arg Arg Gly Gly Gly Thr Gly Glu Thr Leu
              2515                2520                2525

Gly Glu Lys Trp Lys Ala Arg Leu Asn Gln Met Ser Ala Leu Glu Phe
              2530                2535                2540

Tyr Ser Tyr Lys Lys Ser Gly Ile Thr Glu Val Cys Arg Glu Glu Ala
2545                2550                2555                2560

Arg Arg Ala Leu Lys Asp Gly Val Ala Thr Gly Gly His Ala Val Ser
              2565                2570                2575

```
Arg Gly Ser Ala Lys Leu Arg Trp Leu Val Glu Gly Tyr Leu Gln
            2580                2585                2590

Pro Tyr Gly Lys Val Ile Asp Leu Gly Cys Gly Arg Gly Gly Trp Ser
        2595                2600                2605

Tyr Tyr Ala Ala Thr Ile Arg Lys Val Gln Glu Val Lys Gly Tyr Thr
        2610                2615                2620

Lys Gly Gly Pro Gly His Glu Glu Pro Val Leu Val Gln Ser Tyr Gly
2625            2630                2635                2640

Trp Asn Ile Val Arg Leu Lys Ser Gly Val Asp Val Phe His Met Ala
                2645                2650                2655

Ala Glu Pro Cys Asp Thr Leu Leu Cys Asp Ile Gly Glu Ser Ser Ser
            2660                2665                2670

Ser Pro Glu Val Glu Glu Ala Arg Thr Leu Arg Val Leu Ser Met Val
        2675                2680                2685

Gly Asp Trp Leu Glu Lys Arg Pro Gly Ala Phe Cys Ile Lys Val Leu
        2690                2695                2700

Cys Pro Tyr Thr Ser Thr Met Met Glu Thr Leu Glu Arg Leu Gln Arg
2705            2710                2715                2720

Arg Tyr Gly Gly Gly Leu Val Arg Val Pro Leu Ser Arg Asn Ser Thr
                2725                2730                2735

His Glu Met Tyr Trp Val Ser Gly Ala Lys Ser Asn Thr Ile Lys Ser
            2740                2745                2750

Val Ser Thr Thr Ser Gln Leu Leu Leu Gly Arg Met Asp Gly Pro Arg
        2755                2760                2765

Arg Pro Val Lys Tyr Glu Glu Asp Val Asn Leu Gly Ser Gly Thr Arg
        2770                2775                2780

Ala Val Val Ser Cys Ala Glu Ala Pro Asn Met Lys Ile Ile Gly Asn
2785            2790                2795                2800

Arg Ile Glu Arg Ile Arg Ser Glu His Ala Glu Thr Trp Phe Phe Asp
                2805                2810                2815

Glu Asn His Pro Tyr Arg Thr Trp Ala Tyr His Gly Ser Tyr Glu Ala
            2820                2825                2830

Pro Thr Gln Gly Ser Ala Ser Ser Leu Ile Asn Gly Val Val Arg Leu
        2835                2840                2845

Leu Ser Lys Pro Trp Asp Val Val Thr Gly Val Thr Gly Ile Ala Met
2850            2855                2860

Thr Asp Thr Thr Pro Tyr Gly Gln Gln Arg Val Phe Lys Glu Lys Val
2865            2870                2875                2880

Asp Thr Arg Val Pro Asp Pro Gln Glu Gly Thr Arg Gln Val Met Ser
            2885                2890                2895

Met Val Ser Ser Trp Leu Trp Lys Glu Leu Gly Lys His Lys Arg Pro
            2900                2905                2910

Arg Val Cys Thr Lys Glu Glu Phe Ile Asn Lys Val Arg Ser Asn Ala
        2915                2920                2925

Ala Leu Gly Ala Ile Phe Glu Glu Glu Lys Glu Trp Lys Thr Ala Val
        2930                2935                2940

Glu Ala Val Asn Asp Pro Arg Phe Trp Ala Leu Val Asp Lys Glu Arg
2945            2950                2955                2960

Glu His His Leu Arg Gly Glu Cys Gln Ser Cys Val Tyr Asn Met Met
            2965                2970                2975

Gly Lys Arg Glu Lys Lys Gln Gly Glu Phe Gly Lys Ala Lys Gly Ser
        2980                2985                2990

Arg Ala Ile Trp Tyr Met Trp Leu Gly Ala Arg Phe Leu Glu Phe Glu
```

```
                2995                3000                3005
Ala Leu Gly Phe Leu Asn Glu Asp His Trp Met Gly Arg Glu Asn Ser
    3010                3015                3020
Gly Gly Gly Val Glu Gly Leu Gly Leu Gln Arg Leu Gly Tyr Val Leu
3025                3030                3035                3040
Glu Glu Met Ser Arg Ile Pro Gly Gly Arg Met Tyr Ala Asp Asp Thr
                3045                3050                3055
Ala Gly Trp Asp Thr Arg Ile Ser Arg Phe Asp Leu Glu Asn Glu Ala
    3060                3065                3070
Leu Ile Thr Asn Gln Met Glu Lys Gly His Arg Ala Leu Ala Leu Ala
    3075                3080                3085
Ile Ile Lys Tyr Thr Tyr Gln Asn Lys Val Val Lys Val Leu Arg Pro
3090                3095                3100
Ala Glu Lys Gly Lys Thr Val Met Asp Ile Ile Ser Arg Gln Asp Gln
3105                3110                3115                3120
Arg Gly Ser Gly Gln Val Val Thr Tyr Ala Leu Asn Thr Phe Thr Asn
            3125                3130                3135
Leu Val Val Gln Leu Ile Arg Asn Met Glu Ala Glu Val Leu Glu
    3140                3145                3150
Met Gln Asp Leu Trp Leu Leu Arg Arg Ser Glu Lys Val Thr Asn Trp
    3155                3160                3165
Leu Gln Ser Asn Gly Trp Asp Arg Leu Lys Arg Met Ala Val Ser Gly
    3170                3175                3180
Asp Asp Cys Val Val Lys Pro Ile Asp Asp Arg Phe Ala His Ala Leu
3185                3190                3195                3200
Arg Phe Leu Asn Asp Met Gly Lys Val Arg Lys Asp Thr Gln Glu Trp
            3205                3210                3215
Lys Pro Ser Thr Gly Trp Asp Asn Trp Glu Glu Val Pro Phe Cys Ser
            3220                3225                3230
His His Phe Asn Lys Leu His Leu Lys Asp Gly Arg Ser Ile Val Val
        3235                3240                3245
Pro Cys Arg His Gln Asp Glu Leu Ile Gly Arg Ala Arg Val Ser Pro
3250                3255                3260
Gly Ala Gly Trp Ser Ile Arg Glu Thr Ala Cys Leu Ala Lys Ser Tyr
3265                3270                3275                3280
Ala Gln Met Trp Gln Leu Leu Tyr Phe His Arg Arg Asp Leu Arg Leu
        3285                3290                3295
Met Ala Asn Ala Ile Cys Ser Ser Val Pro Val Asp Trp Val Pro Thr
        3300                3305                3310
Gly Arg Thr Thr Trp Ser Ile His Gly Lys Gly Glu Trp Met Thr Thr
        3315                3320                3325
Glu Asp Met Leu Val Val Trp Asn Arg Val Trp Ile Glu Glu Asn Asp
    3330                3335                3340
His Met Glu Asp Lys Thr Pro Val Thr Lys Trp Thr Asp Ile Pro Tyr
3345                3350                3355                3360
Leu Gly Lys Arg Glu Asp Leu Trp Cys Gly Ser Leu Ile Gly His Arg
            3365                3370                3375
Pro Arg Thr Thr Trp Ala Glu Asn Ile Lys Asn Thr Val Asn Met Val
        3380                3385                3390
Arg Arg Ile Ile Gly Asp Glu Glu Lys Tyr Met Asp Tyr Leu Ser Thr
        3395                3400                3405
Gln Val Arg Tyr Leu Gly Glu Glu Gly Ser Thr Pro Gly Val Leu
    3410                3415                3420
```

<210> SEQ ID NO 354
<211> LENGTH: 629
<212> TYPE: PRT
<213> ORGANISM: Artificial Sequence
<220> FEATURE:
<223> OTHER INFORMATION: ZIka prM80E.mmH

<400> SEQUENCE: 354

```
Met His Arg Pro Arg Arg Gly Thr Arg Pro Pro Leu Ala Leu
1               5                   10                  15

Leu Ala Ala Leu Leu Ala Ala Arg Gly Ala Asp Ala Ala Glu Val
                20                  25                  30

Thr Arg Arg Gly Ser Ala Tyr Tyr Met Tyr Leu Asp Arg Asn Asp Ala
            35                  40                  45

Gly Glu Ala Ile Ser Phe Pro Thr Thr Leu Gly Met Asn Lys Cys Tyr
50                  55                  60

Ile Gln Ile Met Asp Leu Gly His Met Cys Asp Ala Thr Met Ser Tyr
65                  70                  75                  80

Glu Cys Pro Met Leu Asp Glu Gly Val Glu Pro Asp Asp Val Asp Cys
                85                  90                  95

Trp Cys Asn Thr Thr Ser Thr Trp Val Val Tyr Gly Thr Cys His His
                100                 105                 110

Lys Lys Gly Glu Ala Arg Arg Ser Arg Arg Ala Val Thr Leu Pro Ser
            115                 120                 125

His Ser Thr Arg Lys Leu Gln Thr Arg Ser Gln Thr Trp Leu Glu Ser
130                 135                 140

Arg Glu Tyr Thr Lys His Leu Ile Arg Val Glu Asn Trp Ile Phe Arg
145                 150                 155                 160

Asn Pro Gly Phe Ala Leu Ala Ala Ala Ala Ile Ala Trp Leu Leu Gly
                165                 170                 175

Ser Ser Thr Ser Gln Lys Val Ile Tyr Leu Val Met Ile Leu Leu Ile
            180                 185                 190

Ala Pro Ala Tyr Ser Ile Arg Cys Ile Gly Val Ser Asn Arg Asp Phe
        195                 200                 205

Val Glu Gly Met Ser Gly Gly Thr Trp Val Asp Ile Val Leu Glu His
210                 215                 220

Gly Gly Cys Val Thr Val Met Ala Gln Asp Lys Pro Thr Val Asp Ile
225                 230                 235                 240

Glu Leu Val Thr Thr Thr Val Ser Asn Met Ala Glu Val Arg Ser Tyr
                245                 250                 255

Cys Tyr Glu Ala Ser Ile Ser Asp Met Ala Ser Asp Ser Arg Cys Pro
            260                 265                 270

Thr Gln Gly Glu Ala Tyr Leu Asp Lys Gln Ser Asp Thr Gln Tyr Val
        275                 280                 285

Cys Lys Arg Thr Leu Val Asp Arg Gly Trp Gly Asn Gly Cys Gly Leu
290                 295                 300

Phe Gly Lys Gly Ser Leu Val Thr Cys Ala Lys Phe Ala Cys Ser Lys
305                 310                 315                 320

Lys Met Thr Gly Lys Ser Ile Gln Pro Glu Asn Leu Glu Tyr Arg Ile
                325                 330                 335

Met Leu Ser Val His Gly Ser Gln His Ser Gly Met Ile Val Asn Asp
            340                 345                 350

Thr Gly His Glu Thr Asp Glu Asn Arg Ala Lys Val Glu Ile Thr Pro
        355                 360                 365
```

Asn Ser Pro Arg Ala Glu Ala Thr Leu Gly Gly Phe Gly Ser Leu Gly
            370                 375                 380

Leu Asp Cys Glu Pro Arg Thr Gly Leu Asp Phe Ser Asp Leu Tyr Tyr
385                 390                 395                 400

Leu Thr Met Asn Asn Lys His Trp Leu Val His Lys Glu Trp Phe His
                405                 410                 415

Asp Ile Pro Leu Pro Trp His Ala Gly Ala Asp Thr Gly Thr Pro His
            420                 425                 430

Trp Asn Asn Lys Glu Ala Leu Val Glu Phe Lys Asp Ala His Ala Lys
            435                 440                 445

Arg Gln Thr Val Val Leu Gly Ser Gln Glu Gly Ala Val His Thr
450                 455                 460

Ala Leu Ala Gly Ala Leu Glu Ala Glu Met Asp Gly Ala Lys Gly Arg
465                 470                 475                 480

Leu Ser Ser Gly His Leu Lys Cys Arg Leu Lys Met Asp Lys Leu Arg
            485                 490                 495

Leu Lys Gly Val Ser Tyr Ser Leu Cys Thr Ala Ala Phe Thr Phe Thr
            500                 505                 510

Lys Ile Pro Ala Glu Thr Leu His Gly Thr Val Thr Val Glu Val Gln
            515                 520                 525

Tyr Ala Gly Thr Asp Gly Pro Cys Lys Val Pro Ala Gln Met Ala Val
            530                 535                 540

Asp Met Gln Thr Leu Thr Pro Val Gly Arg Leu Ile Thr Ala Asn Pro
545                 550                 555                 560

Val Ile Thr Glu Ser Thr Glu Asn Ser Lys Met Met Leu Glu Leu Asp
                565                 570                 575

Pro Pro Phe Gly Asp Ser Tyr Ile Val Ile Gly Val Gly Glu Lys Lys
            580                 585                 590

Ile Thr His His Trp His Arg Ser Gly Glu Gln Lys Leu Ile Ser Glu
            595                 600                 605

Glu Asp Leu Gly Gly Glu Gln Lys Leu Ile Ser Glu Glu Asp Leu His
            610                 615                 620

His His His His
625

<210> SEQ ID NO 355
<211> LENGTH: 624
<212> TYPE: PRT
<213> ORGANISM: Artificial Sequence
<220> FEATURE:
<223> OTHER INFORMATION: ZIka prM80E.BirA.6xHis

<400> SEQUENCE: 355

Met His Arg Pro Arg Arg Gly Thr Arg Pro Pro Leu Ala Leu
1               5                   10                  15

Leu Ala Leu Leu Leu Ala Ala Arg Gly Ala Asp Ala Ala Glu Val
                20                  25                  30

Thr Arg Arg Gly Ser Ala Tyr Tyr Met Tyr Leu Asp Arg Asn Asp Ala
            35                  40                  45

Gly Glu Ala Ile Ser Phe Pro Thr Thr Leu Gly Met Asn Lys Cys Tyr
50                  55                  60

Ile Gln Ile Met Asp Leu Gly His Met Cys Asp Ala Thr Met Ser Tyr
65                  70                  75                  80

Glu Cys Pro Met Leu Asp Glu Gly Val Glu Pro Asp Asp Val Asp Cys
                85                  90                  95

```
Trp Cys Asn Thr Thr Ser Thr Trp Val Val Tyr Gly Thr Cys His His
            100                 105                 110

Lys Lys Gly Glu Ala Arg Arg Ser Arg Arg Ala Val Thr Leu Pro Ser
            115                 120                 125

His Ser Thr Arg Lys Leu Gln Thr Arg Ser Gln Thr Trp Leu Glu Ser
            130                 135                 140

Arg Glu Tyr Thr Lys His Leu Ile Arg Val Glu Asn Trp Ile Phe Arg
145                 150                 155                 160

Asn Pro Gly Phe Ala Leu Ala Ala Ala Ile Ala Trp Leu Leu Gly
                165                 170                 175

Ser Ser Thr Ser Gln Lys Val Ile Tyr Leu Val Met Ile Leu Leu Ile
            180                 185                 190

Ala Pro Ala Tyr Ser Ile Arg Cys Ile Gly Val Ser Asn Arg Asp Phe
            195                 200                 205

Val Glu Gly Met Ser Gly Gly Thr Trp Val Asp Ile Val Leu Glu His
            210                 215                 220

Gly Gly Cys Val Thr Val Met Ala Gln Asp Lys Pro Thr Val Asp Ile
225                 230                 235                 240

Glu Leu Val Thr Thr Thr Val Ser Asn Met Ala Glu Val Arg Ser Tyr
                245                 250                 255

Cys Tyr Glu Ala Ser Ile Ser Asp Met Ala Ser Asp Ser Arg Cys Pro
            260                 265                 270

Thr Gln Gly Glu Ala Tyr Leu Asp Lys Gln Ser Asp Thr Gln Tyr Val
            275                 280                 285

Cys Lys Arg Thr Leu Val Asp Arg Gly Trp Gly Asn Gly Cys Gly Leu
            290                 295                 300

Phe Gly Lys Gly Ser Leu Val Thr Cys Ala Lys Phe Ala Cys Ser Lys
305                 310                 315                 320

Lys Met Thr Gly Lys Ser Ile Gln Pro Glu Asn Leu Glu Tyr Arg Ile
            325                 330                 335

Met Leu Ser Val His Gly Ser Gln His Ser Gly Met Ile Val Asn Asp
            340                 345                 350

Thr Gly His Glu Thr Asp Glu Asn Arg Ala Lys Val Glu Ile Thr Pro
            355                 360                 365

Asn Ser Pro Arg Ala Glu Ala Thr Leu Gly Gly Phe Gly Ser Leu Gly
            370                 375                 380

Leu Asp Cys Glu Pro Arg Thr Gly Leu Asp Phe Ser Asp Leu Tyr Tyr
385                 390                 395                 400

Leu Thr Met Asn Asn Lys His Trp Leu Val His Lys Glu Trp Phe His
            405                 410                 415

Asp Ile Pro Leu Pro Trp His Ala Gly Ala Asp Thr Gly Thr Pro His
            420                 425                 430

Trp Asn Asn Lys Glu Ala Leu Val Glu Phe Lys Asp Ala His Ala Lys
            435                 440                 445

Arg Gln Thr Val Val Val Leu Gly Ser Gln Glu Gly Ala Val His Thr
            450                 455                 460

Ala Leu Ala Gly Ala Leu Glu Ala Glu Met Asp Gly Ala Lys Gly Arg
465                 470                 475                 480

Leu Ser Ser Gly His Leu Lys Cys Arg Leu Lys Met Asp Lys Leu Arg
            485                 490                 495

Leu Lys Gly Val Ser Tyr Ser Leu Cys Thr Ala Ala Phe Thr Phe Thr
            500                 505                 510
```

```
Lys Ile Pro Ala Glu Thr Leu His Gly Thr Val Thr Val Glu Val Gln
            515                 520                 525

Tyr Ala Gly Thr Asp Gly Pro Cys Lys Val Pro Ala Gln Met Ala Val
        530                 535                 540

Asp Met Gln Thr Leu Thr Pro Val Gly Arg Leu Ile Thr Ala Asn Pro
545                 550                 555                 560

Val Ile Thr Glu Ser Thr Glu Asn Ser Lys Met Met Leu Glu Leu Asp
                565                 570                 575

Pro Pro Phe Gly Asp Ser Tyr Ile Val Ile Gly Val Gly Glu Lys Lys
            580                 585                 590

Ile Thr His His Trp His Arg Ser Gly Gly Gly Leu Asn Asp Ile
        595                 600                 605

Phe Glu Ala Gln Lys Ile Glu Trp His Glu His His His His His
    610                 615                 620

<210> SEQ ID NO 356
<211> LENGTH: 330
<212> TYPE: PRT
<213> ORGANISM: Artificial Sequence
<220> FEATURE:
<223> OTHER INFORMATION: hIgG1 Constant region

<400> SEQUENCE: 356

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255
```

```
Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 357
<211> LENGTH: 326
<212> TYPE: PRT
<213> ORGANISM: Artificial Sequence
<220> FEATURE:
<223> OTHER INFORMATION: hIgG4 us

<400> SEQUENCE: 357

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Gly Gly Gly Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser Gln Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Tyr Arg Val Val Ser Val Leu Thr Val Leu His Gln Asp Trp
            180                 185                 190

Leu Asn Gly Lys Glu Tyr Lys Cys Lys Val Ser Asn Lys Gly Leu Pro
        195                 200                 205

Ser Ser Ile Glu Lys Thr Ile Ser Lys Ala Lys Gly Gln Pro Arg Glu
    210                 215                 220

Pro Gln Val Tyr Thr Leu Pro Pro Ser Gln Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Val Leu Asp Ser Asp Gly Ser Phe Phe Leu Tyr Ser Arg
        275                 280                 285
```

Leu Thr Val Asp Lys Ser Arg Trp Gln Glu Gly Asn Val Phe Ser Cys
290                 295                 300

Ser Val Met His Glu Ala Leu His Asn His Tyr Thr Gln Lys Ser Leu
305                 310                 315                 320

Ser Leu Ser Leu Gly Lys
                325

<210> SEQ ID NO 358
<211> LENGTH: 326
<212> TYPE: PRT
<213> ORGANISM: Artificial Sequence
<220> FEATURE:
<223> OTHER INFORMATION: hIgG4 us with YTE

<400> SEQUENCE: 358

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Gly Gly Gly Gly Pro Ser Val Phe Leu Phe Pro Pro Lys Pro Lys Asp
        115                 120                 125

Thr Leu Tyr Ile Thr Arg Glu Pro Glu Val Thr Cys Val Val Val Asp
    130                 135                 140

Val Ser Gln Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Tyr Arg Val Val Ser Val Leu Thr Val Leu His Gln Asp Trp
            180                 185                 190

Leu Asn Gly Lys Glu Tyr Lys Cys Lys Val Ser Asn Lys Gly Leu Pro
        195                 200                 205

Ser Ser Ile Glu Lys Thr Ile Ser Lys Ala Lys Gly Gln Pro Arg Glu
    210                 215                 220

Pro Gln Val Tyr Thr Leu Pro Pro Ser Gln Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Val Leu Asp Ser Asp Gly Ser Phe Phe Leu Tyr Ser Arg
        275                 280                 285

Leu Thr Val Asp Lys Ser Arg Trp Gln Glu Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Leu Gly Lys
            325

<210> SEQ ID NO 359
<211> LENGTH: 449
<212> TYPE: PRT
<213> ORGANISM: Artificial Sequence
<220> FEATURE:
<223> OTHER INFORMATION: mAb1 IgG1 HC

<400> SEQUENCE: 359

Glu Val Gln Leu Gln Gln Ser Gly Pro Glu Leu Val Lys Pro Gly Thr
1               5                   10                  15

Ser Val Lys Ile Ser Cys Lys Thr Ser Gly Tyr Thr Phe Thr Glu Tyr
            20                  25                  30

Thr Ile His Trp Val Lys Gln Ser His Gly Lys Ser Leu Ala Trp Ile
        35                  40                  45

Gly Gly Ile Asp Pro Asn Ser Gly Gly Thr Asn Tyr Ser Pro Asn Phe
    50                  55                  60

Lys Gly Lys Ala Thr Leu Thr Val Asp Lys Ser Ser Ser Thr Ala Tyr
65                  70                  75                  80

Met Asp Leu Arg Ser Leu Ser Ser Glu Asp Ser Ala Val Tyr Phe Cys
                85                  90                  95

Ala Arg Ile Tyr His Tyr Asp Gly Tyr Phe Asp Val Trp Gly Ala Gly
            100                 105                 110

Thr Ala Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
            435                 440                 445

Lys

<210> SEQ ID NO 360
<211> LENGTH: 214
<212> TYPE: PRT
<213> ORGANISM: Artificial Sequence
<220> FEATURE:
<223> OTHER INFORMATION: mAb1 IgG1 LC

<400> SEQUENCE: 360

Asp Ile Lys Met Thr Gln Ser Pro Ser Ser Met Tyr Ala Ser Leu Gly
1               5                   10                  15

Glu Arg Val Thr Ile Thr Cys Lys Ala Ser Gln Asp Ile Asn Ser Tyr
                20                  25                  30

Leu Thr Trp Phe Gln Gln Lys Pro Gly Lys Ser Pro Lys Thr Leu Ile
            35                  40                  45

Tyr Arg Ala Asn Arg Leu Ile Asp Gly Val Pro Ser Arg Phe Ser Gly
        50                  55                  60

Ser Gly Ser Gly Gln Asp Tyr Ser Leu Thr Ile Ser Ser Leu Asp Tyr
65                  70                  75                  80

Glu Asp Met Gly Ile Tyr Tyr Cys Leu Gln Tyr Asp Glu Phe Pro Pro
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 361
<211> LENGTH: 445
<212> TYPE: PRT
<213> ORGANISM: Artificial Sequence
<220> FEATURE:
<223> OTHER INFORMATION: mAb2 IgG4 s HC

<400> SEQUENCE: 361

Glu Val Gln Leu Gln Gln Ser Gly Pro Glu Leu Val Lys Pro Gly Thr
1               5                   10                  15

Ser Val Lys Ile Ser Cys Lys Thr Ser Gly Tyr Thr Phe Thr Glu Tyr
            20                  25                  30

Thr Ile His Trp Val Lys Gln Ser His Gly Lys Ser Leu Ala Trp Ile
        35                  40                  45

Gly Gly Ile Asp Pro Asn Ser Gly Thr Asn Tyr Ser Pro Asn Phe
    50                  55                  60

Lys Gly Lys Ala Thr Leu Thr Val Asp Lys Ser Ser Thr Ala Tyr
65                  70                  75                  80

Met Asp Leu Arg Ser Leu Ser Ser Glu Asp Ser Ala Val Tyr Phe Cys
            85                  90                  95

Ala Arg Ile Tyr His Tyr Asp Gly Tyr Phe Asp Val Trp Gly Ala Gly
            100                 105                 110

Thr Ala Val Thr Val Ser Ser Ala Ser Thr Lys Gly Pro Ser Val Phe
            115                 120                 125

Pro Leu Ala Pro Cys Ser Arg Ser Thr Ser Glu Ser Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
            195                 200                 205

Ser Asn Thr Lys Val Asp Lys Arg Val Glu Ser Lys Tyr Gly Pro Pro
210                 215                 220

Cys Pro Pro Cys Pro Ala Pro Pro Val Ala Gly Pro Ser Val Phe Leu
225                 230                 235                 240

Phe Pro Pro Lys Pro Lys Asp Thr Leu Met Ile Ser Arg Thr Pro Glu
            245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
            275                 280                 285

Pro Arg Glu Glu Gln Phe Asn Ser Thr Tyr Arg Val Val Ser Val Leu
            290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
            325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
            370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln

```
                        405                 410                 415

Glu Gly Asn Val Phe Ser Cys Ser Val Met His Glu Ala Leu His Asn
                420                 425                 430

His Tyr Thr Gln Lys Ser Leu Ser Leu Ser Leu Gly Lys
            435                 440                 445

<210> SEQ ID NO 362
<211> LENGTH: 214
<212> TYPE: PRT
<213> ORGANISM: Artificial Sequence
<220> FEATURE:
<223> OTHER INFORMATION: mAb2 IgG4 s LC

<400> SEQUENCE: 362

Asp Ile Lys Met Thr Gln Ser Pro Ser Ser Met Tyr Ala Ser Leu Gly
1               5                   10                  15

Glu Arg Val Thr Ile Thr Cys Lys Ala Ser Gln Asp Ile Asn Ser Tyr
            20                  25                  30

Leu Thr Trp Phe Gln Gln Lys Pro Gly Lys Ser Pro Lys Thr Leu Ile
        35                  40                  45

Tyr Arg Ala Asn Arg Leu Ile Asp Gly Val Pro Ser Arg Phe Ser Gly
50                  55                  60

Ser Gly Ser Gly Gln Asp Tyr Ser Leu Thr Ile Ser Ser Leu Asp Tyr
65                  70                  75                  80

Glu Asp Met Gly Ile Tyr Tyr Cys Leu Gln Tyr Asp Glu Phe Pro Pro
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 363
<211> LENGTH: 445
<212> TYPE: PRT
<213> ORGANISM: Artificial Sequence
<220> FEATURE:
<223> OTHER INFORMATION: mAb3 IgG4 us HC

<400> SEQUENCE: 363

Glu Val Gln Leu Gln Gln Ser Gly Pro Glu Leu Val Lys Pro Gly Thr
1               5                   10                  15

Ser Val Lys Ile Ser Cys Lys Thr Ser Gly Tyr Thr Phe Thr Glu Tyr
            20                  25                  30

Thr Ile His Trp Val Lys Gln Ser His Gly Lys Ser Leu Ala Trp Ile
        35                  40                  45
```

```
Gly Gly Ile Asp Pro Asn Ser Gly Gly Thr Asn Tyr Ser Pro Asn Phe
    50                  55                  60

Lys Gly Lys Ala Thr Leu Thr Val Asp Lys Ser Ser Ser Thr Ala Tyr
 65              70                  75                  80

Met Asp Leu Arg Ser Leu Ser Ser Glu Asp Ser Ala Val Tyr Phe Cys
                 85                  90                  95

Ala Arg Ile Tyr His Tyr Asp Gly Tyr Phe Asp Val Trp Gly Ala Gly
            100                 105                 110

Thr Ala Val Thr Val Ser Ser Ala Ser Thr Lys Gly Pro Ser Val Phe
            115                 120                 125

Pro Leu Ala Pro Cys Ser Arg Ser Thr Ser Glu Ser Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
            195                 200                 205

Ser Asn Thr Lys Val Asp Lys Arg Val Glu Ser Lys Tyr Gly Pro Pro
210                 215                 220

Cys Pro Pro Cys Pro Ala Pro Gly Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
            275                 280                 285

Pro Arg Glu Glu Gln Phe Asn Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly Lys
            435                 440                 445

<210> SEQ ID NO 364
<211> LENGTH: 214
<212> TYPE: PRT
```

<213> ORGANISM: Artificial Sequence
<220> FEATURE:
<223> OTHER INFORMATION: mAb3 IgG4 us LC

<400> SEQUENCE: 364

```
Asp Ile Lys Met Thr Gln Ser Pro Ser Ser Met Tyr Ala Ser Leu Gly
1               5                   10                  15

Glu Arg Val Thr Ile Thr Cys Lys Ala Ser Gln Asp Ile Asn Ser Tyr
            20                  25                  30

Leu Thr Trp Phe Gln Gln Lys Pro Gly Lys Ser Pro Lys Thr Leu Ile
        35                  40                  45

Tyr Arg Ala Asn Arg Leu Ile Asp Gly Val Pro Ser Arg Phe Ser Gly
50                  55                  60

Ser Gly Ser Gly Gln Asp Tyr Ser Leu Thr Ile Ser Ser Leu Asp Tyr
65                  70                  75                  80

Glu Asp Met Gly Ile Tyr Tyr Cys Leu Gln Tyr Asp Glu Phe Pro Pro
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 365
<211> LENGTH: 326
<212> TYPE: PRT
<213> ORGANISM: Artificial Sequence
<220> FEATURE:
<223> OTHER INFORMATION: IgG4s Fc No YTE

<400> SEQUENCE: 365

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110
```

Pro Val Ala Gly Pro Ser Val Phe Leu Phe Pro Pro Lys Pro Lys Asp
            115                 120                 125

Thr Leu Met Ile Ser Arg Thr Pro Glu Val Thr Cys Val Val Val Asp
130                 135                 140

Val Ser Gln Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Tyr Arg Val Val Ser Val Leu Thr Val Leu His Gln Asp Trp
            180                 185                 190

Leu Asn Gly Lys Glu Tyr Lys Cys Lys Val Ser Asn Lys Gly Leu Pro
        195                 200                 205

Ser Ser Ile Glu Lys Thr Ile Ser Lys Ala Lys Gly Gln Pro Arg Glu
210                 215                 220

Pro Gln Val Tyr Thr Leu Pro Pro Ser Gln Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Val Leu Asp Ser Asp Gly Ser Phe Phe Leu Tyr Ser Arg
        275                 280                 285

Leu Thr Val Asp Lys Ser Arg Trp Gln Glu Gly Asn Val Phe Ser Cys
290                 295                 300

Ser Val Met His Glu Ala Leu His Asn His Tyr Thr Gln Lys Ser Leu
305                 310                 315                 320

Ser Leu Ser Leu Gly Lys
                325

<210> SEQ ID NO 366
<211> LENGTH: 326
<212> TYPE: PRT
<213> ORGANISM: Artificial Sequence
<220> FEATURE:
<223> OTHER INFORMATION: IgG4s Fc + YTE

<400> SEQUENCE: 366

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Tyr Ile Thr Arg Glu Pro Glu Val Thr Cys Val Val Val Asp
130                 135                 140

Val Ser Gln Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
            165                 170                 175

Ser Thr Tyr Arg Val Val Ser Val Leu Thr Val Leu His Gln Asp Trp
            180                 185                 190

Leu Asn Gly Lys Glu Tyr Lys Cys Lys Val Ser Asn Lys Gly Leu Pro
        195                 200                 205

Ser Ser Ile Glu Lys Thr Ile Ser Lys Ala Lys Gly Gln Pro Arg Glu
        210                 215                 220

Pro Gln Val Tyr Thr Leu Pro Pro Ser Gln Glu Glu Met Thr Lys Asn
225                 230                 235                 240

Gln Val Ser Leu Thr Cys Leu Val Lys Gly Phe Tyr Pro Ser Asp Ile
            245                 250                 255

Ala Val Glu Trp Glu Ser Asn Gly Gln Pro Glu Asn Asn Tyr Lys Thr
            260                 265                 270

Thr Pro Pro Val Leu Asp Ser Asp Gly Ser Phe Phe Leu Tyr Ser Arg
        275                 280                 285

Leu Thr Val Asp Lys Ser Arg Trp Gln Glu Gly Asn Val Phe Ser Cys
290                 295                 300

Ser Val Met His Glu Ala Leu His Asn His Tyr Thr Gln Lys Ser Leu
305                 310                 315                 320

Ser Leu Ser Leu Gly Lys
            325

<210> SEQ ID NO 367
<211> LENGTH: 443
<212> TYPE: PRT
<213> ORGANISM: Artificial Sequence
<220> FEATURE:
<223> OTHER INFORMATION: H4H25703N HC (IgG4us No YTE)

<400> SEQUENCE: 367

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Asn Tyr Tyr
            20                  25                  30

Gly Met His Trp Val Arg Gln Ala Pro Gly Lys Gly Leu Glu Trp Val
        35                  40                  45

Ala Val Ile Ser Tyr Asp Gly Thr Asn Lys Tyr Tyr Ala Asp Ser Val
    50                  55                  60

Lys Gly Arg Phe Thr Thr Ser Arg Asp Asn Lys Asn Thr Leu Tyr
65                  70                  75                  80

Leu Gln Met Asn Ser Leu Arg Ala Glu Asp Thr Ala Leu Tyr Tyr Cys
                85                  90                  95

Ala Arg Asp Arg Gly Gly Arg Phe Asp Tyr Trp Gly Gln Gly Ile Gln
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

```
Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Gly Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser Gln Glu Asp Pro Glu Val Gln Phe Asn
            260                 265                 270

Trp Tyr Val Asp Gly Val Glu Val His Asn Ala Lys Thr Lys Pro Arg
        275                 280                 285

Glu Glu Gln Phe Asn Ser Thr Tyr Arg Val Val Ser Val Leu Thr Val
    290                 295                 300

Leu His Gln Asp Trp Leu Asn Gly Lys Glu Tyr Lys Cys Lys Val Ser
305                 310                 315                 320

Asn Lys Gly Leu Pro Ser Ser Ile Glu Lys Thr Ile Ser Lys Ala Lys
                325                 330                 335

Gly Gln Pro Arg Glu Pro Gln Val Tyr Thr Leu Pro Pro Ser Gln Glu
            340                 345                 350

Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Val Leu Asp Ser Asp Gly Ser Phe
385                 390                 395                 400

Phe Leu Tyr Ser Arg Leu Thr Val Asp Lys Ser Arg Trp Gln Glu Gly
                405                 410                 415

Asn Val Phe Ser Cys Ser Val Met His Glu Ala Leu His Asn His Tyr
            420                 425                 430

Thr Gln Lys Ser Leu Ser Leu Ser Leu Gly Lys
        435                 440

<210> SEQ ID NO 368
<211> LENGTH: 215
<212> TYPE: PRT
<213> ORGANISM: Artificial Sequence
<220> FEATURE:
<223> OTHER INFORMATION: H4H25703N LC

<400> SEQUENCE: 368

Glu Ile Val Leu Thr Gln Ser Pro Asp Thr Leu Ser Leu Ser Pro Gly
1               5                   10                  15

Glu Arg Ala Thr Leu Ser Cys Arg Ala Ser Gln Ser Val Ser Ser Asn
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Arg Tyr Gly Thr Ser Pro
                85                  90                  95
```

```
Leu Thr Phe Gly Gly Thr Lys Val Glu Ile Lys Arg Thr Val Ala
            100                 105                 110

Ala Pro Ser Val Phe Ile Phe Pro Pro Ser Asp Glu Gln Leu Lys Ser
115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 369
<211> LENGTH: 443
<212> TYPE: PRT
<213> ORGANISM: Artificial Sequence
<220> FEATURE:
<223> OTHER INFORMATION: H4H25703N HC (IgG4us + YTE)

<400> SEQUENCE: 369

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Asn Tyr Tyr
            20                  25                  30

Gly Met His Trp Val Arg Gln Ala Pro Gly Lys Gly Leu Glu Trp Val
        35                  40                  45

Ala Val Ile Ser Tyr Asp Gly Thr Asn Lys Tyr Tyr Ala Asp Ser Val
    50                  55                  60

Lys Gly Arg Phe Thr Thr Ser Arg Asp Asn Ser Lys Asn Thr Leu Tyr
65                  70                  75                  80

Leu Gln Met Asn Ser Leu Arg Ala Glu Asp Thr Ala Leu Tyr Tyr Cys
                85                  90                  95

Ala Arg Asp Arg Gly Gly Arg Phe Asp Tyr Trp Gly Gln Gly Ile Gln
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Gly Gly Gly Pro Ser Val Phe Leu Phe Pro
225                 230                 235                 240
```

Pro Lys Pro Lys Asp Thr Leu Tyr Ile Thr Arg Glu Pro Glu Val Thr
            245                 250                 255

Cys Val Val Asp Val Ser Gln Glu Asp Pro Glu Val Gln Phe Asn
            260                 265                 270

Trp Tyr Val Asp Gly Val Glu Val His Asn Ala Lys Thr Lys Pro Arg
            275                 280                 285

Glu Glu Gln Phe Asn Ser Thr Tyr Arg Val Val Ser Val Leu Thr Val
            290                 295                 300

Leu His Gln Asp Trp Leu Asn Gly Lys Glu Tyr Lys Cys Lys Val Ser
305                 310                 315                 320

Asn Lys Gly Leu Pro Ser Ser Ile Glu Lys Thr Ile Ser Lys Ala Lys
            325                 330                 335

Gly Gln Pro Arg Glu Pro Gln Val Tyr Thr Leu Pro Pro Ser Gln Glu
            340                 345                 350

Glu Met Thr Lys Asn Gln Val Ser Leu Thr Cys Leu Val Lys Gly Phe
            355                 360                 365

Tyr Pro Ser Asp Ile Ala Val Glu Trp Glu Ser Asn Gly Gln Pro Glu
            370                 375                 380

Asn Asn Tyr Lys Thr Thr Pro Pro Val Leu Asp Ser Asp Gly Ser Phe
385                 390                 395                 400

Phe Leu Tyr Ser Arg Leu Thr Val Asp Lys Ser Arg Trp Gln Glu Gly
            405                 410                 415

Asn Val Phe Ser Cys Ser Val Met His Glu Ala Leu His Asn His Tyr
            420                 425                 430

Thr Gln Lys Ser Leu Ser Leu Ser Leu Gly Lys
            435                 440

<210> SEQ ID NO 370
<211> LENGTH: 446
<212> TYPE: PRT
<213> ORGANISM: Artificial Sequence
<220> FEATURE:
<223> OTHER INFORMATION: H4H25619P HC (IgG4us No YTE)

<400> SEQUENCE: 370

Gln Val Gln Leu Val Glu Ser Gly Gly Gly Val Gln Pro Gly Arg
1               5                   10                  15

Ser Leu Arg Leu Ser Cys Thr Ala Ser Gly Phe Thr Phe Ser Thr Tyr
            20                  25                  30

Gly Met His Trp Val Arg His Val Pro Gly Lys Gly Leu Glu Trp Val
            35                  40                  45

Ala Ile Val Trp Tyr Asp Gly Ser Asp Lys Ser Tyr Ala Ala Ser Val
            50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
            85                  90                  95

Ala Arg Gln Gly Thr Tyr Tyr Tyr Gly Met Asp Val Trp Gly Gln
            100                 105                 110

Gly Thr Thr Val Thr Val Ser Ser Ala Ser Thr Lys Gly Pro Ser Val
            115                 120                 125

Phe Pro Leu Ala Pro Cys Ser Arg Ser Thr Ser Glu Ser Thr Ala Ala
            130                 135                 140

Leu Gly Cys Leu Val Lys Asp Tyr Phe Pro Glu Pro Val Thr Val Ser
145                 150                 155                 160

-continued

```
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Ser Leu Gly Thr Lys Thr Tyr Thr Cys Asn Val Asp His Lys
        195                 200                 205
Pro Ser Asn Thr Lys Val Asp Lys Arg Val Glu Ser Lys Tyr Gly Pro
    210                 215                 220
Pro Cys Pro Pro Cys Pro Ala Pro Gly Gly Gly Pro Ser Val Phe
225                 230                 235                 240
Leu Phe Pro Pro Lys Pro Lys Asp Thr Leu Met Ile Ser Arg Thr Pro
                245                 250                 255
Glu Val Thr Cys Val Val Val Asp Val Ser Gln Glu Asp Pro Glu Val
            260                 265                 270
Gln Phe Asn Trp Tyr Val Asp Gly Val Glu Val His Asn Ala Lys Thr
        275                 280                 285
Lys Pro Arg Glu Glu Gln Phe Asn Ser Thr Tyr Arg Val Val Ser Val
    290                 295                 300
Leu Thr Val Leu His Gln Asp Trp Leu Asn Gly Lys Glu Tyr Lys Cys
305                 310                 315                 320
Lys Val Ser Asn Lys Gly Leu Pro Ser Ser Ile Glu Lys Thr Ile Ser
                325                 330                 335
Lys Ala Lys Gly Gln Pro Arg Glu Pro Gln Val Tyr Thr Leu Pro Pro
            340                 345                 350
Ser Gln Glu Glu Met Thr Lys Asn Gln Val Ser Leu Thr Cys Leu Val
        355                 360                 365
Lys Gly Phe Tyr Pro Ser Asp Ile Ala Val Glu Trp Glu Ser Asn Gly
    370                 375                 380
Gln Pro Glu Asn Asn Tyr Lys Thr Thr Pro Pro Val Leu Asp Ser Asp
385                 390                 395                 400
Gly Ser Phe Phe Leu Tyr Ser Arg Leu Thr Val Asp Lys Ser Arg Trp
                405                 410                 415
Gln Glu Gly Asn Val Phe Ser Cys Ser Val Met His Glu Ala Leu His
            420                 425                 430
Asn His Tyr Thr Gln Lys Ser Leu Ser Leu Ser Leu Gly Lys
        435                 440                 445

<210> SEQ ID NO 371
<211> LENGTH: 215
<212> TYPE: PRT
<213> ORGANISM: Artificial Sequence
<220> FEATURE:
<223> OTHER INFORMATION: H4H25619P LC

<400> SEQUENCE: 371

Asp Ile Gln Met Thr Gln Ser Pro Ser Ser Leu Ser Ala Ser Val Gly
1               5                   10                  15
Asp Arg Val Thr Ile Thr Cys Arg Ser Ser Gln Thr Ile Thr Asn Tyr
                20                  25                  30
Leu Asn Trp Tyr Gln Gln Arg Pro Gly Lys Ala Pro Lys Leu Leu Ile
            35                  40                  45
Tyr Ala Ala Ser Ser Leu Gln Ser Gly Val Pro Ser Arg Phe Ser Gly
        50                  55                  60
Ser Gly Ser Gly Thr Asp Phe Thr Leu Thr Ile Ser Ser Leu Gln Pro
65                  70                  75                  80
```

```
Glu Asp Phe Ala Thr Tyr Tyr Cys Gln Gln Ser Tyr Ser Thr Pro Pro
                85                  90                  95

Ile Thr Phe Gly Gln Gly Thr Lys Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```

<210> SEQ ID NO 372
<211> LENGTH: 446
<212> TYPE: PRT
<213> ORGANISM: Artificial Sequence
<220> FEATURE:
<223> OTHER INFORMATION: H4H25619P HC (IgG4us + YTE)

<400> SEQUENCE: 372

```
Gln Val Gln Leu Val Glu Ser Gly Gly Gly Val Val Gln Pro Gly Arg
1               5                   10                  15

Ser Leu Arg Leu Ser Cys Thr Ala Ser Gly Phe Thr Phe Ser Thr Tyr
            20                  25                  30

Gly Met His Trp Val Arg His Val Pro Gly Lys Gly Leu Glu Trp Val
        35                  40                  45

Ala Ile Val Trp Tyr Asp Gly Ser Asp Lys Ser Tyr Ala Ala Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Arg Gln Gly Thr Tyr Tyr Tyr Gly Met Asp Val Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220
```

Pro Cys Pro Pro Cys Pro Ala Pro Gly Gly Gly Pro Ser Val Phe
225                 230                 235                 240

Leu Phe Pro Pro Lys Pro Lys Asp Thr Leu Tyr Ile Thr Arg Glu Pro
            245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
            325                 330                 335

Lys Ala Lys Gly Gln Pro Arg Glu Pro Gln Val Tyr Thr Leu Pro Pro
        340                 345                 350

Ser Gln Glu Glu Met Thr Lys Asn Gln Val Ser Leu Thr Cys Leu Val
    355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
            405                 410                 415

Gln Glu Gly Asn Val Phe Ser Cys Ser Val Met His Glu Ala Leu His
        420                 425                 430

Asn His Tyr Thr Gln Lys Ser Leu Ser Leu Ser Leu Gly Lys
    435                 440                 445

<210> SEQ ID NO 373
<211> LENGTH: 448
<212> TYPE: PRT
<213> ORGANISM: Artificial Sequence
<220> FEATURE:
<223> OTHER INFORMATION: H4H25598P HC (IgG4us No YTE)

<400> SEQUENCE: 373

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Ser Gly Leu Glu Trp Val
        35                  40                  45

Ser Val Ile Tyr Ser Gly Gly Ile Thr His Tyr Ile Gly Ser Val Lys
    50                  55                  60

Gly Arg Phe Thr Ile Ser Arg His Asn Ser Lys Asn Thr Leu Tyr Leu
65                  70                  75                  80

Gln Met Asn Ser Leu Arg Ala Glu Asp Thr Ala Met Tyr Tyr Cys Ala
            85                  90                  95

Arg Glu Arg Tyr Ser Gly Ile Thr Gly Asn Pro Tyr Gly Phe Asp Phe
        100                 105                 110

Trp Gly Gln Gly Thr Met Val Thr Val Ser Ser Ala Ser Thr Lys Gly
    115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
            165                 170                 175

Pro Ala Val Leu Gln Ser Ser Gly Leu Tyr Ser Leu Ser Ser Val Val
        180                 185                 190

Thr Val Pro Ser Ser Ser Leu Gly Thr Lys Thr Tyr Thr Cys Asn Val
    195                 200                 205

Asp His Lys Pro Ser Asn Thr Lys Val Asp Lys Arg Val Glu Ser Lys
210                 215                 220

Tyr Gly Pro Pro Cys Pro Pro Cys Pro Ala Pro Gly Gly Gly Pro
225                 230                 235                 240

Ser Val Phe Phe Pro Pro Lys Pro Lys Asp Thr Leu Met Ile Ser Arg
            245                 250                 255

Thr Pro Glu Val Thr Cys Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
            325                 330                 335

Ile Ser Lys Ala Lys Gly Gln Pro Arg Glu Pro Gln Val Tyr Thr Leu
        340                 345                 350

Pro Pro Ser Gln Glu Glu Met Thr Lys Asn Gln Val Ser Leu Thr Cys
    355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
            405                 410                 415

Arg Trp Gln Glu Gly Asn Val Phe Ser Cys Ser Val Met His Glu Ala
        420                 425                 430

Leu His Asn His Tyr Thr Gln Lys Ser Leu Ser Leu Ser Leu Gly Lys
    435                 440                 445

<210> SEQ ID NO 374
<211> LENGTH: 214
<212> TYPE: PRT
<213> ORGANISM: Artificial Sequence
<220> FEATURE:
<223> OTHER INFORMATION: H4H25598P LC

<400> SEQUENCE: 374

Asp Ile Gln Leu Thr Gln Ser Pro Ser Phe Leu Ser Ala Ser Val Gly
1               5                   10                  15

Asp Arg Val Thr Ile Thr Cys Trp Ala Ser Gln Asp Ile Ser Ser Tyr
            20                  25                  30

Leu Ala Trp Tyr Gln Gln Lys Pro Gly Ile Ala Pro Lys Leu Leu Ile
        35                  40                  45

Tyr Ser Ala Ser Thr Leu Gln Ser Gly Val Pro Ser Phe Ser Gly
    50                  55                  60

```
Ser Gly Ser Gly Thr Glu Phe Thr Leu Thr Ile Ser Ser Leu Gln Pro
 65                  70                  75                  80

Glu Asp Phe Ala Thr Tyr Tyr Cys Gln Gln Leu Asn Ile Tyr Pro Phe
                 85                  90                  95

Thr Phe Gly Pro Gly Thr Lys Val Asp Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 375
<211> LENGTH: 448
<212> TYPE: PRT
<213> ORGANISM: Artificial Sequence
<220> FEATURE:
<223> OTHER INFORMATION: H4H25598P HC (IgG4us + YTE)

<400> SEQUENCE: 375

```
Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Val Ser Ser Asn
             20                  25                  30

Tyr Met Ser Trp Val Arg Gln Ala Pro Gly Ser Gly Leu Glu Trp Val
         35                  40                  45

Ser Val Ile Tyr Ser Gly Gly Ile Thr His Tyr Ile Gly Ser Val Lys
     50                  55                  60

Gly Arg Phe Thr Ile Ser Arg His Asn Ser Lys Asn Thr Leu Tyr Leu
 65                  70                  75                  80

Gln Met Asn Ser Leu Arg Ala Glu Asp Thr Ala Met Tyr Tyr Cys Ala
                 85                  90                  95

Arg Glu Arg Tyr Ser Gly Ile Thr Gly Asn Pro Tyr Gly Phe Asp Phe
            100                 105                 110

Trp Gly Gln Gly Thr Met Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Lys Thr Tyr Thr Cys Asn Val
        195                 200                 205
```

-continued

```
Asp His Lys Pro Ser Asn Thr Lys Val Asp Lys Arg Val Glu Ser Lys
    210             215                 220
Tyr Gly Pro Pro Cys Pro Pro Cys Pro Ala Pro Gly Gly Gly Gly Pro
225             230                 235             240
Ser Val Phe Phe Pro Pro Lys Pro Lys Asp Thr Leu Tyr Ile Thr Arg
            245                 250             255
Glu Pro Glu Val Thr Cys Val Val Asp Val Ser Gln Glu Asp Pro
            260             265             270
Glu Val Gln Phe Asn Trp Tyr Val Asp Gly Val Glu Val His Asn Ala
        275             280             285
Lys Thr Lys Pro Arg Glu Glu Gln Phe Asn Ser Thr Tyr Arg Val Val
    290             295             300
Ser Val Leu Thr Val Leu His Gln Asp Trp Leu Asn Gly Lys Glu Tyr
305             310             315             320
Lys Cys Lys Val Ser Asn Lys Gly Leu Pro Ser Ser Ile Glu Lys Thr
            325             330             335
Ile Ser Lys Ala Lys Gly Gln Pro Arg Glu Pro Gln Val Tyr Thr Leu
            340             345             350
Pro Pro Ser Gln Glu Glu Met Thr Lys Asn Gln Val Ser Leu Thr Cys
            355             360             365
Leu Val Lys Gly Phe Tyr Pro Ser Asp Ile Ala Val Glu Trp Glu Ser
    370             375             380
Asn Gly Gln Pro Glu Asn Asn Tyr Lys Thr Thr Pro Pro Val Leu Asp
385             390             395             400
Ser Asp Gly Ser Phe Phe Leu Tyr Ser Arg Leu Thr Val Asp Lys Ser
            405             410             415
Arg Trp Gln Gln Gly Asn Val Phe Ser Cys Ser Val Met His Glu Ala
            420             425             430
Leu His Asn His Tyr Thr Gln Lys Ser Leu Ser Leu Ser Leu Gly Lys
        435             440             445
```